US008114862B2

(12) United States Patent
Pellicciari

(10) Patent No.: US 8,114,862 B2
(45) Date of Patent: Feb. 14, 2012

(54) TGR5 MODULATORS AND METHODS OF USE THEREOF

(75) Inventor: Roberto Pellicciari, Perugia (IT)

(73) Assignee: Intercept Pharmaceuticals, Inc., New York, NY (US)

( * ) Notice: Subject to any disclaimer, the term of this patent is extended or adjusted under 35 U.S.C. 154(b) by 44 days.

(21) Appl. No.: 12/622,123

(22) Filed: Nov. 19, 2009

(65) Prior Publication Data

US 2010/0152151 A1   Jun. 17, 2010

(30) Foreign Application Priority Data

Nov. 19, 2008  (EP) ..................................... 08169462

(51) Int. Cl.
*A61K 31/575* (2006.01)
*C07J 9/00* (2006.01)

(52) U.S. Cl. .......................... 514/182; 552/549; 552/550
(58) Field of Classification Search .................. 514/182; 552/549, 550
See application file for complete search history.

(56) References Cited

U.S. PATENT DOCUMENTS

| | | | |
|---|---|---|---|
| 4,892,868 A | 1/1990 | Castagnola et al. |
| 4,921,848 A | 5/1990 | Frigerio et al. |
| 5,061,701 A | 10/1991 | Pellicciari et al. |
| 5,128,481 A | 7/1992 | Oda et al. |
| 5,175,320 A | 12/1992 | Pellicciari et al. |
| 6,200,998 B1 | 3/2001 | Sahoo et al. |
| 6,559,188 B1 | 5/2003 | Gatlin et al. |
| 6,639,078 B1 | 10/2003 | Haffner et al. |
| 6,777,446 B2 | 8/2004 | Houze et al. |
| 6,906,057 B1 | 6/2005 | Forman et al. |
| 6,984,650 B2 | 1/2006 | Haffner et al. |
| 6,987,121 B2 | 1/2006 | Kliewer et al. |
| 7,138,390 B2 | 11/2006 | Pellicciari |
| 2002/0094977 A1 | 7/2002 | Robl et al. |
| 2002/0120137 A1 | 8/2002 | Houze et al. |
| 2002/0132223 A1 | 9/2002 | Forman et al. |
| 2003/0130296 A1 | 7/2003 | Bauer et al. |

FOREIGN PATENT DOCUMENTS

| | | |
|---|---|---|
| EP | 0101554 A2 | 2/1984 |
| EP | 0124068 A1 | 11/1984 |
| EP | 0135782 A2 | 4/1985 |
| EP | 0186023 A2 | 7/1986 |
| EP | 312867 A1 | 4/1989 |
| EP | 0393493 A2 | 10/1990 |
| EP | 1378749 A1 | 1/2004 |
| EP | 1473042 A1 | 11/2004 |
| EP | 1568706 A1 | 8/2005 |
| EP | 1947108 A1 | 7/2008 |
| WO | WO-9728149 A1 | 8/1997 |
| WO | WO-9731907 A | 9/1997 |
| WO | WO-9736579 A1 | 10/1997 |
| WO | WO-9802159 A1 | 1/1998 |
| WO | WO-9938845 A1 | 8/1999 |
| WO | WO-0025134 A1 | 5/2000 |
| WO | WO-0037077 A1 | 6/2000 |
| WO | WO-0040965 A1 | 7/2000 |
| WO | WO-0057915 A1 | 10/2000 |
| WO | WO-0076523 A1 | 12/2000 |
| WO | WO-0130343 A1 | 5/2001 |
| WO | WO-0220463 A2 | 3/2002 |
| WO | WO-02064125 A2 | 8/2002 |
| WO | WO-02072598 A1 | 9/2002 |
| WO | WO-03015771 A1 | 2/2003 |
| WO | WO-03015777 A1 | 2/2003 |
| WO | WO-03016280 A1 | 2/2003 |
| WO | WO-03016288 A1 | 2/2003 |
| WO | WO-03030612 A2 | 4/2003 |
| WO | WO-03043581 A2 | 5/2003 |
| WO | WO-03080803 A2 | 10/2003 |
| WO | WO-03086303 A2 | 10/2003 |
| WO | WO-03090745 A1 | 11/2003 |
| WO | WO-2004007521 A2 | 1/2004 |
| WO | WO-2004048349 A1 | 6/2004 |
| WO | WO-2005032549 A1 | 4/2005 |

(Continued)

OTHER PUBLICATIONS

Aldini et al., "Relationship between structure and intestinal absorption of bile acids with a steroid or side-chain modification", *Steroids*, 61(10):590-597 (1996).
Clerici et al., "Effect of Intraduodenal Administration of 23-Methyl-UDCA Diastereoisomers on Bile Flow in Hamsters", *Dig. Dis. Sci.*, 37(5):791-798 (1992).
Honorio et al., "Hologram QSAR Studies on Farnesoid X Receptor Activators", *Lett. Drug Des. Dis.*, 3(4):261-267 (2006).
Pellicciari et al., "Bile Acid Derivatives as Ligands of the Farnesoid X Receptor. Synthesis, Evaluation, and Structure-Activity Relationship of a Series of Body and Side Chain Modified Analogues of Chenodeoxycholic Acid", *J. Med. Chem.*, 47:4559-4569 (2004).

(Continued)

*Primary Examiner* — Barbara P Badio
(74) *Attorney, Agent, or Firm* — Mintz, Levin, Cohn, Ferris, Glovsky and Popeo, P.C.; Ivor R. Elrifi, Esq.; Jennifer L. Loebach, Esq.

(57) ABSTRACT

The invention relates to compounds of Formula A:

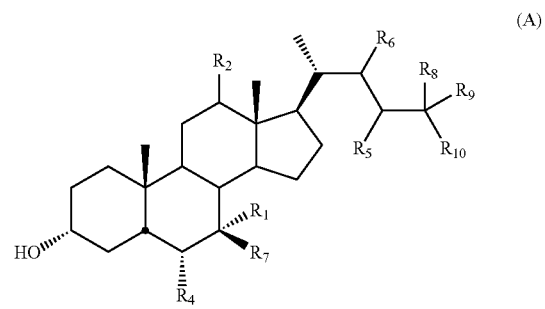

(A)

or a salt, solvate, hydrate, or prodrug thereof. The compounds of Formula A are TGR5 modulators useful for the treatment of various diseases, including metabolic disease, inflammatory disease, liver disease, autoimmune disease, cardiac disease, kidney disease, cancer, and gastrointestinal disease.

9 Claims, 48 Drawing Sheets

FOREIGN PATENT DOCUMENTS

| | | |
|---|---|---|
| WO | WO-2005082925 A2 | 9/2005 |
| WO | WO-2005089316 A2 | 9/2005 |
| WO | WO-2006122977 A2 | 11/2006 |
| WO | WO-2008002573 A2 | 1/2008 |
| WO | WO-2008091540 A2 | 7/2008 |

OTHER PUBLICATIONS

Pellicciari et al.,"Nongenomic Actions of Bile Acids. Synthesis and Preliminary Characterization of 23- and 6,23-Alkyl-Substituted Bile Acid Derivatives as Selective Modulators for the G-Protein Coupled Receptor TGR5", *J. Med. Chem.*, 50:4265-4268 (2007).

Roda et al., "23-Methyl-3α,7β-dihydroxy-5β-cholan-24-oic Acid: Dose-Response Study of Biliary Secretion in Rat", *Hepatol.*, 8(6):1571-1576 (1988).

Roda et al., "Bile acids with a cyclopropyl-containing side chain. IV. Physicochemical and biological properties of the four diastereoisomers of 3α, 7β-dihydroxy-22,23-methylene-5β-cholan-24-oic acid", *J. Lipid Res.*, 28(12):1384-1397 (1987).

Sato et al., "Novel Potent and Selective Bile Acid Derivatives as TGR5 Agonists: Biological Screening, Structure-Activity Relationships, and Molecular Modeling Studies", *J. Med. Chem.*, 51(6):1831-1841 (2008).

Bishop-Bailey et al., "Expression and activation of the farnesoid X receptor in the vasculature", Proc. Natl. Acad. Sci. U.S.A., 101(10):3668-3673 (2004).

Fiorucci et al., "The Nuclear Receptor SHP Mediates Inhibition of Hepaptic Stellate Cells by FXR and Protects Against Liver Fibrosis", *Gastroenterology*, 127:1497-1512 (2004).

Forman et al., "Identification of a Nuclear Receptor That is Activated by Farnesol Metabolites", *Cell*, 81:687-693 (1995).

Kliewer et al., "Peroxisome Proliferator-Activated Receptors: From Genes to Physiology", *Endo J.*, 56:239-263 (2001).

Mangelsdorf et al., "The RXR Heterodimers and Orphan Receptors", *Cell*, 83:841-850 (1995).

Mi et al., "Structural Basis for Bile Acid Binding and Activation of the Nuclear Receptor FXR", *Mol. Cell*, 11:1093-1100 (2003).

Nesto et al., "Thiazolidinedione Use, Fluid Retention, and Congestive Heart Failure", *Diabetes Care*, 27(1):256-263 (2004).

Pellicciari et al., "6α-Ethyl-Chenodeoxycholic Acid (6-ECDCA), a Potent and Selective FXR Agonist Endowed with Anticholestatic Activity", *J. Med. Chem.*, 45(17):3569-3572 (2002).

Raskin et al., "A Randomized Trial of Rosiglitazone Therapy in Patients With Inadequately Controlled Insulin-Treated Type 2 Diabetes", *Diabetes Care*, 24(7):1226-1232 (2001).

Rubin et al., "Combination Therapy With Pioglitazone and Insulin in Patients With Type 2 Diabetes", *Diabetes*, 48(Suppl. 1):A110 (1999) (Abstract Only).

Souillac et al., "Characterization of Delivery Systems, Differential Scanning Calorimetry", in *Encyclopedia of Controlled Drug Delivery*, John Wiley & Sons, pp. 212-227 (1999).

Vippagunta et al., "Crystalline solids", *Adv. Drug Del. Rev.*, 48:3-26 (2001).

Willson et al., "The PPARs: From Orphan Receptors to Drug Discovery", *J. Med. Chem.*, 43(4):527-550 (2000).

Center, S.A., et al., "Chronic Liver Disease: Current Concepts of Disease Mechanisms", J. Small Anim. Pract., 40(3), 106-114 (1999).

Downes, M., et al., A Chemical, Genetic, and Structural Analysis of the Nuclear Bile Acid Receptor FXR, Mol. Cell., 11(4), 1079-1092 (2003).

Fukuchi et al., "5β-Cholane activators of the farnesol X receptor," *J. Steroid Biochem. Mol. Biol.*, 94(4):311-318 (2005).

Haslewood et al., "Specificity and some characteristics of a 7.alpha.-hydroxysteroid dehydrogenase from *E. coli*", Database CA [online], Database accession No. 1978:419015.

Kihira et al., "Synthesis of sulfonate analogs of bile acids", *Steroids*, 57(4):193-198 (1992).

Kim et al., "Hypocholesterolemic Effect of Bile Acid Sulfonate Analogs in Hamsters", *Biol. Pharm. Bull.*, 24(3):218-220 (2001).

Liu, Y. et al., "Hepatoprotection by the Farnesoid X Receptor Agonist GW4064 in Rat Models of Intra- and Extrahepatic Cholestasis", J. Clin. Invest., 112(11), 1678-1687 (2003).

Mikami et al., "Effect of some sulfonate analogues of ursodeoxycholic acid on biliary lipid secretion in the rat", *J. Lipid Res.*, 37(6):1181-1188 (1996).

Miki et al., "Sulfonate analogues of chenodeoxycholic acid: metabolism of sodium 3α,7α-dihydroxy-25-homo-5β-cholane-25-sulfonate and sodium 3α,7α-dihydroxy-24-nor-5β-cholane-23-sulfonate in the hamster", *J. Lipid Res.*, 33(11):1629-1637 (1992).

Schmider et al., "Evidence for an additional sinusoidal bile salt transport system", Database CA [online], Database accession No. 2000:260886.

Stenner et al., "The effect of ursodeoxycholic acid on fibrosis markers in alcoholic liver disease", *Flak Symposium*, pp. 229-235 (2002).

Urizar, N.L. et al., A Natural Product that Lowers Cholesterol as an Antagonist Ligand for FXR, Science, 296(5573), 1703-1706 (2002).

A ▨ CHOW DIET + VEHICLE   C ▤ HF DIET + VEHICLE
B ▨ CHOW DIET + 6-Et,23(S)-Me CA   D ▨ HF DIET + 6-Et,23(S)-Me CA
Fig. 2
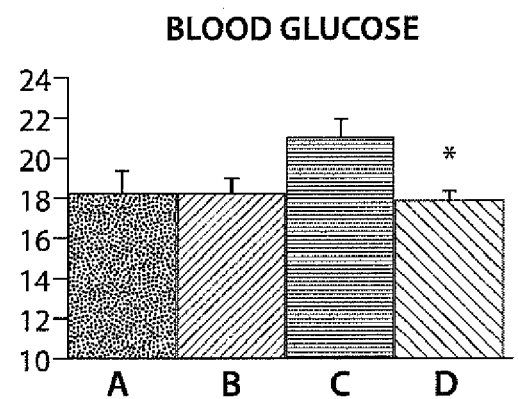
Fig. 2A
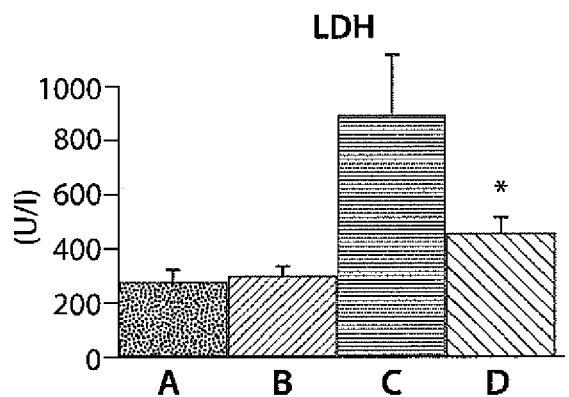
Fig. 2B A  CD          C  HF
B  CD + COMPOUND Ih3e   D  HF + COMPOUND Ih3e A ▨ CD         C ▤ HF
B ▧ CD + COMPOUND Ih3e    D ▨ HF + COMPOUND Ih3e
Fig. 9
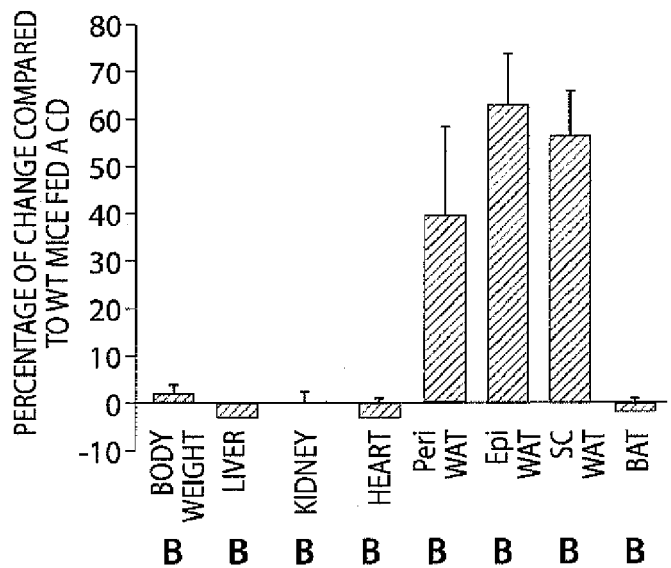
Fig. 9A
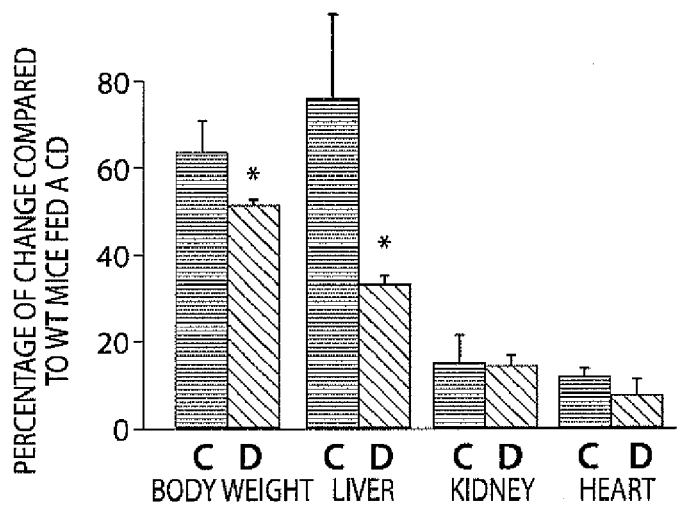
Fig. 9B

TGR5 MODULATORS AND METHODS OF USE THEREOF

RELATED APPLICATION

This application claims priority under 35 U.S.C. §119 to European Application No. 08169462.2, filed Nov. 19, 2008, the contents of which are incorporated herein.

FIELD OF THE INVENTION

The invention relates to compounds that modulate TGR5 and compositions useful in methods for the treatment and/or prevention of various diseases.

BACKGROUND OF THE INVENTION

TGR5 receptor is a G-protein-coupled receptor that has been identified as a cell-surface receptor that is responsive to bile acids (BAs). The primary structure of TGR5 and its responsiveness to bile acids has been found to be highly conserved in TGR5 among human, bovine, rabbit, rat, and mouse, and thus suggests that TGR5 has important physiological functions. TGR5 has been found to be widely distributed in not only lymphoid tissues but also in other tissues. High levels of TGR5 mRNA have been detected in placenta, spleen, and monocytes/macrophages. Bile acids have been shown to induce internalization of the TGR5 fusion protein from the cell membrane to the cytoplasm. Kawamata et al. 2003, J. Bio. Chem., 278, 9435. TGR5 has been found to be identical to hGPCR19 reported by Takeda et al. 2002, FEBS Lett. 520, 97-101.

TGR5 is associated with the intracellular accumulation of cAMP, that is widely expressed in diverse cell types. While the activation of this membrane receptor in macrophages decreases pro-inflammatory cytokine production, (Kawamata, Y., et al. *J. Biol. Chem.* 2003, 278, 9435-9440) the stimulation of TGR5 by BAs in adipocytes and myocytes enhances energy expenditure (Watanabe, M. et al. *Nature.* 2006, 439, 484-489). This latter effect involves the cAMP-dependent induction of type 2 iodothyronine deiodinase (D2), which by, locally converting T4 into T3, gives rise to increased thyroid hormone activity. Consistent with the role of TGR5 in the control of energy metabolism, female TGR5 knock-out mice show a significant fat accumulation with body weight gain when challenged with a high fat diet, indicating that the lack of TGR5 decreases energy expenditure and elicits obesity (Maruyama, T., et al. *J. Endocrinol.* 2006, 191, 197-205). In addition and in line with the involvement of TGR5 in energy homeostasis, bile acid activation of the membrane receptor has also been reported to promote the production of glucagon-like peptide 1 (GLP-1) in murine enteroendocrine cell lines (Katsuma, S., *Biochem. Biophys. Res. Commun.* 2005, 329, 386-390). On the basis of all the above observations, TGR5 is an attractive target for the treatment of disease e.g., obesity, diabetes and metabolic syndrome.

In addition to the use of TGR5 agonists for the treatment and prevention of metabolic diseases, compounds that modulate TGR5 modulators are also useful for the treatment of other diseases e.g., central nervous diseases as well as inflammatory diseases (WO 01/77325 and WO 02/84286). Modulators of TGR5 also provide methods of regulating bile acid and cholesterol homeostasis, fatty acid absorption, and protein and carbohydrate digestion.

Relatively few examples of TGR5 agonists have been described in literature. Recently, 23-alkyl-substituted and 6,23-alkyl-disubstituted derivatives of chenodeoxycholic acid (CDCA), such as the compound 6α-ethyl-23(S)-methyl-chenodeoxycholic acid shown below, have been reported as potent and selective agonists of TGR5 (Pellicciari, R.; et al. *J. Med. Chem.* 2007, 50, 4265-4268).

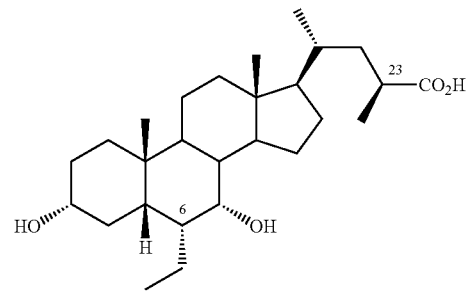

In particular, the methylation (S-configuration) at the $C_{23}$-position of natural bile acids (BAs) confers a marked selectivity to TGR5 over FXR (farnesoid X receptor) activation, whereas the 6α-alkyl substitution increases the potency at both receptors. Some examples of other TGR5 agonists include 6-Methyl-2-oxo-4-thiophen-2-yl-1,2,3,4-tetrahydro-pyrimidine-5-carboxylic acid benzyl ester (WO004067008, Takeda Chemical Industries LTD, Japan, 2004) and oleanoic acid (Sato, H. et al. *Biochem. and Biophys. Res. Commun.* 2007, 362, 793-798; Ito, F. et al. WO2004067008, 2004). More recently, the first synthesis of enantiomeric chenodeoxycholic acid (CDCA) and lithocholic acid (LCA) has allowed access to studying the specificity of the interaction of natural BAs with TGR5 (Katona, B. W. et al. *J. Med. Chem.* 2007, 50, 6048-6058).

Recently developed TGR5 agonists have also provided for the first time a pharmacological differentiation of genomic versus nongenomic effects of BAs and have also allowed for informative structure-activity relationship studies, for example, the presence of an accessory binding pocket in TGR5 has been found to play a pivotal role in determining ligand selectivity (See, Pellicciari, et al. *J. Med. Chem.* 2007, 50, 4265-4268). In this context, the availability of more potent and selective TGR5 modulators is necessary to further identify additional features affecting receptor activation and characterize the physiological and pharmacological actions of this receptor in order to better understand its relationship to the prevention and treatment of disease.

To this end, of particular interest were the biological and physicochemical properties of the compound cholic acid (CA), which has the structure shown below:

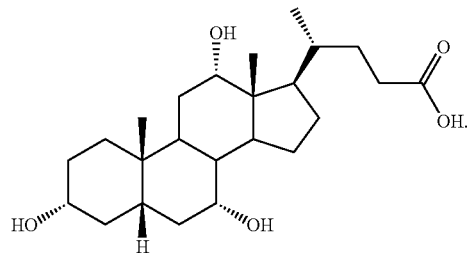

Cholic acid is a primary bile acid in human and many animal species, also reported as one of the main components together with bilirubin of *Calculus Bovis*, a highly valued traditional Chinese medicine (Chen, X., *Biochem. Pharmacol.* 2002, 63, 533-541). Cholic acid (CA) differs from chenodeoxycholic acid (CDCA) and its derivatives described above by the presence at C-12 of an additional alpha-hydroxyl group oriented on the polar side of the molecule. This "minor" structural difference accounts for the remarkably different physicochemical and biological features of these two bile acids. With respect to CDCA, protonated CA is about 4-fold more soluble and relatively less detergent as a result of its hydrophobic/hydrophilic balance and polarity. Moreover, Calif. is devoid of activity toward FXR receptor (EC50>100 µM) while showing moderate agonistic activity on TGR5 (EC50=13.6 µM). As an even more important consideration, it was previously reported that the pharmacological administration of CA at 0.5% w/w in diet-induced obese mice efficiently prevents and treats metabolic syndrome (Katsuma, S., *Biochem. Biophys. Res. Commun.* 2005, 329, 386). While this study provided interesting results related to the endocrine functions of bile acids, the high dosage required (0.5% w/w) still limited the proof of concept concerning the therapeutic relevance of TGR5 in the context of metabolic diseases, since the modulation of other and unknown targets could not be ruled out at that dose. An additional issue was also the risk associated with testing a high dose of CA in clinical trials due to the production of the toxic secondary metabolite BA DCA via extensive and efficient intestinal bacteria 7α-dehydroxylation (Nagengast, F. M., *Eur. J. Cancer,* 1995, 31A, 1067).

Thus, there is a need for the development of TGR5 modulators for the treatment and/or prevention of various diseases. The present invention has identified compounds that modulate TGR5 as well as methods of using these compounds to treat or prevent disease.

SUMMARY OF THE INVENTION

The present invention relates to TGR5 modulators and their use to treat and/or prevent various diseases. The invention relates to compounds according to formula A:

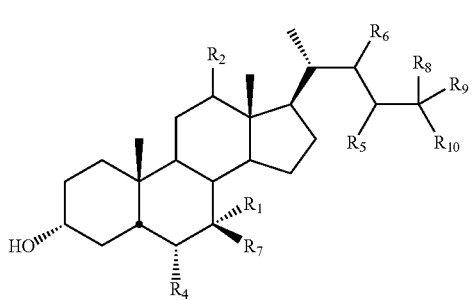

(A)

or a salt, solvate, hydrate, or prodrug thereof. In formula A, variables $R_1$, $R_2$, $R_3$, $R_4$, $R_5$, $R_6$, $R_7$, $R_8$, $R_9$, and $R_{10}$ can be selected from the respective groups of chemical moieties later defined in the detailed description. The invention includes a composition comprising a compound of the invention or a pharmaceutically acceptable salt, solvate, hydrate, or prodrug thereof, and at least one pharmaceutically acceptable excipient. The invention also includes the use of a composition or compound of the invention or a pharmaceutically acceptable salt, solvate, hydrate, or prodrug thereof, in the manufacture of a medicament for a treating or preventing a disease in a subject. In one aspect, the disease is selected from metabolic disease, inflammatory disease, liver disease, autoimmune disease, cardiac disease, kidney disease, cancer, and gastrointestinal disease.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples.

BRIEF DESCRIPTION OF THE FIGURES

FIG. 2 is a legend for a series of nine graphs (FIGS. 2A-2I) that shows changes in the metabolic profile of high fat fed mice and chow diet fed mice treated with vehicle and compound Ih3e. FIG. 2A is a bar graph that shows a comparison of the plasma levels of blood glucose. FIG. 2B is a bar graph that shows a comparison of the levels of the liver enzyme LDH.

FIG. 9 is a legend for a series of graphs (FIGS. 9A-9C) that shows changes in body, organ, and tissue weights for chow and high fat fed mice treated and not treated with compound Ih3c. FIG. 9A is a bar graph that shows the percentage change in body weight, organ weight (liver, kidney, and heart), and adipose tissue weight (peri WAT, epi WAT, Sc WAT, and BAT) in mice fed a chow diet plus compound Ih3e. FIG. 9B is a bar graph that shows the percentage change in body weight and organ weight (liver, kidney, and heart) in mice fed a high fat diet and in mice fed a high fat diet plus compound Ih3e.

FIG. 14 is a series of graphs (A-D) related to compound Ih3e and its metabolites.

DESCRIPTION OF THE INVENTION

Figure 1:
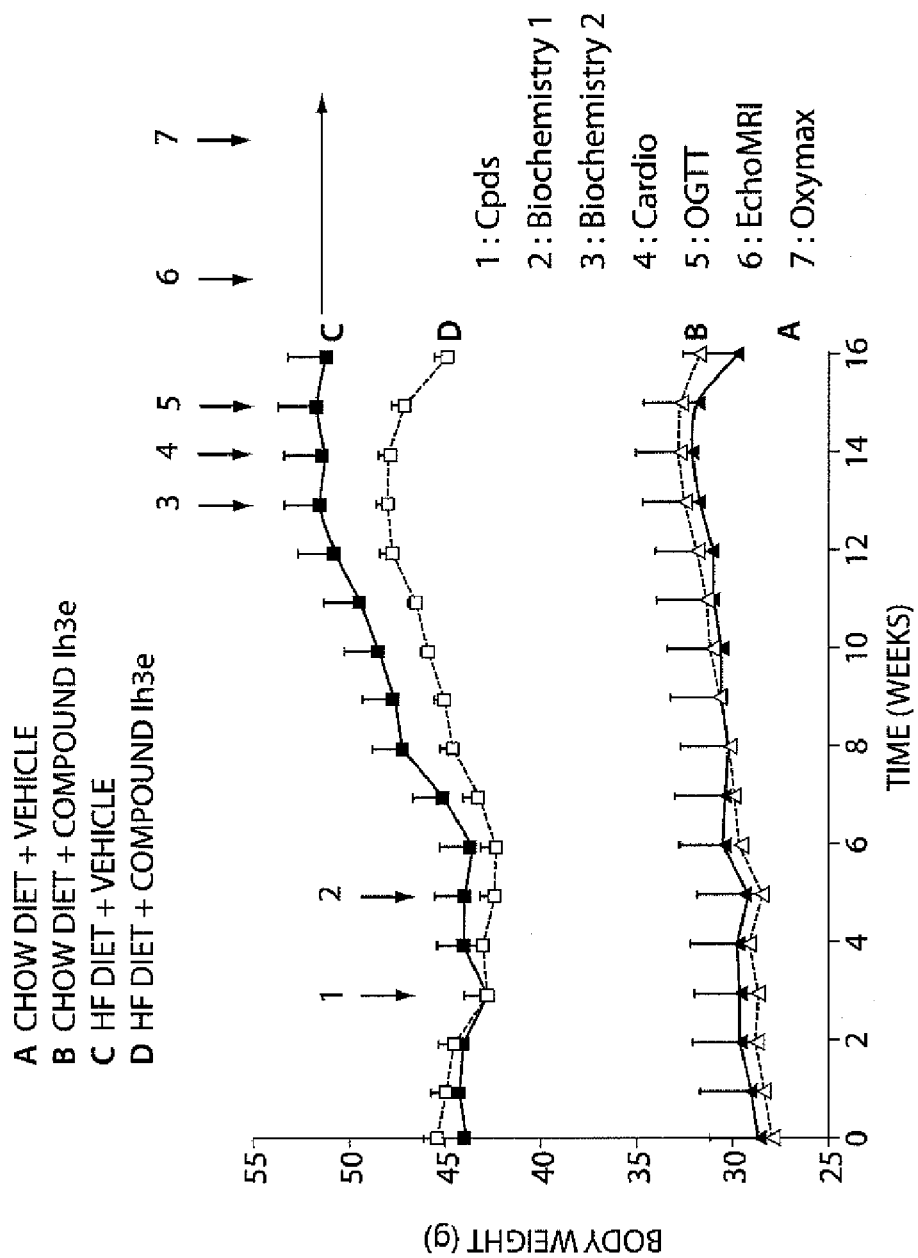
FIG. 1 is a graph that shows the impact of compound Ih3e on body weight gain in chow and high fat fed mice.
Figure 2C:
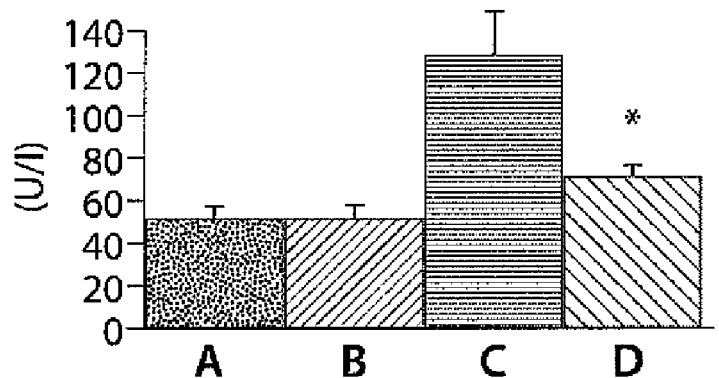
FIG. 2C is a bar graph that shows a comparison of the levels of the liver enzyme ASAT.
Figure 2D:
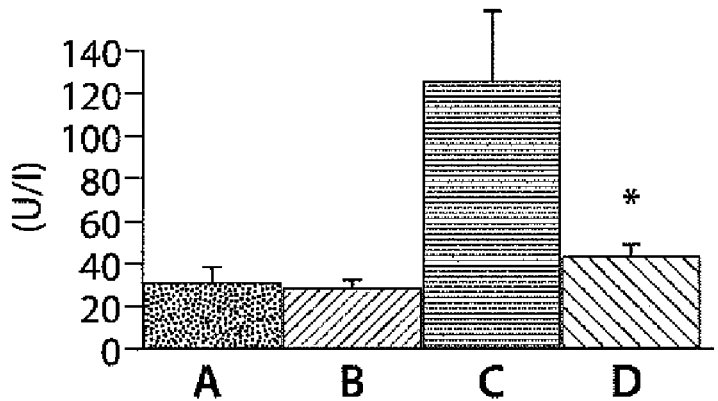
FIG. 2D is a bar graph that shows a comparison of the levels of the liver enzyme ALAT.
Figure 2E:
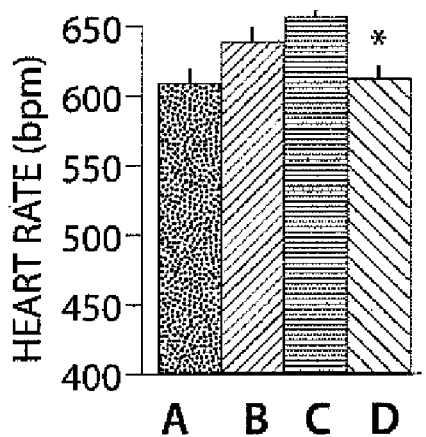
FIG. 2E is a bar graph that shows a comparison of the heart rate.
Figure 2F:
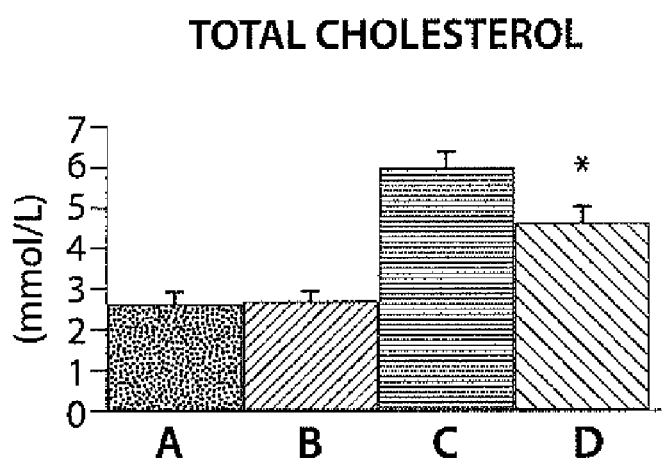
FIG. 2F is a bar graph that shows a comparison of total cholesterol.
Figure 2G:
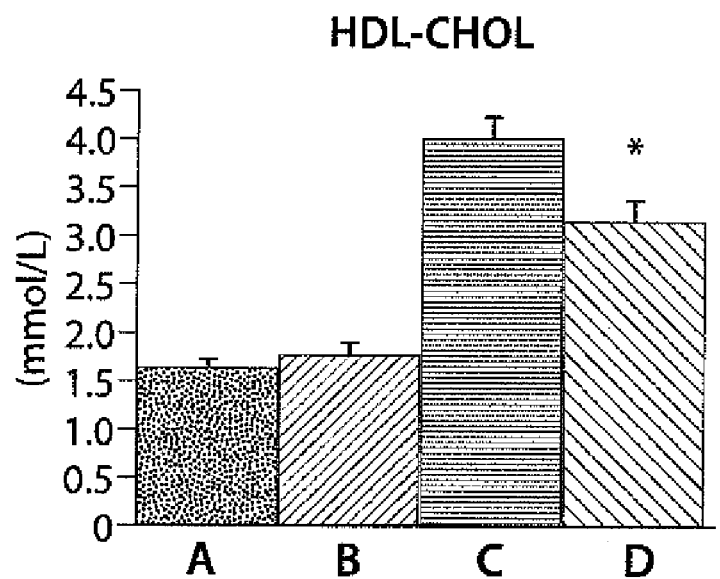
FIG. 2G is a bar graph that shows a comparison of the levels of HDL-cholesterol.
Figure 2H:
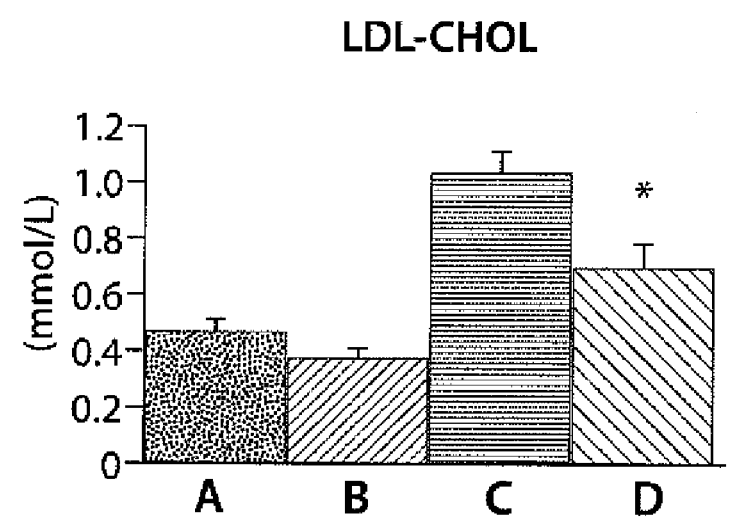
FIG. 2H is a bar graph that shows a comparison of the levels of LDL-cholesterol.
Figure 2I:
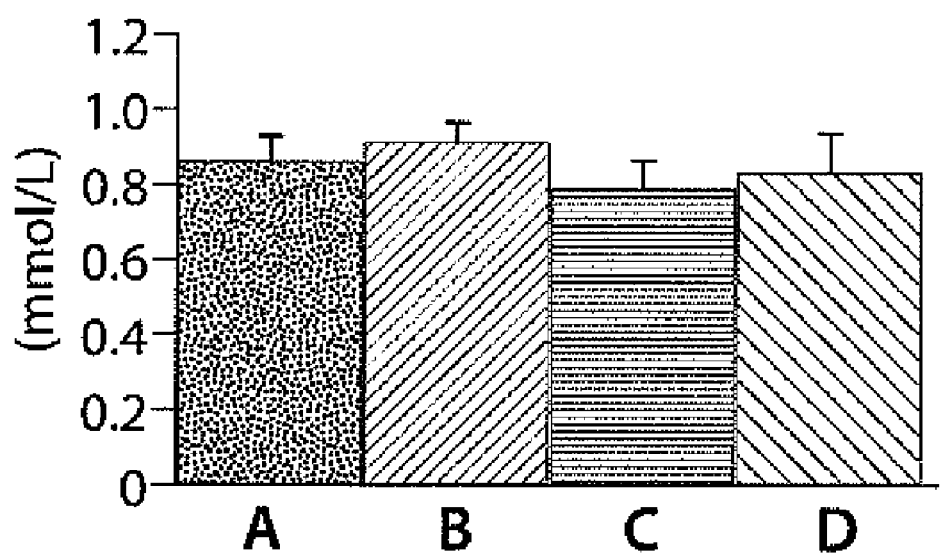
FIG. 2I is a bar graph that shows a comparison of the levels of triglycerides.

The details of one or more embodiments of the invention are set forth in the accompanying description below. Although any methods and materials similar or equivalent to those described herein can be used in the practice or testing of the present invention, the methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

DEFINITIONS

For convenience, certain terms used in the specification, examples and appended claims are collected here.

The term "treating", as used herein, means relieving, lessening, reducing, eliminating, modulating, or ameliorating, i.e. causing regression of the disease state or condition.

The term "preventing", as used herein means, to completely or almost completely stop a disease state or condition, from occurring in a patient or subject, especially when the patient or subject is predisposed to such or at risk of contracting a disease state or condition. Preventing can also include inhibiting, i.e. arresting the development, of a disease state or condition, and relieving or ameliorating, i.e. causing regression of the disease state or condition, for example when the disease state or condition may already be present.

The term "6-Et,23(S)-MeCA" refers to the compound Ih3e having the chemical structure:

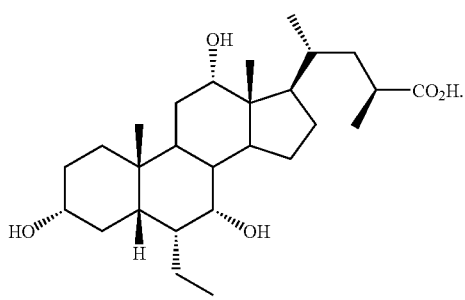

Alternatively, compound Ih3e may also be referred to as 6α-ethyl-(23S)-methyl-3α,7α,12α trihydroxy-5β-cholan-24-oic acid.

As used herein, "BA" means bile acid and bile acid derivatives. Bile acids are steroid carboxylic acids derived from cholesterol. The primary bile acids are cholic and chenodeoxycholic acids. In the body, these acids are conjugated with glycine or taurine before they are secreted into the bile.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has six or fewer carbon atoms in its backbone, referred to as "lower alkyl" (e.g., $C_1$-$C_6$ for straight chain meaning 1, 2, 3, 4, 5, or 6 carbon atoms, $C_3$-$C_6$ for branched chain meaning 3, 4, 5, or 6 carbon atoms). In some examples, a straight chain or branched chain alkyl has four or fewer carbon atoms in its backbone. Further, cycloalkyls have 3, 4, 5, 6, 7, or 8 carbon atoms in their ring structure.

The term "substituted alkyl" refers to an alkyl moieties having a substituent replace one or more hydrogen atoms on at least one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at least one ring position with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

Unless the number of carbons is otherwise specified, "lower alkyl" includes an alkyl group, as defined above, but having from one to ten, for example, from one to six, carbon atoms in its backbone structure.

The term "alkoxy" or "alkoxyl" includes alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

An "anionic group," as used herein, refers to a group that is negatively charged at physiological pH. Anionic groups include carboxylate, sulfate, sulfonate, sulfinate, sulfamate, tetrazolyl, phosphate, phosphonate, phosphinate, or phosphorothioate or functional equivalents thereof "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). Another anionic group is a carboxylate.

The term "unstable functionality" refers to a substitution pattern that contains a labile linkage, e.g., a functionality or bond that is susceptible to hydrolysis or cleavage under physiological conditions (e.g., aqueous solutions in the neutral pH range). Examples of unstable functionalities include acetals and ketals.

The terms "crystal polymorphs" or "polymorphs" refer to the existence of more than one crystal form for a compound, salt or solvate thereof. Crystal polymorphs of the bile acid analog compounds are prepared by crystallization under different conditions.

The term "R-EMCA" refers to the compound 6α-ethyl-23(R)-methylcholic acid having the structure:

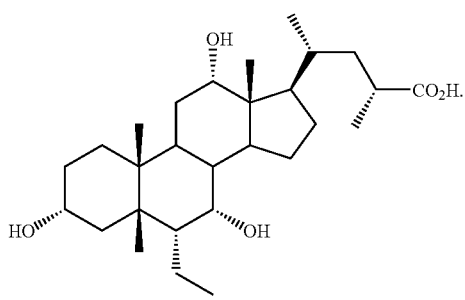

Alternatively may be referred to as 6α-ethyl-(23R)-methyl-3α,7α,12α trihydroxy-5β-cholan-24-oic acid Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

It will be noted that the structure of some of the compounds of the invention include asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Enantiomers (R- and S-configurations) are named according to the system developed by R. S. Cahn, C. Ingold, and V. Prelog.

Further, the structures and other compounds discussed in this application include all atropic isomers thereof. Atropic isomers are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Stable compound" and "stable structure" are meant to indicate a compound that is sufficiently robust to survive isolation to a useful degree of purity from a reaction mixture, and formulation into an efficacious therapeutic agent.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

As defined herein, the term "derivative", e.g., in the term "bile acid derivatives", refers to compounds that have a common core 4-membered ring structure, and are substituted with various groups as described herein.

The term "bioisostere" refers to a compound resulting from the exchange of an atom or of a group of atoms with another, broadly similar, atom or group of atoms. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

"Combination therapy" (or "co-therapy") includes the administration of a compound of the invention and at least a second agent as part of a specific treatment regimen intended to provide the beneficial effect from the co-action of these therapeutic agents (i.e., the compound of the invention and at least a second agent). The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or mechanical treatments). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The terms "parenteral administration" and "administered parenterally" as used herein refer to modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "pulmonary" as used herein refers to any part, tissue or organ whose primary function is gas exchange with the external environment, e.g., $O_2/CO_2$ exchange, within a patient. "Pulmonary" typically refers to the tissues of the respiratory tract. Thus, the phrase "pulmonary administration" refers to administering the formulations described herein to any part, tissue or organ whose primary function is gas exchange with the external environment (e.g., mouth, nose, pharynx, oropharynx, laryngopharynx, larynx, trachea, carina, bronchi, bronchioles, alveoli). For purposes of the present invention, "pulmonary" also includes a tissue or cavity that is contingent to the respiratory tract, in particular, the sinuses.

A "therapeutically effective amount" of a compound of the invention, or a combination of compounds is an amount (quantity or concentration) of compound or compounds. In one embodiment, when a therapeutically effective amount of a compound is administered to a subject in need of treatment symptoms arising from the disease are ameliorated immediately or after administration of the compound one or more times. The amount of the compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

The term "prophylactically effective amount" means an amount (quantity or concentration) of a compound of the present invention, or a combination of compounds, that is administered to prevent or reduce the risk of a disease—in other words, an amount needed to provide a preventative or prophylactic effect. The amount of the present compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

The term "reducing the risk of", as used herein, means to lower the likelihood or probability of a central nervous system disease, inflammatory disease and/or metabolic disease from occurring in a patient, especially when the patient or subject is predisposed to such occurrence.

A "pharmaceutically acceptable salt" or "salt" of a compound of the invention is a product of the compound that contains an ionic bond, and is typically produced by reacting the compound with either an acid or a base, suitable for administering to a subject.

As used herein, "pharmaceutically acceptable salts" refer to derivatives of the compounds of the invention wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., USA, p. 1445 (1990).

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A "composition" or "pharmaceutically acceptable composition" is a formulation containing a compound of the invention or salt, solvate, hydrate, or prodrug thereof. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the invention or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In another embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). Typically, the subject is human.

Compounds of the invention also include prodrugs or physiologically equivalent derivatives. A "prodrug" or "physiologically equivalent derivative" includes a precursor form of the drug which is metabolically converted in vivo to produce the active drug. The invention further contemplates the use of prodrugs which are converted in vivo to the TGR5 modulating compounds used in the methods of the invention (see, e.g., R. B. Silverman, 1992, "The Organic Chemistry of Drug Design and Drug Action", Academic Press, Chp. 8).

Such prodrugs can be used to alter the biodistribution (e.g., to allow compounds which would not typically cross the blood-brain barrier to cross the blood-brain barrier) or the pharmacokinetics of the TGR5 modulating compound. For example, an anionic group, e.g., a carboxylate, sulfate or sulfonate, can be esterified, e.g., with an alkyl group (e.g., a methyl group) or a phenyl group, to yield an ester. When the ester is administered to a subject, the ester is cleaved, enzymatically or non-enzymatically, reductively or hydrolytically, to reveal the anionic group. Such an ester can be cyclic, e.g., a cyclic sulfate or sulfone, or two or more anionic moieties may be esterified through a linking group. An anionic group can be esterified with moieties (e.g., acyloxymethyl esters) which are cleaved to reveal an intermediate TGR5 modulating compound which subsequently decomposes to yield the active TGR5 modulating compound. In one embodiment, the prodrug is a reduced form of a carboxylate, sulfate or sulfonate, e.g., an alcohol or thiol, which is oxidized in vivo to the TGR5 modulating compound. Furthermore, an anionic moiety can be esterified to a group which is actively transported in vivo, or which is selectively taken up by target organs.

As used herein, the term "amino acid conjugates" refers to conjugates of the compounds of the invention with any suitable amino acid. Taurine ($NH(CH_2)_2SO_3H$) and glycine ($NHCH_2CO_2H$) are examples of amino acid conjugates. Suitable amino acid conjugates of the compounds have the added advantage of enhanced integrity in bile or intestinal fluids. Suitable amino acids are not limited to taurine and glycine. The invention encompasses amino acid conjugates of the compounds of the invention. More specifically, the invention includes amino acid conjugates of compound Ih3e. Even more specifically, the invention includes the taurine and glycine conjugates of compound Ih3e.

The term "compounds of the invention" refers to compounds having the formulae described herein.

The term "TGR5 modulator" means any compound that interacts with the TGR5 receptor. The interaction is not limited to a compound acting as an antagonist, agonist, partial agonist, or inverse agonist of the TGR5 receptor. In one aspect, the compounds of the present invention act as an antagonist of the TGR5 receptor. In another aspect, the compounds of the present invention act as an agonist of the TGR5 receptor. In another aspect, the compounds of the present invention act as a partial agonist of the TGR5 receptor. In another aspect, the compounds of the present invention as an inverse agonist of the TGR5 receptor. The profile of a ligand, traditionally, endogenous or synthetic, is characterized by its intrinsic efficacy 'e' originally described by Furchgott in 1966. It is used to express the degree to which the different ligands produce varying biological responses while occupying the same number of receptors. Generally, the term "agonist" means a compound that enhances the activity of another molecule or receptor site. An agonist, by classical definition, whether a orthosteric, allosteric, inverse or a co-agonist has a property to bind to the receptor, alter its receptor state and result in a biological action. Consequently, agonism is defined as a property of an agonist or a ligand to produce a biological action. In contrast to this, an "antagonist" is essentially an agonist with high affinity to the same receptor macromolecule, but with very less or negligible intrinsic efficacy, and thus sterically prevents the biological actions of an agonist. As a property, antagonism may be functional or physiological, where an agonist has a direct competition for the receptor site in former and opposing effects via a different receptor-messenger system in the later. More specifically, a TGR5 agonist is a receptor ligand or compound that binds to TGR5 and increases the concentration of cyclic adenosine monophosphate (cAMP) by at least 20% in cells expressing the receptor." Conversely, a TGR5 antagonist would be a compound that antagonizes or blocks the activity of an agonist, thereby effecting a reduction in the concentration of cAMP The present invention relates to compounds having TGR5 receptor modulating activity and their use to treat and/or prevent various diseases including metabolic disease, inflammatory disease, liver disease, autoimmune disease, cardiac disease, kidney disease, cancer, and gastrointestinal disease. Further, the present invention relates to compounds of the formulae described herein.

Compounds and Compositions

In one aspect, the invention relates to a compound of formula A:

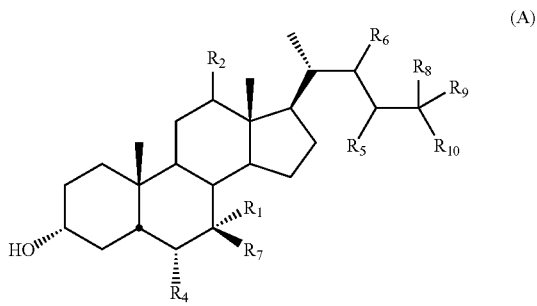

(A)

or a salt, solvate, hydrate, or prodrug thereof, wherein: $R_1$ is hydrogen, hydroxy, substituted or unsubstituted alkyl, or halogen; $R_2$ is hydrogen or α-hydroxy; $R_3$ is hydrogen, hydroxy, $NH(CH_2)_mSO_3H$, or $NH(CH_2)_nCO_2H$; $R_4$ is hydrogen, substituted or unsubstituted alkyl, or halogen; $R_5$ is unsubstituted or substituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; $R_8$ is hydrogen, substituted or unsubstituted alkyl; $R_9$ is hydrogen, substituted or unsubstituted alkyl or taken together $R_8$ and $R_9$ form a carbonyl; $R_{10}$ is $R_3$ or $SO_3H$; m is an integer 0, 1, 2, 3, 4, or 5; and n is an integer 0, 1, 2, 3, 4, or 5. In one aspect, when $R_5$ is methyl, $R_1$ is hydroxyl, and $R_3$ is hydroxyl or $NHCH_2CH_2SO_3H$, then $R_4$ is not hydrogen.

In one aspect of the invention, $R_1$ is hydrogen or hydroxy. $R_1$ is hydroxy. $R_1$ is hydrogen. $R_2$ is α-hydroxy. $R_1$ is hydroxy and $R_2$ is α-hydroxy. $R_1$ is hydroxy and $R_2$ is H. $R_1$ is hydroxy and $R_2$ is H. At least one of $R_1$ or $R_2$ is hydroxy. At least one of $R_1$ or $R_2$ is hydrogen. $R_1$ and $R_2$ are the same. $R_1$ and $R_2$ are each α-hydroxy. $R_1$ and $R_2$ are each hydrogen.

In another aspect of the invention, $R_{10}$ is $R_3$. $R_3$ is hydroxyl, $NH(CH_2)_mSO_3H$, or $NH(CH_2)_nCO_2H$. $R_3$ is hydroxyl. $R_3$ is not hydroxyl. $R_3$ is $NH(CH_2)_mSO_3H$. $R_3$ is $NH(CH_2)_mSO_3H$ and m is 2. $R_3$ is $NH(CH_2)_nCO_2H$. $R_3$ is $NH(CH_2)_nCO_2H$ and n is 1.

In another aspect of the invention, $R_4$ is hydrogen or unsubstituted alkyl. $R_4$ is hydrogen. $R_4$ is unsubstituted alkyl. $R_4$ is unsubstituted alkyl. $R_4$ is methyl or ethyl. $R_4$ is methyl. $R_4$ is ethyl. $R_3$ and $R_4$ are the same. $R_3$ and $R_4$ are different. $R_3$ and $R_4$ are each hydrogen. $R_3$ is hydroxyl and $R_4$ is hydrogen. $R_3$ is $NH(CH_2)_mSO_3H$ and $R_4$ is hydrogen. $R_3$ is $NH(CH_2)_mSO_3H$, $R_4$ is hydrogen, and m is 2. $R_3$ is $NH(CH_2)_nCO_2H$ and $R_4$ is hydrogen. $R_3$ is $NH(CH_2)_nCO_2H$, $R_4$ is hydrogen, and n is 1. $R_3$ is H and $R_4$ is unsubstituted alkyl. $R_3$ is OH and $R_4$ is methyl. $R_3$ is OH and $R_4$ is ethyl. $R_3$ is OH and $R_4$ is methyl.

In another aspect, $R_5$ is unsubstituted or substituted alkyl. $R_5$ is in the S-configuration. $R_5$ is in the R-configuration. $R_5$ is methyl or ethyl. $R_5$ is S-methyl. $R_5$ is R-methyl. $R_5$ is S-ethyl. $R_5$ is R-ethyl. $R_5$ is substituted alkyl substituted with phenyl. $R_5$ is benzyl. $R_5$ is S-benzyl. $R_5$ is R-benzyl. $R_5$ is aryl. $R_5$ is phenyl. $R_4$ and $R_5$ are each unsubstituted alkyl. $R_4$ and $R_5$ are each unsubstituted alkyl, wherein $R_5$ is in the S-configuration and $R_4$ is in the alpha-configuration. $R_4$ and $R_5$ are each unsubstituted alkyl and $R_1$ is hydroxy. $R_4$ and $R_5$ are each unsubstituted alkyl and $R_2$ is hydrogen. $R_4$ and $R_5$ are each unsubstituted alkyl, $R_1$ is hydroxy, and $R_2$ is hydrogen.

In one aspect of the invention, $R_1$, $R_2$, $R_3$, and $R_4$ are hydrogen. $R_2$, $R_3$, and $R_4$ are hydrogen. $R_2$ and $R_3$ are hydrogen. At least one of $R_1$, $R_2$, $R_3$, or $R_4$ is hydrogen. At least two of $R_1$, $R_2$, $R_3$, or $R_4$ are hydrogen. At least three of $R_1$, $R_2$, $R_3$, or $R_4$ are hydrogen. At least four of $R_1$, $R_2$, $R_3$, or $R_4$ are hydrogen.

In one aspect of the invention, $R_1$, $R_2$, and $R_4$ are hydrogen and $R_3$ is OH. $R_2$ and $R_4$ are hydrogen and $R_3$ is OH. $R_2$ is hydrogen and $R_3$ is OH. At least one of $R_1$, $R_2$, or $R_4$ is hydrogen and $R_3$ is OH. At least two of $R_1$, $R_2$, or $R_4$ are hydrogen and $R_3$ is OH. $R_1$, $R_2$ and $R_4$ are hydrogen and $R_3$ is OH.

In another aspect of the invention, at least one of $R_1$ or $R_7$ is unsubstituted alkyl. At least one of $R_1$ or $R_7$ is methyl. At least one of $R_1$ or $R_7$ is ethyl. At least one of $R_1$ or $R_7$ is propyl. $R_1$ is methyl. $R_1$ is ethyl. $R_1$ is propyl. $R_7$ is methyl. $R_7$ is ethyl. $R_7$ is propyl. Both $R_1$ and $R_7$ are unsubstituted alkyl. Both $R_1$ and $R_7$ are methyl. Both $R_1$ and $R_7$ are ethyl. $R_7$ is hydrogen. $R_7$ is hydroxy. $R_1$ is hydrogen. $R_1$ is hydroxyl. One of $R_1$ or $R_7$ is unsubstituted alkyl and the other $R_1$ or $R_7$ is hydrogen. One of $R_1$ or $R_7$ is unsubstituted alkyl and the other $R_1$ or $R_7$ is hydroxy. At least one of $R_1$ or $R_7$ is unsubstituted alkyl and $R_5$ is unsubstituted or substituted alkyl. At least one of $R_1$ or $R_7$ is methyl and $R_5$ is methyl. $R_7$ is hydroxy and both $R_1$ and $R_5$ are unsubstituted alkyl. $R_1$ is hydroxyl and both $R_7$ and $R_5$ are unsubstituted alkyl. At least one of $R_1$ or $R_7$ is unsubstituted alkyl and $R_5$ is unsubstituted or substituted alkyl, further wherein $R_5$ is in the S-configuration. At least one of $R_1$ or $R_7$ is unsubstituted alkyl and $R_5$ is unsubstituted or substituted alkyl, further wherein $R_5$ is in the R-configuration.

In another aspect, $R_1$ is hydroxy and $R_7$ is methyl. $R_1$ is methyl and $R_7$ is hydroxy. $R_6$ is unsubstituted alkyl. $R_6$ is methyl. $R_6$ is ethyl. $R_6$ is propyl.

In another aspect, $R_8$ is hydrogen. $R_8$ is unsubstituted alkyl. $R_8$ is methyl. $R_8$ is ethyl. $R_8$ is propyl. $R_2$ is α-hydroxy and $R_8$ is unsubstituted alkyl. In another aspect, $R_8$ and $R_9$ form a carbonyl.

In one aspect, $R_{10}$ is $R_3$. $R_3$ is hydroxyl. At least one of $R_8$ or $R_9$ is hydrogen. $R_8$ and $R_9$ are both hydrogen. At least one of $R_8$ or $R_9$ is unsubstituted alkyl. At least one of $R_8$ or $R_9$ is methyl. At least one of $R_8$ or $R_9$ is ethyl. In another aspect, $R_{10}$ is $SO_3H$.

In another aspect of the present invention, when $R_2$, $R_4$ and $R_6$ are each hydrogen, $R_3$ is hydroxyl, and one of $R_1$ and $R_7$ is hydrogen or hydroxyl, then the other $R_1$ or $R_7$ is not methyl. In another aspect, when $R_2$ is α-OH; $R_3$ is hydroxyl; $R_4$ and $R_6$ are each hydrogen; and one of $R_1$ and $R_7$ is hydrogen or hydroxyl, then the other $R_1$ or $R_7$ is not methyl. In another aspect, the present invention does not include the following compounds: 3α,7α-dihydroxy-7β-methyl-5β-cholanoic acid, 3α,7β-dihydroxy-7α-methyl-5β-cholanoic acid, 3α-hydroxy-7ε-methyl-5β-cholanoic acid, 3α,7β,12α-trihydroxy-7α-methyl-5β-cholan-24-oic acid; 3α,7α,12α-trihydroxy-7β-methyl-5β-cholan-24-oic acid; and 3α,12α-dihydroxy-7ε-methyl-5β-cholan-24-oic acid.

In another aspect of the present invention, when R$_3$ is hydroxyl and one of R$_1$ and R$_7$ is methyl and the other R$_1$ and R$_7$ is hydrogen or hydroxyl, then R$_2$, R$_4$ and R$_6$ are not all hydrogen. In another aspect, when R$_2$ is α-OH, R$_3$ is hydroxyl, and one of R$_1$ and R$_7$ is methyl and the other R$_1$ and R$_7$ is hydrogen or hydroxyl, then R$_4$ and R$_6$ are not all hydrogen.

According to one aspect, the present invention provides a compound of formula I:

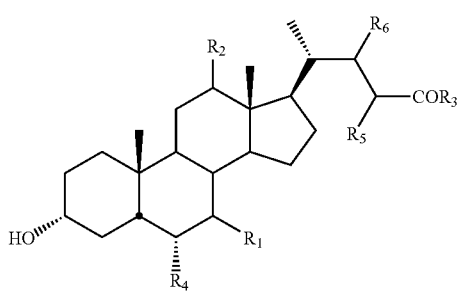

(I)

or a salt, solvate, hydrate, or prodrug thereof, wherein: R$_1$ is hydrogen, hydroxy, or halogen; R$_2$ is hydrogen or α-hydroxy; R$_3$ is hydroxy, NH(CH$_2$)$_m$SO$_3$H, or NH(CH$_2$)$_n$CO$_2$H; R$_4$ is hydrogen, unsubstituted or substituted alkyl, or halogen; R$_5$ is unsubstituted or substituted alkyl, or aryl; R$_6$ is hydrogen or R$_5$ and R$_6$ taken together with the carbons to which they are attached form a ring of size 3, 4, 5, or 6 atoms; m is an integer 0, 1, 2, 3, 4, or 5, and n is an integer 0, 1, 2, 3, 4, or 5. In one aspect, when R$_5$ is methyl, R$_1$ is hydroxyl, and R$_3$ is hydroxyl or NHCH$_2$CH$_2$SO$_3$H, then R$_4$ is not hydrogen.

In one aspect, the present invention provides compounds where R$_1$ is hydrogen or hydroxy. R$_1$ is hydroxy. R$_1$ is hydrogen. R$_1$ is α-hydroxy. R$_1$ is β-hydroxy.

In another aspect, the present invention provides compounds where R$_1$ is halogen. R$_1$ is fluorine. R$_1$ is α-fluorine. R$_1$ is β-fluorine. The stereochemistry of R$_1$ in the α- and β-configurations is shown below:

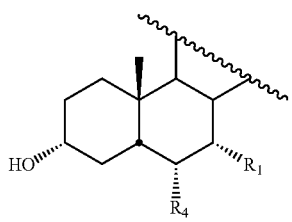

R$_1$ alpha (α-) configuration

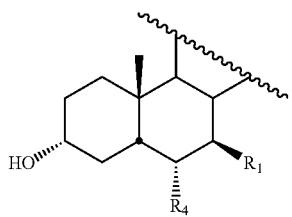

R$_1$ beta (β-) configuration

In another aspect, the present invention provides compounds where R$_2$ is α-hydroxy. R$_2$ is hydrogen. R$_1$ is β-hydroxy and R$_2$ is α-hydroxy. R$_1$ is β-hydroxy and R$_2$ is H. R$_1$ is α-hydroxy and R$_2$ is H.

In another aspect, the present invention provides compounds where at least one of R$_1$ or R$_2$ is hydroxy. In another aspect, at least one of R$_1$ or R$_2$ is hydrogen. R$_1$ and R$_2$ are the same. R$_1$ and R$_2$ are each α-hydroxy. R$_1$ and R$_2$ are each hydrogen.

In another aspect, the present invention provides compounds where R$_3$ is hydrogen, hydroxyl, NH(CH$_2$)$_m$SO$_3$H, or NH(CH$_2$)$_n$CO$_2$H. R$_3$ is hydroxyl. R$_3$ is not hydroxyl. R$_3$ is NH(CH$_2$)$_m$SO$_3$H. In another aspect, R$_3$ is NH(CH$_2$)$_m$SO$_3$H and m is 2. R$_3$ is NH(CH$_2$)$_n$CO$_2$H. In another aspect, R$_3$ is NH(CH$_2$)$_n$CO$_2$H and n is 1.

In another aspect, R$_4$ is hydrogen or alkyl. R$_4$ is hydrogen. R$_4$ is lower alkyl. R$_4$ is lower alkyl and the lower alkyl group is in the alpha configuration. R$_4$ in the alpha configuration means that R$_4$ has the stereochemistry shown in the structure below.

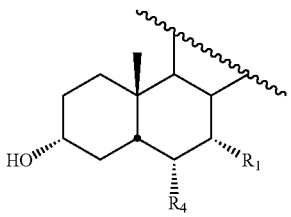

R$_4$ alpha (α-) configuration

In another aspect, R$_4$ is halogen. R$_4$ is fluorine. R$_4$ is halogen and the halogen is in the alpha configuration. R$_4$ is α-fluorine.

In another aspect, R$_4$ is methyl or ethyl. R$_4$ is methyl. R$_4$ is ethyl. R$_4$ is α-methyl. R$_4$ is α-ethyl. R$_3$ and R$_4$ are the same. R$_3$ and R$_4$ are different. R$_3$ and R$_4$ are each hydrogen. R$_3$ is NH(CH$_2$)$_m$SO$_3$H and R$_4$ is hydrogen. R$_3$ is hydroxyl and R$_4$ is hydrogen. In another aspect, R$_3$ is NH(CH$_2$)$_m$SO$_3$H, R$_4$ is hydrogen and m is 2. R$_3$ is NH(CH$_2$)$_n$CO$_2$H and R$_4$ is hydrogen. In another aspect, R$_3$ is NH(CH$_2$)$_n$CO$_2$H, R$_4$ is hydrogen and n is 1.

In another aspect, R$_3$ is OH and R$_4$ is alkyl. R$_3$ is OH and R$_4$ is lower alkyl. Lower alkyl is in the alpha configuration. R$_3$ is OH and R$_4$ is methyl. R$_3$ is OH and R$_4$ is ethyl. R$_3$ is OH and R$_4$ is α-methyl. R$_3$ is OH and R$_4$ is α-ethyl.

In another aspect, R$_5$ is unsubstituted or substituted alkyl. R$_5$ is unsubstituted or substituted lower alkyl. R$_5$ is in the S-configuration. R$_5$ is in the R-configuration. R$_5$ is methyl or ethyl. R$_5$ is S-methyl. R-methyl. R$_5$ is S-ethyl. R-ethyl. R$_5$ is alkyl substituted with phenyl. R$_5$ is lower alkyl substituted with phenyl. R$_5$ is benzyl. R$_5$ is S-benzyl. R$_5$ is R-benzyl.

In another aspect, R$_5$ is aryl. R$_5$ is phenyl.

In another aspect, R$_4$ and R$_5$ are each unsubstituted alkyl. R$_4$ and R$_5$ are each lower unsubstituted alkyl. R$_4$ and R$_5$ are each lower unsubstituted alkyl and R$_5$ is in the S-configuration. R$_4$ and R$_5$ are each lower unsubstituted alkyl and R$_4$ is in the alpha configuration. In another aspect, R$_4$ and R$_5$ are not hydrogen.

In another aspect, R$_4$ and R$_5$ are each lower unsubstituted alkyl and R$_1$ is α-hydroxy. R$_4$ and R$_5$ are each lower unsubstituted alkyl and R$_2$ is hydrogen. R$_4$ and R$_5$ are each lower unsubstituted alkyl, R$_1$ is α-hydroxy, and R$_2$ is hydrogen.

In another aspect, R$_5$ and R$_6$ taken together with the carbons to which they are attached form a ring size of 3, 4, 5, or 6 atoms. R$_5$ and R$_6$ taken together with the carbons to which they are attached form a 3-membered ring. The 3-membered ring has the following stereochemistry:

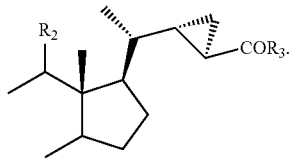

The 3-membered ring has the following stereochemistry:

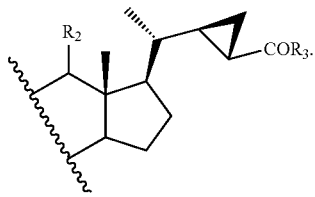

In another aspect, $R_1$, $R_2$, $R_3$, and $R_4$ are hydrogen. $R_2$, $R_3$, and $R_4$ are hydrogen. $R_2$ and $R_3$ are hydrogen. In another aspect, $R_1$, $R_2$, and $R_4$ are hydrogen and $R_3$ is OH. $R_2$ and $R_4$ are hydrogen and $R_3$ is OH. $R_2$ is hydrogen and $R_3$ is OH.

In another aspect, at least one of $R_1$, $R_2$, $R_3$, or $R_4$ is hydrogen. In another aspect, at least two of $R_1$, $R_2$, $R_3$, or $R_4$ are hydrogen. In another aspect, at least three of $R_1$, $R_2$, $R_3$, or $R_4$ are hydrogen. In another aspect, $R_1$, $R_2$, $R_3$, and $R_4$ are hydrogen. In another aspect, at least one of $R_1$, $R_2$, or $R_4$ is hydrogen and $R_3$ is OH. In another aspect, at least two of $R_1$, $R_2$, or $R_4$ are hydrogen and $R_3$ is OH. In another aspect, $R_1$, $R_2$, and $R_4$ are hydrogen and $R_3$ is OH. In another aspect, the present invention does not include when $R_5$ is methyl, $R_4$ is hydrogen, and $R_2$ is H or OH.

In another aspect of the present invention, the compound is selected from Compounds Ia, Ib, Ic, Ig, Ih, Ii, Io, Ip, Iq, Ia1, Ib1, Ic1, Ig1, Ih1, Ii1, Il1, Im1, In1, Io1, Ip1, Iq1, Ia2, Ib2, Ic2, Id2, Ie2, If2, Ig2, Ih2, Ii2, Il2, Im2, In2, Io2, Ip2, Iq2, Ia3, Ib3, Ic3, Id3, Ie3, If3, Ig3, Ih3, Ii3, Il3, Im3, In3, Ia4, Ib4, Ic4, Id4, Ie4, If4, Ig4, Ih4, Ii4, Il4, Im4, In4, Ia5, Ib5, Ic5, Id5, Ie5, If5, Ig5, Ih5, Ii5, Il5, Im5, In5, Ib3e, Ic3e, Id3e, Ie3e, If3e, Ig3e, Ih3e, Ii3e, Il3e, Im3e, In3e, Ia4e, Ib4e, Ic4e, Id4e, Ie4e, If4e, Ig4e, Ih4e, Ii4e, Il4e, Im4e, In4e, Ia5e, Ib5e, Ic5e, Id5e, Ie5e, If5e, Ig5e, Ih5e, Ii5e, Il5e, Im5e, Io5, Ip5, Iq5, and Ir5.

In another aspect of the present invention, the compound is not selected from Compounds Id, Ie, If, Id1, Il, Im, and In. In another aspect, the compound is not selected from Ie1 and If1.

Another aspect of the present invention includes a composition or medicament comprising a compound of formula I:

(I)

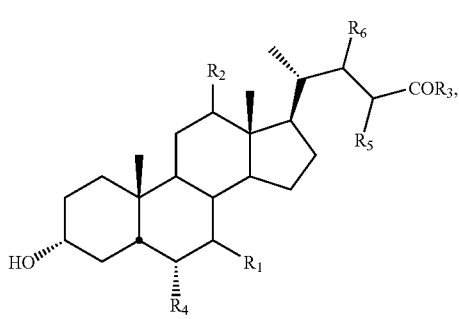

or a salt, solvate, hydrate, or prodrug thereof, and at least one pharmaceutically acceptable excipient wherein $R_1$ is hydrogen, hydroxy, or halogen; $R_2$ is hydrogen or α-hydroxy; $R_3$ is hydroxy, $NH(CH_2)_mSO_3H$, or $NH(CH_2)_nCO_2H$; $R_4$ is hydrogen, unsubstituted or substituted alkyl, or halogen; $R_5$ is unsubstituted or substituted lower alkyl, or aryl; $R_6$ is hydrogen or $R_5$ and $R_6$ taken together with the carbons to which they are attached form a ring of size 3, 4, 5, or 6 atoms; m is an integer 0, 1, 2, 3, 4, or 5; and n is an integer 0, 1, 2, 3, 4, or 5. In another aspect, the present invention includes a composition or medicament comprising a compound of formula I with proviso that when $R_5$ is methyl, $R_1$ is hydroxyl, and $R_3$ is hydroxy or $NHCH_2CH_2SO_3H$, then $R_4$ is not hydrogen.

Another aspect of the invention includes compounds of Formula IA:

(IA)

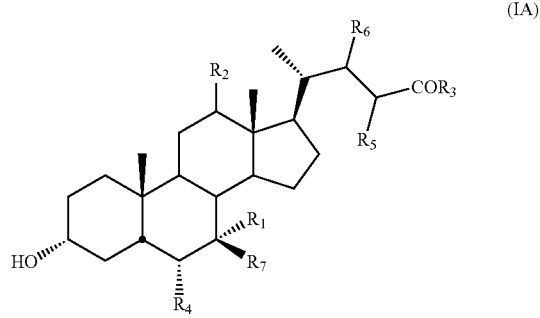

or a salt, solvate, hydrate, or prodrug thereof, wherein: $R_1$ is hydrogen, hydroxy, substituted or unsubstituted alkyl, or halogen; $R_2$ is hydrogen or α-hydroxy; $R_3$ is hydroxy, hydrogen, $NH(CH_2)_mSO_3H$, or $NH(CH_2)_nCO_2H$; $R_4$ is hydrogen, substituted or unsubstituted alkyl, or halogen; $R_5$ is unsubstituted or substituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; m is an integer 0, 1, 2, 3, 4, or 5; and n is an integer 0, 1, 2, 3, 4, or 5. In one aspect, when $R_5$ is methyl, $R_1$ is hydroxyl, and $R_3$ is hydroxy or $NHCH_2CH_2SO_3H$, then $R_4$ is not hydrogen.

In one aspect, $R_1$ is hydrogen or hydroxy. $R_1$ is hydroxy. $R_1$ is hydrogen. $R_1$ is hydroxy and $R_2$ is α-hydroxy. $R_1$ is hydroxy and $R_2$ is H. $R_1$ is hydroxy and $R_2$ is H. At least one of $R_1$ or $R_2$ is hydroxy. At least one of $R_1$ or $R_2$ is hydrogen. $R_1$ and $R_2$ are the same. $R_1$ is hydroxyl and $R_2$ is α-hydroxy. $R_1$ and $R_2$ are each hydrogen.

In one aspect, $R_3$ is hydrogen, hydroxy, $NH(CH_2)_mSO_3H$, or $NH(CH_2)_nCO_2H$. $R_3$ is hydroxy. $R_3$ is not hydroxy. $R_3$ is $NH(CH_2)_mSO_3H$. $R_3$ is $NH(CH_2)_mSO_3H$ and m is 2. $R_3$ is $NH(CH_2)_nCO_2H$. $R_3$ is $NH(CH_2)_1CO_2H$ and n is 1.

In another aspect, $R_4$ is hydrogen or unsubstituted alkyl. $R_4$ is hydrogen. $R_4$ is unsubstituted alkyl. $R_4$ is unsubstituted alkyl. $R_4$ is methyl or ethyl. $R_4$ is methyl. $R_4$ is ethyl. $R_3$ and $R_4$ are the same. $R_3$ and $R_4$ are different. $R_3$ and $R_4$ are each hydrogen. $R_3$ is OH and $R_4$ is hydrogen.

In another aspect, $R_3$ is $NH(CH_2)_mSO_3H$ and $R_4$ is hydrogen. $R_3$ is $NH(CH_2)_mSO_3H$, $R_4$ is hydrogen, and m is 2. $R_3$ is $NH(CH_2)_nCO_2H$ and $R_4$ is hydrogen. $R_3$ is $NH(CH_2)_nCO_2H$, $R_4$ is hydrogen, and n is 1. $R_3$ is OH and $R_4$ is unsubstituted alkyl. $R_3$ is OH and $R_4$ is unsubstituted alkyl. $R_3$ is OH and $R_4$ is methyl. $R_3$ is OH and $R_4$ is ethyl. $R_3$ is OH and $R_4$ is methyl.

In one aspect, $R_5$ is unsubstituted or substituted alkyl. $R_5$ is in the S-configuration. $R_5$ is in the R-configuration. $R_5$ is methyl or ethyl. $R_5$ is S-methyl. $R_5$ is R-methyl. $R_5$ is S-ethyl. $R_5$ is R-ethyl. $R_5$ is substituted with phenyl. $R_5$ is benzyl. $R_5$ is S-benzyl. $R_5$ is R-benzyl. In another aspect, $R_5$ is aryl. For example, $R_5$ is phenyl.

$R_4$ and $R_5$ are each unsubstituted alkyl. $R_4$ and $R_5$ are each unsubstituted alkyl, further wherein $R_5$ is in the S-configuration. $R_4$ and $R_5$ are each unsubstituted alkyl. $R_4$ and $R_5$ are each unsubstituted alkyl and $R_1$ is hydroxy. $R_4$ and $R_5$ are each unsubstituted alkyl and $R_2$ is hydrogen. $R_4$ and $R_5$ are each unsubstituted alkyl, $R_1$ is hydroxy, and $R_2$ is hydrogen.

In one aspect, $R_1$, $R_2$, $R_3$, and $R_4$ are hydrogen. $R_2$, $R_3$, and $R_4$ are hydrogen. $R_2$ and $R_3$ are hydrogen. At least one of $R_1$, $R_2$, $R_3$, or $R_4$ is hydrogen. At least two of $R_1$, $R_2$, $R_3$, or $R_4$ is hydrogen. At least three of $R_1$, $R_2$, $R_3$, or $R_4$ is hydrogen. $R_1$, $R_2$, $R_3$, and $R_4$ is hydrogen.

In one aspect, $R_1$, $R_2$, and $R_4$ are hydrogen and $R_3$ is OH. $R_2$ and $R_4$ are hydrogen and $R_3$ is OH. $R_2$ is hydrogen and $R_3$ is OH. At least one of $R_1$, $R_2$, or $R_4$ is hydrogen and $R_3$ is OH. At least two of $R_1$, $R_2$, or $R_4$ is hydrogen and $R_3$ is OH. All of $R_1$, $R_2$, and $R_4$ are hydrogen and $R_3$ is OH.

In another aspect, at least one of $R_1$ or $R_7$ is unsubstituted alkyl. At least one of $R_1$ or $R_7$ is methyl. At least one of $R_1$ or $R_7$ is ethyl. At least one of $R_1$ or $R_7$ is propyl. Both $R_1$ and $R_7$ are unsubstituted alkyl. Both $R_1$ and $R_7$ are methyl. Both $R_1$ and $R_7$ are ethyl. $R_1$ and $R_7$ are the same. $R_1$ and $R_7$ are different. $R_7$ is hydrogen. $R_7$ is hydroxy. One of $R_1$ or $R_7$ is unsubstituted alkyl and the remaining $R_1$ or $R_7$ is hydrogen. One of $R_1$ or $R_7$ is unsubstituted alkyl and the remaining $R_1$ or $R_7$ is hydroxy. At least one of $R_1$ or $R_7$ is unsubstituted alkyl and $R_5$ is unsubstituted or substituted alkyl. At least one of $R_1$ or $R_7$ is methyl and $R_5$ is methyl.

Both $R_1$ and $R_5$ are unsubstituted alkyl and $R_7$ is hydroxy. Both $R_7$ and $R_5$ are unsubstituted alkyl and $R_1$ is hydroxy. $R_1$ or $R_7$ is unsubstituted alkyl and $R_5$ is unsubstituted or substituted alkyl further wherein $R_5$ is in the S-configuration. $R_1$ or $R_7$ is unsubstituted alkyl and $R_5$ is unsubstituted or substituted alkyl, further wherein $R_5$ is in the R-configuration.

In another aspect, $R_1$ is hydroxy and $R_7$ is methyl. $R_1$ is methyl and $R_7$ is hydroxy. $R_6$ is unsubstituted alkyl. $R_6$ is methyl. $R_6$ is ethyl. $R_2$, and $R_6$ are each hydrogen. $R_2$ and $R_6$ are hydrogen and $R_5$ is unsubstituted alkyl. $R_2$ and $R_6$ are hydrogen, $R_5$ is unsubstituted alkyl, and at least one of $R_1$ or $R_7$ is unsubstituted alkyl.

In one aspect, the compound is selected from Compounds Ia6, Ib6, Ic6, Ig6, Ih6, Ii6, Io6, Ip6, Iq6, Ia7, Ib7, Ic7, Ig7, Ih7, Ii7, Il7, Im7, In7, Io7, Ip7, Iq7, Ia8, Ib8, Ic8, Id8, Ie8, If8, Ig8, Ih8, Ii8, Il8, Im8, In8, Io8, Ip8, Iq8, Ia9, Ib9, Ic9, Id9, Ie9, If9, Ig9, Ih9, Ii9, Il9, Im9, In9, Ia10, Ib10, Ic10, Id10, Ie10, If10, Ig10, Ih10, Ii10, Il10, Im10, In10, Ia11, Ib11, Ic11, Id11, Ie11, If11, Ig11, Ih11, Ii11, Il11, Im11, In11, Ia9e, Ib9e, Ic9e, Id9e, Ie9e, If9e, Ig9e, Ih9e, Ii9e, Il9e, Im9e, In9e, Ia10e, Ib10e, Ic10e, Id10e, Ie10e, If10e, Ig10e, Ih10e, Ii10e, Il10e, Im10e, In10e, Ia11e, Ib11e, Ic11e, Id11e, Ie11e, If11e, Ig11e, Ih11e, Ii11e, Il11e, Im11e, and In11e.

In another aspect of the present invention, when $R_2$, $R_4$, and $R_6$ are each hydrogen, $R_3$ is hydroxyl, and one of $R_1$ and $R_7$ is hydrogen or hydroxyl, then the other $R_1$ or $R_7$ is not methyl. In another aspect, when $R_2$ is α-OH; $R_3$ is hydroxyl; $R_4$ and $R_6$ are each hydrogen; and one of $R_1$ and $R_7$ is hydrogen or hydroxyl, then the other $R_1$ or $R_7$ is not methyl. In another aspect, the present invention does not include the following compounds: 3α,7α-dihydroxy-7β-methyl-5β-cholanoic acid, 3α,7β-dihydroxy-7α-methyl-5β-cholanoic acid, 3α-hydroxy-7ε-methyl-5β-cholanoic acid, 3α,7β,12α-trihydroxy-7α-methyl-5β-cholan-24-oic acid; 3α,7α,12α-trihydroxy-7β-methyl-5β-cholan-24-oic acid; and 3α,12α-dihydroxy-7ε-methyl-5β-cholan-24-oic acid.

In another aspect of the present invention, when $R_3$ is hydroxyl and one of $R_1$ and $R_7$ is methyl and the other $R_1$ and $R_7$ is hydrogen or hydroxyl, then $R_2$, $R_4$ and $R_6$ are not all hydrogen. In another aspect, when $R_2$ is α-OH, $R_3$ is hydroxyl, and one of $R_1$ and $R_7$ is methyl and the other $R_1$ and $R_7$ is hydrogen or hydroxyl, then $R_4$ and $R_6$ are not hydrogen.

Another aspect of the invention includes a composition or medicament comprising a compound of formula IA:

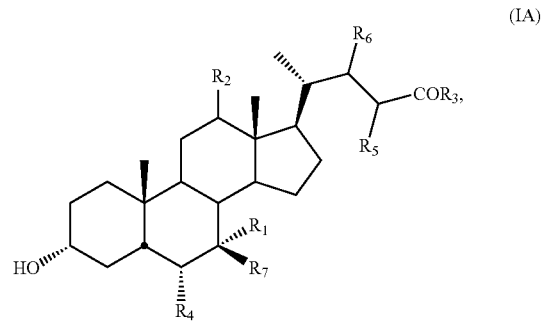

(IA)

or a salt, solvate, hydrate, or prodrug thereof, and at least one pharmaceutically acceptable excipient wherein: $R_1$ is hydrogen, hydroxy, substituted or unsubstituted alkyl or halogen; $R_2$ is hydrogen or α-hydroxy; $R_3$ is hydroxy, $NH(CH_2)_mSO_3H$, or $NH(CH_2)_nCO_2H$; $R_4$ is hydrogen, substituted or unsubstituted alkyl, or halogen; $R_5$ is unsubstituted or substituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; and m is an integer 0, 1, 2, 3, 4, or 5; and n is an integer 0, 1, 2, 3, 4, or 5.

In one aspect of the invention, when $R_5$ is methyl, $R_1$ is hydroxyl, and $R_3$ is hydroxyl or $NHCH_2CH_2SO_3H$, then $R_4$ is not hydrogen.

Another aspect of the present invention includes a compound of Formula II:

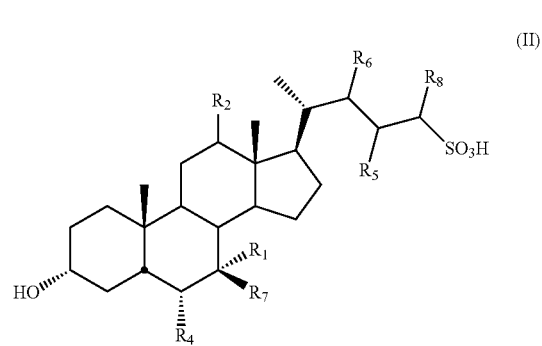

(II)

or a salt, solvate, hydrate, or prodrug thereof, wherein: $R_1$ is hydrogen, hydroxy, substituted or unsubstituted alkyl, or halogen; $R_2$ is hydrogen or α-hydroxy; $R_4$ is hydrogen, substituted or unsubstituted alkyl, or halogen; $R_5$ is unsubstituted or substituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; and $R_8$ is hydrogen, substituted or unsubstituted alkyl. In one aspect, when $R_5$ is methyl and $R_1$ is hydroxyl, then $R_4$ is not hydrogen.

In one aspect, $R_1$ is hydrogen or hydroxy. $R_1$ is hydroxy. $R_1$ is hydrogen. $R_1$ is β-hydroxy. $R_2$ is α-hydroxy. $R_1$ is hydroxy and $R_2$ is α-hydroxy. $R_1$ is hydroxy and $R_2$ is H. At least one of $R_1$ or $R_2$ is hydroxy. At least one of $R_1$ or $R_2$ is hydrogen. $R_1$ and $R_2$ are the same. $R_1$ is hydroxyl and $R_2$ is α-hydroxy. $R_1$ and $R_2$ are each hydrogen.

In another aspect, $R_4$ is hydrogen or unsubstituted alkyl. $R_4$ is hydrogen. $R_4$ is unsubstituted alkyl. $R_4$ is unsubstituted alkyl. $R_4$ is methyl or ethyl. $R_4$ is methyl. $R_4$ is ethyl.

In one aspect, $R_5$ is unsubstituted or substituted alkyl. $R_5$ is in the S-configuration. $R_5$ is in the R-configuration. $R_5$ is methyl or ethyl. $R_5$ is S-methyl. $R_5$ is R-methyl. $R_5$ is S-ethyl. $R_5$ is R-ethyl. $R_5$ is substituted with phenyl. $R_5$ is benzyl. $R_5$ is S-benzyl. $R_5$ is R-benzyl. $R_5$ is aryl. $R_5$ is phenyl. $R_4$ and $R_5$ are each unsubstituted alkyl. $R_4$ and $R_5$ are each unsubstituted alkyl, further wherein $R_5$ is in the S-configuration. $R_4$ and $R_5$ are each unsubstituted alkyl and $R_1$ is hydroxy. $R_4$ and $R_5$ are each unsubstituted alkyl and $R_2$ is hydrogen. $R_4$ and $R_5$ are each unsubstituted alkyl, $R_1$ is hydroxy and $R_2$ is hydrogen.

In one aspect, $R_1$, $R_2$, and $R_4$ are hydrogen. $R_2$ and $R_4$ are hydrogen. $R_2$ is hydrogen. At least one of $R_1$, $R_2$, or $R_4$ is hydrogen. At least two of $R_1$, $R_2$, or $R_4$ is hydrogen. All of $R_1$, $R_2$, or $R_4$ is hydrogen.

In one aspect, $R_1$ or $R_7$ is unsubstituted alkyl. $R_1$ or $R_7$ is methyl. $R_1$ or $R_7$ is ethyl. $R_1$ or $R_7$ is propyl. Both $R_1$ and $R_7$ are unsubstituted alkyl. $R_7$ is hydrogen. $R_7$ is hydroxy. One of $R_1$ or $R_7$ is unsubstituted alkyl and the remaining $R_1$ or $R_7$ is hydrogen. One of $R_1$ or $R_7$ is unsubstituted alkyl and the remaining $R_1$ or $R_7$ is hydroxy. At least one of $R_1$ or $R_7$ is unsubstituted alkyl and $R_5$ is unsubstituted or substituted alkyl. At least one of $R_1$ or $R_7$ is methyl and $R_5$ is methyl. $R_7$ is hydroxy and both $R_1$ and $R_5$ are unsubstituted alkyl. $R_1$ is hydroxy and both $R_7$ and $R_5$ are unsubstituted alkyl. At least one of $R_1$ or $R_7$ is unsubstituted alkyl and $R_5$ is unsubstituted or substituted alkyl, further wherein $R_5$ is in the S-configuration. At least one of $R_1$ or $R_7$ is unsubstituted alkyl and $R_5$ is unsubstituted or substituted alkyl, further wherein $R_5$ is in the R-configuration. $R_7$ is hydroxy and both $R_1$ and $R_5$ are unsubstituted alkyl, further wherein $R_5$ is in the S-configuration. $R_7$ is hydroxy and both $R_1$ and $R_5$ are unsubstituted alkyl, further wherein $R_5$ is in the R-configuration. $R_1$ is hydroxy and both $R_7$ and $R_5$ are unsubstituted alkyl, further wherein $R_5$ is in the S-configuration. $R_1$ is hydroxy and both $R_7$ and $R_5$ are unsubstituted alkyl, further wherein $R_5$ is in the R-configuration. $R_1$ is hydroxy and $R_7$ is methyl. $R_1$ is methyl and $R_7$ is hydroxy.

In another aspect, $R_6$ is unsubstituted alkyl. $R_6$ is methyl. $R_6$ is ethyl. $R_8$ is hydrogen.

$R_8$ is unsubstituted alkyl. $R_8$ is methyl. $R_8$ is ethyl. $R_2$ is α-hydroxy and $R_8$ is unsubstituted alkyl.

In another aspect of the invention, the compound is selected from Compounds Ia12, Ib12, Ic12, Ig12, Ih12, Ii12, Io12, Ip12, Ig12, Ia13, Ib13, Ic13, Ig13, Ih13, Ii13, Il13, Im13, In13, Io13, Ip13, Iq13, Ia14, Ib14, Ic14, Id14, Ie14, If14, Ig14, Ih14, Ii14, Il14, Im14, In14, Io14, Ip14, Iq14, Ia15, Ib15, Ic15, Id15, Ie15, If15, Ig15, Ih15, Ii15, Il15, Im15, In15, Iath, Ib16, Ic16, Id16, Ie16, If16, Ig16, Ih16, Ii16, Il16, Im16, In16, Ia17, Ib17, Ic17, Id17, Ie17, Il17, Ig17, Ih17, Ii17, Il17, Im17, In17, Ia15e, Ib15e, Ic15e, Id15e, Ie15e, If15e, Ig15e, Ih15e, Ii15e, Il15e, Im15e, In15e, Ia16e, Ib16e, Ic16e, Id16e, Ie16e, If16e, Ig16e, Ih16e, Ii16e, Il16e, Im16e, In16e, Ia17e, Ib17e, Ic17e, Id17e, Ie17e, If17e, Ig17e, Ih17e, Ii17e, Il17e, Im17e, and In17e.

Another aspect of the invention includes a composition or medicament comprising a compound of formula II:

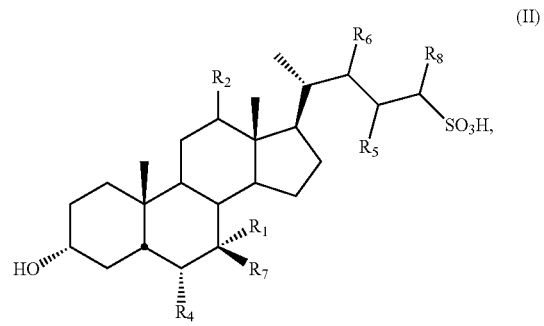

(II)

or a salt, solvate, hydrate, or prodrug thereof, and at least one pharmaceutically acceptable excipient wherein: $R_1$ is hydrogen, hydroxy, substituted or unsubstituted alkyl or halogen; $R_2$ is hydrogen or α-hydroxy; $R_4$ is hydrogen, substituted or unsubstituted alkyl, or halogen; $R_5$ is unsubstituted or substituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_2$ is hydrogen, substituted or unsubstituted alkyl, or hydroxy; and $R_8$ is hydrogen or substituted or unsubstituted alkyl. In one aspect, when $R_5$ is methyl, $R_1$ is hydroxyl, and $R_3$ is hydroxyl or $NHCH_2CH_2SO_3H$, then $R_4$ is not hydrogen.

Another aspect of the invention includes a compound according to formula III:

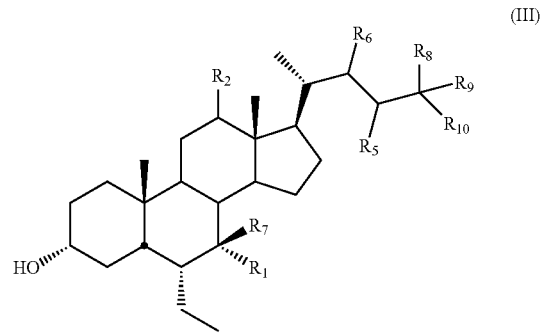

(III)

or a salt, solvate, hydrate, or prodrug thereof, wherein $R_1$ is hydrogen, hydroxy, or halogen; $R_2$ is hydrogen or α-hydroxy; $R_3$ is hydroxy, $NH(CH_2)_mSO_3H$, or $NH(CH_2)_nCO_2H$; $R_5$ is unsubstituted or substituted alkyl, or aryl; $R_6$ is hydrogen or $R_5$ and $R_6$ taken together with the carbons to which they are attached form a ring of size 3, 4, 5, or 6 atoms; $R_2$ is hydrogen, unsubstituted or substituted alkyl or hydroxy; $R_8$ is hydrogen, unsubstituted or substituted alkyl; $R_9$ is hydrogen, unsubstituted or substituted alkyl or $R_8$ and $R_9$ taken together with the carbon to which they are attached form a carbonyl; $R_{10}$ is $R_3$ or $SO_3H$; m is an integer 0, 1, 2, 3, 4, or 5; and n is an integer 0, 1, 2, 3, 4, or 5.

Another aspect of the invention includes a compound according to formula IIIA:

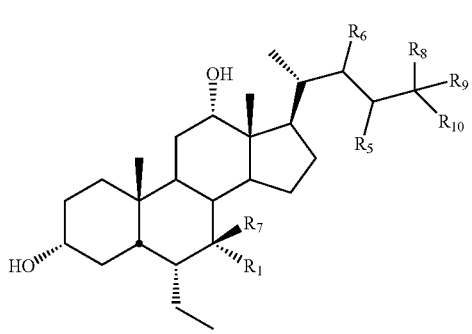

(IIIA)

or a salt, solvate, hydrate, or prodrug thereof, wherein $R_1$ is hydrogen, hydroxy, or halogen; $R_3$ is hydroxy, $NH(CH_2)_mSO_3H$, or $NH(CH_2)_nCO_2H$; $R_5$ is unsubstituted or substituted alkyl, or aryl; $R_6$ is hydrogen or $R_5$ and $R_6$ taken together with the carbons to which they are attached form a ring of size 3, 4, 5, or 6 atoms; $R_7$ is hydrogen, unsubstituted or substituted alkyl or hydroxy; $R_8$ is hydrogen, unsubstituted or substituted alkyl; $R_9$ is hydrogen, unsubstituted or substituted alkyl or $R_8$ and $R_9$ taken together with the carbon to which they are attached form a carbonyl; $R_{10}$ is $R_3$ or $SO_3H$; m is an integer 0, 1, 2, 3, 4, or 5; and n is an integer 0, 1, 2, 3, 4, or 5.

One aspect of the invention includes a compound or a salt, solvate, hydrate, or prodrug thereof, wherein $R_1$ is hydroxyl. Another aspect of the invention includes a compound or a salt, solvate, hydrate, or prodrug thereof, wherein $R_8$ and $R_9$ taken together with the carbon to which they are attached form a carbonyl and $R_{10}$ is $R_3$. In one aspect, $R_3$ is selected from hydroxy, $NH(CH_2)_2SO_3H$, and $NHCH_2CO_2H$. In one aspect, $R_3$ is hydroxy. In one aspect, $R_3$ is $NH(CH_2)_2SO_3H$. In one aspect, $R_3$ is $NHCH_2CO_2H$. One aspect of the invention includes a compound or a salt, solvate, hydrate, or prodrug thereof, wherein $R_6$ is hydrogen. One aspect of the invention includes a compound or a salt, solvate, hydrate, or prodrug thereof, wherein $R_5$ is unsubstituted alkyl. In one aspect, $R_5$ is methyl. One aspect of the invention includes a compound or a salt, solvate, hydrate, or prodrug thereof, wherein $R_5$ is in the S-configuration. One aspect of the invention includes a compound or a salt, solvate, hydrate, or prodrug thereof, wherein $R_5$ is in the S-configuration and $R_5$ is methyl. One aspect of the invention includes a compound or a salt, solvate, hydrate, or prodrug thereof, wherein $R_7$ is hydrogen.

One aspect of the invention includes a compound selected from Compounds Ig3e, Ih3e, Ii3e, Ig4e, Ih4e, Ii4e, Ig5e, Ih5e, and Ii5e.

Another aspect of the invention includes a compound according to formula IIIB

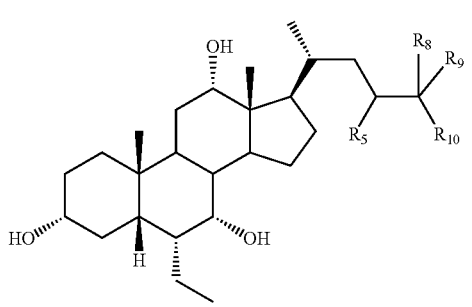

(IIIB)

or a salt, solvate, hydrate, or prodrug thereof, wherein $R_3$ is hydroxy, $NH(CH_2)_mSO_3H$, or $NH(CH_2)_nCO_2H$; $R_5$ is unsubstituted or substituted alkyl, or aryl; $R_8$ is hydrogen, unsubstituted or substituted alkyl; $R_9$ is hydrogen, unsubstituted or substituted alkyl or $R_8$ and $R_9$ taken together with the carbon to which they are attached form a carbonyl; $R_{10}$ is $R_3$ or $SO_3H$; m is an integer 0, 1, 2, 3, 4, or 5; and n is an integer 0, 1, 2, 3, 4, or 5. One aspect of the invention includes a compound or a salt, solvate, hydrate, or prodrug thereof, wherein $R_5$ is unsubstituted alkyl. In one aspect, $R_5$ is methyl. One aspect of the invention includes a compound or salt, solvate, hydrate, or prodrug thereof, wherein $R_5$ is in the S-configuration. One aspect of the invention includes a compound or salt, solvate, hydrate, or prodrug thereof, wherein $R_5$ is in the S-configuration and $R_5$ is methyl. One aspect of the invention includes a compound or a salt, solvate, hydrate, or prodrug thereof, wherein $R_8$ and $R_9$ taken together with the carbon to which they are attached form a carbonyl. One aspect of the invention includes a compound or a salt, solvate, hydrate, or prodrug thereof, wherein $R_{10}$ is $R_3$. In one aspect, $R_3$ is selected from hydroxy, $NH(CH_2)_2SO_3H$, and $NHCH_2CO_2H$. In one aspect, $R_3$ is hydroxy. In one aspect, $R_3$ is $NH(CH_2)_2SO_3H$. In one aspect, $R_3$ is $NHCH_2CO_2H$.

Another aspect of the invention includes a compound according to formula IIIC:

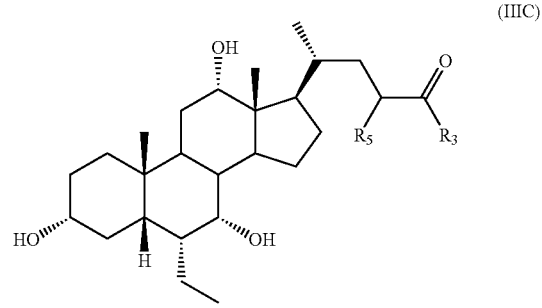

(IIIC)

or a salt, solvate, hydrate, or prodrug thereof, wherein $R_3$ is hydroxy, $NH(CH_2)_mSO_3H$, or $NH(CH_2)_nCO_2H$; $R_5$ is unsubstituted or substituted alkyl, or aryl; m is an integer 0, 1, 2, 3, 4, or 5; and n is an integer 0, 1, 2, 3, 4, or 5. One aspect of the invention includes a compound or a salt, solvate, hydrate, or prodrug thereof, wherein $R_3$ is selected from hydroxy, $NH(CH_2)_2SO_3H$, and $NHCH_2CO_2H$. In one aspect, $R_3$ is hydroxy. In one aspect, $R_3$ is $NH(CH_2)_2SO_3H$. In one aspect, $R_3$ is $NHCH_2CO_2H$. One aspect of the invention includes a compound or a salt, solvate, hydrate, or prodrug thereof, wherein $R_5$ is unsubstituted alkyl. In one aspect, $R_5$ is methyl. One aspect of the invention includes a compound or salt, solvate, hydrate, or prodrug thereof, wherein $R_5$ is in the S-configuration. One aspect of the invention includes a compound or salt, solvate, hydrate, or prodrug thereof, wherein $R_5$ is in the S-configuration and $R_5$ is methyl.

Another aspect of the invention includes a compound according to formula IV:

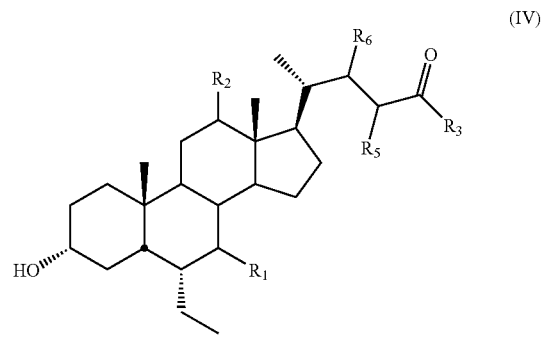

(IV)

or a salt, solvate, hydrate, or prodrug thereof, wherein: $R_1$ is hydrogen, hydroxy, or halogen; $R_2$ is hydrogen or α-hydroxy; $R_3$ is hydroxy, $NH(CH_2)_mSO_3H$, or $NH(CH_2)_nCO_2H$; $R_5$ is unsubstituted or substituted alkyl, or aryl; $R_6$ is hydrogen or $R_5$ and $R_6$ taken together with the carbons to which they are attached form a ring of size 3, 4, 5, or 6 atoms; m is an integer 0, 1, 2, 3, 4, or 5; and n is an integer 0, 1, 2, 3, 4, or 5.

In one aspect, the invention includes a compound or a salt, solvate, hydrate, or prodrug thereof, wherein $R_1$ is hydroxy. In another aspect, the invention includes a compound or a salt, solvate, hydrate, or prodrug thereof, wherein $R_1$ is alpha hydroxy. In one aspect, the invention includes a compound or a salt, solvate, hydrate, or prodrug thereof, wherein $R_1$ is beta hydroxy. In one aspect, the invention includes a compound or a salt, solvate, hydrate, or prodrug thereof, wherein $R_1$ is methyl.

In one aspect, the invention includes a compound or a salt, solvate, hydrate, or prodrug thereof, wherein $R_5$ is unsubstituted alkyl. In one aspect, the invention includes a compound or a salt, solvate, hydrate, or prodrug thereof, wherein $R_5$ is methyl. In one aspect, the invention includes a compound or a salt, solvate, hydrate, or prodrug thereof, wherein $R_5$ is in the R-configuration. In one aspect, the invention includes a compound or a salt, solvate, hydrate, or prodrug thereof, wherein $R_5$ is in the S-configuration.

In one aspect, the invention includes a compound or a salt, solvate, hydrate, or prodrug thereof, wherein $R_6$ is hydrogen. In one aspect, the invention includes a compound or a salt, solvate, hydrate, or prodrug thereof, wherein $R_2$ is hydrogen. In one aspect, the invention includes a compound or a salt, solvate, hydrate, or prodrug thereof, wherein $R_2$ is alpha hydroxy. In one aspect, the invention includes a compound or a salt, solvate, hydrate, or prodrug thereof, wherein $R_3$ is hydroxyl.

One aspect of the invention includes a compound selected from Compounds Ib3e, Ic3e, Id3e, Ie3e, If3e, Ig3e, Ih3e, Ii3e, Il3e, Im3e, In3e, Ia4e, Ib4e, Ic4e, Id4e, Ie4e, If4e, Ig4e, Ih4e, If4e, Il4e, Im4e, In4e, Ia5e, Ib5e, Ic5e, Id5e, Ie5e, If5e, Ig5e, Ih5e, Ii5e, Il5e, Im5e, In5e, Ia9e, Ib9e, Ic9e, Id9e, Ie9e, If9e, Ig9e, Ih9e, Ii9e, Il9e, Im9e, In9e, Ia10e, Ib10e, Ic10e, Id10e, Ie10e, If10e, Ig10e, Ih10e, Ii10e, Il10e, Im10e, In10e, Ia11e, Ib11e, Ic11e, Id11e, Ie11e, If11e, Ig11e, Ih11e, Ii11e, Il11e, Im11e, In11e, Ia15e, Ib15e, Ic15e, Id15e, Ie15e, If15e, Ig15e, Ih15e, Ii15e, Il15e, Im15e, In15e, Ia16e, Ib16e, Ic16e, Id16e, Ie16e, If16e, Ig16e, Ih16e, Ii16e, Il16e, Im16e, In16e, Ia17e, Ib17e, Ic17e, Id17e, Ie17e, If17e, Ig17e, Ih17e, Ii17e, Il17e, Im17e, and In17e.

The invention includes Compound Ih3e:

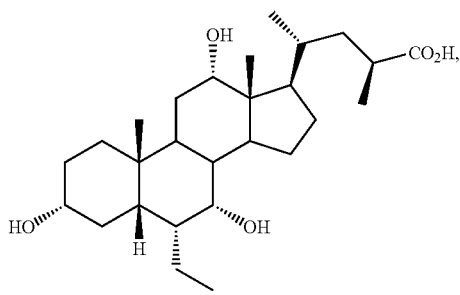

or a salt, solvate, hydrate, or prodrug thereof. In one aspect, the invention includes the taurine conjugate of Compound Ih3e:

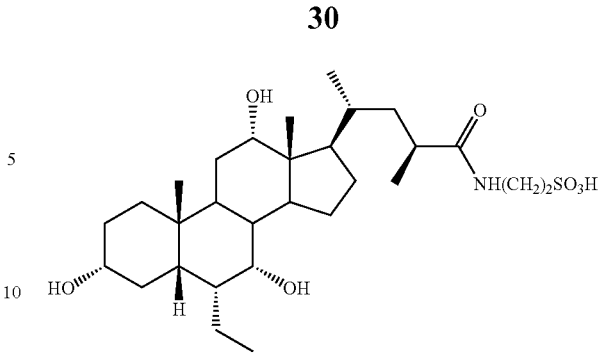

or a salt, solvate, hydrate, or prodrug thereof. In one aspect, includes the glycine conjugate of Compound Ih3e:

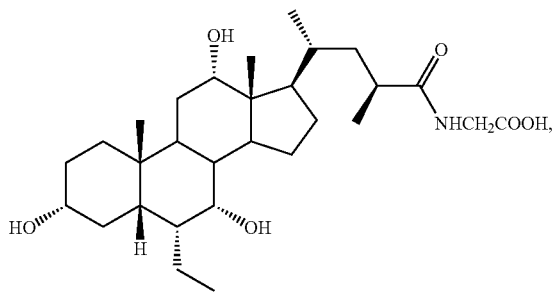

or a salt, solvate, hydrate, or prodrug thereof.

One aspect of the invention includes Compounds Ib3e, Ic3e, Id3e, Ie3e, If3e, Ig3e, Ih3e, Ii3e, Il3e, Im3e, In3e, Ia4e, Ib4e, Ic4e, Id4e, Ie4e, If4e, Ig4e, Ih4e, If4e, Il4e, Im4e, In4e, Ia5e, Ib5e, Ic5e, Id5e, Ie5e, If5e, Ig5e, Ih5e, Ii5e, Il5e, Im5e, and In5e.

One aspect of the invention includes Compounds Ia9e, Ib9e, Ic9e, Id9e, Ie9e, If9e, Ig9e, Ih9e, Ii9e, Il9e, Im9e, In9e, Ia10e, Ib10e, Ic10e, Id10e, Ie10e, If10e, Ig10e, Ih10e, Ii10e, Il10e, Im10e, In10e, Ia11e, Ib11e, Ic11e, Id11e, Ie11e, If11e, Ig11e, Ih11e, Ii11e, Il11e, Im11e, and In11e.

One aspect of the invention includes Compounds Ia15e, Ib15e, Ic15e, Id15e, Ie15e, If15e, Ig15e, Ih15e, Ii15e, Il15e, Im15e, In15e, Ia16e, Ib16e, Ic16e, Id16e, Ie16e, If16e, Ig16e, Ih16e, Ii16e, Il16e, Im16e, In16e, Ia17e, Ib17e, Ic17e, Id17e, Ie17e, If17e, Ig17e, Ih17e, Ii17e, Il17e, Im17e, and In17e.

In one aspect, the invention includes a compound of the invention, wherein the compound is a pharmaceutically acceptable salt.

One aspect of the invention includes a composition comprising a compound of the invention or a pharmaceutically acceptable salt, solvate, hydrate, or prodrug thereof, and at least one pharmaceutically acceptable excipient.

The present invention also includes radiolabeled compounds of the invention Radiolabeled compounds can be prepared using conventional techniques. For example, radiolabeled compounds of the invention can be prepared by reacting the compound of the invention with tritium gas in the presence of an appropriate catalyst to produce radiolabeled compounds having the formulae described herein. In one embodiment, the compounds of the invention are tritiated.

Use and Methods

The invention includes the use of a compound or a pharmaceutically acceptable salt, solvate, hydrate, or prodrug thereof, in the manufacture of a medicament for a treating or preventing disease in a subject. The invention also includes a method of treating or preventing disease in a subject by administering a compound of the invention or a pharmaceutically acceptable salt, hydrate, or prodrug thereof.

One aspect of the invention includes the use or method, wherein the disease is selected from metabolic disease, inflammatory disease, liver disease, autoimmune disease, cardiac disease, kidney disease, cancer, and gastrointestinal disease.

In one aspect, the invention includes a metabolic disease selected from obesity, diabetes, diabesity, metabolic syndrome, insulin resistance, including pre-diabetic insulin resistance, hypertension, and dyslipidemia. In one aspect, the metabolic disease is obesity. In another aspect, the metabolic disease is diabetes. In one aspect, diabetes is selected from pre-diabetes and type II diabetes. In one aspect, the metabolic disease is metabolic syndrome. In one aspect, the metabolic disease is insulin resistance. In one aspect, the metabolic disease is dyslipidemia. In one aspect, the metabolic disease is diabesity. The term "diabesity" refers to a condition wherein the subject has both diabetes and excessive weight.

In one aspect, the invention includes an inflammatory disease selected from allergy, osteoarthritis (OA), chronic obstructive pulmonary disease (COPD), appendicitis, bronchial asthma, pancreatitis, allergic rash, and psoriasis.

In one aspect, the invention includes an autoimmune disease selected from rheumatoid arthritis, multiple sclerosis, and type I diabetes.

In one aspect, the invention includes a gastrointestinal disease selected from inflammatory bowel disease (Crohn's disease, ulcerative colitis), short bowel syndrome (post-radiation colitis), microscopic colitis, irritable bowel syndrome (malabsorption), and bacterial overgrowth.

In one aspect, the invention includes kidney disease selected from diabetic nephropathy, chronic renal failure, glomerular nephritis, hypertensive nephrosclerosis, chronic glomerulonephritis, chronic transplant glomerulopathy, chronic interstitial nephritis, and polysystic kidney disease.

In one aspect, the invention includes cancer selected from colorectal cancer, liver cancer, heptacellular carcinoma, cholangio carcinoma, renal cancer, gastric cancer, pancreatic cancer, prostate cancer, and insulanoma.

In one aspect, the invention includes liver disease selected from nonalcoholic steatohepatitis, nonalcoholic fatty liver disease, chronic viral hepatitis, alcoholic liver disease, drug induced hepatitis, hemochromatosis, primary biliary cirrhosis, primary sclerosing cholangitis, portal hypertension, bile desaturation, Gaucher's disease, Wilson's disease, α1-antitrypsin deficiency, total parenteral nutrition (TPN), cholelithiasis, TPN-associated cholestasis and sepsis.

In one aspect, the invention includes the autoimmune disease erythematosus.

In one aspect, the invention includes cardiac disease selected from congestive heart failure, myocardial infarction, atherosclerosis, angina pectoris, arteriosclerosis and cerebrovascular disease (hemorrhage, stroke, cerebrovascular infarction).

In one aspect, the invention includes a use or method, wherein the compound of the invention is a TGR5 agonist. In one aspect, the selectivity ratio of TGR5 $EC_{50}$ to FXR $EC_{50}$ is less than 0.05.

In one aspect, the invention includes a use or method, wherein the compound or composition is administered to the subject orally, parentally, intravenously, or topically. In one aspect, the subject is human.

One aspect of the invention includes a use or method comprising administering to a subject a therapeutically effective amount of the compound of the invention. In one aspect, the invention includes a use or method comprising administering to subject in need thereof. The present invention includes a use or method comprising administering to a subject a prophylatically effective amount of the compound of the invention.

The compounds and compositions of the present invention can be administered by various routes, e.g., oral, subcutaneous, intramuscular, intravenous, or intraperitoneal. The referred routes of administering the pharmaceutical compositions are oral, subcutaneous, and intravenous at daily doses of about 0.01-5000 mg, preferably 5-500 mg, of the FXR ligand for a 70 kg adult human per day. The appropriate dose may be administered in a single daily dose or as divided doses presented at appropriate intervals, for example as two, three, four, or more subdoses per day.

For preparing pharmaceutical compositions containing a compound of the invention, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., a compound of the invention. In tablets, the active ingredient is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient of the compound of the invention. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound with encapsulating material as a carrier providing a capsule in which the compound of the invention (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., a compound of the invention) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 and 8.

The pharmaceutical compositions containing compounds of the invention can be administered for prophylactic and/or therapeutic treatments. In therapeutic applications, compositions are administered in an amount sufficient to cure, reverse, or at least partially slow or arrest the symptoms of the disease and its complications. An amount adequate to cure, reverse, or at least partially slow or arrest the symptom of the disease and its complications is defined as a "therapeutically effective dose." In prophylatic applications, compositions are administered in an amount sufficient to prevent the symptoms of the disease and its complications. An amount adequate to prevent the symptom of the disease and its complications is defined as a "prophylatically effective dose."

Amounts effective for therapeutic use will depend on the severity of the disease or condition and the weight and general state of the patient, but generally range from about 0.1 mg to about 2,000 mg of the compound per day for a 70 kg patient, with dosages of from about 5 mg to about 500 mg of the compound per day for a 70 kg patient being more commonly used.

In prophylactic applications, pharmaceutical compositions containing compounds of the invention are administered to a patient susceptible to or otherwise at risk of developing disease, in an amount sufficient to delay or prevent the onset of the disease symptoms. Such an amount is defined to be a "prophylactically effective dose." In this use, the precise amounts of the compound again depend on the patient's state of health and weight, but generally range from about 0.1 mg to about 2,000 mg for a 70 kg patient per day, more commonly from about 5 mg to about 500 mg for a 70 kg patient per day.

Single or multiple administrations of the compositions can be carried out with dose levels and pattern being selected by the treating physician. In any event, the pharmaceutical formulations should provide a quantity of a compound of the invention sufficient to effectively treat or prevent disease in the patient.

The invention also provides kits for preventing or treating disease according to the use and method of the present invention. In one aspect, the invention includes kit for treating or preventing disease in a subject, wherein the kit comprises a compound of the invention or a salt, solvate, hydrate, or prodrug thereof. The kits typically include a pharmaceutical composition that contains an effective amount of a compound of the invention, as well as informational material containing instructions of how to dispense the pharmaceutical composition, including description of the type of patients who may be treated, the schedule (e.g., dose and frequency) and route of administration, and the like.

Some representative compounds of the invention are shown below.

The following compounds below Ia-Ir5 pertain to at least formula I:

Ia: $R_1=\alpha$-OH, $R_2$=H, $R_3$=OH, $R_4$=H, $R_5$=(S,R)Me, $R_6$=H
Ib: $R_1=\alpha$-OH, $R_2$=H, $R_3$=OH, $R_4$=H, $R_5$=(S)Me, $R_6$=H
Ic: $R_1=\alpha$-OH, $R_2$=H, $R_3$=OH, $R_4$=H, $R_5$=(R)Me, $R_6$=H
Id: $R_1=\beta$-OH, $R_2$=H, $R_3$=OH, $R_4$=H, $R_5$=(S,R)Me, $R_6$=H
Ie: $R_1=\beta$-OH, $R_2$=H, $R_3$=OH, $R_4$=H, $R_5$=(S)Me, $R_6$=H
If: $R_1=\beta$-OH, $R_2$=H, $R_3$=OH, $R_4$=H, $R_5$=(R)Me, $R_6$=H
Ig: $R_1=\alpha$-OH, $R_2=\alpha$-OH, $R_3$=OH, $R_4$=H, $R_5$=(S,R)Me, $R_6$=H
Ih: $R_1=\alpha$-OH, $R_2=\alpha$-OH, $R_3$=OH, $R_4$=H, $R_5$=(S)Me, $R_6$=H
Ii: $R_1=\alpha$-OH, $R_2=\alpha$-OH, $R_3$=OH, $R_4$=H, $R_5$=(R)Me, $R_6$=H
Il: $R_1=\beta$-OH, $R_2=\alpha$-OH, $R_3$=OH, $R_4$=H, $R_5$=(S,R)Me, $R_6$=H
Im: $R_1=\beta$-OH, $R_2=\alpha$-OH, $R_3$=OH, $R_4$=H, $R_5$=(S)Me, $R_6$=H
In: $R_1=\beta$-OH, $R_2=\alpha$-OH, $R_3$=OH, $R_4$=H, $R_5$=(R)Me, $R_6$=H
Io: $R_1$=H, $R_2$=H, $R_3$=OH, $R_4$=H, $R_5$=(S,R)Me, $R_6$=H
Ip: $R_1$=H, $R_2$=H, $R_3$=OH, $R_4$=H, $R_5$=(S)Me, $R_6$=H
Iq: $R_1$=H, $R_2$=H, $R_3$=OH, $R_4$=H, $R_5$=(R)Me, $R_6$=H
Ia1: $R_1=\alpha$-OH, $R_2$=H, $R_3$=NHCH$_2$CH$_2$SO$_3$H, $R_4$=H, $R_5$=(S,R)Me, $R_6$=H
Ib1: $R_1=\alpha$-OH, $R_2$=H, $R_3$=NHCH$_2$CH$_2$SO$_3$H, $R_4$=H, $R_5$=(S)Me, $R_6$=H
Ic1: $R_1=\alpha$-OH, $R_2$=H, $R_3$=NHCH$_2$CH$_2$SO$_3$H, $R_4$=H, $R_5$=(R)Me, $R_6$=H
Id1: $R_1=\beta$-OH, $R_2$=H, $R_3$=NHCH$_2$CH$_2$SO$_3$H, $R_4$=H, $R_5$=(S,R)Me, $R_6$=H
Ie1: $R_1=\beta$-OH, $R_2$=H, $R_3$=NHCH$_2$CH$_2$SO$_3$H, $R_4$=H, $R_5$=(S)Me, $R_6$=H
If1: $R_1=\beta$-OH, $R_2$=H, $R_3$=NHCH$_2$CH$_2$SO$_3$H, $R_4$=H, $R_5$=(R)Me, $R_6$=H
Ig1: $R_1=\alpha$-OH, $R_2=\alpha$-OH, $R_3$=NHCH$_2$CH$_2$SO$_3$H, $R_4$=H, $R_5$=(S,R)Me, $R_6$=H
Ih1: $R_1=\alpha$-OH, $R_2=\alpha$-OH, $R_3$=NHCH$_2$CH$_2$SO$_3$H, $R_4$=H, $R_5$=(S)Me, $R_6$=H
Ii1: $R_1=\alpha$-OH, $R_2=\alpha$-OH, $R_3$=NHCH$_2$CH$_2$SO$_3$H, $R_4$=H, $R_5$=(R)Me, $R_6$=H
Il1: $R_1=\beta$-OH, $R_2=\alpha$-OH, $R_3$=NHCH$_2$CH$_2$SO$_3$H, $R_4$=H, $R_5$=(S,R)Me, $R_6$=H
Im1: $R_1=\beta$-OH, $R_2=\alpha$-OH, $R_3$=NHCH$_2$CH$_2$SO$_3$H, $R_4$=H, $R_5$=(S)Me, $R_6$=H
In1: $R_1=\beta$-OH, $R_2=\alpha$-OH, $R_3$=NHCH$_2$CH$_2$SO$_3$H, $R_4$=H, $R_5$=(R)Me, $R_6$=H
Io1: $R_1$=H, $R_2$=H, $R_3$=NHCH$_2$CH$_2$SO$_3$H, $R_4$=H, $R_5$=(S,R)Me, $R_6$=H
Ip1: $R_1$=H, $R_2$=H, $R_3$=NHCH$_2$CH$_2$SO$_3$H, $R_4$=H, $R_5$=(S)Me, $R_6$=H
Iq1: $R_1$=H, $R_2$=H, $R_3$=NHCH$_2$CH$_2$SO$_3$H, $R_4$=H, $R_5$=(R)Me, $R_6$=H
Ia2: $R_1=\alpha$-OH, $R_2$=H, $R_3$=NHCH$_2$CO$_2$H, $R_4$=H, $R_5$=(S,R)Me, $R_6$=H
Ib2: $R_1=\alpha$-OH, $R_2$=H, $R_3$=NHCH$_2$CO$_2$H, $R_4$=H, $R_5$=(S)Me, $R_6$=H
Ic2: $R_1=\alpha$-OH, $R_2$=H, $R_3$=NHCH$_2$CO$_2$H, $R_4$=H, $R_5$=(R)Me, $R_6$=H
Id2: $R_1=\beta$-OH, $R_2$=H, $R_3$=NHCH$_2$CO$_2$H, $R_4$=H, $R_5$=(S,R)Me, $R_6$=H
Ie2: $R_1=\beta$-OH, $R_2$=H, $R_3$=NHCH$_2$CO$_2$H, $R_4$=H, $R_5$=(S)Me, $R_6$=H
If2: $R_1=\beta$-OH, $R_2$=H, $R_3$=NHCH$_2$CO$_2$H, $R_4$=H, $R_5$=(R)Me, $R_6$=H
Ig2: $R_1=\alpha$-OH, $R_2=\alpha$-OH, $R_3$=NHCH$_2$CO$_2$H, $R_4$=H, $R_5$=(S,R)Me, $R_6$=H
Ih2: $R_1=\alpha$-OH, $R_2=\alpha$-OH, $R_3$=NHCH$_2$CO$_2$H, $R_4$=H, $R_5$=(S)Me, $R_6$=H
Ii2: $R_1=\alpha$-OH, $R_2=\alpha$-OH, $R_3$=NHCH$_2$CO$_2$H, $R_4$=H, $R_5$=(R)Me, $R_6$=H
Il2: $R_1=\beta$-OH, $R_2=\alpha$-OH, $R_3$=NHCH$_2$CO$_2$H, $R_4$=H, $R_5$=(S,R)Me, $R_6$=H
Im2: $R_1=\beta$-OH, $R_2=\alpha$-OH, $R_3$=NHCH$_2$CO$_2$H, $R_4$=H, $R_5$=(S)Me, $R_6$=H In2: $R_1=\beta$-OH, $R_2=\alpha$-OH, $R_3=$NHCH$_2$CO$_2$H, $R_4=$H, $R_5=$(R)Me, $R_6=$H
Io2: $R_1=$H, $R_2=$H, $R_3=$NHCH$_2$CO$_2$H, $R_4=$H, $R_5=$(S,R)Me, $R_6=$H
Ip2: $R_1=$H, $R_2=$H, $R_3=$NHCH$_2$CO$_2$H, $R_4=$H, $R_5=$(S)Me, $R_6=$H
Iq2: $R_1=$H, $R_2=$H, $R_3=$NHCH$_2$CO$_2$H, $R_4=$H, $R_5=$(R)Me, $R_6=$H
Ia3: $R_1=\alpha$-OH, $R_2=$H, $R_3=$OH, $R_4=\alpha$-Me, $R_5=$(S,R)Me, $R_6=$H
Ib3: $R_1=\alpha$-OH, $R_2=$H, $R_3=$OH, $R_4=\alpha$-Me, $R_5=$(S)Me, $R_6=$H
Ic3: $R_1=\alpha$-OH, $R_2=$H, $R_3=$OH, $R_4=\alpha$-Me, $R_5=$(R)Me, $R_6=$H
Id3: $R_1=\beta$-OH, $R_2=$H, $R_3=$OH, $R_4=\alpha$-Me, $R_5=$(S,R)Me, $R_6=$H
Ie3: $R_1=\beta$-OH, $R_2=$H, $R_3=$OH, $R_4=\alpha$-Me, $R_5=$(S)Me, $R_6=$H
If3: $R_1=\beta$-OH, $R_2=$H, $R_3=$OH, $R_4=\alpha$-Me, $R_5=$(R)Me, $R_6=$H
Ig3: $R_1=\alpha$-OH, $R_2=\alpha$-OH, $R_3=$OH, $R_4=\alpha$-Me, $R_5=$(S,R)Me, $R_6=$H
Ih3: $R_1=\alpha$-OH, $R_2=\alpha$-OH, $R_3=$OH, $R_4=\alpha$-Me, $R_5=$(S)Me, $R_6=$H
Ii3: $R_1=\alpha$-OH, $R_2=\alpha$-OH, $R_3=$OH, $R_4=\alpha$-Me, $R_5=$(R)Me, $R_6=$H
Il3: $R_1=\beta$-OH, $R_2=\alpha$-OH, $R_3=$OH, $R_4=\alpha$-Me, $R_5=$(S,R)Me, $R_6=$H
Im3: $R_1=\beta$-OH, $R_2=\alpha$-OH, $R_3=$OH, $R_4=\alpha$-Me, $R_5=$(S)Me, $R_6=$H
In3: $R_1=\beta$-OH, $R_2=\alpha$-OH, $R_3=$OH, $R_4=\alpha$-Me, $R_5=$(R)Me, $R_6=$H
Ia4: $R_1=\alpha$-OH, $R_2=$H, $R_3=$NHCH$_2$CH$_2$SO$_3$H, $R_4=\alpha$-Me, $R_5=$(S,R)Me, $R_6=$H
Ib4: $R_1=\alpha$-OH, $R_2=$H, $R_3=$NHCH$_2$CH$_2$SO$_3$H, $R_4=\alpha$-Me, $R_5=$(S)Me, $R_6=$H
Ic4: $R_1=\alpha$-OH, $R_2=$H, $R_3=$NHCH$_2$CH$_2$SO$_3$H, $R_4=\alpha$-Me, $R_5=$(R)Me, $R_6=$H
Id4: $R_1=\beta$-OH, $R_2=$H, $R_3=$NHCH$_2$CH$_2$SO$_3$H, $R_4=\alpha$-Me, $R_5=$(S,R)Me, $R_6=$H
Ie4: $R_1=\beta$-OH, $R_2=$H, $R_3=$NHCH$_2$CH$_2$SO$_3$H, $R_4=\alpha$-Me, $R_5=$(S)Me, $R_6=$H
If4: $R_1=\beta$-OH, $R_2=$H, $R_3=$NHCH$_2$CH$_2$SO$_3$H, $R_4=\alpha$-Me, $R_5=$(R)Me, $R_6=$H
Ig4: $R_1=\alpha$-OH, $R_2=\alpha$-OH, $R_3=$NHCH$_2$CH$_2$SO$_3$H, $R_4=\alpha$-Me, $R_5=$(S,R)Me, $R_6=$H
Ih4: $R_1=\alpha$-OH, $R_2=\alpha$-OH, $R_3=$NHCH$_2$CH$_2$SO$_3$H, $R_4=\alpha$-Me, $R_5=$(S)Me, $R_6=$H
Ii4: $R_1=\alpha$-OH, $R_2=\alpha$-OH, $R_3=$NHCH$_2$CH$_2$SO$_3$H, $R_4=\alpha$-Me, $R_5=$(R)Me, $R_6=$H
Il4: $R_1=\beta$-OH, $R_2=\alpha$-OH, $R_3=$NHCH$_2$CH$_2$SO$_3$H, $R_4=\alpha$-Me, $R_5=$(S,R)Me, $R_6=$H
Im4: $R_1=\beta$-OH, $R_2=\alpha$-OH, $R_3=$NHCH$_2$CH$_2$SO$_3$H, $R_4=\alpha$-Me, $R_5=$(S)Me, $R_6=$H
In4: $R_1=\beta$-OH, $R_2=\alpha$-OH, $R_3=$NHCH$_2$CH$_2$SO$_3$H, $R_4=\alpha$-Me, $R_5=$(R)Me, $R_6=$H
Ia5: $R_1=\alpha$-OH, $R_2=$H, $R_3=$NHCH$_2$CO$_2$H, $R_4=\alpha$-Me, $R_5=$(S,R)Me, $R_6=$H
Ib5: $R_1=\alpha$-OH, $R_2=$H, $R_3=$NHCH$_2$CO$_2$H, $R_4=\alpha$-Me, $R_5=$(S)Me, $R_6=$H
Ic5: $R_1=\alpha$-OH, $R_2=$H, $R_3=$NHCH$_2$CO$_2$H, $R_4=\alpha$-Me, $R_5=$(R)Me, $R_6=$H
Id5: $R_1=\beta$-OH, $R_2=$H, $R_3=$NHCH$_2$CO$_2$H, $R_4=\alpha$-Me, $R_5=$(S,R)Me, $R_6=$H
Ie5: $R_1=\beta$-OH, $R_2=$H, $R_3=$NHCH$_2$CO$_2$H, $R_4=\alpha$-Me, $R_5=$(S)Me, $R_6=$H
If5: $R_1=\beta$-OH, $R_2=$H, $R_3=$NHCH$_2$CO$_2$H, $R_4=\alpha$-Me, $R_5=$(R)Me, $R_6=$H
Ig5: $R_1=\alpha$-OH, $R_2=\alpha$-OH, $R_3=$NHCH$_2$CO$_2$H, $R_4=\alpha$-Me, $R_5=$(S,R)Me, $R_6=$H
Ih5: $R_1=\alpha$-OH, $R_2=\alpha$-OH, $R_3=$NHCH$_2$CO$_2$H, $R_4=\alpha$-Me, $R_5=$(S)Me, $R_6=$H
Ii5: $R_1=\alpha$-OH, $R_2=\alpha$-OH, $R_3=$NHCH$_2$CO$_2$H, $R_4=\alpha$-Me, $R_5=$(R)Me, $R_6=$H
Il5: $R_1=\beta$-OH, $R_2=\alpha$-OH, $R_3=$NHCH$_2$CO$_2$H, $R_4=\alpha$-Me, $R_5=$(S,R)Me, $R_6=$H
Im5: $R_1=\beta$-OH, $R_2=\alpha$-OH, $R_3=$NHCH$_2$CO$_2$H, $R_4=\alpha$-Me, $R_5=$(S)Me, $R_6=$H
In5: $R_1=\beta$-OH, $R_2=\alpha$-OH, $R_3=$NHCH$_2$CO$_2$H, $R_4=\alpha$-Me, $R_5=$(R)Me, $R_6=$H
Ib3e: $R_1=\alpha$-OH, $R_2=$H, $R_3=$OH, $R_4=\alpha$-Et, $R_5=$(S)Me, $R_6=$H
Ic3e: $R_1=\alpha$-OH, $R_2=$H, $R_3=$OH, $R_4=\alpha$-Et, $R_5=$(R)Me, $R_6=$H
Id3e: $R_1=\beta$-OH, $R_2=$H, $R_3=$OH, $R_4=\alpha$-Et, $R_5=$(S,R)Me, $R_6=$H
Ie3e: $R_1=\beta$-OH, $R_2=$H, $R_3=$OH, $R_4=\alpha$-Et, $R_5=$(S)Me, $R_6=$H
If3e: $R_1=\beta$-OH, $R_2=$H, $R_3=$OH, $R_4=\alpha$-Et, $R_5=$(R)Me, $R_6=$H
Ig3e: $R_1=\alpha$-OH, $R_2=\alpha$-OH, $R_3=$OH, $R_4=\alpha$-Et, $R_5=$(S,R)Me, $R_6=$H
Ih3e: $R_1=\alpha$-OH, $R_2=\alpha$-OH, $R_3=$OH, $R_4=\alpha$-Et, $R_5=$(S)Me, $R_6=$H
Ii3e: $R_1=\alpha$-OH, $R_2=\alpha$-OH, $R_3=$OH, $R_4=\alpha$-Et, $R_5=$(R)Me, $R_6=$H
Il3e: $R_1=\beta$-OH, $R_2=\alpha$-OH, $R_3=$OH, $R_4=\alpha$-Et, $R_5=$(S,R)Me, $R_6=$H
Im3e: $R_1=\beta$-OH, $R_2=\alpha$-OH, $R_3=$OH, $R_4=\alpha$-Et, $R_5=$(S)Me, $R_6=$H
In3e: $R_1=\beta$-OH, $R_2=\alpha$-OH, $R_3=$OH, $R_4=\alpha$-Et, $R_5=$(R)Me, $R_6=$H
Ia4e: $R_1=\alpha$-OH, $R_2=$H, $R_3=$NHCH$_2$CH$_2$SO$_3$H, $R_4=\alpha$-Et, $R_5=$(S,R)Me, $R_6=$H
Ib4e: $R_1=\alpha$-OH, $R_2=$H, $R_3=$NHCH$_2$CH$_2$SO$_3$H, $R_4=\alpha$-Et, $R_5=$(S)Me, $R_6=$H
Ic4e: $R_1=\alpha$-OH, $R_2=$H, $R_3=$NHCH$_2$CH$_2$SO$_3$H, $R_4=\alpha$-Et, $R_5=$(R)Me, $R_6=$H
Id4e: $R_1=\beta$-OH, $R_2=$H, $R_3=$NHCH$_2$CH$_2$SO$_3$H, $R_4=\alpha$-Et, $R_5=$(S,R)Me, $R_6=$H
Ie4e: $R_1=\beta$-OH, $R_2=$H, $R_3=$NHCH$_2$CH$_2$SO$_3$H, $R_4=\alpha$-Et, $R_5=$(S)Me, $R_6=$H
If4e: $R_1=\beta$-OH, $R_2=$H, $R_3=$NHCH$_2$CH$_2$SO$_3$H, $R_4=\alpha$-Et, $R_5=$(R)Me, $R_6=$H
Ig4e: $R_1=\alpha$-OH, $R_2=\alpha$-OH, $R_3=$NHCH$_2$CH$_2$SO$_3$H, $R_4=\alpha$-Et, $R_5=$(S,R)Me, $R_6=$H
Ih4e: $R_1=\alpha$-OH, $R_2=\alpha$-OH, $R_3=$NHCH$_2$CH$_2$SO$_3$H, $R_4=\alpha$-Et, $R_5=$(S)Me, $R_6=$H
Ii4e: $R_1=\alpha$-OH, $R_2=\alpha$-OH, $R_3=$NHCH$_2$CH$_2$SO$_3$H, $R_4=\alpha$-Et, $R_5=$(R)Me, $R_6=$H
Il4e: $R_1=\beta$-OH, $R_2=\alpha$-OH, $R_3=$NHCH$_2$CH$_2$SO$_3$H, $R_4=\alpha$-Et, $R_5=$(S,R)Me, $R_6=$H
Im4e: $R_1=\beta$-OH, $R_2=\alpha$-OH, $R_3=$NHCH$_2$CH$_2$SO$_3$H, $R_4=\alpha$-Et, $R_5=$(S)Me, $R_6=$H
In4e: $R_1=\beta$-OH, $R_2=\alpha$-OH, $R_3=$NHCH$_2$CH$_2$SO$_3$H, $R_4=\alpha$-Et, $R_5=$(R)Me, $R_6=$H
Ia5e: $R_1=\alpha$-OH, $R_2=$H, $R_3=$NHCH$_2$CO$_2$H, $R_4=\alpha$-Et, $R_5=$(S,R)Me, $R_6=$H
Ib5e: $R_1=\alpha$-OH, $R_2=$H, $R_3=$NHCH$_2$CO$_2$H, $R_4=\alpha$-Et, $R_5=$(S)Me, $R_6=$H
Ic5e: $R_1=\alpha$-OH, $R_2=$H, $R_3=$NHCH$_2$CO$_2$H, $R_4=\alpha$-Et, $R_5=$(R)Me, $R_6=$H Id5e: $R_1=\beta$-OH, $R_2$=H, $R_3$=NHCH$_2$CO$_2$H, $R_4$=$\alpha$-Et, $R_5$=(S,R)Me, $R_6$=H
Ie5e: $R_1=\beta$-OH, $R_2$=H, $R_3$=NHCH$_2$CO$_2$H, $R_4$=$\alpha$-Et, $R_5$=(S)Me, $R_6$=H
If5e: $R_1=\beta$-OH, $R_2$=H, $R_3$=NHCH$_2$CO$_2$H, $R_4$=$\alpha$-Et, $R_5$=(R)Me, $R_6$=H
Ig5e: $R_1=\alpha$-OH, $R_2=\alpha$-OH, $R_3$=NHCH$_2$CO$_2$H, $R_4$=$\alpha$-Et, $R_5$=(S,R)Me, $R_6$=H
Ih5e: $R_1=\alpha$-OH, $R_2=\alpha$-OH, $R_3$=NHCH$_2$CO$_2$H, $R_4$=$\alpha$-Et, $R_5$=(S)Me, $R_6$=H
Ii5e: $R_1=\alpha$-OH, $R_2=\alpha$-OH, $R_3$=NHCH$_2$CO$_2$H, $R_4$=$\alpha$-Et, $R_5$=(R)Me, $R_6$=H
Il5e: $R_1=\beta$-OH, $R_2=\alpha$-OH, $R_3$=NHCH$_2$CO$_2$H, $R_4$=$\alpha$-Et, $R_5$=(S,R)Me, $R_6$=H
Im5e: $R_1=\beta$-OH, $R_2=\alpha$-OH, $R_3$=NHCH$_2$CO$_2$H, $R_4$=$\alpha$-Et, $R_5$=(S)Me, $R_6$=H
In5e: $R_1=\beta$-OH, $R_2=\alpha$-OH, $R_3$=NHCH$_2$CO$_2$H, $R_4$=$\alpha$-Et, $R_5$=(R)Me, $R_6$=H

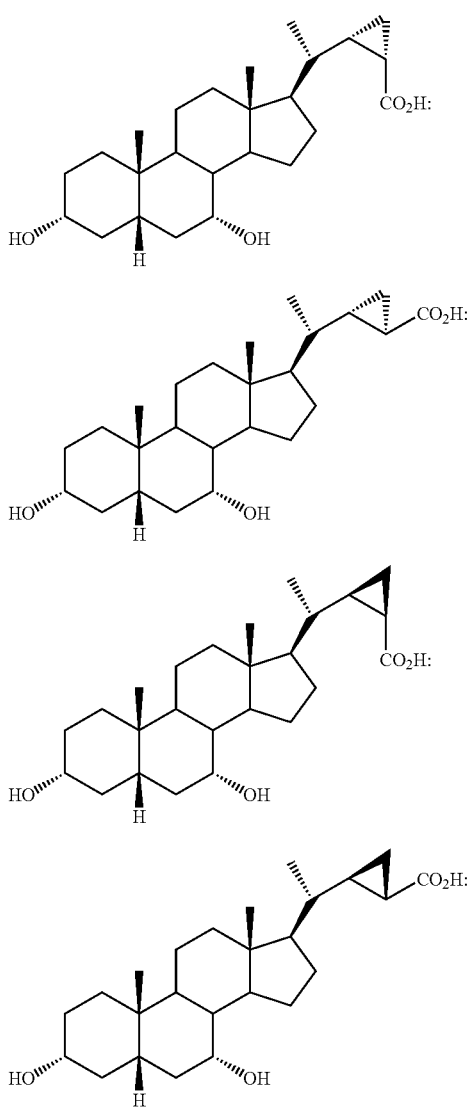

Io5

Ip5

Iq5

Ir5

The following compounds In6-In11e pertain to at least formula IA:

Ia6: $R_1$=OH, $R_2$=H, $R_3$=OH, $R_4$=H, $R_5$=(S,R)Me, $R_6$=H, $R_7$=Me
Ib6: $R_1$=OH, $R_2$=H, $R_3$=OH, $R_4$=H, $R_5$=(S)Me, $R_6$=H, $R_2$=Me
Ic6: $R_1$=OH, $R_2$=H, $R_3$=OH, $R_4$=H, $R_5$=(R)Me, $R_6$=H, $R_2$=Me
Id6: $R_1$=Me, $R_2$=H, $R_3$=OH, $R_4$=H, $R_5$=(S,R)Me, $R_6$=H, $R_7$=OH
Ie6: $R_1$=Me, $R_2$=H, $R_3$=OH, $R_4$=H, $R_5$=(S)Me, $R_6$=H, $R_7$=OH
If6: $R_1$=Me $R_2$=H, $R_3$=OH, $R_4$=H, $R_5$=(R)Me, $R_6$=H, $R_7$=OH
Ig6: $R_1$=OH, $R_2=\alpha$-OH, $R_3$=OH, $R_4$=H, $R_5$=(S,R)Me, $R_6$=H, $R_2$=Me
Ih6: $R_1$=OH, $R_2=\alpha$-OH, $R_3$=OH, $R_4$=H, $R_5$=(S)Me, $R_6$=H, $R_2$=Me
Ii6: $R_1$=OH, $R_2=\alpha$-OH, $R_3$=OH, $R_4$=H, $R_5$=(R)Me, $R_6$=H, $R_2$=Me
Il6: $R_1$=Me, $R_2=\alpha$-OH, $R_3$=OH, $R_4$=H, $R_5$=(S,R)Me, $R_6$=H, $R_7$=OH
Im6: $R_1$=Me, $R_2=\alpha$-OH, $R_3$=OH, $R_4$=H, $R_5$=(S)Me, $R_6$=H, $R_7$=OH
In6: $R_1$=Me, $R_2=\alpha$-OH, $R_3$=OH, $R_4$=H, $R_5$=(R)Me, $R_6$=H, $R_7$=OH
Io6: $R_1$=H, $R_2$=H, $R_3$=OH, $R_4$=H, $R_5$=(S,R)Me, $R_6$=H, $R_2$=Me
Ip6: $R_1$=H, $R_2$=H, $R_3$=OH, $R_4$=H, $R_5$=(S)Me, $R_6$=H, $R_2$=Me
Iq6: $R_1$=H, $R_2$=H, $R_3$=OH, $R_4$=H, $R_5$=(R)Me, $R_6$=H, $R_2$=Me
Ia7: $R_1$=OH, $R_2$=H, $R_3$=NHCH$_2$CH$_2$SO$_3$H, $R_4$=H, $R_5$=(S,R)Me, $R_6$=H, $R_2$=Me
Ib7: $R_1$=OH, $R_2$=H, $R_3$=NHCH$_2$CH$_2$SO$_3$H, $R_4$=H, $R_5$=(S)Me, $R_6$=H, $R_2$=Me
Ic7: $R_1$=OH, $R_2$=H, $R_3$=NHCH$_2$CH$_2$SO$_3$H, $R_4$=H, $R_5$=(R)Me, $R_6$=H, $R_2$=Me
Id7: $R_1$=Me, $R_2$=H, $R_3$=NHCH$_2$CH$_2$SO$_3$H, $R_4$=H, $R_5$=(S,R)Me, $R_6$=H, $R_7$=OH
Ie7: $R_1$=Me, $R_2$=H, $R_3$=NHCH$_2$CH$_2$SO$_3$H, $R_4$=H, $R_5$=(S)Me, $R_6$=H, $R_7$=OH
If7: $R_1$=Me, $R_2$=H, $R_3$=NHCH$_2$CH$_2$SO$_3$H, $R_4$=H, $R_5$=(R)Me, $R_6$=H, $R_7$=OH
Ig7: $R_1$=OH, $R_2=\alpha$-OH, $R_3$=NHCH$_2$CH$_2$SO$_3$H, $R_4$=H, $R_5$=(S,R)Me, $R_6$=H, $R_2$=Me
Ih7: $R_1$=OH, $R_2=\alpha$-OH, $R_3$=NHCH$_2$CH$_2$SO$_3$H, $R_4$=H, $R_5$=(S)Me, $R_6$=H, $R_2$=Me
Ii7: $R_1$=OH, $R_2=\alpha$-OH, $R_3$=NHCH$_2$CH$_2$SO$_3$H, $R_4$=H, $R_5$=(R)Me, $R_6$=H, $R_2$=Me
Il7: $R_1$=Me, $R_2=\alpha$-OH, $R_3$=NHCH$_2$CH$_2$SO$_3$H, $R_4$=H, $R_5$=(S,R)Me, $R_6$=H, $R_7$=OH
Im7: $R_1$=Me, $R_2=\alpha$-OH, $R_3$=NHCH$_2$CH$_2$SO$_3$H, $R_4$=H, $R_5$=(S)Me, $R_6$=H, $R_7$=OH
In7: $R_1$=Me, $R_2=\alpha$-OH, $R_3$=NHCH$_2$CH$_2$SO$_3$H, $R_4$=H, $R_5$=(R)Me, $R_6$=H, $R_7$=OH
Io7: $R_1$=H, $R_2$=H, $R_3$=NHCH$_2$CH$_2$SO$_3$H, $R_4$=H, $R_5$=(S,R)Me, $R_6$=H, $R_7$=Me
Ip7: $R_1$=H, $R_2$=H, $R_3$=NHCH$_2$CH$_2$SO$_3$H, $R_4$=H, $R_5$=(S)Me, $R_6$=H, $R_7$=Me
Iq7: $R_1$=H, $R_2$=H, $R_3$=NHCH$_2$CH$_2$SO$_3$H, $R_4$=H, $R_5$=(R)Me, $R_6$=H, $R_7$=Me
Ia8: $R_1$=OH, $R_2$=H, $R_3$=NHCH$_2$CO$_2$H, $R_4$=H, $R_5$=(S,R)Me, $R_6$=H, $R_7$=Me
Ib8: $R_1$=OH, $R_2$=H, $R_3$=NHCH$_2$CO$_2$H, $R_4$=H, $R_5$=(S)Me, $R_6$=H, $R_7$=Me
Ic8: $R_1$=OH, $R_2$=H, $R_3$=NHCH$_2$CO$_2$H, $R_4$=H, $R_5$=(R)Me, $R_6$=H, $R_7$=Me
Id8: $R_1$=Me, $R_2$=H, $R_3$=NHCH$_2$CO$_2$H, $R_4$=H, $R_5$=(S,R)Me, $R_6$=H, $R_7$=OH Ie8: $R_1$=Me, $R_2$=H, $R_3$=NHCH$_2$CO$_2$H, $R_4$=H, $R_5$=(S)Me, $R_6$=H, $R_7$=OH
If8: $R_1$=Me, $R_2$=H, $R_3$=NHCH$_2$CO$_2$H, $R_4$=H, $R_5$=(R)Me, $R_6$=H, $R_7$=OH
Ig8: $R_1$=OH, $R_2$=α-OH, $R_3$=NHCH$_2$CO$_2$H, $R_4$=H, $R_5$=(S,R)Me, $R_6$=H, $R_7$=Me
Ih8: $R_1$=OH, $R_2$=α-OH, $R_3$=NHCH$_2$CO$_2$H, $R_4$=H, $R_5$=(S)Me, $R_6$=H, $R_7$=Me
Ii8: $R_1$=OH, $R_2$=α-OH, $R_3$=NHCH$_2$CO$_2$H, $R_4$=H, $R_5$=(R)Me, $R_6$=H, $R_7$=Me
Il8: $R_1$=Me, $R_2$=α-OH, $R_3$=NHCH$_2$CO$_2$H, $R_4$=H, $R_5$=(S,R)Me, $R_6$=H, $R_7$=OH
Im8: $R_1$=Me, $R_2$=α-OH, $R_3$=NHCH$_2$CO$_2$H, $R_4$=H, $R_5$=(S)Me, $R_6$=H, $R_7$=OH
In8: $R_1$=Me, $R_2$=α-OH, $R_3$=NHCH$_2$CO$_2$H, $R_4$=H, $R_5$=(R)Me, $R_6$=H, $R_7$=OH
Io8: $R_1$=H, $R_2$=H, $R_3$=NHCH$_2$CO$_2$H, $R_4$=H, $R_5$=(S,R)Me, $R_6$=H, $R_7$=Me
Ip8: $R_1$=H, $R_2$=H, $R_3$=NHCH$_2$CO$_2$H, $R_4$=H, $R_5$=(S)Me, $R_6$=H, $R_7$=Me
Iq8: $R_1$=H, $R_2$=H, $R_3$=NHCH$_2$CO$_2$H, $R_4$=H, $R_5$=(R)Me, $R_6$=H, $R_7$=Me
Ia9: $R_1$=OH, $R_2$=H, $R_3$=OH, $R_4$=α-Me, $R_5$=(S,R)Me, $R_6$=H, $R_7$=Me
Ib9: $R_1$=OH, $R_2$=H, $R_3$=OH, $R_4$=α-Me, $R_5$=(S)Me, $R_6$=H, $R_7$=Me
Ic9: $R_1$=OH, $R_2$=H, $R_3$=OH, $R_4$=α-Me, $R_5$=(R)Me, $R_6$=H, $R_7$=Me
Id9: $R_1$=Me, $R_2$=H, $R_3$=OH, $R_4$=α-Me, $R_5$=(S,R)Me, $R_6$=H, $R_7$=OH
Ie9: $R_1$=Me, $R_2$=H, $R_3$=OH, $R_4$=α-Me, $R_5$=(S)Me, $R_6$=H, $R_7$=OH
If9: $R_1$=Me, $R_2$=H, $R_3$=OH, $R_4$=α-Me, $R_5$=(R)Me, $R_6$=H, $R_7$=OH
Ig9: $R_1$=OH, $R_2$=α-OH, $R_3$=OH, $R_4$=α-Me, $R_5$=(S,R)Me, $R_6$=H, $R_7$=Me
Ih9: $R_1$=OH, $R_2$=α-OH, $R_3$=OH, $R_4$=α-Me, $R_5$=(S)Me, $R_6$=H, $R_7$=Me
Ii9: $R_1$=OH, $R_2$=α-OH, $R_3$=OH, $R_4$=α-Me, $R_5$=(R)Me, $R_6$=H, $R_7$=Me
Il9: $R_1$=Me, $R_2$=α-OH, $R_3$=OH, $R_4$=α-Me, $R_5$=(S,R)Me, $R_6$=H, $R_7$=OH
Im9: $R_1$=Me, $R_2$=α-OH, $R_3$=OH, $R_4$=α-Me, $R_5$=(S)Me, $R_6$=H, $R_7$=OH
In9: $R_1$=Me, $R_2$=α-OH, $R_3$=OH, $R_4$=α-Me, $R_5$=(R)Me, $R_6$=H, $R_7$=OH
Ia10: $R_1$=OH, $R_2$=H, $R_3$=NHCH$_2$CH$_2$SO$_3$H, $R_4$=α-Me, $R_5$=(S,R)Me, $R_6$=H, $R_7$=Me
Ib10: $R_1$=OH, $R_2$=H, $R_3$=NHCH$_2$CH$_2$SO$_3$H, $R_4$=α-Me, $R_5$=(S)Me, $R_6$=H, $R_7$=Me
Ic10: $R_1$=OH, $R_2$=H, $R_3$=NHCH$_2$CH$_2$SO$_3$H, $R_4$=α-Me, $R_5$=(R)Me, $R_6$=H, $R_7$=Me
Id10: $R_1$=Me, $R_2$=H, $R_3$=NHCH$_2$CH$_2$SO$_3$H, $R_4$=α-Me, $R_5$=(S,R)Me, $R_6$=H, $R_7$=OH
Ie10: $R_1$=Me, $R_2$=H, $R_3$=NHCH$_2$CH$_2$SO$_3$H, $R_4$=α-Me, $R_5$=(S)Me, $R_6$=H, $R_7$=OH
If10: $R_1$=Me, $R_2$=H, $R_3$=NHCH$_2$CH$_2$SO$_3$H, $R_4$=α-Me, $R_5$=(R)Me, $R_6$=H, $R_7$=OH
Ig10: $R_1$=OH, $R_2$=α-OH, $R_3$=NHCH$_2$CH$_2$SO$_3$H, $R_4$=α-Me, $R_5$=(S,R)Me, $R_6$=H, $R_7$=Me
Ih10: $R_1$=OH, $R_2$=α-OH, $R_3$=NHCH$_2$CH$_2$SO$_3$H, $R_4$=α-Me, $R_5$=(S)Me, $R_6$=H, $R_7$=Me
Ii10: $R_1$=OH, $R_2$=α-OH, $R_3$=NHCH$_2$CH$_2$SO$_3$H, $R_4$=α-Me, $R_5$=(R)Me, $R_6$=H, $R_7$=Me
Il10: $R_1$=Me, $R_2$=α-OH, $R_3$=NHCH$_2$CH$_2$SO$_3$H, $R_4$=α-Me, $R_5$=(S,R)Me, $R_6$=H, $R_7$=OH
Im10: $R_1$=Me, $R_2$=α-OH, $R_3$=NHCH$_2$CH$_2$SO$_3$H, $R_4$=α-Me, $R_5$=(S)Me, $R_6$=H, $R_7$=OH
In10: $R_1$=Me, $R_2$=α-OH, $R_3$=NHCH$_2$CH$_2$SO$_3$H, $R_4$=α-Me, $R_5$=(R)Me, $R_6$=H, $R_7$=OH
Ia11: $R_1$=OH, $R_2$=H, $R_3$=NHCH$_2$CO$_2$H, $R_4$=α-Me, $R_5$=(S,R)Me, $R_6$=H, $R_7$=Me
Ib11: $R_1$=OH, $R_2$=H, $R_3$=NHCH$_2$CO$_2$H, $R_4$=α-Me, $R_5$=(S)Me, $R_6$=H, $R_7$=Me
Ic11: $R_1$=OH, $R_2$=H, $R_3$=NHCH$_2$CO$_2$H, $R_4$=α-Me, $R_5$=(R)Me, $R_6$=H, $R_7$=Me
Id11: $R_1$=Me, $R_2$=H, $R_3$=NHCH$_2$CO$_2$H, $R_4$=α-Me, $R_5$=(S,R)Me, $R_6$=H, $R_7$=OH
Ie11: $R_1$=Me, $R_2$=H, $R_3$=NHCH$_2$CO$_2$H, $R_4$=α-Me, $R_5$=(S)Me, $R_6$=H, $R_7$=OH
If11: $R_1$=Me, $R_2$=H, $R_3$=NHCH$_2$CO$_2$H, $R_4$=α-Me, $R_5$=(R)Me, $R_6$=H, $R_7$=OH
Ig11: $R_1$=OH, $R_2$=α-OH, $R_3$=NHCH$_2$CO$_2$H, $R_4$=α-Me, $R_5$=(S,R)Me, $R_6$=H, $R_7$=Me
Ih11: $R_1$=OH, $R_2$=α-OH, $R_3$=NHCH$_2$CO$_2$H, $R_4$=α-Me, $R_5$=(S)Me, $R_6$=H, $R_7$=Me
Ii11: $R_1$=OH, $R_2$=α-OH, $R_3$=NHCH$_2$CO$_2$H, $R_4$=α-Me, $R_5$=(R)Me, $R_6$=H, $R_7$=Me
Il11: $R_1$=Me, $R_2$=α-OH, $R_3$=NHCH$_2$CO$_2$H, $R_4$=α-Me, $R_5$=(S,R)Me, $R_6$=H, $R_7$=OH
Im11: $R_1$=Me, $R_2$=α-OH, $R_3$=NHCH$_2$CO$_2$H, $R_4$=α-Me, $R_5$=(S)Me, $R_6$=H, $R_7$=OH
In11: $R_1$=Me, $R_2$=α-OH, $R_3$=NHCH$_2$CO$_2$H, $R_4$=α-Me, $R_5$=(R)Me, $R_6$=H, $R_7$=OH
Ia9e: $R_1$=OH, $R_2$=H, $R_3$=OH, $R_4$=α-Et, $R_5$=(S,R)Me, $R_6$=H, $R_7$=Me
Ib9e: $R_1$=OH, $R_2$=H, $R_3$=OH, $R_4$=α-Et, $R_5$=(S)Me, $R_6$=H, $R_7$=Me
Ic9e: $R_1$=OH, $R_2$=H, $R_3$=OH, $R_4$=α-Et, $R_5$=(R)Me, $R_6$=H, $R_7$=Me
Id9e: $R_1$=Me, $R_2$=H, $R_3$=OH, $R_4$=α-Et, $R_5$=(S,R)Me, $R_6$=H, $R_7$=OH
Ie9e: $R_1$=Me, $R_2$=H, $R_3$=OH, $R_4$=α-Et, $R_5$=(S)Me, $R_6$=H, $R_7$=OH
If9e: $R_1$=Me, $R_2$=H, $R_3$=OH, $R_4$=α-Et, $R_5$=(R)Me, $R_6$=H, $R_7$=OH
Ig9e: $R_1$=OH, $R_2$=α-OH, $R_3$=OH, $R_4$=α-Et, $R_5$=(S,R)Me, $R_6$=H, $R_7$=Me
Ih9e: $R_1$=OH, $R_2$=α-OH, $R_3$=OH, $R_4$=α-Et, $R_5$=(S)Me, $R_6$=H, $R_7$=Me
Ii9e: $R_1$=OH, $R_2$=α-OH, $R_3$=OH, $R_4$=α-Et, $R_5$=(R)Me, $R_6$=H, $R_7$=Me
Il9e: $R_1$=Me, $R_2$=α-OH, $R_3$=OH, $R_4$=α-Et, $R_5$=(S,R)Me, $R_6$=H, $R_7$=OH
Im9e: $R_1$=Me, $R_2$=α-OH, $R_3$=OH, $R_4$=α-Et, $R_5$=(S)Me, $R_6$=H, $R_7$=OH
In9e: $R_1$=Me, $R_2$=α-OH, $R_3$=OH, $R_4$=α-Et, $R_5$=(R)Me, $R_6$=H, $R_7$=OH
Ia10e: $R_1$=OH, $R_2$=H, $R_3$=NHCH$_2$CH$_2$SO$_3$H, $R_4$=α-Et, $R_5$=(S,R)Me, $R_6$=H, $R_7$=Me
Ib10e: $R_1$=OH, $R_2$=H, $R_3$=NHCH$_2$CH$_2$SO$_3$H, $R_4$=α-Et, $R_5$=(S)Me, $R_6$=H, $R_7$=Me
Ic10e: $R_1$=OH, $R_2$=H, $R_3$=NHCH$_2$CH$_2$SO$_3$H, $R_4$=α-Et, $R_5$=(R)Me, $R_6$=H, $R_7$=Me
Id10e: $R_1$=Me, $R_2$=H, $R_3$=NHCH$_2$CH$_2$SO$_3$H, $R_4$=α-Et, $R_5$=(S,R)Me, $R_6$=H, $R_7$=OH
Ie10e: $R_1$=Me, $R_2$=H, $R_3$=NHCH$_2$CH$_2$SO$_3$H, $R_4$=α-Et, $R_5$=(S)Me, $R_6$=H, $R_7$=OH
If10e: $R_1$=Me, $R_2$=H, $R_3$=NHCH$_2$CH$_2$SO$_3$H, $R_4$=α-Et, $R_5$=(R)Me, $R_6$=H, $R_7$=OH
Ig10e: $R_1$=OH, $R_2$=α-OH, $R_3$=NHCH$_2$CH$_2$SO$_3$H, $R_4$=α-Et, $R_5$=(S,R)Me, $R_6$=H, $R_7$=Me Ih10e: $R_1$=OH, $R_2$=α-OH, $R_3$=NHCH$_2$CH$_2$SO$_3$H, $R_4$=α-Et, $R_5$=(S)Me, $R_6$=H, $R_7$=Me
Ii10e: $R_1$=OH, $R_2$=α-OH, $R_3$=NHCH$_2$CH$_2$SO$_3$H, $R_4$=α-Et, $R_5$=(R)Me, $R_6$=H, $R_7$=Me
Il10e: $R_1$=Me, $R_2$=α-OH, $R_3$=NHCH$_2$CH$_2$SO$_3$H, $R_4$=α-Et, $R_5$=(S,R)Me, $R_6$=H, $R_7$=OH
Im10e: $R_1$=Me, $R_2$=α-OH, $R_3$=NHCH$_2$CH$_2$SO$_3$H, $R_4$=α-Et, $R_5$=(S)Me, $R_6$=H, $R_7$=OH
In10e: $R_1$=Me, $R_2$=α-OH, $R_3$=NHCH$_2$CH$_2$SO$_3$H, $R_4$=α-Et, $R_5$=(R)Me, $R_6$=H, $R_7$=OH
Ia11e: $R_1$=OH, $R_2$=H, $R_3$=NHCH$_2$CO$_2$H, $R_4$=α-Et, $R_5$=(S,R)Me, $R_6$=H, $R_7$=Me
Ib11e: $R_1$=OH, $R_2$=H, $R_3$=NHCH$_2$CO$_2$H, $R_4$=α-Et, $R_5$=(S)Me, $R_6$=H, $R_7$=Me
Ic11e: $R_1$=OH, $R_2$=H, $R_3$=NHCH$_2$CO$_2$H, $R_4$=α-Et, $R_5$=(R)Me, $R_6$=H, $R_7$=Me
Id11e: $R_1$=Me, $R_2$=H, $R_3$=NHCH$_2$CO$_2$H, $R_4$=α-Et, $R_5$=(S,R)Me, $R_6$=H, $R_7$=OH
Ie11e: $R_1$=Me, $R_2$=H, $R_3$=NHCH$_2$CO$_2$H, $R_4$=α-Et, $R_5$=(S)Me, $R_6$=H, $R_7$=OH
If11e: $R_1$=Me, $R_2$=H, $R_3$=NHCH$_2$CO$_2$H, $R_4$=α-Et, $R_5$=(R)Me, $R_6$=H, $R_7$=OH
Ig11e: $R_1$=OH, $R_2$=α-OH, $R_3$=NHCH$_2$CO$_2$H, $R_4$=α-Et, $R_5$=(S,R)Me, $R_6$=H, $R_7$=Me
Ih11e: $R_1$=OH, $R_2$=α-OH, $R_3$=NHCH$_2$CO$_2$H, $R_4$=α-Et, $R_5$=(S)Me, $R_6$=H, $R_7$=Me
Ii11e: $R_1$=OH, $R_2$=α-OH, $R_3$=NHCH$_2$CO$_2$H, $R_4$=α-Et, $R_5$=(R)Me, $R_6$=H, $R_7$=Me
Il11e: $R_1$=Me, $R_2$=α-OH, $R_3$=NHCH$_2$CO$_2$H, $R_4$=α-Et, $R_5$=(S,R)Me, $R_6$=H, $R_7$=OH
Im11e: $R_1$=Me, $R_2$=α-OH, $R_3$=NHCH$_2$CO$_2$H, $R_4$=α-Et, $R_5$=(S)Me, $R_6$=H, $R_7$=OH
In11e: $R_1$=Me, $R_2$=α-OH, $R_3$=NHCH$_2$CO$_2$H, $R_4$=α-Et, $R_5$=(R)Me, $R_6$=H, $R_7$=OH The following compounds Ia12-1 n17e pertain to at least formula II:

Ia12: $R_1$=OH, $R_2$=H, $R_4$=H, $R_5$=(S,R)Me, $R_6$=H, $R_7$=Me, $R_8$=H
Ib12: $R_1$=OH, $R_2$=H, $R_4$=H, $R_5$=(S)Me, $R_6$=H, $R_7$=Me, $R_5$=H
Ic12: $R_1$=OH, $R_2$=H, $R_4$=H, $R_5$=(R)Me, $R_6$=H, $R_7$=Me, $R_5$=H
Id12: $R_1$=Me, $R_2$=H, $R_4$=H, $R_5$=(S,R)Me, $R_6$=H, $R_7$=OH, $R_5$=H
Ie12: $R_1$=Me, $R_2$=H, $R_4$=H, $R_5$=(S)Me, $R_6$=H, $R_7$=OH, $R_5$=H
If12: $R_1$=Me, $R_2$=H, $R_4$=H, $R_5$=(R)Me, $R_6$=H, $R_7$=OH, $R_5$=H
Ig12: $R_1$=OH, $R_2$=α-OH, $R_4$=H, $R_5$=(S,R)Me, $R_6$=H, $R_7$=Me, $R_5$=H
Ih12: $R_1$=OH, $R_2$=α-OH, $R_4$=H, $R_5$=(S)Me, $R_6$=H, $R_7$=Me, $R_5$=H
Ii12: $R_1$=OH, $R_2$=α-OH, $R_4$=H, $R_5$=(R)Me, $R_6$=H, $R_7$=Me, $R_5$=H
Il12: $R_1$=Me, $R_2$=α-OH, $R_4$=H, $R_5$=(S,R)Me, $R_6$=H, $R_7$=OH, $R_5$=H
Im12: $R_1$=Me, $R_2$=α-OH, $R_4$=H, $R_5$=(S)Me, $R_6$=H, $R_7$=OH, $R_5$=H
In12: $R_1$=Me, $R_2$=α-OH, $R_4$=H, $R_5$=(R)Me, $R_6$=H, $R_7$=OH, $R_5$=H
Io12: $R_1$=H, $R_2$=H, $R_4$=H, $R_5$=(S,R)Me, $R_6$=H, $R_7$=Me, $R_5$=H
Ip12: $R_1$=H, $R_2$=H, $R_4$=H, $R_5$=(S)Me, $R_6$=H, $R_7$=Me, $R_5$=H
Iq12: $R_1$=H, $R_2$=H, $R_4$=H, $R_5$=(R)Me, $R_6$=H, $R_7$=Me, $R_5$=H

Ia13: $R_1$=OH, $R_2$=H, $R_4$=H, $R_5$=(S,R)Me, $R_6$=H, $R_7$=Me, $R_5$=H
Ib13: $R_1$=OH, $R_2$=H, $R_4$=H, $R_5$=(S)Me, $R_6$=H, $R_7$=Me, $R_5$=H
Ic13: $R_1$=OH, $R_2$=H, $R_4$=H, $R_5$=(R)Me, $R_6$=H, $R_7$=Me, $R_5$=H
Id13: $R_1$=Me, $R_2$=H, $R_4$=H, $R_5$=(S,R)Me, $R_6$=H, $R_7$=OH, $R_5$=H
Ie13: $R_1$=Me, $R_2$=H, $R_4$=H, $R_5$=(S)Me, $R_6$=H, $R_7$=OH, $R_5$=H
If13: $R_1$=Me, $R_2$=H, $R_4$=H, $R_5$=(R)Me, $R_6$=H, $R_7$=OH, $R_5$=H
Ig13: $R_1$=OH, $R_2$=α-OH, $R_4$=H, $R_5$=(S,R)Me, $R_6$=H, $R_7$=Me, $R_5$=H
Ih13: $R_1$=OH, $R_2$=α-OH, $R_4$=H, $R_5$=(S)Me, $R_6$=H, $R_7$=Me, $R_5$=H
Ii13: $R_1$=OH, $R_2$=α-OH, $R_4$=H, $R_5$=(R)Me, $R_6$=H, $R_7$=Me, $R_5$=H
Il13: $R_1$=Me, $R_2$=α-OH, $R_4$=H, $R_5$=(S,R)Me, $R_6$=H, $R_7$=OH, $R_5$=H
Im13: $R_1$=Me, $R_2$=α-OH, $R_4$=H, $R_5$=(S)Me, $R_6$=H, $R_7$=OH, $R_5$=H
In13: $R_1$=Me, $R_2$=α-OH, $R_4$=H, $R_5$=(R)Me, $R_6$=H, $R_7$=OH, $R_5$=H Io13: $R_1$=H, $R_2$=H, $R_4$=H, $R_5$=(S,R)Me, $R_6$=H, $R_7$=Me, $R_5$=H
Ip13: $R_1$=H, $R_2$=H, $R_4$=H, $R_5$=(S)Me, $R_6$=H, $R_7$=Me, $R_5$=H
Iq13: $R_1$=H, $R_2$=H, $R_4$=H, $R_5$=(R)Me, $R_6$=H, $R_7$=Me, $R_5$=H
Ia14: $R_1$=OH, $R_2$=H, $R_4$=H, $R_5$=(S,R)Me, $R_6$=H, $R_7$=Me, $R_5$=H
Ib14: $R_1$=OH, $R_2$=H, $R_4$=H, $R_5$=(S)Me, $R_6$=H, $R_7$=Me, $R_5$=H
Ic14: $R_1$=OH, $R_2$=H, $R_4$=H, $R_5$=(R)Me, $R_6$=H, $R_7$=Me, $R_5$=H
Id14: $R_1$=Me, $R_2$=H, $R_4$=H, $R_5$=(S,R)Me, $R_6$=H, $R_7$=OH, $R_8$=H
Ie14: $R_1$=Me, $R_2$=H, $R_4$=H, $R_5$=(S)Me, $R_6$=H, $R_7$=OH, $R_8$=H
If14: $R_1$=Me, $R_2$=H, $R_4$=H, $R_5$=(R)Me, $R_6$=H, $R_7$=OH, $R_8$=H
Ig14: $R_1$=OH, $R_2$=α-OH, $R_4$=H, $R_5$=(S,R)Me, $R_6$=H, $R_2$=Me, $R_8$=H
Ih14: $R_1$=OH, $R_2$=α-OH, $R_4$=H, $R_5$=(S)Me, $R_6$=H, $R_2$=Me, $R_8$=H
Ii14: $R_1$=OH, $R_2$=α-OH, $R_4$=H, $R_5$=(R)Me, $R_6$=H, $R_2$=Me, $R_8$=H
Il14: $R_1$=Me, $R_2$=α-OH, $R_4$=H, $R_5$=(S,R)Me, $R_6$=H, $R_7$=OH, $R_8$=H
Im14: $R_1$=Me, $R_2$=α-OH, $R_4$=H, $R_5$=(S)Me, $R_6$=H, $R_7$=OH, $R_8$=H
In14: $R_1$=Me, $R_2$=α-OH, $R_4$=H, $R_5$=(R)Me, $R_6$=H, $R_7$=OH, $R_8$=H
Io14: $R_1$=H, $R_2$=H, $R_4$=H, $R_5$=(S,R)Me, $R_6$=H, $R_2$=Me, $R_8$=H
Ip14: $R_1$=H, $R_2$=H, $R_4$=H, $R_5$=(S)Me, $R_6$=H, $R_2$=Me, $R_8$=H
Iq14: $R_1$=H, $R_2$=H, $R_4$=H, $R_5$=(R)Me, $R_6$=H, $R_2$=Me, $R_8$=H
Ia15: $R_1$=OH, $R_2$=H, $R_4$=α-Me, $R_5$=(S,R)Me, $R_6$=H, $R_2$=Me, $R_8$=H
Ib15: $R_1$=OH, $R_2$=H, $R_4$=α-Me, $R_5$=(S)Me, $R_6$=H, $R_2$=Me, $R_8$=H
Ic15: $R_1$=OH, $R_2$=H, $R_4$=α-Me, $R_5$=(R)Me, $R_6$=H, $R_2$=Me, $R_8$=H
Id15: $R_1$=Me, $R_2$=H, $R_4$=α-Me, $R_5$=(S,R)Me, $R_6$=H, $R_7$=OH, $R_8$=H

Ie15: $R_1$=Me, $R_2$=H, $R_4$=α-Me, $R_5$=(S)Me, $R_6$=H, $R_7$=OH, $R_8$=H
If15: $R_1$=Me, $R_2$=H, $R_4$=α-Me, $R_5$=(R)Me, $R_6$=H, $R_7$=OH, $R_8$=H
Ig15: $R_1$=OH, $R_2$=α-OH, $R_4$=α-Me, $R_5$=(S,R)Me, $R_6$=H, $R_7$=Me, $R_8$=H
Ih15: $R_1$=OH, $R_2$=α-OH, $R_4$=α-Me, $R_5$=(S)Me, $R_6$=H, $R_7$=Me, $R_8$=H
Ii15: $R_1$=OH, $R_2$=α-OH, $R_4$=α-Me, $R_5$=(R)Me, $R_6$=H, $R_7$=Me, $R_8$=H
Il15: $R_1$=Me, $R_2$=α-OH, $R_4$=α-Me, $R_5$=(S,R)Me, $R_6$=H, $R_7$=OH, $R_8$=H
Im15: $R_1$=Me, $R_2$=α-OH, $R_4$=α-Me, $R_5$=(S)Me, $R_6$=H, $R_7$=OH, $R_8$=H
In15: $R_1$=Me, $R_2$=α-OH, $R_4$=α-Me, $R_5$=(R)Me, $R_6$=H, $R_7$=OH, $R_8$=H
Ia16: $R_1$=OH, $R_2$=H, $R_4$=α-Me, $R_5$=(S,R)Me, $R_6$=H, $R_7$=Me, $R_8$=H
Ib16: $R_1$=OH, $R_2$=H, $R_4$=α-Me, $R_5$=(S)Me, $R_6$=H, $R_7$=Me, $R_8$=H
Ic16: $R_1$=OH, $R_2$=H, $R_4$=α-Me, $R_5$=(R)Me, $R_6$=H, $R_7$=Me, $R_8$=H
Id16: $R_1$=Me, $R_2$=H, $R_4$=α-Me, $R_5$=(S,R)Me, $R_6$=H, $R_7$=OH, $R_8$=H
Ie16: $R_1$=Me, $R_2$=H, $R_4$=α-Me, $R_5$=(S)Me, $R_6$=H, $R_7$=OH, $R_8$=H
If16 $R_1$=Me, $R_2$=H, $R_4$=α-Me, $R_5$=(R)Me, $R_6$=H, $R_7$=OH, $R_8$=H
Ig16: $R_1$=OH, $R_2$=α-OH, $R_4$=α-Me, $R_5$=(S,R)Me, $R_6$=H, $R_7$=Me, $R_8$=H
Ih16: $R_1$=OH, $R_2$=α-OH, $R_4$=α-Me, $R_5$=(S)Me, $R_6$=H, $R_7$=Me, $R_8$=H
Ii16: $R_1$=OH, $R_2$=α-OH, $R_4$=α-Me, $R_5$=(R)Me, $R_6$=H, $R_7$=Me, $R_8$=H
Il16: $R_1$=Me, $R_2$=α-OH, $R_4$=α-Me, $R_5$=(S,R)Me, $R_6$=H, $R_7$=OH, $R_8$=H
Im16: $R_1$=Me, $R_2$=α-OH, $R_4$=α-Me, $R_5$=(S)Me, $R_6$=H, $R_7$=OH, $R_8$=H
In16: $R_1$=Me, $R_2$=α-OH, $R_4$=α-Me, $R_5$=(R)Me, $R_6$=H, $R_7$=OH, $R_8$=H
Ia17: $R_1$=OH, $R_2$=H, $R_4$=α-Me, $R_5$=(S,R)Me, $R_6$=H, $R_7$=Me, $R_8$=H
Ib17: $R_1$=OH, $R_2$=H, $R_4$=α-Me, $R_5$=(S)Me, $R_6$=H, $R_7$=Me, $R_8$=H
Ic17: $R_1$=OH, $R_2$=H, $R_4$=α-Me, $R_5$=(R)Me, $R_6$=H, $R_7$=Me, $R_8$=H
Id17: $R_1$=Me, $R_2$=H, $R_4$=α-Me, $R_5$=(S,R)Me, $R_6$=H, $R_7$=OH, $R_8$=H
Ie17: $R_1$=Me, $R_2$=H, $R_4$=α-Me, $R_5$=(S)Me, $R_6$=H, $R_7$=OH, $R_8$=H
If17: $R_1$=Me, $R_2$=H, $R_4$=α-Me, $R_5$=(R)Me, $R_6$=H, $R_7$=OH, $R_8$=H
Ig17: $R_1$=OH, $R_2$=α-OH, $R_4$=α-Me, $R_5$=(S,R)Me, $R_6$=H, $R_7$=Me, $R_8$=H
Ih17: $R_1$=OH, $R_2$=α-OH, $R_4$=α-Me, $R_5$=(S)Me, $R_6$=H, $R_7$=Me, $R_8$=H
Ii17: $R_1$=OH, $R_2$=α-OH, $R_4$=α-Me, $R_5$=(R)Me, $R_6$=H, $R_7$=Me, $R_8$=H
Il17: $R_1$=Me, $R_2$=α-OH, $R_4$=α-Me, $R_5$=(S,R)Me, $R_6$=H, $R_7$=OH, $R_8$=H
Im17: $R_1$=Me, $R_2$=α-OH, $R_4$=α-Me, $R_5$=(S)Me, $R_6$=H, $R_7$=OH, $R_8$=H
In17: $R_1$=Me, $R_2$=α-OH, $R_4$=α-Me, $R_5$=(R)Me, $R_6$=H, $R_7$=OH, $R_8$=H
Ia15e: $R_1$=OH, $R_2$=H, $R_4$=α-Et, $R_5$=(S,R)Me, $R_6$=H, $R_7$=Me, $R_8$=H
Ib15e: $R_1$=OH, $R_2$=H, $R_4$=α-Et, $R_5$=(S)Me, $R_6$=H, $R_7$=Me, $R_8$=H
Ic15e: $R_1$=OH, $R_2$=H, $R_4$=α-Et, $R_5$=(R)Me, $R_6$=H, $R_7$=Me, $R_8$=H
Id15e: $R_1$=Me, $R_2$=H, $R_4$=α-Et, $R_5$=(S,R)Me, $R_6$=H, $R_7$=OH, $R_8$=H
Ie15e: $R_1$=Me, $R_2$=H, $R_4$=α-Et, $R_5$=(S)Me, $R_6$=H, $R_7$=OH, $R_8$=H
If15e: $R_1$=Me, $R_2$=H, $R_4$=α-Et, $R_5$=(R)Me, $R_6$=H, $R_7$=OH, $R_8$=H
Ig15e: $R_1$=OH, $R_2$=α-OH, $R_4$=α-Et, $R_5$=(S,R)Me, $R_6$=H, $R_7$=Me, $R_8$=H
Ih15e: $R_1$=OH, $R_2$=α-OH, $R_4$=α-Et, $R_5$=(S)Me, $R_6$=H, $R_7$=Me, $R_8$=H
Ii15e: $R_1$=OH, $R_2$=α-OH, $R_4$=α-Et, $R_5$=(R)Me, $R_6$=H, $R_7$=Me, $R_8$=H
Il15e: $R_1$=Me, $R_2$=α-OH, $R_4$=α-Et, $R_5$=(S,R)Me, $R_6$=H, $R_7$=OH, $R_8$=H
Im15e: $R_1$=Me, $R_2$=α-OH, $R_4$=α-Et, $R_5$=(S)Me, $R_6$=H, $R_7$=OH, $R_8$=H
In15e: $R_1$=Me, $R_2$=α-OH, $R_4$=α-Et, $R_5$=(R)Me, $R_6$=H, $R_7$=OH, $R_8$=H
Ia16e: $R_1$=OH, $R_2$=H, $R_4$=α-Et, $R_5$=(S,R)Me, $R_6$=H, $R_7$=Me, $R_8$=H
Ib16e: $R_1$=OH, $R_2$=H, $R_4$=α-Et, $R_5$=(S)Me, $R_6$=H, $R_7$=Me, $R_8$=H
Ic16e: $R_1$=OH, $R_2$=H, $R_4$=α-Et, $R_5$=(R)Me, $R_6$=H, $R_7$=Me, $R_8$=H
Id16e: $R_1$=Me, $R_2$=H, $R_4$=α-Et, $R_5$=(S,R)Me, $R_6$=H, $R_7$=OH, $R_8$=H
Ie16e: $R_1$=Me, $R_2$=H, $R_4$=α-Et, $R_5$=(S)Me, $R_6$=H, $R_7$=OH, $R_8$=H
If16e: $R_1$=Me, $R_2$=H, $R_4$=α-Et, $R_5$=(R)Me, $R_6$=H, $R_7$=OH, $R_8$=H
Ig16e: $R_1$=OH, $R_2$=α-OH, $R_4$=α-Et, $R_5$=(S,R)Me, $R_6$=H, $R_7$=Me, $R_8$=H
Ih16e: $R_1$=OH, $R_2$=α-OH, $R_4$=α-Et, $R_5$=(S)Me, $R_6$=H, $R_7$=Me, $R_8$=H
Ii16e: $R_1$=OH, $R_2$=α-OH, $R_4$=α-Et, $R_5$=(R)Me, $R_6$=H, $R_7$=Me, $R_8$=H
Il16e: $R_1$=Me, $R_2$=α-OH, $R_4$=α-Et, $R_5$=(S,R)Me, $R_6$=H, $R_7$=OH, $R_8$=H
Im16e: $R_1$=Me, $R_2$=α-OH, $R_4$=α-Et, $R_5$=(S)Me, $R_6$=H, $R_7$=OH, $R_8$=H
In16e: $R_1$=Me, $R_2$=α-OH, $R_4$=α-Et, $R_5$=(R)Me, $R_6$=H, $R_7$=OH, $R_8$=H
Ia17e: $R_1$=OH, $R_2$=H, $R_4$=α-Et, $R_5$=(S,R)Me, $R_6$=H, $R_7$=Me, $R_8$=H
Ib17e: $R_1$=OH, $R_2$=H, $R_4$=α-Et, $R_5$=(S)Me, $R_6$=H, $R_7$=Me, $R_8$=H
Ic17e: $R_1$=OH, $R_2$=H, $R_4$=α-Et, $R_5$=(R)Me, $R_6$=H, $R_7$=Me, $R_8$=H
Id17e: $R_1$=Me, $R_2$=H, $R_4$=α-Et, $R_5$=(S,R)Me, $R_6$=H, $R_7$=OH, $R_8$=H
Ie17e: $R_1$=Me, $R_2$=H, $R_4$=α-Et, $R_5$=(S)Me, $R_6$=H, $R_7$=OH, $R_8$=H
If17e: $R_1$=Me, $R_2$=H, $R_4$=α-Et, $R_5$=(R)Me, $R_6$=H, $R_7$=OH, $R_8$=H
Ig17e: $R_1$=OH, $R_2$=α-OH, $R_4$=α-Et, $R_5$=(S,R)Me, $R_6$=H, $R_7$=Me, $R_8$=H
Ih17e: $R_1$=OH, $R_2$=α-OH, $R_4$=α-Et, $R_5$=(S)Me, $R_6$=H, $R_7$=Me, $R_8$=H
Ii17e: $R_1$=OH, $R_2$=α-OH, $R_4$=α-Et, $R_5$=(R)Me, $R_6$=H, $R_7$=Me, $R_8$=H
Il17e: $R_1$=Me, $R_2$=α-OH, $R_4$=α-Et, $R_5$=(S,R)Me, $R_6$=H, $R_7$=OH, $R_8$=H

Im17e: $R_1$=Me, $R_2$=α-OH, $R_4$=α-Et, $R_5$=(S)Me, $R_6$=H, $R_7$=OH, $R_8$=H

In17e: $R_1$=Me, $R_2$=α-OH, $R_4$=α-Et, $R_5$=(R)Me, $R_6$=H, $R_7$=OH, $R_8$=H

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Example 1

Synthesis of TGR5 Modulators

The compounds of the invention, and related derivatives, can be synthesized by methods known to one skilled in the art. Detailed methods for synthesizing these compounds are described below. See, also, WO 02/072598, WO 2004/0007521, EP 1568706 and EP 135782. In the case of the compound where $R_1$ is hydrogen, $R_2$ and $R_3$ are hydroxy and $R_4$ is a lower alkyl group, the compound of formula (I) can be obtained in accordance with the following scheme:

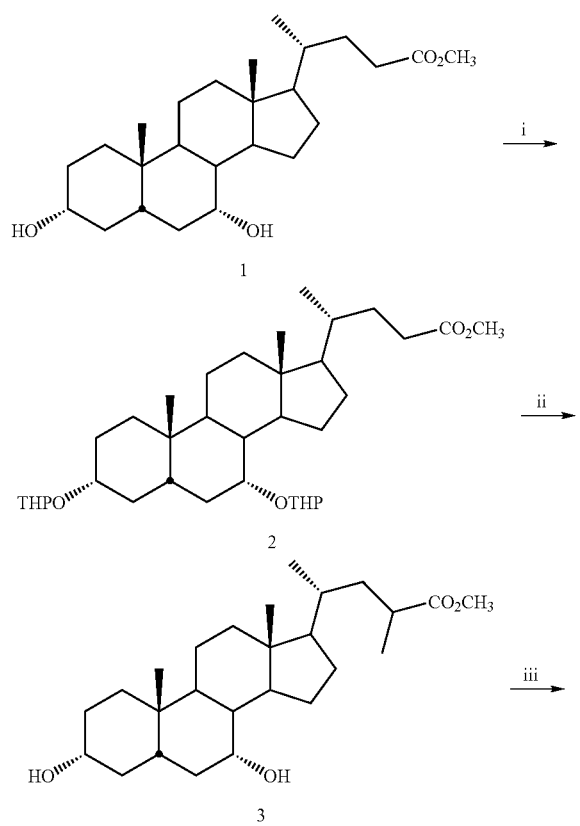

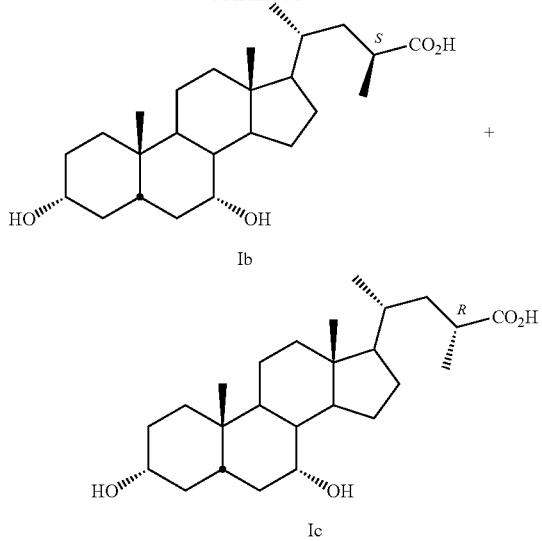

Scheme 1.
(i) 3,4-DHP, p-TSA, dioxane, r.t.; (ii) a) LDA, CH3I, -78° C.; b) HCl, CH3OH, r.t.;
iii) NaOH, CH3OH, reflux.

Methyl chenodeoxycholanoate (1) was protected in 3- and 7-position by treatment with 3,4-dihydro-2H-pyran in dioxane in presence of catalytic amount of p-toluenesulfonic acid (p-TSA) to give the corresponding 3α,7α-tetrahydropyranyloxy analog (2). Reaction of 2 with methyl iodide (or with an appropriate alkyl halide), at −78° C. using lithium diisopropylamide as a base and tetrahydrofuran (THF) as solvent, followed by treatment with methanolic HCl afforded the corresponding methyl 23-methyl-3α,7α-dihydroxy-5(3-cholan-24-oate (3). Hydrolysis with alkali of the methyl ester 3 and purification by flash chromatography yielded the desired 23(S)-methyl-3α,7α-dihydroxy-5β-cholan-24-oic acid (Ib) and 23(R)-methyl-3α,7α-dihydroxy-5(3-cholan-24-oic acid (Ic).

Preparation of 23(R)- and 23(S)-methyl-3α,7α-dihydroxy-5β-cholan-24-oic acid (Ib, Ic)

a) Methyl 3α,7α-ditetrahydropyranyloxy-5β-cholan-24-oate (2)

p-Toluenesulfonic acid (78 mg, 0.41 mmol), 3,4-dihydro-2H-pyrane (20.1 ml, 0.098 mol) were added to a solution of methyl 3α,7α-dihydroxy-5β-cholan-24-oate (1) (2.0 g, 4.9 mmol) in dioxane (6 mL). The reaction mixture was stirred at room temperature for 15 min. H$_2$O (50 mL) was then added and the mixture was partially concentrated under vacuum and extracted with EtOAc (3×50 mL). The combined organic fractions were washed with brine (1×50 mL), dried (Na$_2$SO$_4$) and evaporated under vacuum. The residue was purified by chromatography on silica gel column. Elution with light petroleum/ethyl acetate 80/20 afforded 2.5 g of the pure compound 2 (90% yield).

$^1$H-NMR (CDCl$_3$) δ: 0.64 (s, 3H, CH$_3$-18), 0.89 (s, 3H, CH$_3$-19), 0.92 (d, 3H, CH$_3$-21), 3.31-3.67 (m, 4H, —CH$_2$OCH—), 3.65 (s, 3H, CO$_2$CH$_3$), 3.67 (m, 1H, CH-3), 3.88 (brs, 1H, CH-7), 4.67 (brs, 1H, —O—CH—O—), 4.73 (brs, 1H, —O—CH—O—).

b) Methyl 23(R,S)-methyl-3α,7α-dihydroxy-5β-cholan-24-oate (3)

n-Butyl lithium (4.3 mL, 2.2 M solution in hexane) were added dropwise at ±78° C. to a solution of diisopropylamine (1.4 mL, 10.1 mmol) in dry THF (50 mL). The system was kept to −78° C. for additional 30 min and then, methyl 3α,7α,12α-tetrahydropyranyloxy-5β-cholan-24-oate (2) (1.8 g, 3.2 mmol) dissolved in dry THF (14 mL) was added dropwise to the mixture. After 20 min methyl iodide (1.4 mL, 22.0 mmol) dissolved in dry THF (7 mL) was slowly added and the mixture was allowed to warm to room temperature overnight. The solvents were removed under vacuum and acidified by 10% HCl and extracted with EtOAc (5×50 mL), washed with 5% $Na_2S_2O_3$ solution (2×50 mL), dried (over anhydrous $Na_2SO_4$), filtered, and evaporated under vacuum. The crude residue was then treated with a solution of 2N HCl in MeOH (50 mL) for 12 h. The residue was evaporated under vacuum and taken up with EtOAc (100 mL), washed with a saturated $NaHCO_3$ solution (2×50 mL), dried ($Na_2SO_4$) and evaporated under vacuum. The residue was purified by silica gel flash chromatography. Elution with light petroleum/ethyl acetate 70/30 afforded 1.1 g (2.7 mmol) of the pure compound 3 (84% yield).

$^1$H-NMR ($CDCl_3$) δ: 0.62 (s, 3H, $CH_3$-18), 0.87 (s, 3H, $CH_3$-19), 0.92 (d, 3H, $CH_3$-21), 2.38 (m, 1H, CH-23), 3.27-3.40 (m, 1H, CH-3), 3.55 (brs, 1H, CH-7), 3.63 (s, 3H, $CO_2CH_3$).

c) 23(R)-Methyl-3α,7α-dihydroxy-5β-cholan-24-oic acid (Ib) and 23(S)-Methyl-3α,7α-dihydroxy-5β-cholan-24-oic acid (Ic)

Methyl 23-methyl-3α,7α-dihydroxy-5β-cholan-24-oate 0.97 g (2.3 mmol) was dissolved in MeOH (25 mL) and added with 10% NaOH in MeOH (5.7 mL, 14.2 mmol). The mixture was refluxed for 16 h. The mixture was acidified with 3N HCl and extracted with EtOAc (3×20 mL). The combined organic fractions were washed with brine (1×50 mL), dried ($Na_2SO_4$) and evaporated under vacuum. The residue was purified by silica gel flash chromatography. Elution with $CHCl_3$:MeOH (95/5) afforded 1.5 g (65%) of 23(S)-Methyl-3α,7α-dihydroxy-5β-cholan-24-oic acid and 330 mg of 23(R)-Methyl-3α,7α-dihydroxy-5β-cholan-24-oic acid.

23(S)-Methyl-3α,7α-dihydroxy-5β-cholan-24-oic acid (Ib): mp: 125-126° C. $^1$H-NMR ($CDCl_3$+$CD_3OD$) δ: 0.44 (s, 3H, $CH_3$-18), 0.69 (s, 3H, $CH_3$-19), 0.73-0.76 (d, 3H $CH_3$-21), 0.93-0.97 (d, 3H, —$CH_3$), 2.36 (m, 1H, CH-23), 3.15-3.38 (m, 1H, CH-3), 3.62 (brs, 1H, CH-7). $^{13}$C-NMR ($CDCl_3$+$CD_3OD$) δ: 11.55, 18.43, 18.87, 20.49, 22.69, 28.15, 28.57, 30.14, 32.65, 34.43, 34.61, 34.94, 35.23, 37.06, 39.17, 39.60, 40.81, 41.40, 42.57, 46.54, 50.29, 56.63, 68.24, 71.62, 179.99.

23(R)-Methyl-3α,7α-dihydroxy-5β-cholan-24-oic acid (Ic): mp: 163-164° C. $^1$H-NMR ($CDCl_3$+$CD_3OD$) δ: 0.43 (s, 3H, $CH_3$-18), 0.65 (s, 3H, $CH_3$-19), 0.65-0.69 (d, 3H $CH_3$-21), 0.83-0.86 (d, 3H, —$CH_3$), 2.20 (m, 1H, CH-23), 3.09-3.15 (m, 1H, CH-3), 3.58 (brs, 1H, CH-7). $^{13}$C-NMR ($CDCl_3$+$CD_3OD$) δ: 11.94, 16.40, 18.30, 20.93, 23.06, 23.89, 28.85, 30.52, 33.08, 34.16, 34.91, 35.38, 35.68, 37.14, 39.49, 39.64, 40.04, 40.17, 41.92, 43.05, 50.69, 57.10, 68.51, 72.01, 181,09.

Example 2

Preparation of 23(S)- and 23(R)-methyl-6α-methyl-3α,7α-dihydroxy-5β-cholan-24-oic acid (Ib3, Ic3)

The following compounds were prepared by alkylation of 6α-methyl-3α,7α-dihydroxy-5β-cholan-24-oic acid according to the procedure of Example 1.

23(S)-Methyl-6α-methyl-3α,7α-dihydroxy-5β-cholan-24-oic acid (Ib3): mp: 98-100° C. $^1$H-NMR ($CDCl_3$) δ: 0.63 (s, 3H, $CH_3$-18), 0.89 (s, 3H, $CH_3$-19), 0.92-1.00 (m, 6H, $CH_3$-21 and $CH_3$-6), 1.15-1.19 (d, 3H, —$CH_3$), 2.45-2.73 (m, 1H, CH-23), 3.31-3.52 (m, 1H, CH-3), 3.58 (brs, 1H, CH-7). $^{13}$C-NMR ($CDCl_3$) δ: 11.76, 15.72, 18.58, 18.88, 20.63, 23.11, 23.65, 28.19, 30.21, 30.47, 32.64, 33.79, 33.97, 34.61, 35.42, 35.66, 37.03, 39.60, 40.01, 40.71, 42.71, 47.35, 50.44, 56.60, 72.34, 72.87, 182.37.

23(R)-Methyl-3α,7α-dihydroxy-5β-cholan-24-oic acid (Ic3): mp: 89-90° C. $^1$H-NMR ($CDCl_3$+$CD_3OD$) δ: 0.65 (s, 3H, $CH_3$-18), 0.88 (s, 3H, $CH_3$-19), 0.88-0.92 (m, 3H, $CH_3$-6), 0.95-0.99 (d, 3H, $CH_3$-21), 1.08-1.14 (d, 3H-$CH_3$), 2.35 (m, 1H, CH-23), 3.29-3.48 (m, 1H, CH-3), 3.57 (brs, 1H, CH-7). $^{13}$C-NMR ($CDCl_3$+$CD_3OD$) δ: 11.70, 15.66, 16.02, 18.00, 20.61, 23.09, 23.60, 28.51, 30.39, 32.61, 33.72, 33.92, 35.38, 35.65, 36.33, 39.57, 39.94, 42.77, 47.30, 50.39, 56.53, 72.22, 72.83, 180.50.

Example 3

Preparation of 23(R)- and 23(S)-methyl-3α,7α,12α-trihydroxy-5β-cholan-24-oic acid (Ih, Ii)

The following compounds were prepared by alkylation of 3α,7α,12α-trihydroxy-5β-cholan-24-oic acid according to the procedure of Example 1.

23(S)-Methyl-3α,7α,12α-trihydroxy-5β-cholan-24-oic acid (Ih): mp: 237-239° C. $^1$H-NMR ($CDCl_3$) δ: 0.63 (s, 3H, $CH_3$-18), 0.87 (s, 3H, $CH_3$-19), 0.96-0.98 (m, 3H, $CH_3$-21), 1.07-1.11 (d, 3H, —$CH_3$), 2.44-2.73 (m, 1H, CH-23), 3.35-3.50 (m, 1H, CH-3), 3.82 (brs, 1H, CH-7) 3.95 (brs, 1H, CH-12). $^{13}$C-NMR (DMSO) δ: 12.72, 17.60, 19.24, 19.24, 23.00, 23.19, 26.59, 27.78, 28.88, 30.72, 34.77, 35.22, 35.66, 37.19, 41.84, 46.19, 47.27, 49.01, 66.69, 70.88, 71.45, 178.25.

23(R)-Methyl-3α,7α,12α-trihydroxy-5β-cholan-24-oic acid (Ii): mp: 221-223° C. $^1$H-NMR ($CDCl_3$) δ: 0.63 (s, 3H, $CH_3$-18), 0.87 (s, 3H, $CH_3$-19), 0.96-0.98 (m, 3H, $CH_3$-21), 1.07-1.11 (d, 3H, —$CH_3$), 2.44-2.73 (m, 1H, CH-23), 3.35-3.50 (m, 1H, CH-3), 3.82 (brs, 1H, CH-7) 3.95 (brs, 1H, CH-12). $^{13}$C-NMR (DMSO) δ: 12.76, 16.88, 17.31, 23.04, 23.24, 26.62, 28.12, 28.94, 30.81, 33.97, 34.80, 35.28, 35.71, 37.20, 41.85, 46.29, 47.44, 66.67, 70.86, 71.45, 178.77.

Example 4

Preparation of 23(R)- and 23(S)-methyl-6α-methyl-3α,7α,12α-trihydroxy-5β-cholan-24-oic acid (Ih3, Ii3)

The following compounds were prepared by alkylation of 6α-methyl-3α,7α,12α-trihydroxy-5β-cholan-24-oic acid according to the procedure of Example 1.

23(S)-Methyl-6α-methyl-3α,7α,12α-trihydroxy-5β-cholan-24-oic acid (Ih3): mp: 131-134° C. $^1$H-NMR ($CDCl_3$+$CD_3OD$) δ: 0.65 (s, 3H, $CH_3$-18), 0.87 (s, 3H, $CH_3$-19), 0.97-1.00 (m, 3H, $CH_3$-21), 1.14-1.18 (d, 3H, —$CH_3$), 1.23 (m, 1H, CH-6), 2.52 (m, 1H, CH-23), 3.32-3.50 (m, 1H, CH-3), 3.55 (brs, 1H, CH-7) 3.94 (brs, 1H, CH-12). $^{13}$C-NMR ($CDCl_3$+$CD_3OD$) δ: 12.43, 145.66, 17.62, 18.92, 22.70, 23.14, 26.21, 27.45, 28.01, 30.03, 33.44, 34.11, 34.42, 35.30, 36.71, 39.97, 40.45, 41.73, 46.45, 47.25, 72.13, 72.76, 73.01, 180.53.

23(R)-Methyl-6α-methyl-3α,7α,12α-trihydroxy-5β-cholan-24-oic acid (Ii3): mp: 109-110° C. $^1$H-NMR ($CD_3OD$) δ: 0.72 (s, 3H, $CH_3$-18), 0.91 (s, 3H, $CH_3$-19), 1.07-1.11 (m, 6H, —$CH_3$ and $CH_3$-21), 2.37-2.53 (m, 1H, CH-23), 3.15-3.42 (m, 1H, CH-3), 3.53 (brs, 1H, CH-7) 3.97 (brs, 1H, CH-12). $^{13}$C-NMR ($CD_3OD$) δ: 11.61, 15.04, 15.32, 16.15, 22.04, 22.75, 26.27, 27.62, 28.18, 29.61, 32.91, 33.74, 34.31, 35.06, 35.18, 36.56, 39.70, 40.25, 41.68, 46.19, 46.31, 71.76, 71.77, 72.62, 180.11.

Example 5

Preparation of 23(R)- and 23(S)-methyl-3α-hydroxy-5β-cholan-24-oic acid (Ip, Iq)

The following compounds were prepared by alkylation of 3α-hydroxy-5β-cholan-24-oic acid according to the procedure of Example 1.

23(S)-Methyl-3α-hydroxy-5β-cholan-24-oic acid (Ip): mp: 161-162° C. $^1$H-NMR (CDCl$_3$+CD$_3$OD) δ: 0.60 (s, 3H, CH$_3$-18), 0.88 (s, 3H, CH$_3$-19), 0.92-1.01 (m, 3H, CH$_3$-21), 1.13-1.16 (d, 3H, —CH$_3$), 2.55 (m, 1H, CH-23), 3.60 (m, 1H, CH-3). $^{13}$C-NMR (CDCl$_3$+CD$_3$OD) δ: 11.97, 18.52, 18.87, 20.73, 23.30, 24.14, 26.34, 27.10, 28.15, 30.18, 34.48, 34.50, 35.23, 35.74, 36.06, 37.01, 40.13, 40.34, 40.74, 41.99, 42.68, 56.43, 56.75, 71.70, 181.42.

23(R)-Methyl-3α-hydroxy-5β-cholan-24-oic acid (Iq): mp: 152-153° C. $^1$H-NMR (CDCl$_3$+CD$_3$OD) δ: 0.63 (s, 3H, CH$_3$-18), 0.89 (s, 3H, CH$_3$-19), 0.94-1.03 (m, 3H, CH$_3$-21), 2.45 (m, 1H, CH-23), 3.59 (m, 1H, CH-3). $^{13}$C-NMR (CD$_3$OD) δ: 11.98, 15.97, 18.00, 20.75, 23.31, 24.14, 26.34, 27.11, 28.48, 30.26, 33.68, 34.50, 35.26, 35.77, 36.15, 36.46, 39.59, 40.13, 40.36, 42.01, 42.79, 56.45, 56.76, 71.71, 181.02.

Example 6

Preparation of 23(S)-methyl-3α,7α,12α-trihydroxy-6α-ethyl-5β-cholan-24-oic acid (Ih3e)

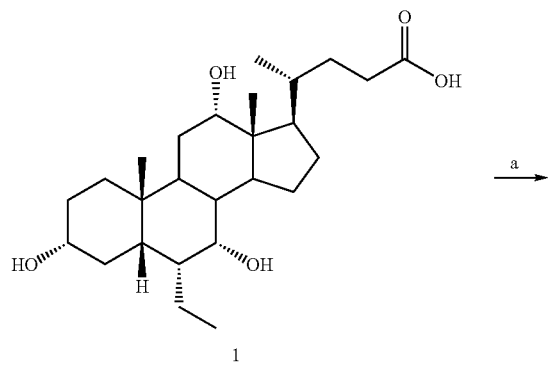

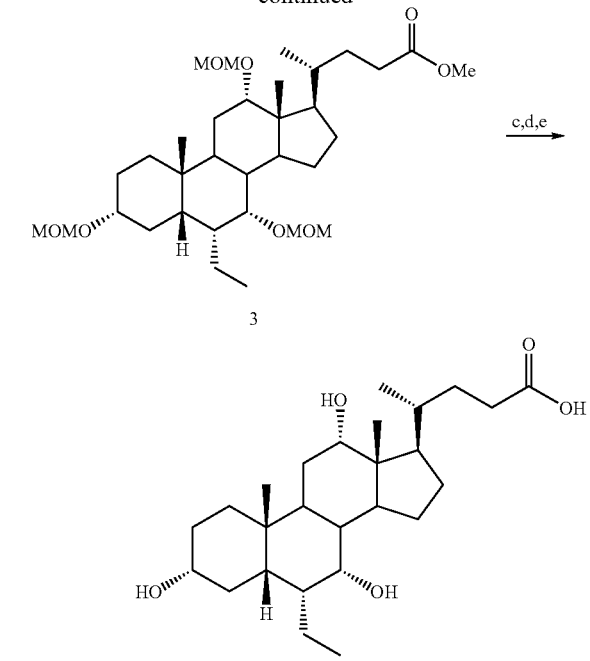

Reagents and conditions: a) pTSA, MeOH, ultrasound, quant. b) CH$_2$(OCH$_3$)$_2$, P$_2$O$_5$, CHCl$_3$, 97%. c) LDA, MeI, -78° C. d) MeOH, HCl, 45° C. e) MeOH, NaOH, 45° C., 41%. Overall yield: 39.7%.

Synthesis of 23(S)-methyl-3α,7α,12α-trihydroxy-6α-ethyl-5β-cholan-24-oate (2)

To a solution of 1 (2.78 g, 6.37 mmol) in MeOH (120 ml), pTSA (0.12 g, 0.63 mmol) was added, and the mixture was treated with ultrasound for 90'. The mixture was then concentrated under reduced pressure, and the resulting residue was diluted with AcOEt (120 ml), washed with H$_2$O (3×100 ml), brine (100 ml), dried over anhydrous Na$_2$SO$_4$, and concentrated under reduced pressure to give 2 (quantitative yield) that was used for the next step without further purification.

$^1$H-NMR (CDCl$_3$) δ 0.63 (3H, s, 18-CH$_3$), 0.84-0.88 (6H, s, 19-CH$_3$+CH$_3$CH$_2$), 0.97 (3H, d, J=6.62 Hz, 21-CH$_3$), 3.30 (1H, m. 3-CH), 3.48 (3H, s, COOCH$_3$), 3.62 (1H, m, 7-CH), 3.97 (1H, m, 12-CH).

Methyl 3α,7α,12α-trihydroxy-6α-ethyl-5β-24-oate (3)

To a solution of 2 (2.50 g, 5.55 mmol) in CHCl3 (60 ml) and dimethoxymethane (34.10 ml, 166.66 mmol), P$_2$O$_5$ (14.18 g, 99.90 mmol) was added portion-wise, and the resulting suspension was mechanically stirred for 45'. The mixture was then decanted, and the organic layer was treated with NaHCO$_3$ 10% (50 ml) for 10'. The organic layer was then separated, and the aqueous layer was extracted with CHCl$_3$ (3×50 ml). The collected organic layers were washed with brine (100 ml), dried over anhydrous Na$_2$SO$_4$, and concentrated under reduced pressure to give 3 (3.14 g, 97%), that was used for the next step without further purification.

$^1$H-NMR (CDCl$_3$) δ: 0.67 (3H, s, 18-CH$_3$), 0.88-1.04 (9H, m, 19-CH$_3$+CH$_3$CH$_2$+21-CH$_3$), 3.30 (1H, m. 3-CH), 3.30-3.40 (7H, m, 3-CH+2×CH$_3$OCH$_2$O), 3.45 (3H, s, CH$_3$OCH$_2$O), 3.50 (1H, m, 7-CH), 3.66 (3H, s, COOCH$_3$), 3.79 (1H, m, 12-CH), 4.57-4.75 (6H, m, 3×CH$_3$OCH$_2$O).

23(S)-methyl-3α,7α,12α-trihydroxy-6α-ethyl-5β-cholan-24-oic acid (Ih3e)

To a solution of diisopropylamine (0.56 ml, 4.026 mmol) in freshly distilled THF (15 ml) cooled at −78° C. and under $N_2$ atmosphere, $^{11}$BuLi 2.5N in hexane (1.53 ml, 3.840 mmol) was added dropwise. The reaction was stirred at −78° C. for 30' and then a solution of 3 (350 mg, 0.601 mmol) dissolved in freshly distilled THF (7 ml) was added dropwise. The resulting solution was stirred at −78° for 90'. Iodomethane (0.56 ml, 9.015 mmol) was added, the reaction mixture was stirred at −78° C. for 60', and then slowly warmed to room temperature overnight. The mixture was then concentrated under reduced pressure, and the resulting residue was diluted with $H_2O$ (30 ml) and extracted with AcOEt (3×30 ml). The collected organic layers were washed with brine (30 ml), dried over anhydrous $Na_2SO_4$, and concentrated under reduced pressure. The residue was then treated with a solution of MeOH/HCl 37% (20 ml, 20:1 vol/vol) at 45° for 8 h. The mixture was concentrated under reduced pressure, and the resulting residue was diluted with $H_2O$ (30 ml) and extracted with AcOEt (3×30 ml). The combined organic layers were washed with brine (100 ml), dried over anhydrous $Na_2SO_4$, and concentrate under reduced pressure. The resulting residue was treated with a solution of NaOH 10% in MeOH (15 ml) at 45° C. for 24 h. The mixture was then concentrated under reduced pressure, and the resulting residue was diluted with $H_2O$ (20 ml), washed with $^iPr_2O$ (3×15 ml), acidify with HCl 3N, and finally extracted with $CHCl_3$ (3×20 ml). The organic layers were washed with brine (100 ml), dried over anhydrous $Na_2SO_4$, and concentrated. The resulting residue was purified by medium pressure chromatography (column: "RP-18 Lobar B", MeOH/$H_2O$ from 5:5 to 6:4, 50 psi) to give 4 (47 mg, 41%).

Mp: 195-197° C.

$^1$H-NMR (CDCl$_3$+CD$_3$OD) δ: 0.63 (3H, s, 18-CH$_3$), 0.84-0.88 (6H, m, 19-CH$_3$+CH$_3$CH$_2$), 0.98 (3H, d, J=6.60 Hz, 21-CH$_3$), 1.10 (3H, d, J=6.80 Hz, CH(CH$_3$)COOH), 2.61 (m, 1H, CH(CH$_3$)COOH), 3.35 (1H, m. 3-CH), 3.65 (1H, m, 7-CH), 3.92 (1H, m, 12-CH).

$^{13}$C-NMR (CDCl$_3$+CD$_3$OD) δ: 11.51, 12.34, 17.52, 19.19, 22.09, 22.67, 23.11, 26.65, 27.40, 28.05, 29.83, 33.31, 34.56, 35.06, 35.40, 38.67, 39.90, 41.11, 41.39, 41.69, 45.10, 46.39, 47.32, 70.65, 71.79, 72.90, 182.07.

Example 7

Synthesis of compounds Io5, Ip5, Iq5, and Ir5

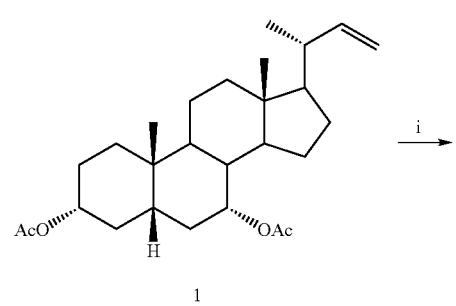

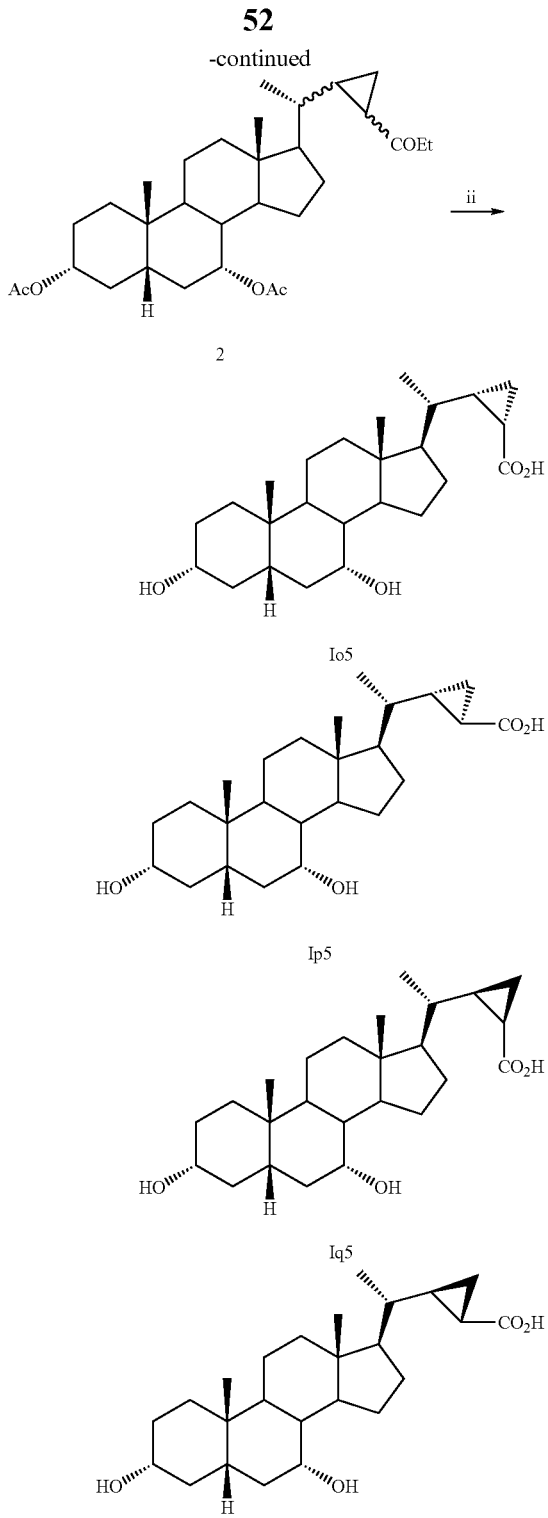

(i) EDA, Rh$_2$(OAc)$_4$, CH$_2$Cl$_2$, room temp; (ii) (a) NaOH, EtOH, reflux, (b) MPLC

3α,7α-Dihydroxy-22,23-methylene-5β-cholan-24-oic Acids (Io5, Ip5, Iq5, and Ir5)

Ethyl diazoacetate (0.478 g, 1.19 mmol) in dry $CH_2Cl_2$ (15 mL) was slowly added dropwise to a stirred suspension of 3α,7α-diacetoxy-5-norcholan-22,23-ene (1) (0.6 g, 1.39 mmol) in the presence of dirhodium (II) tetraacetate (9 mg, 0.02 mmol) in dry $CH_2Cl_2$ (15 mL) under nitrogen at room temperature. The reaction mixture was filtered and washed with $H_2O$ (20 mL), dried ($Na_2SO_4$), and evaporated under vacuum, thus affording a mixture of the four diastereoisomeric esters 2. The esters 2 were successively dissolved in EtOH (15 mL) and treated with a solution of 10 N NaOH (10 mL) at reflux for 4 h, cooled, poured onto cold $H_2O$ (50 mL), acidified with 2 N HCl, and extracted with EtOAc (3×15 mL). The organic phase was washed with brine (10 mL), dried ($Na_2SO_4$), and concentrated under vacuum. The residue was chromatographated on silica gel. Elution with $CH_2Cl_2$/MeOH 96/4 with AcOH 0.1% afforded 0.087 g (15% yield) of (22S,23S)-3α,7α-dihydroxy-22,23-methylene-5β-cholan-24-oic acid (Io5) and 0.065 g (11.5% yield) of (22R,23R)-3α,7α-dihydroxy-22,23-methylene-5β-cholan-24-oic acid (Iq5). Elution with $CH_2Cl_2$/MeOH 95.5/4.5 with 0.1% AcOH afforded 0.18 g (32% yield) of (22S,23R)-3α,7α-dihydroxy-22,23-methylene-5β-cholan-24-oic acid (Ip5) and 0.15 g (26.7% yield) of (22R,23S)-3α,7α-dihydroxy-22,23-methylene-5β-cholan-24-oic acid (Ir5) as white solids.

Io5. Mp: 148-150° C. $[\alpha]^{20}_D$+5.16 (c 1, EtOH). $^1$H NMR ($CD_3OD$ and $CDCl_3$) δ: 0.67 (s, 3H, 18-$CH_3$), 090 (s, 3H, 19-$CH_3$), 0.96 (d, J=6.68 Hz, 3H, 21-$CH_3$), 3.40-3.50 (m, 1H, 3-CH), 3.85 (m, 1H, 7-CH). $^{13}$C NMR ($CDCl_3$) δ: 12.20, 16.80, 17.08, 20.80, 21.00, 23.15, 24.10, 28.30, 30.80, 31.30, 33.30, 34.80, 34.90, 35.40, 35.70, 39.80, 39.90, 41.80, 43.40, 50.55, 58.20, 68.90, 72.30, 177.00.

Iq5. MP: >230° C. $[\alpha]^{20}_D$−38.19 (c 1.1, $CH_3Cl$/MeOH 1:1). $^1$H NMR ($CD_3OD$ and $CDCl_3$) δ: 0.50 (s, 3H, 18-$CH_3$), 0.86 (s, 3H, 19-$CH_3$), 0.96 (d, J=6.40 Hz, 3H, 21-$CH_3$), 3.40-3.60 (m, 1H, 3-CH), 3.80 (m, 1H, 7-CH). $^{13}$C NMR ($CDCl_3$) δ: 12.00, 12.50, 20.90, 21.00, 21.10, 23.00, 23.80, 27.10, 30.50, 31.00, 32.10, 33.10, 34.80, 35.30, 35.60, 39.50, 39.70, 39.85, 41.80, 43.00, 50.40, 58.50, 68.60, 72.00, 176.90.

Ip5. Mp: 221-225° C. $[\alpha]^{20}_D$−40.22 (c1, EtOH). $^1$H NMR ($CD_3OD$ and $CDCl_3$) δ: 0.56 (s, 3H, 18-$CH_3$), 0.86 (s, 3H, 19-$CH_3$), 1.16 (d, J=6.60 Hz, 3H, 21-$CH_3$), 3.10-3.30 (m, 1H, 3-CH), 3.85 (m, 1H, 7-CH). $^{13}$C NMR ($CDCl_3$) δ: 12.10, 18.30, 18.55, 20.00, 20.90, 23.10, 24.00, 28.20, 30.70, 31.70, 33.20, 34.80, 35.40, 35.70, 39.80, 40.10, 41.80, 43.15, 50.40, 57.80, 68.90, 72.20, 178.40.

Ir5. Mp: 136-140° C. $[\alpha]^{20}_D$+13.66 (c 1, EtOH). $^1$H NMR ($CD_3OD$ and $CDCl_3$) δ: 0.56 (s, 3H, 18-$CH_3$), 0.86 (s, 3H, 19-$CH_3$), 0.96 (d, J=6.66 Hz, 3H, 21-$CH_3$), 3.40-3.60 (m, 1H, 3-CH), 3.80 (m, 1H, 7-CH). $^{13}$C NMR ($CDCl_3$) δ: 12.00, 13.50, 19.90, 20.90, 22.50, 23.10, 24.00, 28.00, 30.70, 31.60, 33.20, 34.90, 35.40, 35.65, 39.70, 39.73, 41.80, 43.10, 50.40, 58.00, 68.80, 72.20, 177.60.

Example 8

In Vitro TGR5 and FXR Activity

The potency and efficacy of the compounds of the invention on TGR5 receptor was evaluated using in vitro assays.

Table 1 shows that compounds of the invention are potent and selective TGR5 modulators. The introduction of an alkyl group at the C-23 position of bile acid gives selectivity for the TGR5 receptor with respect to FXR. This is evident by the observation of the biological results obtained for CDCA, 6-MeCDCA and 6,23-diMe-CDCA (23-R,S isomers mixture) on FXR and TGR5 as shown in Table 1. 6,23-diMe-CDCA is 100-fold more potent on TGR5 with respect to the FXR receptor For a description of TGR5 receptor binding using an in vitro assay, See, e.g., Kawamata, J. Biol. Chem. 2003, Vol. 278 No. 11, p. 9435-9440). Activity on FXR was assayed by fluorescence resonance energy transfer (FRET) for recruitment of the SRC-1 peptide to human FXR using a cell-free ELiSA. See, Blanchard et al. WO 00/37077.

TABLE 1

$EC_{50}$ (μM) of Example Compounds on FXR and TGR5 Receptor

| Compound | Structure | FXR Data | TGR5 Data |
|---|---|---|---|
| CDCA (ChenoDeoxyCholicAcid) | 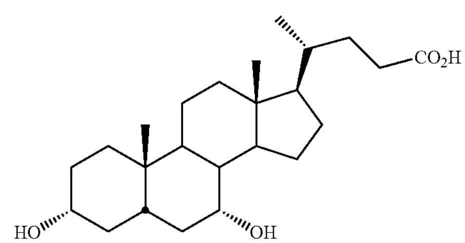 | $EC_{50}$: 8.6 μM Efficacy: 100% | $EC_{50}$: 4.0 μM Efficacy: 100% |
| 6α-MeCDCA | 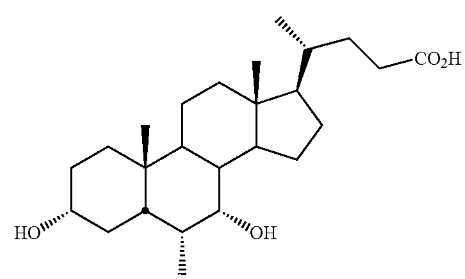 | $EC_{50}$: 0.21 μM Efficacy: 148% | $EC_{50}$: 0.37 μM Efficacy: 119% |

TABLE 1-continued

EC$_{50}$ (μM) of Example Compounds on FXR and TGR5 Receptor

| Compound | Structure | FXR Data | TGR5 Data |
|---|---|---|---|
| 23(R + S)-Me-6MeCDCA (13a) | (R + S) | EC$_{50}$: 15.62 μM Efficacy: 60% | EC$_{50}$: 0.11 μM Efficacy: 123% |

Tables 2 and 3 show additional compounds evaluated for TGR5 activity. Luciferase activity was determined in CHO cells stably expressing hTGR5 or transiently cotransfected with a hTGR5 expression vector and a cAMP-responsive element (CRE)-driven luciferase reporter gene. Some of the compounds were further submitted to a luciferase reporter assay to score for their capacity to activate the nuclear bile acid receptor FXR.

TABLE 2

| Name | R$_1$ | R$_2$ | R$_3$ | TGR5 EC$_{50}$ | TGR5 Efficacy |
|---|---|---|---|---|---|
| 22S,23S-CCDCA* (Io5) | α-OH | —H | | 1.33 | 110 |
| 22S,23R-CCDCA* (Ip5) | α-OH | —H | | 2.91 | 102 |
| 22R,23R-CCDCA* (Iq5) | α-OH | —H | | 75.7 | 5 |
| 22R,23S-CCDCA* (Ir5) | α-OH | —H | | >100 | 4 |

*Data represent average values of at least three independent experiments of CRE-driven luciferase reporter assays in TGR5-transfected CHO cells. Units are μM for EC$_{50}$ and % of 10 μM LCA value for efficacy.

TABLE 3

TGR5 and FXR Activities$^a$

| Name | FXR EC$_{50}$ μM | FXR Efficacy | TGR5 EC$_{50}$ μM | TGR5 Efficacy | EC50 ratio (TGR5/FXR) |
|---|---|---|---|---|---|
| Ih3 | 22.8 | 0.76 | 0.8 | 75.6 | 0.035 |

TABLE 3-continued

TGR5 and FXR Activities[a]

| Name | FXR EC$_{50}$ μM | FXR Efficacy | TGR5 EC$_{50}$ μM | TGR5 Efficacy | EC50 ratio (TGR5/FXR) |
|---|---|---|---|---|---|
| Ib | >100 | 0[b] | 3.58 | 110 | 0.036 |
| Ic | 10.5 | 49 | 25.5 | 100 | 2.4 |
| Ib3 | 11.6 | 23 | 0.140 | 105 | 0.012 |
| Ib3e | 3.97 | 64.4 | 0.51 | 165 | 0.128 |

TABLE 3-continued

TGR5 and FXR Activities[a]

| Name | FXR EC$_{50}$ µM | FXR Efficacy | TGR5 EC$_{50}$ µM | TGR5 Efficacy | EC50 ratio (TGR5/FXR) |
|---|---|---|---|---|---|
| Ih (structure) | | | 4.39 | 105 | |
| Ii (structure) | | | >51.9 | 75[b] | |

[a]Data represents average values of at least three independent experiments. Value for efficacy are expressed as % of activity vs. 10 µM LCA (TGR5) or 10 µM 6ECDCA (FXR).
[b]Plateau activation level not reached; the maximum concentration tested was 125 µM for Ib and 100 mM for Ii.

The data in Tables 2 and 3 can be determined using methods known in the art, for example, as described below.

Plasmids

The NIH Mammalian Gene Collection clone MGC:40597 (also named pCMVSPORT6/hTGR5 or pTGR5) and pcDNA3.1(+) were obtained from Invitrogen (Carlsbad, Calif.). pCRE-Luc and pCMVβ were obtained from Clontech (Palo Alto, Calif.). pCMX-hFXR and pCMX-mRXRα were kind gifts from Dr. David J. Mangelsdorf (Howard Hughes Medical Institute, University of Texas Southwestern Medical Center). pEcREx7-Luc was a kind gift from Dr. Richard A. Heyman (X-ceptor Therapeutics, Calif.).

Cell Culture

Chinese hamster ovary (CHO) cells, NCI-H716 cells, Hep3B cells and COS1 cells were obtained from American Type Culture Collection (Manassas, Va.). Cell culture medium, serum and supplements were from Invitrogen or Sigma-Aldrich. All CHO cells were maintained in minimum essential medium α (α-MEM) supplemented with 10% (v/v) fetal bovine serum (FBS) and 100 µM nonessential amino acids (NEAA). NCI-H716 cells were maintained in suspension in RPMI-1640 supplemented with 10% (v/v) FBS, 10 mM HEPES and 1 mM sodium pyruvate. Hep3B cells were maintained in Eagle's medium supplemented with 10% (v/v) FBS and 100 µM NEAA. COS1 cells were maintained in Dulbecco's modified Eagle's medium (DMEM) supplemented with 10% (v/v) FBS. All cell culture medium was supplemented with 100 units/ml penicillin and 100 µg/ml streptomycin sulfate. Cells were grown at 37° C. in an atmosphere of 5% CO2, passed every 2-6 days and freshly plated for each experiment.

Transient Transfections

CHO cells were plated in 96-well plates at a density of 3.5×104 cells/well, cultured for 24 h, and then transfected with 150 ng of human (h) TGR5 expression plasmid (pCMVSPORT6/hTGR5) and 100 ng of cAMP-responsive element (CRE)-driven luciferase reporter plasmid (pCRE-Luc) in each well using Lipofectamine 2000 reagent (Invitrogen) according to the manufacturer's instructions. After 6 h incubation, cells were washed once with phosphate-buffered saline (PBS) and medium was exchanged for DMEM containing 0.1% (w/v) bovine serum albumin (BSA). After incubation for another 18 h, cells were treated for 5 h with different concentrations of each compound in fresh DMEM containing 0.1% (w/v) BSA. After treatment, the cells were lysed with 50 µl of lysis buffer (25 mM Tris-C1(pH7.6), 2 mM EDTA, 1 mM dithiothreitol (DTT), 10% (v/v) glycerol and 1% (v/v) triton X-100) by a freeze-thaw cycle and subjected to luciferase assays as described below.

COS1 cells were plated in 96-well plates at a density of 2.5×104 cells/well in DMEM supplemented with 10% (v/v) charcoal-stripped FBS, cultured for 24 h, and then transfected with 25 ng of hFXR expression plasmid (pCMX-hFXR), 25 ng of mouse (m) retinoid X receptor α (RXRα) expression plasmid (pCMX-mRXRa), 50 ng of reporter plasmid (pEcREx7-Luc) and 50 ng of pCMVβ as internal control in each well, using the Lipofectamine 2000 reagent. After 24 h, cells were washed twice with PBS and treated with different concentrations of each compound in fresh DMEM supplemented with 10% (v/v) charcoal-stripped FBS for 24 h. After treatment, the cells were lysed with 50 µl of lysis buffer by a freeze-thaw cycle and subjected to both luciferase and β-galactosidase assays as described below. Normalized luciferase values were determined by dividing the luciferase activity by the β-galactosidase activity.

Luciferase and β-Galactosidase Assays

For luciferase assays, 20 µl of cell lysate was mixed with 100 µl of luciferase reaction buffer [235 µM luciferine, 265 µM ATP and 135 µM coenzyme A (CoA)] and luminescence was determined with CentroXS3 LB960 (Berthold Technologies, Bad Wildbad, Germany) For β-galactosidase assays, 10 µl of cell lysate was mixed with 100 µl of Buffer Z [60 mM Na2HPO4, 10 mM KCl, 1 mM MgSO4, 50 mM β-mercaptoethanol and 0.75 mg/ml o-nitrophenyl-β-D-galactopyranoside (ONPG)] and incubated at 37° C. for 0.5-3 h. Reactions were stopped by adding 50 µl of Stop buffer (1M Na2CO3) and the optical density at 420 nm was determined Establishing CHO Cells Stably Expressing Human TGR5 (CHO-TGR5 Cells)

CHO cells were transfected with 3.8 µg of hTGR5 expression plasmid (pCMVSPORT6/hTGR5), 3.8 µg of CRE-driven luciferase reporter plasmid (pCRE-Luc) and 0.4 µg of neomycin-resistant gene expression plasmid [pcDNA3.1(+)] using Lipofectamine 2000. The transfectants were selected with 400 µg/ml G418 sulfate and single clones were grown in 96-well plate, independently. TGR5-expressing CHO cell lines were screened by LCA treatments, followed by luciferase assays.

cAMP Production Analysis

NCI-H716 cells were plated in 96-well plates coated with 0.75 mg/ml Matrigel (BD Biosciences) according to manufacturer's instructions just prior to use, at a density of 6×104 cells/well in DMEM supplemented with 10% (v/v) FBS, 100 units/ml penicillin and 100 µg/ml streptomycin sulfate, and cultured for 24 h, which allowed cell adhesion to the bottom of the plate. CHO-TGR5 cells were plated in 96-well plates at a density of 3.5×104 cells/well in α-MEM supplemented with 10% (v/v) FBS, 100 µM NEAA, 100 units/ml penicillin and 100 µg of streptomycin sulfate, and cultured for 24 h. The cells were washed twice with PBS and medium was exchanged for cAMP assay medium [DMEM containing 0.1% (w/v) BSA and 0.5 mM 3-isobutyl-1-methylxanthine (IBMX)]. After incubation for 30 minutes at 37° C., the cells were treated with each compound in fresh cAMP assay medium for 30 minutes. After treatment, medium was discarded and cAMP amounts were determined using cAMP-Screen kit (Applied Biosystems, Foster City, Calif.) according to manufacturer's instructions.

50% Effective Concentrations (EC50) and Efficacy Determination

Assays were performed in triplicate or quadruplicate for each condition. EC50 values were determined by probit analysis. Efficacy was determined by calculating percentages of 10 µM LCA value for TGR5 agonist study and 10 µM 6α-Et-CDCA value for FXR agonist study, respectively. After subtracting the average value of the basal (vehicle-treated) condition, values were applied to EC50 and/or efficacy determinations. Calculation of average EC50 and comparison of the EC50 between different compounds were performed after logarithm transformation.

Statistical Analysis

Statistical analysis was performed by Student's t-test and $p < 0.05$ was considered statistically significant.

TABLE 3A

| Compound (Reference Standard) | Alphascreen Assay hFXR (CDCA = 10-20 µM) EC50 (µM) | FRET (cAMP) NCI-H716 hTGR5 (LCA = 48 µM) EC50 (µM) | Transactivation Assay hTGR5 (LCA = 16 µM) EC50 (µM) | FRET-cAMPon TGR5 overexpressing Hek293 cells hTGR5 (LCA = 0.35 µM) EC50 (µM) |
|---|---|---|---|---|
| 1h3e | 175 | 0.9 | 1.7 | 0.001 |

The data in Table 3A were generated by using methods described below.

FRET Assay (Detection of Intracellular cAMP Levels).

The receptor binding assay was performed by measuring the level of cyclic AMP (cAMP) using FRET assay. Human intestinal cell lines (NCI-H716) were plated in 96-well plates coated with 0.75 mg/ml Matrigel (BD Biosciences) according to manufacturer's instructions just prior to use, at a density of $12 \times 10^3$ cells/well in DMEM supplemented with 10% (v/v) FBS, 100 units/ml penicillin and 100 µg/ml streptomycin sulfate, and cultured for 24 h, which allowed cell adhesion to the bottom of the plate. The cells were washed twice with PBS and medium was exchanged for cAMP assay medium [OPTIMEM containing 0.1% (w/v) BSA and 1 mM 3-isobutyl-1-methylxanthine (IBMX)]. After incubation for 60 minutes at 37° C., the cells were treated with increasing concentrations of compound Ih3 in stimulation buffer (5 mM HEPES, 0.1% BSA in HBSS pH 7.4) containing the europium chelate—Streptavidin and the ALEXA Fluor 647-conjugated antibody anti-cAMP (PerkinElmer) for 1 hour at room temperature. The level of intracellular cAMP was determined with Lance kit (PerkinElmer). Litocholic acid was used as control ligand. Z' factor was used to validate assays. Non linear regression curves, without constraints, were performed by using four parameter equation and GraphPad Prism Software (GraphPad Inc.), to obtain the EC50 values.

Alphascreen Assay

Activity on FXR was assayed by using Alphascreen technology in a recruitment coactivator assay. AlphaScreen is a bead-based chemistry assay used to study biomolecular interactions. Binding of molecules captured on the beads leads to an energy transfer from one bead to the other, ultimately producing a luminescent signal. When the partners interact, chemical energy is transferred from Donor to Acceptor beads and a signal is produced. Upon bile acids stimulation the GST-FXR-LBD interacts with the Src-1 peptide. Anti-GST-coated Acceptor beads were used to capture the GST-fusion FXR-LBD whereas the biotinylated-SRC-1 peptide was captured by the streptavidin Donor beads. Upon illumination at 680 nm chemical energy is transferred from Donor to Acceptor beads across the complex streptavidin-Donor/Src-1-Biotin/GSTFXR-LBD/Anti-GST-Acceptor and a signal is produced. The assay was performed in white, low-volume, 384-well Optiplates (PerkinElmer) using a final volume of 25 µl containing final concentrations of 10 nM of purified GST-tagged FXR-LBD protein, 30 nM biotinylated Src-1 peptide, 20 µg/ml anti-GST acceptor beads acceptor beads and 10 µg/ml of streptavidin donor bead (PerkinElmer). The assay buffer contained 50 mM Tris (pH 7.4), 50 mM KCl, 0.1%

BSA, and 1 mM DTT. The stimulation times with 1 μl of ligands (solubilized in 100% DMSO) were fixed to 30' a room temperature. The concentration of DMSO in each well was maintained at a final concentration of 4%. After the addition of the detection mix (acceptor and donor beads) the plates were incubated in the dark for 4 h at room temperature and then were read in an Envision microplate analyzer (PerkinElmer). Dose response curves were performed in triplicate and Z' factor was used to validate the assays. Non linear regression curves, without constraints, were performed by using four parameter equation and GraphPad Prism Software (GraphPad Inc.), to obtain the EC50 values.

Cell Culture, Transfection and Luciferase Assay

HEPG2 and HEK293T cells were cultured in E-MEM and DMEM respectively, either supplemented with 1% penicillin/streptomycin, 1% L-glutamine and 10% fetal bovine serum. (high glucose) (Invitrogen, Carlsbad, Calif.). Cells were grown at 37° C. in 5% CO2. All the transfections were made using 5:2 Fugene HD Trasfection reagent (n1) to DNA (ng) respectively (Roche). Twenty-four hours before transfection HEK293T or HepG2 cells were seeded onto a 96-well plate at a density of 10.000 or 15.000 cells/well, respectively. Transient transfections were performed using 100 ng of reporter vector pGL4.29[luc2P/CRE/Hygro] (Promega), 40 ng of pGL4.74 (Renilla), as internal control for transfection efficiency, and 10 ng of expression plasmid pCMV-SPORT6-hTGRS The NIH Mammalian Gene Collection clone MGC: 40597 (Invitrogen). The pGEM vector was added to normalize the amounts of DNA transfected in each assay (2 μg). Twenty-four hours post-transfection the cells were stimulated with increasing concentrations of compound Ih3e for 18 h. Control cultures received vehicle (0.1% DMSO) alone. The cells were then lysed by adding 75 μl of Dual-Glo Luciferase Reagent (Promega) to 75 μl of medium containing cells/well. Renilla luciferase activity was measured by adding a volume of Dual-Glo Stop & Glo reagent and original culture medium. Luciferase activities were expressed as ratio between luciferase unit and renilla luciferase unit. Each data point is the average of triplicate assays. Each experiment was repeated at least three times.

TABLE 3A

Direct comparison of 6-ethyl vs. 6-methyl substituted 23-methyl cholic acid

| Cmpd No | Reference Standard LCA (4.5 ± 2.4 μM) CA (69 ± 24 μM) | TGR5 I exp (EC50 = μM) | TGR5 II exp (EC50 = μM) | FXR I exp (EC50 = μM) | FXR II exp (EC50 = μM) |
|---|---|---|---|---|---|
| Ih3e | [structure] | 0.8 | 1.1 | 53 | 23 |
| Ih3 | [structure] | 1.7 | 3 | 10 | 7.8 |

*The results show in Table 3A were generated using the procedures described directly above.

Compound having an alpha-ethyl group at the C-6 position on the bile acid ring are preferred. More specifically, compounds having an alpha ethyl group at the C-6 position of the 23-methyl cholic acid are the most preferred. As shown in Table 3A above, compounds having an alpha-ethyl group at the C-6 position are surprisingly and unexpectedly more potent than the corresponding C-6 alpha-methyl derivative.

Example 9

Metabolic Activities of Oleanolic Acid and 6-Ethyl, 23-Methyl-cholic Acid (Ih3e) in a Diet-Induced Obesity Mouse Model The goal of the study is to define whether TGR5 agonists (oleanolic acid (OA) or 6 ethyl, 23-methyl cholic acid (Ih3e) correct the development of obesity and associated insulin-resistance in vivo. To test this possibility, OA/Ih3e were administered via food administration for 16 weeks to male C57BL6J mice that had been previously subjected for 10 weeks to a high fat diet.

II—Protocol

In a previous study, OA was observed as a selective TGR5 agonist that did not cause food aversion Animals treated with a dose of 100 mg/kg/day of OA showed, however, some signs of toxicity, whereas a lower dose was well tolerated. Therefore, OA was administered at the dose of 50 mg/kg/d in this study.

In vitro studies have identified Ih3e as a potent and selective TGR5 ligand. No problems with toxicity were expected with Ih3e, which was administered at ~50 fold lower concentration.

For this study, 48 male C57BL6J mice (5 weeks of age) were divided in two groups: one group of 24 (group 1, 2&3) animals received chow diet whereas the other 24 received a high fat diet for a period of 10 weeks (group 4,5&6). The animals were then analyzed during a period of 16 weeks. Five groups of 10 animals were assigned as follows:
1: chow diet
2: chow diet+OA 50 mg/kg/day
3: chow diet+6Et23MeCA (Ih3e) 30 mg/kg/day
4: high fat diet
5: high fat diet+OA 50 mg/kg/day
6: high fat diet+6Et23MeCA (Ih3e) 30 mg/kg/day
During the entire study, body weight and food intake was monitored twice weekly.

Week-2: Body composition was analyzed, for all groups, by dual energy X-ray absorptiometry (dexascan).

Week-1: Serum levels of transaminases, glucose, triglycerides, cholesterol, HDL-C, LDL-C and insulin were measured in all groups after a fasting period of 12 h and mice were then placed on the diets as indicated (Day 0).

Week 2: Serum levels of transaminases, glucose, triglycerides, cholesterol, HDL-C, LDL-C and insulin was measured in all groups after a fasting period of 12 h (Day 14).

Week 4: Glucose tolerance was determined by subjecting all the animals to an intraperitoneal glucose tolerance test (IPGTT). Animals were fasted for 12 h prior to this test. Nocturnal energy expenditure of groups 1, 4, 5 and 6 (chow diet, high fat diet and high fat diet OA/6Et23MeCDCA (Ih3e) was measured by indirect calorimetry.

Week 8: Body weight composition was again analyzed by dexascan for all groups. Serum levels of transaminases, glucose, triglycerides, cholesterol, HDL-C, LDL-C and insulin were measured in all groups after a fasting period of 12 h (Day 56).

Week 9: Circadian activity of groups 4, 5 and 6 (high fat diet fed mice) was studied during a period of 30 h.

Week 10: Measurement of blood pressure and heart rate was performed on groups 4, 5 and 6.

Week 11: Rectal temperature of all animals was measured at room temperature at 10:00 am.

Circadian activity measurement was performed on groups 1, 2, 3 and 4.

Week 12: Glucose tolerance was analyzed by performing an intraperitoneal glucose tolerance test (IPGTT) on groups 4, 5 and 6. During the IPGTT, blood was also collected to analyze insulin levels. Animals were fasted 12 h prior to these tests. Feces were collected in all groups over a 24 h time period and fecal lipids content was measured.

Week 16: Cold test was performed on all animals by measuring body temperature of animals exposed to 4° C.

Three days later, animals were sacrificed. At sacrifice, blood was collected and analyzed for: plasma lipids (TC, TG, HDL-C, FFAs); liver functions (ALAT, ASAT, alkaline Pase, γ-GT); glucose and insulin; lipoprotein profiles of selected groups of plasma (size-exclusion chromatography).

Liver, small intestine, adipose tissues (WAT and BAT), pancreas, heart and muscle were collected, weighed and kept for further analyses including: standard histology (HE staining, succinate dehydrogenase staining, oil-red-O staining and cell morphology); tissue lipid content; electron microscopy on BAT and muscle to analyze mitochondria; RNA isolation for expression studies of selected genes involved in metabolism and energy homeostasis by quantitative RT-PCR; Protein extraction for the study of post-translational modifications such as acetylation of proteins of interest (e.g. PGC-1α).

III—Detailed Procedures

A—Animal Procedure and Diets

Animals Housing and Handling

Mice were group housed (5 animals/cage) in specific pathogen-free conditions with a 12 h:12 h (on at 7:00) light-dark cycle, in a temperature (20-22° c.) and humidity controlled vivarium, according to the European Community specifications. Animals were allowed free access to water and food.

Drinking Water

Chemical composition of the tap water was regularly analyzed to verify the absence of potential toxic substances at the Institut d'Hydrologie, ULP, Strasbourg. Drinking water was treated with HCl and $HClO_4$ to maintain pH between 5 and 5.5 and chlorin concentration between 5 and 6 ppm.

Diet

The standard rodent chow diet was obtained from UAR and the high fat diet was obtained from Research Diet. Mice were fed, either with chow diet (16% protein, 3% fat, 5% fiber, 5% ash) or with high fat diet (20% protein, 20% carbohydrate, 60% fat). Oleanolic acid and 6Et23MeCDCA (Ih3e) were mixed with either powdered chow diet or either powdered high fat diet in the following proportions: 0.5 g of OA/kg of food for the 50 mg/kg/day treatment and 0.08 g of 6Et23MeCA (Ih3e)/kg of food for the 10 mg/kg/day treatment. Pellets were then reconstituted. Control groups received food pellets as provided by the company. Due to the consistency of the high fat diet, no water was added in the mix with OA. In the case of the chow diet, which is harder to reconstitute, a minimal amount of water was added to the powder to reconstitute pellets, which were then air-dried. New batches of food were prepared weekly.

Blood Collection

Blood was collected either from the retro-orbital sinus under anesthesia or from the tail vein.

Anesthesia

For the dexa scanning experiment, animals were anesthesized with a mixture of ketamine (200 mg/kg)/Xylasine (10 mg/kg) administred by intra-peritoneal injection.

For the venipuncture, animals were anesthesized by inhalation of an isoflurane-$O_2$ mixture.

B-Biochemistry

The tests were performed with an Olympus AU-400 automated laboratory work station using commercial reagents (Olympus).

Analysis of Lipids and Lipoproteins

Serum triglycerides, total and HDL cholesterol were determined by enzymatic assays. Serum HDL cholesterol content was determined after precipitation of apo B-containing lipoproteins with phosphotungstic acid/Mg (e.g., Roche Diagnostics, Mannheim, Germany). Free fatty acids level was determined with a kit from Wako (e.g., Neuss, Germany) as specified by the provider.

Metabolic and Endocrine Exploration

Blood glucose concentration was measured by a Precision Q.I.D analyzer (e.g., Medisense system), using Medisense Precis electrodes (e.g., Abbot Laboratories, Medisense products, Bedford, USA). This method was validated, by comparing Precision Q.I.D analyzer values with classical glucose measurements. The Precision Q.I.D method was chosen since it requires a minimal amount of blood and can hence be employed for multiple measurements such as during an IPGTT. Plasma insulin (e.g., Mercodia, Uppsala, Sweden) was determined by ELISA according to the manufacturer's specifications.

C-Metabolic Testing

Lipoprotein Profiles

Lipoprotein profiles were obtained by fast protein liquid chromatography, allowing separation of the three major lipoprotein classes VLDL, LDL, and HDL.

Intraperitoneal Glucose Tolerance Test (IPGTT)—Oral Glucose Tolerance Test

IPGTT was performed in mice which were fasted overnight (12 h). Mice were either injected intraperitoneally (IP-GTT) with a solution of 20% glucose in sterile saline (0.9% NaCl) at a dose of 2 g glucose/kg body weight. Blood was collected from the tail vein, for glucose and insulin monitoring, prior and 15, 30, 45, 75, 90, 120, 150, 180 min after administration of the glucose solution. The incremental area of the glucose curve was calculated as a measure of insulin sensitivity, whereas the corresponding insulin levels indicate insulin secretory reserves.

Energy Expenditure

Energy expenditure was evaluated through indirect calorimetry by measuring oxygen consumption with the Oxymax apparatus (e.g., Columbus Instruments, Columbus, Ohio) during 12 h. This system consists of an open circuit with air coming in and out of plastic cages (one mouse per cage). Animals were allowed free access to food and water. A very precise $CO_2$ and $O_2$ sensor measured the difference in $O_2$ and $CO_2$ concentrations in both air volumes, which gave the amount of oxygen consumed in a period of time given that the air flow of air coming in the cage was constant. The data coming out of the apparatus was processed in a connected computer, analyzed, and shown in an exportable Excel file. The values were expressed as $ml \cdot kg^{-1} \cdot h^{-1}$, which is commonly known as the $VO_2$.

Determination of Body Fat Content by Dexa Scanning

The Dexa analyses were performed by the ultra high resolution PIXIMUS Series Densitometer (0.18×0.18 mm pixels, GE Medical Systems, Madison, Wis., USA). Bone mineral density (BMD in $g/cm^2$) and body composition were determined by using the PIXIMUS software (version 1.4×, GE Medical Systems).

D-Non-Invasive Blood Pressure Measurement and Pulse

The Visitech BP-2000 Blood Pressure Analysis System is a computer-automated tail'cuff system that is used for taking multiple measurements on 4 awake mice simultaneously without operator intervention. The mice were contained in individual dark chambers on a heated platform with their tails threaded through a tail cuff. The system measures blood pressure by determining the cuff pressure at which the blood flow to the tail was eliminated. A photoelectric sensor detects the specimen's pulse. The system generates results that have been shown to correspond closely with mean intra-arterial pressure measured simultaneously in the carotid artery. This allows reproducible values of systolic blood pressure and heart beat rate to be obtained. This required training of the animals for one week in the system.

E—Circadian Activity

Spontaneous locomotor activity was measured using individual boxes, each composed with a sliding floor, a detachable cage, and equipped with infra-red captors allowing measurement of ambulatory locomotor activity and rears. Boxes were linked to a computer using an electronic interface (e.g., Imetronic, Pessac, France). Mice were tested for 32 hours in order to measure habituation to the apparatus as well as nocturnal and diurnal activities. The quantity of water consumed was measured during the test period using an automated lickometer.

Figure 3A:
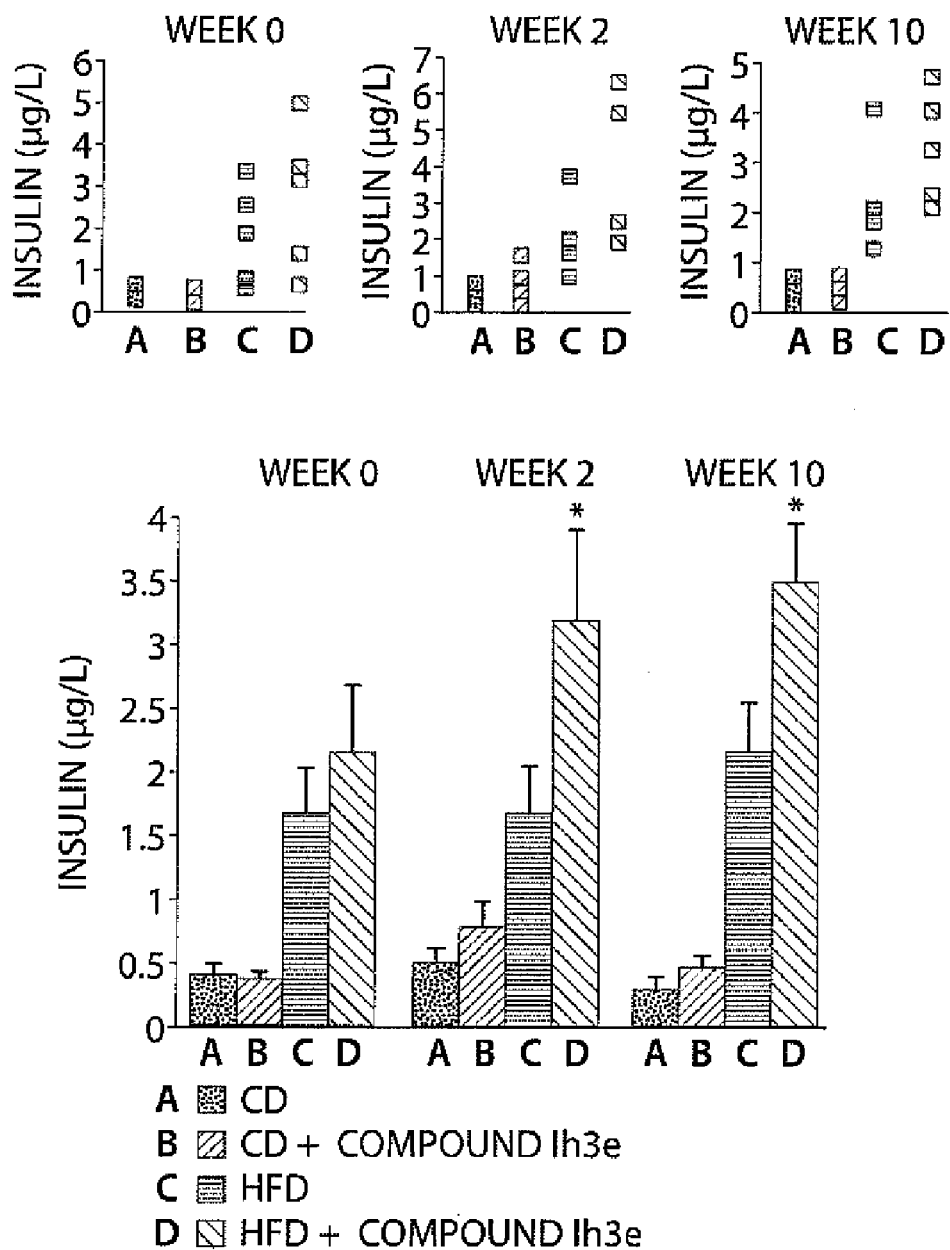
FIG. 3 is a series of graphs (A-B) that show the results of plasma insulin analysis and oral glucose tolerance test in chow and high fat fed mice treated with compound Ih3e.
Figure 3B:
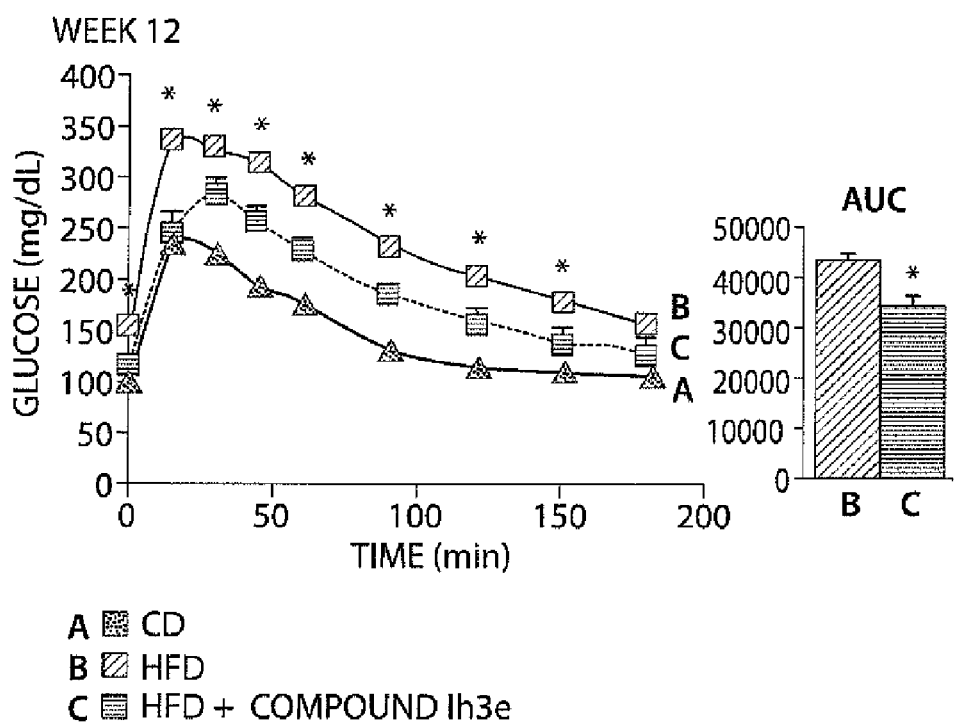
Figure 4:
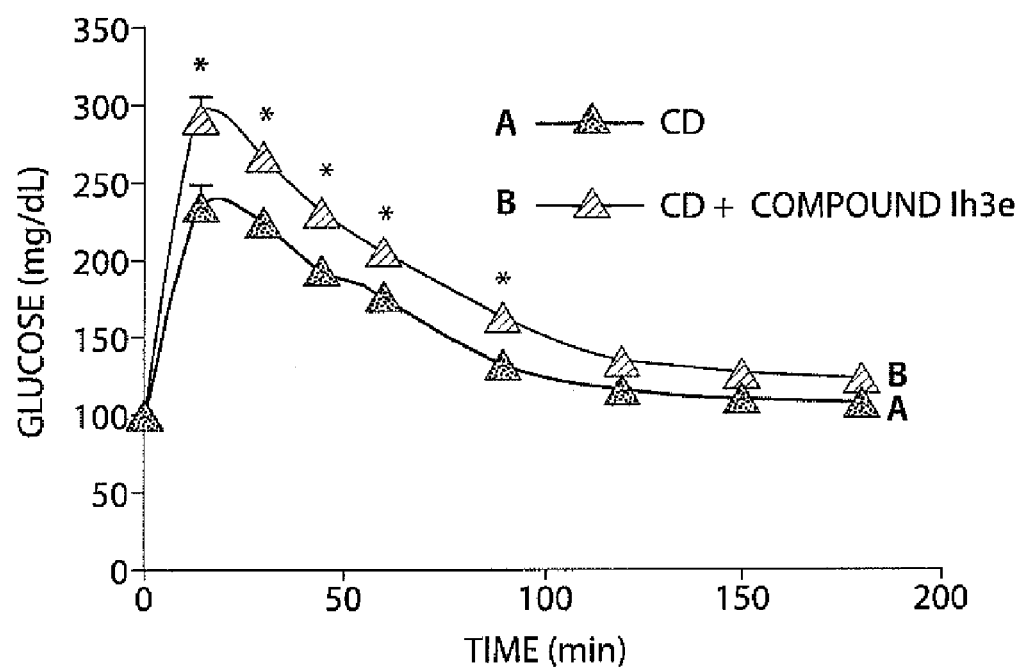
FIG. 4 is a graph that shows changes in glucose levels in chow diet mice treated with compound Ih3e.
Figure 5A:
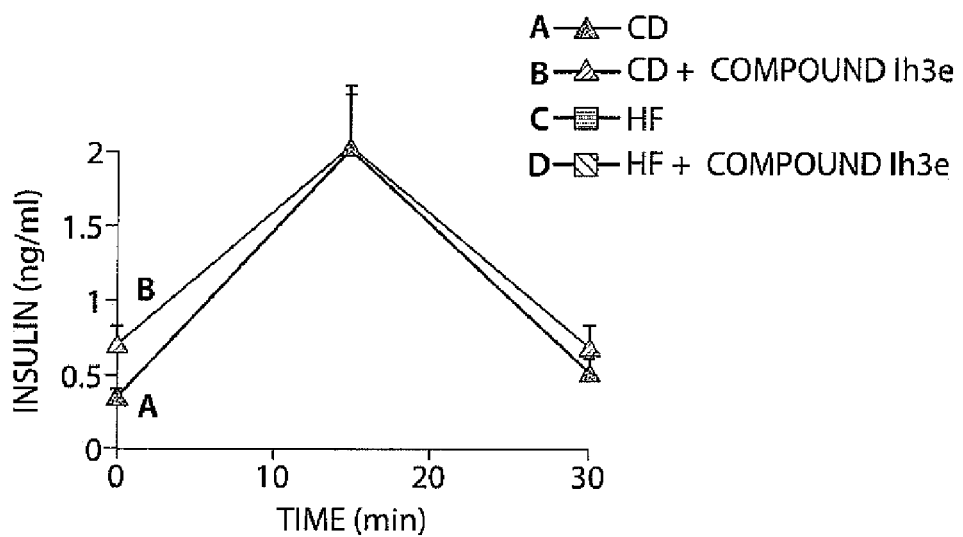
FIG. 5 is a series of graphs (A-D) that show insulin release in vivo after a test meal in chow and high fat fed mice treated with compound Ih3e.
Figure 5B:
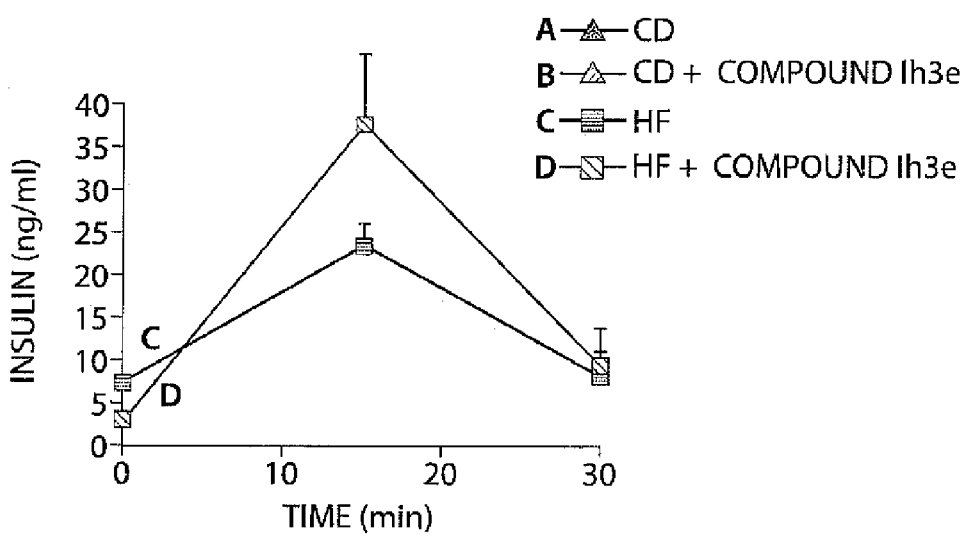
Figure 5C:
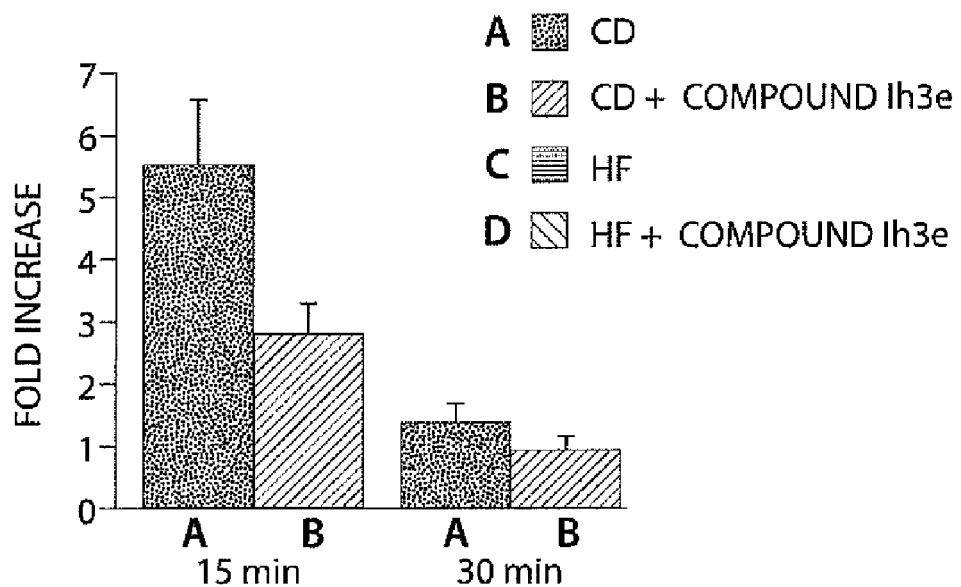
Figure 5D:
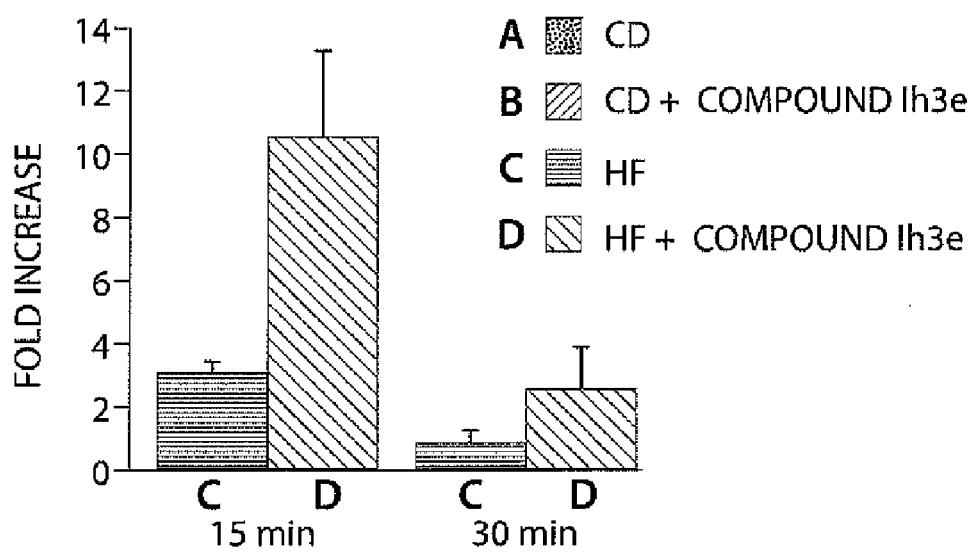
Figure 6:
FIG. 6 is a legend for a series of graphs (FIGS. 6A-6D) that shows oxygen consumption and CO2 production as measured by indirect calorimetry in chow and high fat fed mice treated with compound Ih3e.
Figure 6:
Figure 6:
Figure 6:
Figure 8A:
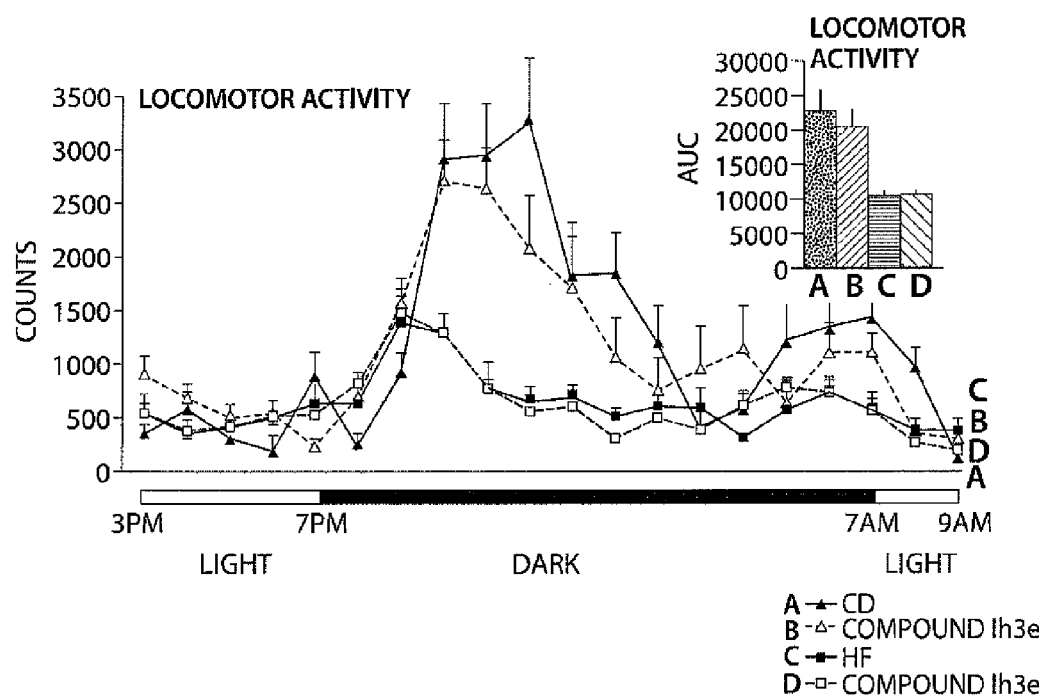
FIG. 8 is a series of graphs (A-B) that show locomotor activity and food and water intake for chow and high fat fed mice treated with compound Ih3e.
Figure 8B:
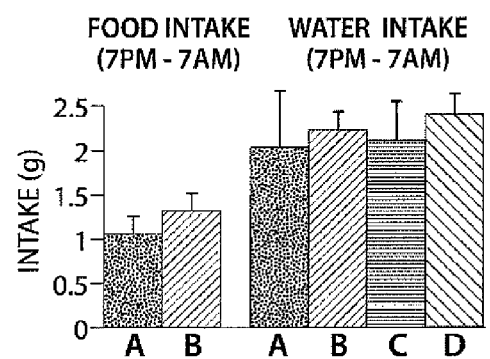
Figure 9C:
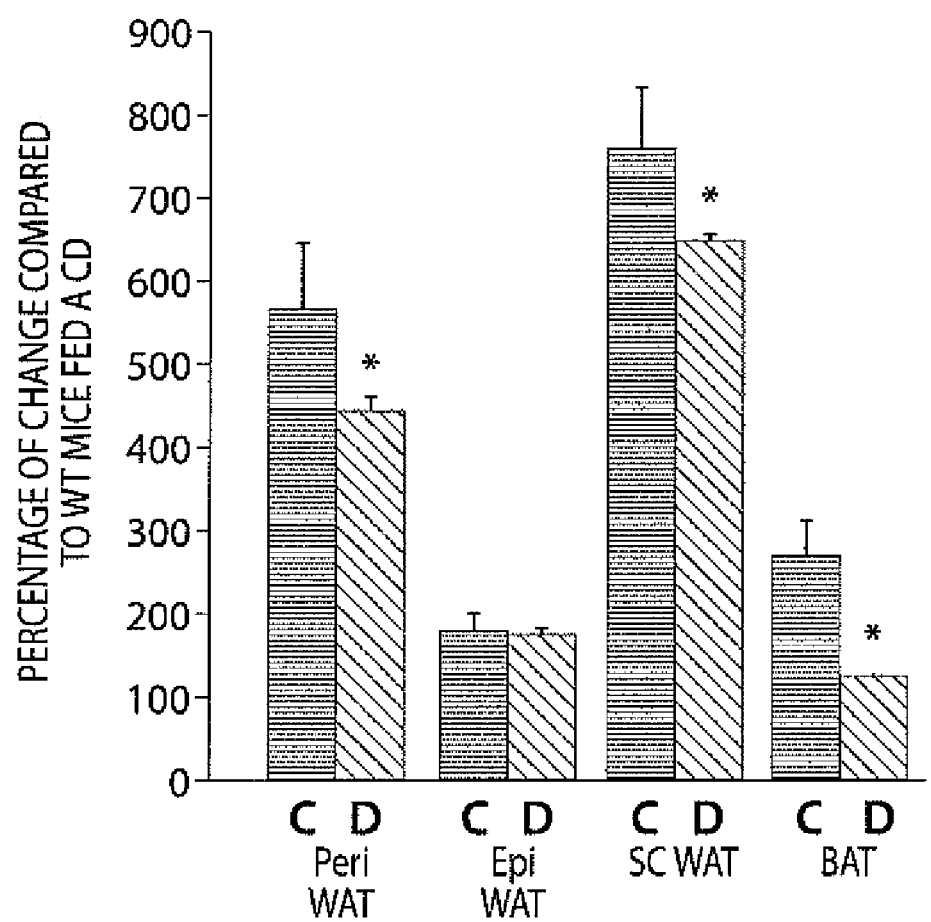
FIG. 9C is a bar graph that shows the percentage change in adipose tissue weight (peri WAT, epi WAT, Sc WAT, and BAT) in mice fed a high fat diet and in mice fed a high fat diet plus compound Ih3e.

The results of the study are shown in FIGS. 1-9. FIG. 1 shows the impact of compound Ih3e on body weight gain in chow and high fat fed mice. Body weight gain was measured over 16 weeks. High fat fed mice treated with compound Ih3e showed less weight gain than high fat fed mice treated with vehicle. FIG. 2 shows that compound Ih3e improves the metabolic profile of high fat fed mice. The results of blood plasma and heart rate analysis in diet-induced obese mice treated with compound Ih3e is shown in FIG. 2, including levels of blood glucose, liver enzymes (LDH, ASAT, and ALAT) and plasmid lipids (total cholesterol, HDL-chol, LDL-chol, and triglycerides). High fat fed mice treated with compound Ih3e showed lower blood glucose, liver enzymes, and plasma lipids than high fat fed mice treated with vehicle. The heart rate of high fed mice treated with compound Ih3e also showed a lower heart rate in comparision with high fat fed mice treated with vehicle. FIG. 3 shows that compound Ih3e improves glucose tolerance in high fat fed mice. After 10 weeks, plasma insulin levels were increased in both the chow fed and high fat fed mice treated with compound Ih3e in comparison to mice treated with vehicle as shown in FIG. 3A. After 12 weeks, glucose levels were shown to be lower in high fat fed mice treated with compound Ih3e as shown in FIG. 3B. FIG. 4 shows oral glucose tolerance test (OGTT) results as glucose levels over a period of 200 min in chow diet fed mice treated with compound Ih3e. FIG. 5 (graphs A-D) shows insulin release in vivo after a test meal. FIG. 5A shows insulin release over 30 min. FIG. 5B shows fold increase in insulin release compared to basal insulin level. Insulin levels peaked to higher levels at ~12 minutes in high fat fed mice treated compound Ih3e in comparison with mice treated with vehicle. FIGS. 5C and 5D show the fold increase in insulin release compared to basal insulin levels. The fold increase in high fat fed mice treated with compound Ih3e was greater at both 15 and 30 min time points as shown in FIG. 5D. FIGS. 6 (graphs A-D) and 7 (graphs A-C) show that compound Ih3e treated mice have an increase in respiratory exchange ratio (RER) upon HFD (high fat diet) which can be explained as linked to their improved insulin sensitivity which maintains their ability to oxidize glucose. FIG. 8 (graphs A and B) show locomotor activity and food/water intake of treated high fat fed and treated chow fed mice in comparison to vehicle treated. Food/water intake for mice fed a high fat diet and treated with compound Ih3e showed a slight increase in intake verses mice treated with vehicle. FIG. 9 (graphs A-C) shows changes in organ weight. FIGS. 9B and 9C show the percentage of change in body weight, liver, kidney, heart, peri WAT, epi WAT, Sc WAT, and BAT compared to weight in mice fed a chow diet. In all organs, high fat fed mice treated with compound Ih3e showed a reduced percentage change.

Example 10

Physico-Chemical Properties

Water Solubility

Solid BA (in protonated form for compound Ih3e) were suspended in 5 ml of 0.1 M HCl. The saturated solutions, after incubation for 1 week, were filtered on a Millipore filter (0.22 µpm) and the concentration of BA was measured by HPLC-ESI-MS/MS using C18 column (150 mm×2 mm i.d., 4 µm) and mobile phases of water containing 15 mM acetic acid pH 5 and acetonitrile. The flow rate was 150 µl/min. The mass spectrometry acquisition was performed in the multiple reaction monitoring mode using the ESI source in negative ionization. Water solubility was expressed as µmol/liter.

The water solubility of compound Ih3e is 99 pM a value higher than corresponding dihydroxy BA and comparable with that of CA (see Table 4).

TABLE 4

| Bile Acid | Ws[a] (µM) | CMC[b] 0.15 M Na+ (mM) | $ST_{CMC}$[c] Dyne/cm | $LogP_A$-[d] | Albumin Binding[e] (%) |
|---|---|---|---|---|---|
| CDCA | 32 | 3.2 | 45.5 | 2.2 | 93 |
| UDCA | 7.5 | 6.0 | 50.5 | 2.2 | 94 |
| CA | 273* | 11* | — | 1.1* | 50* |
| TCDCA | hs | 3.0* | — | 0.9* | 70* |
| TUDCA | hs | 2.2* | — | 1.1* | 67* |
| 6MUDCA | 28* | 4.2* | — | 1.3* | 80* |
| Ih3e | 99 | 1.4 | 50.1 | 1.4 | 62 |

[a]Ws: water solubility refers to BA as protonated species and therefore not evaluated for TCDCA, and TUDCA which are highly soluble (hs).
[b]CMC: Critical Micellar Concentration determined in 0.15 M NaCl water solution.
[c]$ST_{CMC}$: Surface Tension at CMC in 0.15 M NaCl water solution.
[d]$LogP_A$: 1-octanol-water partition coefficient of the studied bile acids as ionized species.
*values from literature.

The presence of a 23-methyl group in the compound Ih3e does not compromise the water solubility. Compound Ih3e exhibits a solubility value in the range of natural occurring BA and previous studied synthetic analogues. Further, given the relatively good albumin binding of compound Ih3e, circulation of compound Ih3e in the blood may be facilitated, thereby favoring the systemic targeting of TGR5 in peripheral tissues such as muscle and brown adipose tissue. Examples 9, 16 and 17 further support this hypothesis.

Critical Micellar Concentration (CMC)

The detergency i.e. the tendency to form micelles was evaluated for all the charged molecules which are soluble in water as Sodium salt (2 unit up the pKa). The critical micellar concentration (CMC) was determined by surface tension (ST) measurements using a maximum bubble-pressure method which give surface tension values slightly affected by potential impurities like static methods are. The tensiometer was a Sensadyne 6000 (Chem-Dyne Research Corp., Milwaukee, Wis.) equipped with two glass probes of 0.5 and 4.0 mm diameters connected to a source of nitrogen. The bubble frequency was 1 bubble/second in distilled water at 26° C. (P=2.7 atm) and the calibration was made with double-distilled water and methanol. The surface tension of BA sodium salts solutions in NaCl 0.15 M was measured at various concentrations inside the 0.13-50 mM range. The surface tension values were plotted against the logarithm of the bile salt concentration; the regression lines corresponding to the two parts of the curve (monomeric and micellar phases) were calculated using the method of least squares, and the intersection of the lines was taken as the CMC value. From the ST vs concentration curves the value of the surface tension at the CMC (equilibrium between monomers and multimers species) was also calculated giving information about the detergency power which is related to the size of the micelles with associate surface tension lowering capacity.

Figure 10:
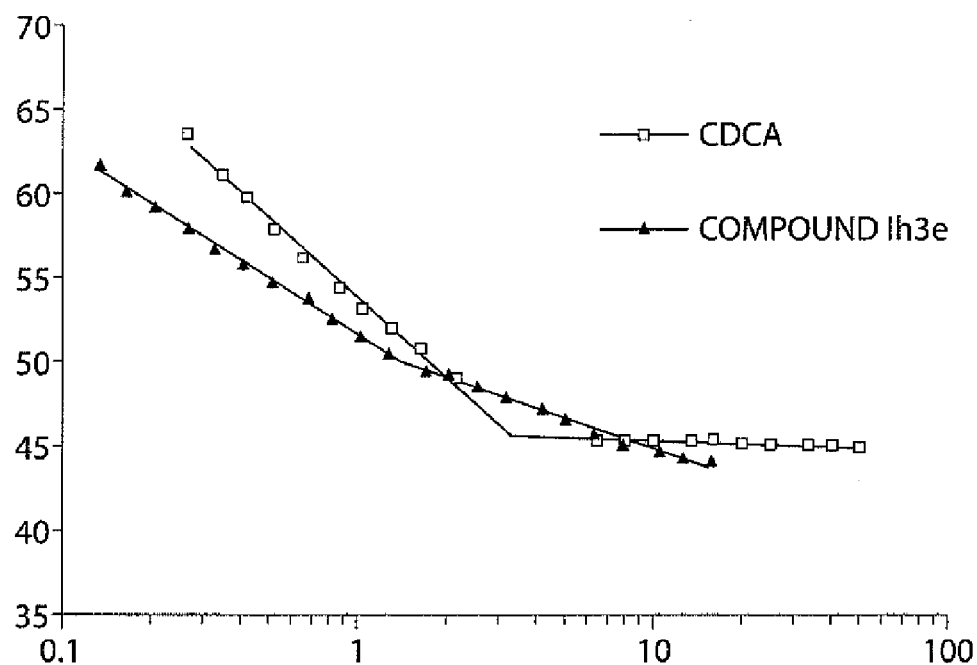
FIG. 10 is a graph that depicts the surface tension plotted against the logarithm of the concentrating of compound Ih3e (mM) in NaCl 0.15M.
Figure 11:
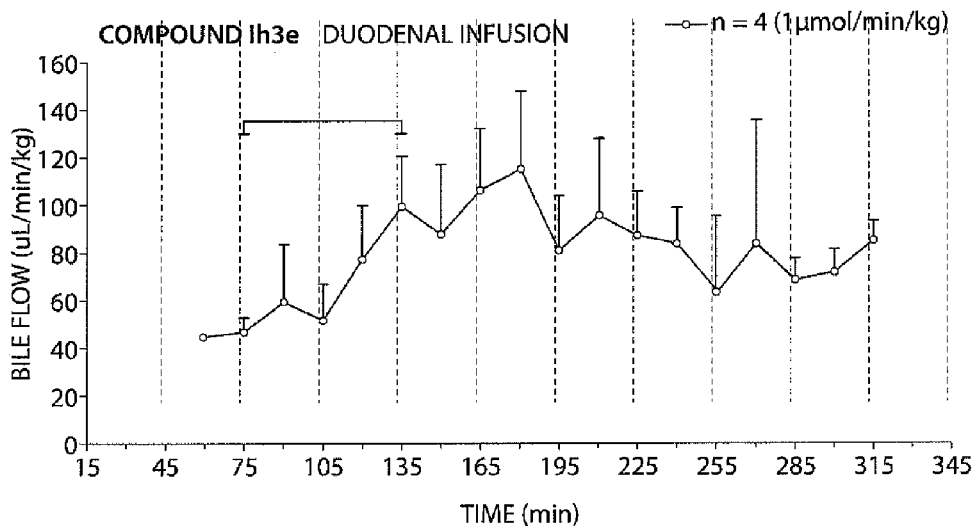
FIG. 11 is a bile flow chart for a duodenal infusion experiment performed using compound Ih3e.

The CMC was evaluated by surface tension measurements in non equilibrium conditions i.e. in conditions that impurities slightly affect the surface tension results (FIG. 10). Compound Ih3e presents a low CMC but a moderate detergency and surface tension lowering capacity as shown by the surface tension values at the CMC (low detergency means low toxicity to membrane or cells).

Octanol/Water Partition Coefficient

Since the sulphate and sulphonated analogues are always ionised at all pH values the octanol/water partition coefficient was measured for all molecules in ionized form and therefore the carboxy analogues were studied at high pH. 1-Octanol/water partition coefficient (log P) was evaluated using a conventional shake-flask procedure. The experiments were carried out on 0.1 mM bile salt solution buffered at pH 8 with 0.1 M phosphate buffer to ensure complete ionization of the BA; the log P values refer to the BA in the ionized form, not to the protonated species, and the initial concentration of each BA was below its own CMC value. The aqueous buffer was previously pre-saturated with 1-octanol, 5 ml of 1-octanol pre-saturated with water was then added and the samples were left to equilibrate for 2 weeks under continuous stirring at room temperature After centrifugation the two phases were carefully separated. BA concentration in the water phase was measured with HPLC-ESI-ES/MS using C18 column (150 mm×2 mm i.d., 4 µm) and, as mobile phases, water containing 15 mM acetic acid pH 5 and acetonitrile. The flow rate was 150 µal/min and the column was maintained at 45° C. The mass spectrometry acquisition was performed in the multiple reaction monitoring mode using the ESI source in negative ionization.

The carboxylated compound Ih3e with three hydroxyl groups in 3α,7α and 12α position presents a slightly higher lipophilicity in respect to the natural analogue CA, 1.4 vs 1.1 as a result of the presence of an ethyl in 6 position and a methyl in 23 position.

Albumin Binding

The extent of albumin binding was evaluated by equilibrium dialysis at a fixed BA-albumin ratio. BA was dissolved at a concentration of 100 µM in 5% bovine serum albumin-saline solution (pH 7.2) and left to stand for 24 h at 25° C. Two milliliters of this solution was dialyzed in cellulose sacs having a molecular weight cut-off of 12-14,000 against 25 ml of saline solution. The system was equilibrated by mechanical gently shaking for 72 h at 25° C. BA concentrations of the dialyzed solution (corresponding to the free unbound fraction) and of the starting solution were determined with HPLC-ESI-MS/MS in the same conditions of the previous analysis.

The percent of albumin binding was calculate from the initial BA concentration and from the unbound concentration in the dialyzed fraction. Data are reported in Table 4.

The percent albumin binding of compound Ih3e is slightly higher than CA and this derives from the presence of the 23 methyl and 6 ethyl groups.

Example 11

In Vitro Metabolic Stability in Human Stools Culture

Stability to Intestinal Bacteria

Example 11a

7α-dehydroxylation

Homogenized fresh human stools (500 mg) were transferred into sterile vials to which 5 mL of sterilized chopped meat-glucose medium (Scott Lab., Fiskville, R.I.) was added. BA was then added at a final concentration of 0.05 mM. Vials were incubated at 37° C.; then, at 0, 1, 2, 4, 8 and 24 h after the addition of the BA, the reaction was stopped with 150 µL of 30% KOH. The samples were centrifuged at 3500 rpm for 10 min; from the supernatant the BA were isolated by C-18 solid-phase extraction and analyzed by TLC and HPLC-ES-MS/MS.

Thin-layer chromatography (TLC), utilizing silica gel 0.25 mm thickness plates (Merck, Darmstat, Germany), was employed as the first screening test. The solvent system used for the separation of conjugated BA was composed of propionic acid/isoamyl acetate/water/N-propanol (3:4:1:2, v/v/v/v; solvent I), and that of the unconjugated BA was acetic acid/carbon tetrachloride/isopropyl ether/isoamyl acetate/water/N-propanol/benzene (1:4:6:8:2:2, v/v/v/v/v/v; solvent II). Separated BA were revealed with 5% phosphomolybdic acid ethanol solution.

Compound Ih3e was very stable when incubated in human stool cultures and even after 24 hour, more than 85% of the compound was recovered unmodified. On the contrary the reference natural analogue CDCA presented a half-life time of almost one hour and after 8 hours of incubation was almost completely metabolized (7-dehydroxylated) to form lithocholic acid.

After long time incubation for Ih3e, the 7-dehydroxylation and the intermediate formation of a 7-oxo derivative were practically abolished.

Example 11b

Figure 15:
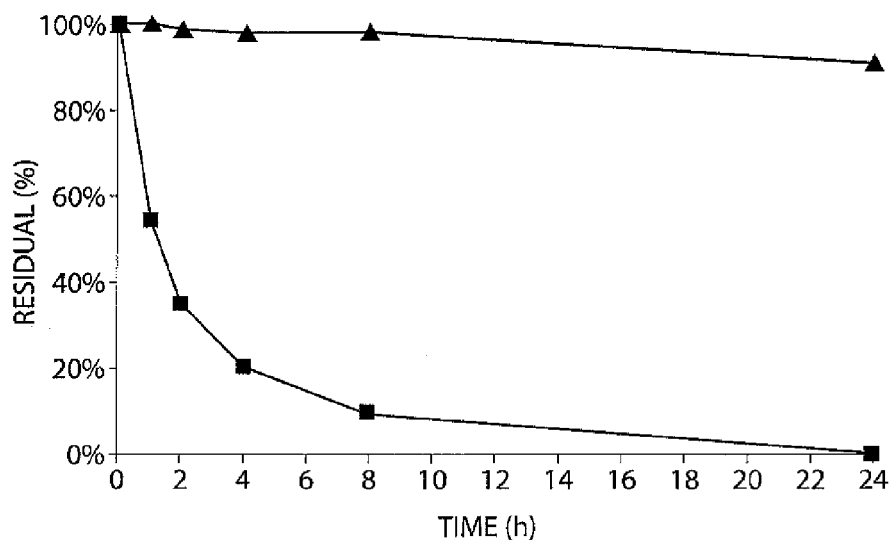
FIG. 15 is a graph that shows the stability of compound Ih3e (triangle) and CA (square) in human stool culture.

It is known that intestinal bacteria hydrolyze the C24 amide bond of taurine and glycine conjugated BAs and remove the 7α-hydroxyl group of CA, leading to the formation of toxic lipophilic secondary BAs such as deoxycholic acid (DCA) (Ridlon, J. M., et al., J. Lipid Res. 2006, 47, 241-259). To determine the sensitivity of compound Ih3e to intestinal flora-mediated 7-dehydroxylation, its metabolic stability was assessed in human stool broth culture as described in Roda, A., et al., J. Lipid Res. 1994, 35, 2268-2279. Compound Ih3e appears not to be sensitive to this process and was shown to be highly stable with more than 95% of the compound unmodified after 12 h of incubation. By comparison, more than 50% of CA (cholic acid) was metabolized after 1 h and up to 90% within 8 h (FIG. 15). It is likely that the extended stability of compound Ih3e is related to the alkylation of the C6 position which provides steric hindrance to the bacterial 7α-dehydroxylation process.

Side Chain Stability

According to these results the side chain of compound Ih3e was not modified by intestinal bacteria enzymatic activities.

These data suggest that the presence of the ethyl group in the C-6 position protects the 7-hydroxyl group toward oxidation or removal by steric hindrance. In addition compound Ih3e is very stable also for side chain metabolism. No minor metabolites have been found by HPLC-ES-MS/MS. These data suggest that in the lower intestinal content in presence of anaerobic bacteria these analogues are stable.

Example 12

Biliary Secretion and Metabolism of Compound Ih3e in Bile-Fistula Rat After Duodenal (id) and Femoral (iv) Administration

Example 12A

Aim and Rationale

Structural modifications of bile acids could affect their hepatic uptake, hepatic transports and secretion and intestinal absorption. Therefore the knowledge of the biliary secretion after both iv and id administration together their metabolism is a key point in compound selection for additional studies.

To evaluate the mode and efficiency of the intestinal absorption of compound Ih3e, the compound was administered both intravenously (femoral infusion) and orally (duodenal infusion) at the same dose and its biliary secretion rate was evaluated in bile fistula rat model.

The differences in the area under the curve of the biliary secretion vs time between iv and id administration account for its intestinal absorption and give information about its biovailability. Moreover, the hepatic and intestinal metabolism could be also quite different and therefore, the biliary secretion of compound Ih3e and its main hepatic metabolites was determined Choleretic Effect Duodenal Infusion The bile fistula rat model was developed at the University of Bologna Lab facilities. Compound Ih3e was administered at a dose of 1 μmol/kg/min (1 hour infusion) to a rat group via duodenal infusion (id). Rats had a bile fistula to collect bile samples at different times before, during, and after the infusion. For duodenal infusion experiment 6 rats (250±10 g) were treated. Bile samples were collected every 15 minutes for four hours. In addition, 3 control rats were treated with saline solution under the same conditions for times and sampling (duodenal control rats).

The duodenal infusion of compound Ih3e significantly increased the bile flow rate which reached the maximum value of about 120 μL/min/kg. This phenomenon started during the infusion period and continued for at least 3 hours.

Compound Ih3e presented the a potent choleretic effect and this is believed to be related to its structure; a methyl group in the C-23 position partially prevents conjugation and this molecule can undergo a cholehepatic shunt pathway. For comparison, the duodenal infusion of CDCA slightly increased the bile flow, which did not exceed 80 μL/min/kg.

Intravenous Infusion

Figure 12:
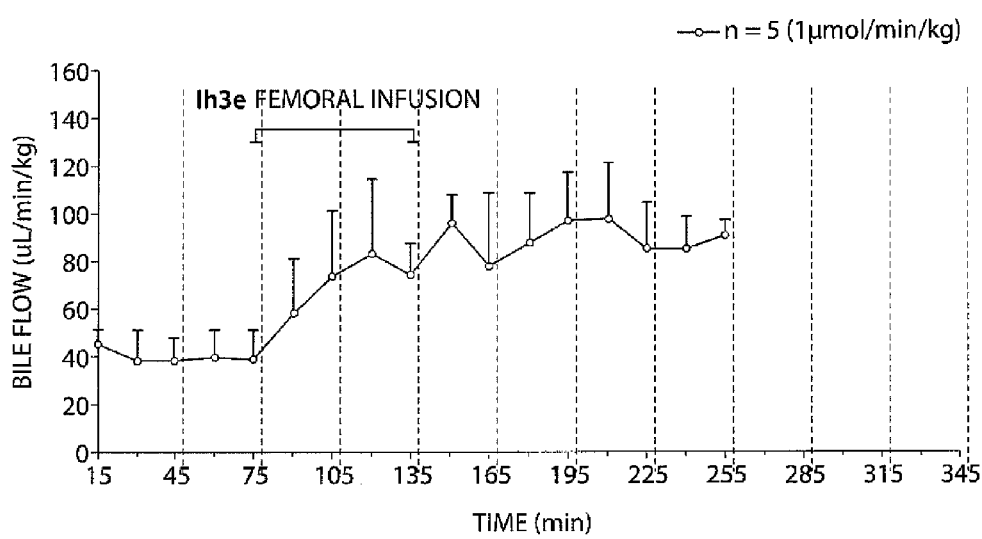
FIG. 12 is a bile flow chart for a femoral infusion experiment performed using compound Ih3e.

For femoral infusion experiment, 6 rats were treated. FIG. 12 shows bile flow during the study. Femoral infusion started after 75 minutes of steady-state and continued for 60 min. Bile samples were collected every 15 minutes for four hours. In addition, 3 rats were treated with 3% BSA saline solution under the same conditions for times and sampling (femoral control rats). The bile flow during iv infusion of 3% BSA saline vehicle (control, n=1) maintained a value ranging from 40 to 80 μL/min/kg for the entire period of the experiment.

The iv infusion of compound Ih3e significantly increased the bile flow rate and the phenomenon started 15 minutes after the beginning of the infusion period and continued for at least two hours. The choleretic effect was quite similar to that achieved in the id infusion experiment.

Biliary Secretion

Bile samples collected during the iv and id experiments were analyzed to determine the biliary secretion of compound Ih3e and its metabolites.

HPLC-ES-MS/MS Analysis

Pure crystalline powder of compound Ih3e was obtained from the R. Pellicciari laboratory of Perugia. Stock solutions in methanol at 1 mmol/L were prepared and working solutions were prepared by diluting appropriate volumes of the primary solution. Methanol and acetonitrile were of HPLC-grade purity. Ammonia was 30% and acetic acid was 99.8%. All reagents were obtained from Carlo Erba Reagents. HPLC-grade water was prepared by a Milli-Q system.

Sample Preparation

Rat bile samples were brought to room temperature, briefly stirred, and diluted 1:100 v/v (bile samples from duodenal orinfusion) and 1:100 or 1:200 v/v (bile samples from femoralr infusion) with 15 mM ammonium acetate buffer (pH=5.0):acetonitrile=70:30 (v/v). The final solution was transferred in an autosampler vial, and 10 μL was injected into the chromatographic column.

HPLC-ESI-MS/MS Method

Bile rat samples were analyzed by liquid chromatography-tandem mass spectrometry (HPLC-MS/MS) using electrospray (ESI) source in negative ionization mode. For liquid chromatography a Waters Alliance 2695 separation module coupled with autosampler was used. Autosampler was maintained at 7° C. Separation was performed on a Synergi Hydro-RP $C_{18}$ column (150×2.0 mm i.d., 4 μm particle size), protected by a SecurityGuard ODS 4×2.0 mm i.d. precolumn, both supplied from Phenomenex. Analyte was eluted using 15 mM ammonium acetate buffer (pH=5.00) as mobile phase A and acetonitrile as mobile phase B. Mobile phase B was increased from 30% to 64% in 10 min, then to 100% in 10 min, and held constant for 10 min. Flow rate was 150 μL/min and the column was maintained at 45° C. The column effluent was introduced into ESI source connected to a triple quadruple mass spectrometer (Quattro-LC, Micromass) operating in Multiple Reaction Monitoring (MRM) acquisition mode. Nitrogen was used as nebulizer gas at 100 L/h flow rate and as desolvation gas at 930 L/h. Ion source block and desolvation temperatures were set respectively to 80° C. and 180° C. Capillary voltage was 3.0 kV. MassLynx software version 4.0 was used for data acquisition and processing. In addition, using mass spectrometry both in single MS or tandem MS/MS configuration experiments were performed to identify metabolites.

Quantification

A 5-point calibration curve was prepared daily and injected in duplicate. Calibration samples were obtained in the 0.1 to 20 μmol/L concentration range prepared in mobile phase. Linear calibration curve parameters were obtained from the plot of the analyte peak area versus analyte concentration using a least squares regression analysis (weight=$1/x^2$). Correlation coefficients were ≧0.981.

The taurine conjugated metabolites of compound Ih3e were also estimated. Corrective factors, to take into account the different responses in ES-MS/MS between free and taurine conjugated species, were estimated and applied to the area values obtained from HPLC-MRM dataset chromatograms. Finally, calibration curves obtained for the free bile acids were used to estimate the taurine conjugated metabolites.

Pharmacokinetic (Biliary Secretion) of the Administered Analogues: iv Versus id Comparison The data refer to the secretion rate of the compound recovered in bile as such after duodenal and femoral infusion at a dose of 1 umol/Kg/min.

Table 5 shows concentration and secretion values for compound Ih3e obtained from bile rat samples collected during the duodenal infusion (1 h ranging from 75 to 135 min)

TABLE 5

Compound Ih3e concentration and secretion values obtained from rat bile samples collected during the duodenal infusion
(1 hour ranging from 75 to 135 minutes)

| | Ih3e (n = 4) | |
|---|---|---|
| Time (min) | Conc. (mmol/L) | Secretion (μmol/kg/min) |
| 90 | 0.007 | 0.0003 |
| 120 | 0.69 | 0.057 |
| 150 | 1.88 | 0.167 |
| 180 | 1.29 | 0.150 |
| 210 | 0.79 | 0.077 |
| 240 | 0.39 | 0.033 |
| 270 | 0.27 | 0.026 |
| 300 | 0.20 | 0.015 |

Table 6 shows concentration and secretion values obtained from bile rat samples collected during the femoral infusion (1 h ranging from 75 to 135 min)

TABLE 6

Compound Ih3e concentration and secretion values obtained from rat bile samples collected during the femoral infusion
(1 hour ranging from 75 to 135 minutes).

| | Ih3e (n = 5) | |
|---|---|---|
| Time (min) | Conc. (mmol/L) | Secretion (μmol/kg/min) |
| 75 | n.a. | —[a] |
| 90 | 1.9 | 0.1 |
| 120 | 3.1 | 0.23 |
| 150 | 3.4 | 0.31 |
| 180 | 2.3 | 0.2 |
| 210 | 1.06 | 0.105 |
| 240 | 0.55 | 0.049 |
| 270 | 0.27 | 0.018 |

[a]—: not calculated

TABLE 6A

Tauro-Ih3e concentration and secretion values estimated from rat bile samples collected during the duodenal infusion
(1 hour ranging from 75 to 135 minutes)

| | Ih3e (n = 4) | |
|---|---|---|
| Time (min) | Conc. (mmol/L) | Secretion (μmol/kg/min) |
| 90 | 0.017 | 0.001 |
| 120 | 0.63 | 0.051 |
| 150 | 0.68 | 0.053 |
| 180 | 0.75 | 0.091 |
| 210 | 0.68 | 0.063 |
| 240 | 0.60 | 0.054 |
| 270 | 0.64 | 0.074 |
| 300 | 0.74 | 0.053 |

TABLE 6B

Tauro-Ih3e concentration and secretion values estimated from rat bile samples collected during the femoral infusion
(1 hour ranging from 75 to 135 minutes)

| | Ih3e (n = 5) | |
|---|---|---|
| Time (min) | Conc. (mmol/L) | Secretion (μmol/kg/min) |
| 90 | 0.29 | 0.0101 |
| 120 | 0.50 | 0.044 |
| 150 | 0.43 | 0.043 |
| 180 | 0.51 | 0.045 |
| 210 | 0.33 | 0.031 |
| 240 | 0.21 | 0.019 |
| 270 | 0.059 | 0.0039 |

Figure 13:
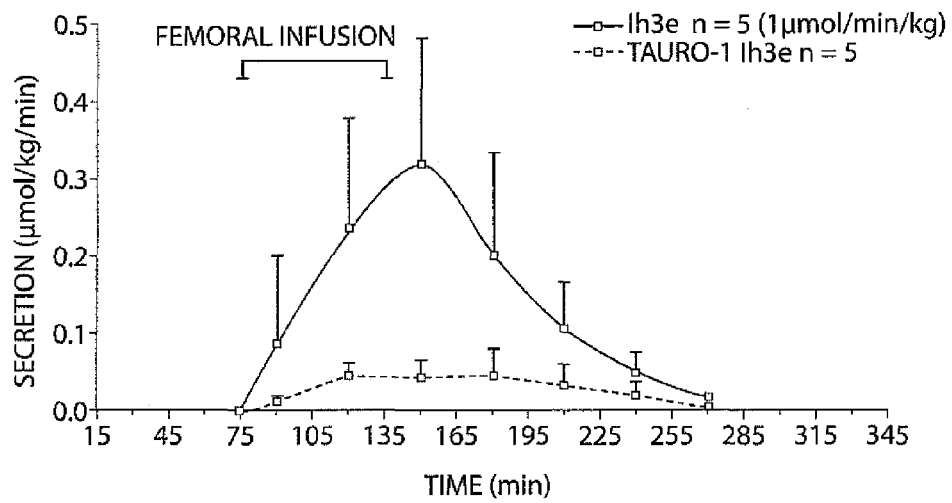
FIG. 13 is a graph that depicts secretion rates verses time in femoral and duodenal infusion experiments performed using compound Ih3e.
Figure 14A:
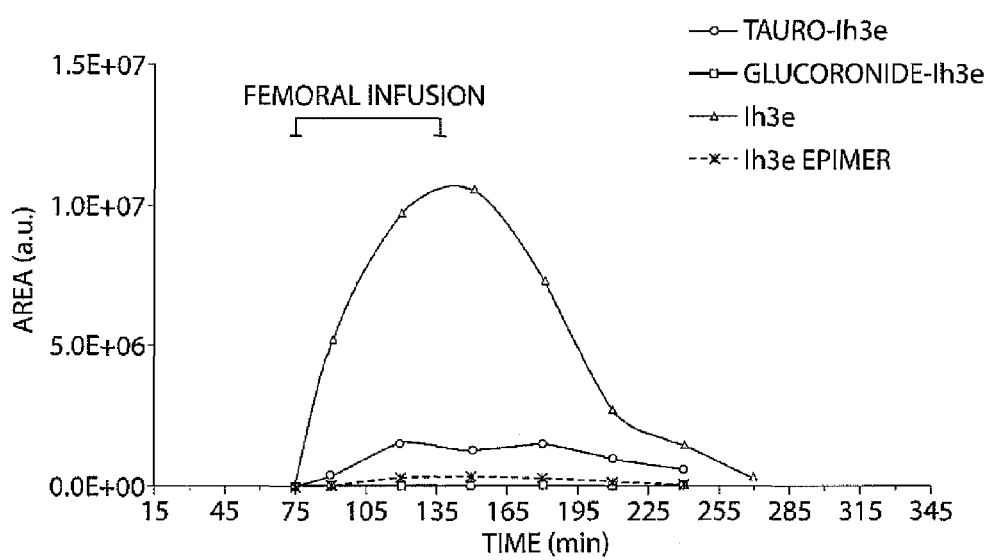
FIG. 14A that shows compound Ih3e and its main metabolites identified in bile using mass spectrometry in the iv experiment. Data are reported as absolute area values.
Figure 14B:
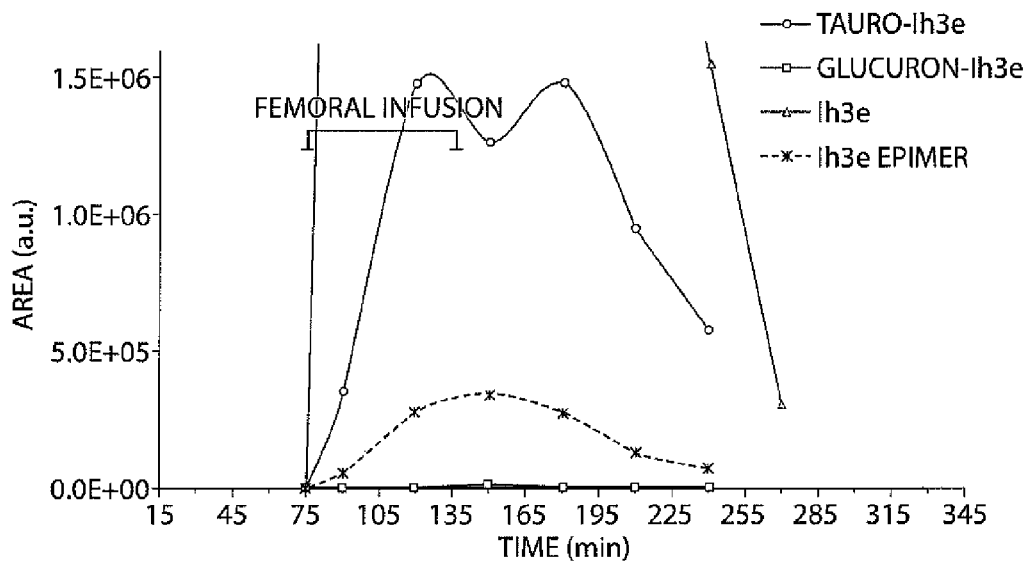
FIG. 14b is a zoom display of FIG. 14A.

The biliary secretion of compound Ih3e after iv administration was efficient and the compound was recovered in bile in a relatively high percentage. The kinetic profile indicated that the compound was efficiently taken up by the liver and secreted in bile partially as such and also, to a less extent, metabolized to for more polar compounds (FIGS. 13, 14a and 14b). Without wishing to be bound by any particular theory, it is believed that the presence of the methyl group in C-23 position hinders the conjugation process with taurine and glycine which is in part relevant for an efficient secretion of almost all natural occurring carboxylated BA; this is fundamental for dihydroxy BA and to a less extent for trihydroxy BA. The extent of its recovery in bile is also related to the administered dose. After id administration the recovery in bile is was slightly lower than the recovery after iv administration suggesting that the compound is not efficiently absorbed by the intestine (FIGS. 13, 14c and 14d) Considering the physicochemical properties, we expected that this compound could be absorbed by passive diffusion mechanism (LogP=1.44) and an active mechanism did not seem to be involved. The presence of three hydroxyl group allows the molecule on one side to be efficiently taken up by the liver and partially secreted into bile. It also prevents the molecule from being absorbed by the intestine.

Example 12B

The results in the Table shown below reveal that compound Ih3e has a potent choleretic effect, with the maximum bile secretion rate (SVO) being significantly higher than those of CDCA and CA.

TABLE

Biliary Lipid Secretion Parameters after iv and id Infusion at a Dose of 1 (μmol/min)/kg bw over 1 h of BAs[a]

| Compd | $SV_0$ id (iv) | $S_{BA}$ id (iv) | % free id (iv) | % conjug id (iv) |
|---|---|---|---|---|
| CDCA | 57 ± 7 | 0.7 ± 0.2 | 3 ± 1 | 96 ± 8 |
| | (51 ± 9) | (0.8 ± 0.1) | (4 ± 1) | (98 ± 5) |
| CA | 64 ± 6 | 1.0 ± 0.4 | 12 ± 2 | 90 ± 4 |
| | (78 ± 8) | (1.3 ± 0.2) | (8 ± 3) | (92 ± 6) |
| Ih3e | 112 ± 12 | 0.5 ± 0.2 | 94 ± 6 | 10 ± 5 |
| | (131 ± 11) | (0.7 ± 0.3) | (93 ± 5) | (7 ± 3) |
| R-EMCA | 81 ± 8 | 0.4 ± 0.2 | 68 ± 8 | 32 ± 7 |
| | (90 ± 5) | (0.5 ± 0.1) | (65 ± 4) | (26 ± 6) |
| Saline | 46 ± 4 | 0.4 ± 0.1 | | |
| | (48 ± 4) | (0.4 ± 0.1) | | |

[a]Data represent average values and standard deviations of six independent experiments.
The vehicle used for the id administration was saline solution.
The vehicle used for the iv administration was 3% BSA saline solution, pH 7.2.
$SV_0$: maximum bile secretion rate ((μL/min)/kg bw).
$S_{BA}$: maximum BA secretion rate ((μmol/min)/kg bw).
% free: percentage of the administered dose recovered in bile of the molecules as such.
% conjugate: percentage of the administered dose recovered as conjugated BA.

Accordingly, the results in the table above show that compound Ih3e is resistant to conjugation, with more than 90% of the compound being secreted into the bile in its unconjugated form after intravenous or intraduodenal infusion. In contrast CDCA and CA cannot be secreted into bile as such, requiring the conjugation step. Thus, it is envisaged that the C23(S) methyl group of compound Ih3e prevents carboxyl CoA activation and subsequent conjugation, thereby favoring its cholehepatic shunt pathway with a ductular absorption and a potent choleretic effect.

To further study the influence of the configuration of the C23 methyl group on the side chain amidation and choleretic effect of the compound, similar analyses were also carried out on the other epimer, namely, 6α-ethyl-23(R)-methylcholic acid (R-EMCA in the table above). The inspection of the maximum bile secretion rate (SVO) shows that the choleretic effect of R-EMCA is still higher than CA, though lower than compound Ih3e. As a result, these data suggest that the orientation of the C-23 methyl group is important for the conjugation of the carboxyl group, with the methyl moiety fitting poorly in the catalytic pocket of the conjugating enzyme in the case of the C23(S) epimer. Altogether, these results show that compound Ih3e is efficiently absorbed and undergoes enterohepatic cycling albeit with relatively little liver conjugation. The low rate of conjugation may also allow compound Ih3e to escape hepatic first pass clearance and reach the systemic blood circulation.

Hepatic Metabolism

For a preliminary screening the search of the possible metabolites was performed on the basis of the expected compounds according to previous experiments and data and the structure and physicochemical properties of compound Ih3e.

Compound Ih3e is mainly secreted as parent compound (unmodified) and was only slightly metabolized by the liver. The main metabolite was the taurine conjugate and the mono glucuronide was present in a low amount. The metabolism is similar for both iv and id administration. Considering the recovery in bile, we expected to identify other metabolites. The presence of the methyl group in the C-23 position hinders the conjugation process with taurine and glycine which is in part required for an efficient secretion of almost all natural occurring carboxylated BAs; this is fundamental for dihydroxy BA and to a less extent for trihydroxy BA since they are already quite polar. Formation of glucuronides could became relevant if administered higher doses.

Figure 14C:
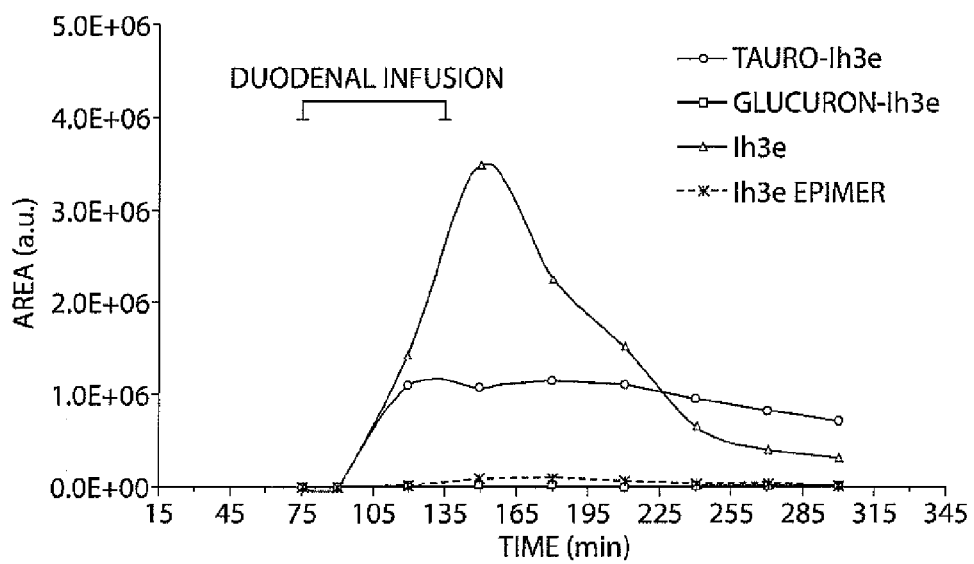
FIG. 14C shows compound Ih3e and its main metabolites identified in bile using mass spectrometry.
Figure 14D:
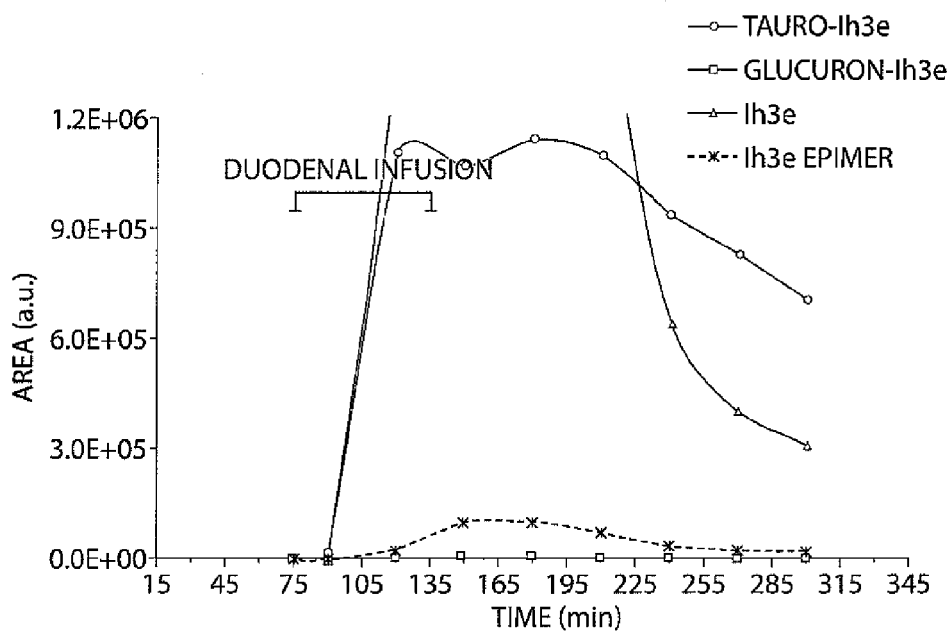
FIG. 14D is a zoom display of FIG. 14C.

FIG. 14a shows compound Ih3e and its main metabolites identified in bile using mass spectrometry in the iv experiment. Data are reported as absolute area values (n=5). FIG. 14b is a zoom display of FIG. 14a. FIG. 14c shows compound Ih3e and its main metabolites identified in bile using mass spectrometry in the di experiment. Data are reported as absolute area values. FIG. 14d is a zoom display of FIG. 14c.

In summary, compound Ih3e is moderately hydrophilic and has a mild detergency. Its hepatic uptake seems efficient. The biliary secretion is also efficient considering that the compound is secreted mainly unmodified and, to a limited extent, conjugated with taurine. The intestinal absorption is also efficient, even if it is not complete, and the molecule does not require extensive hepatic metabolism at the administered dose to be secreted into bile. The presence of the methyl group in the C-23 position prevents extensive conjugation with taurine for biliary secretion. Therefore, there is an increase in the hepatic resonance time of the molecule which undergoes a cholehepatic shunt pathway, which is responsible for its potent choleretic effect.

Example 13

In Vitro Toxicity on HepG2 Cell

Compounds of the invention were evaluated for in vitro toxicity using a HepG2 cell assay. HepG2 cell cytotoxicity was determined by monitoring ATP decrease and HepG2 cell apotosis was determined by monitoring caspase-3 activation. The results are shown in Table 7.

Cytotoxicity

Cell viability was measured using Perkinelmer ATP-Lite 1 STEP. ATP is a marker for cell viability because it is present in all metabolically active cells and the concentration declines very rapidly when the cells undergo necrosis or apoptosis. HepG2 cells ($1\times10^4$) were seeded in 96 wells plate and stimulated with 10-fold dilutions from 1 nM to 300 μM of the compound Ih3e for 4 h at 37° C. The plates were equilibrate at RT for 10 minutes and 100 μl of ATP-Lite 1 STEP Reagent was added to 100 μl of culture medium containing cells. Luminescence was read with Victor Light (PerkinElemr). The experimental signal was subtracted from background. Tamoxifen was used as positive control of cellular cytotoxicity, while negative control was the non treated cells.

Apoptosis

Caspases participate in the molecular control of apoptosis and TruPoint Caspase-3 Substrate enables sensitive, robust and homogeneous time-resolved fluorescence assay of caspase-3 activity. Human Hepatocytes cells (HepG2) were seeded ($1\times10^4$) in 96 well plate with HepG2 medium without sodium pyruvate. The cells were stimulated 4 h at 37° C. with serial dilutions of test compound Ih3e from 1 nM to 300 μM in triplicate. Staurosporin was used as positive control of apoptotic cells. Negative controls were: 1. Unstimulated cells; 2. Medium alone without cells; 3. Cells incubated without the caspase substrate. Lyses buffer and Caspase-3 Substrate were added to the cells and 1 hour and 24 hours after fluorescence was measured with EnVision.

Necrosis

The cellular necrosis was analyzed by measuring the release of Lactato DeHydroxegenase (LDH) from the necrotic cells using Promega's CytoTox ONE Homogeneous Membrane Integrity Assay. HepG2 cells ($1\times10^4$) were seeded in a 96 well plate. After 18 hours of incubation fresh medium without Sodium Pyruvate and Serum free was replaced and compound Ih3e were added in dose response from 0.1 μM to 500 μM. Triton 1% was used as maximum LDH release control. Tamoxifen was used as inducer necrosis. The plated cells were placed back into the incubator for an additional 4 hours. The supernatant was transferred in a new plate and the same volume of CytoTox-ONE Reagent was added to the plate. After 1 h of incubation the fluorescence was read with the EnVision multilabel plate reader with an excitation wavelength of 560 nm and an emission of 590 nm.

TABLE 7

In Vitro Toxicity on HepG2 cells

| Compound | CYTOTOXICITY ATP decrease $EC_{50}$ (μM) | APOPTOSIS Caspase-3 activation $EC_{50}$ (μM) | NECROSIS LDH release $EC_{50}$ (μM) |
|---|---|---|---|
| Staurosporine$^{(apoptosis)}$ | 15 | 3 | n.d. |
| Tamoxifen$^{(Necrosis)}$ | 47 | 4 | 35 |
| LCA | 84 | 65 | 105 |
| CDCA | 650 | 890 | >1000 |
| UDCA | >1000 | n.d. | n.d. |
| CA | >1000 | n.d. | n.d. |
| Compound Ih3e | >1000 | n.d. | n.d. |

Example 14

NR Selectivity Assays

The selectivity of compounds of the invention was evaluated using assay methods known in the art. Specifically, the following assay methods were used:

FXR and LXR: Coactivator Recruitment (alphascreen);

TGR5: cAMP level on human intestinal cell line (NCI-H716);

PXR: Ligands Competition assay (Binding Assay)

CAR: Coactivator Recruitment (Lanthascreen)

Table 8 shows the results of these assays.

TR-FRET Coactivator Assay

Lanthascreen assay (Invitrogen) was used for nulear receptor selectivity assay. The kit uses a terbium-labeled anti-GST antibody, a fluorescein-labeled coactivator peptide, and a NR ligand-binding domain that is tagged with glutathione-S-transferase (GST) in a homogenous mix-and-read assay format. The assays were performed in 384 microwell plate (PerkinElmer). A 20 μl total assay reaction included 5 nM GST-tagged NRs, 125 nM of coregulator peptide, 5 nM of TB-anti-GST tagged antibody (terbium-anti-glutathione S transferase tagged), 5 mM DTT and varying concentration of compound Ih3e in the assay buffer supplied by Invitrogen. The negative control was devoid of the compound Ih3e but contained everything else contained in the agonist well. Following 1 hour incubation in the dark, TR-FRET measurements were made in the Envision. The emission ratio 520/495 was plotted against varying ligand concentrations. The data was analyzed using GraphPad Prism using the sigmoidal curve equation with variable slope to obtain $EC_{50}$ values.

TABLE 8

NR Selectivity Assays

| Compound (Reference Standard) | FXR Activation (CDCA = 10-20 µM) $EC_{50}$ (µM) | TGR5 Activation (LCA = 4-8 µM) $EC_{50}$ (µM) | LXRα Activation (T0901317 = 0.08 µM) $EC_{50}$ (µM) | PXR Binding (SR-12183 = 0.013 µM) $IC_{50}$ (µM) | CAR Activation (CITCO = 0.005 µM) $EC_{50}$ (µM) | PPARδ Activation (GW0742 = 0.004 µM) $EC_{50}$ (µM) | VDR Activation (Di-HydroxyVitD3 = 0.005 µM) $EC_{50}$ (µM) |
|---|---|---|---|---|---|---|---|
| CDCA | 20 | 30 | No activity | >250 | >250 | No activity | No activity |
| LCA | No activity | 4-8 | No activity | 23 | No activity | No activity | No activity |
| CA | No activity | 30 | No activity | No activity | No activity | No activity | No activity |
| UDCA | >150 | No activity | No activity | >250 | >250 | No activity | No activity |
| Compound Ih3e | 175 | 0.9 | No activity | 110 | >250 | No activity | No activity |

FXR, LXR, CAR, PPARδ, VDR: Coactivator Recruitment Assay;
TGR-5: cAMP level on human intestinal cell line, NCI-H716;
PXR: Ligands Competition assay;

Example 15

Compound Stability

The stability of compound Ih3e was determined using methods known in the art. Cellular fraction concentration was 1 mg/ml over a time course of 0-15-30-60-120-240-360-1440 minutes. Positive controls were testosterone (1000 ng/ml); 7-hydroxy coumarine (1296 ng/ml); benzoic acid (2440 ng/ml) over a time course of 0-10-20-40-60-120. The analytical method used was LC/MS separation on C18 column by gradient polarity; acquisition performed in Single Ion Monitoring. The results are shown below in Table 9.

TABLE 9

| | Ih3e | Positive Controls | | |
|---|---|---|---|---|
| | | Testosterone | 7-Hydroxy Coumarine | Benzoice Acid |
| | | $T^{1/2}$ (expressed in minutes) | | |
| Human liver S9 fraction | 725 | 39 | 8.5 | 236 |
| Human liver Microsomes | 1942 | 8-20 | — | — |

Example 16

Release of GLP-1 Ex Vivo

Figure 16:
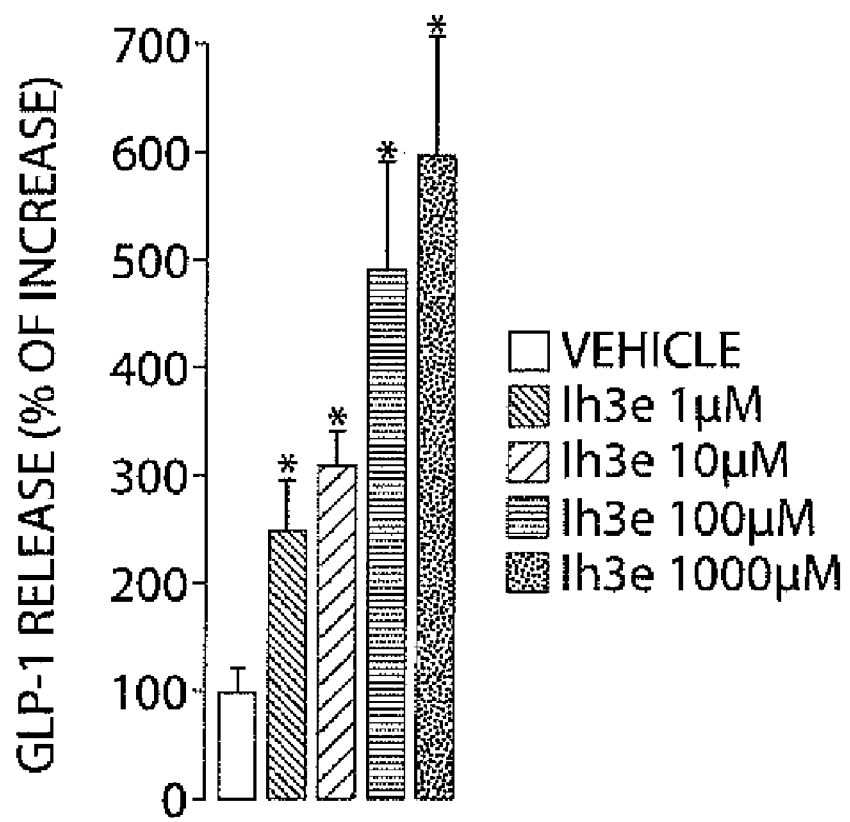
FIG. 16 is a bar graph that shows the dose-dependent release of GLP-1 ex vivo induced by compound Ih3e.

FIG. 16 shows that compound Ih3e dramatically and dose-dependently induces the release of GLP-1 ex vivo. FIG. 16 shows the impact of 1 h exposure to indicated concentration of compound Ih3e on GLP-1 release ex vivo in ileal explants isolated from 18-weeks HF-fed TGR5-Tg male mice (n=4). The data are represented as mean±SE: Student's unpaired t-test, (*) P<0.05, compound Ih3e treated ileal explants vs vehicle treated.

The following Experimental Procedures are utilized in Examples 17-21.
Chemicals and Reagents All biochemical reagents were purchased from Sigma-Aldrich unless indicated. The DPP4 inhibitor (DPP4i) sitagliptin was a kind gift from Dr. C. Ullmer (Hoffmann-La Roche). Compound Ih3e was synthesized as previously described (Macchiarulo et al., 2008; Pellicciari et al., 2007).
Cell Culture In vitro experiments were carried out in STC-1 or NCI-H716 cells treated with vehicle (DMSO) or Compound Ih3e.

Compound Ih3e was assessed for its agonistic activity on TGR5 as previously described (Macchiarulo et al., 2008, J. Chem. Inf. Model. 48, 1792; Pellicciari et al., 2007, J. Med. Chem. 50, 4265-4268). cAMP production was performed as described (Sato et al., 2008, J. Med. Chem. 51, 1831; Watanabe et al., 2006, Nature 439, 484). Cox activity was evaluated by following the oxidation of fully reduced cytochrome c (Sigma) at 550 nm (Feige et al., 2008b, Cell Metab. 8, 347). ATP/ADP ratio and GLP-1 release were measured according to the manufacturers' instructions (Biovision and Millipore, respectively). Primary brown adipocytes were prepared as previously described (Watanabe et al., 2006, Nature 439, 484), and ileal explants were prepared according to an established method (Cima et al., 2004, J. Exp. Med. 200, 1635-1646).
Intracellular Calcium Quantification NCI-H716 (40,000 cells) was seeded in 96-well black plates coated with Matrigel (BD Biosciences). Seventy-two hours after transfection, cells were washed twice in assay buffer (HBSS1x, 20 mM HEPES [pH 7.4]) and assayed for intracellular calcium with Fluo-4 AM according to the manufacturer's protocol (Invitrogen).
Biochemistry and Histochemistry Plasma parameters and hepatic and fecal lipid content were measured as described (Mataki et al., 2007, Mol. Cell. Biol. 27, 8330-8339). Hematoxylin and eosin (H&E), Sirius red, and oil red 0 staining were performed as described (Mark al., 2007, Curr. Protoc. Mol. Biol. Chapter 29, Unit 29B, 24), and micrographs were taken on wide-field microscopes (Leica) with a CCD camera. For pancreatic sections, islets were sized and counted from four HE-stained alternated sections spaced of 150 µM using ImageJ software (five animals per group). Immunofluorescent staining of insulin was performed as described (Fajas et al., 2004, J. Clin. Invest. 113, 1288). Additionally, pancreatic islets were isolated by collagenase digestion of pancreas from HF-fed TGR5-Tg mice according to online-available procedures (for example, see JOVE (Journal of Visualized Experiments website)). Insulin was extracted after O/N incubation at −20° C. in acid ethanol and measured by ELISA on PBS-diluted samples according to the manufacturer's instructions (Mercodia). GLP-1 release was measured in vitro, ex vivo, and in vivo according to methods known in the art.
Oxygen Consumption Measurement Cellular oxygen consumption was measured using a Seahorse Bioscience XF24 analyzer with ten biological replicates per condition (Feige et al., 2008b, Cell Metab. 8, 347).

Animal Experiments

Animals were housed and bred according to standardized procedures (Argmann and Auwerx, 2006b). Age-matched male mice were used for all experiments. Genetically engineered mouse models (GEMMs), i.e., TGR5-Tg and TGR5$^{-/-}$ mice, were generated as described in the Supplemental Data. DIO in the GEMMs or C57BL/6J mice (Charles River) was induced by feeding 8-week-old mice with a HF diet (60% cal/fat, D12492; Research Diets) for at least 8 weeks, as mentioned in the text and figure legends. In the dietary intervention experiments, Compound Ih3e was mixed with diet (Feige et al., 2008a, Curr. Protoc. Mol. Biol. Chapter 29, Unit 29B, 25) at the dose sufficient to reach an in vivo dose of 30 mg/kg/d. Mouse phenotyping experiments were performed according to EMPRESS protocols (see, for example, Empress (European Mouse Phenotyping Resource of Standardised Screening) website) and were aimed to assess food and water intake, body composition (Argmann et al., 2006a, Curr. Protoc. Mol. Biol. Chapter 29, Unit 29A, 23), energy expenditure (Argmann et al., 2006a, Curr. Protoc. Mol. Biol. Chapter 29, Unit 29A, 23), glucose and lipid homeostasis (Argmann et al., 2006b, Curr. Protoc. Mol. Biol. Chapter 29, Unit 29A, 22); Heikkinen et al., 2007, Curr. Protoc. Mol. Chapter. 29, Unit 29B, 23; Mataki et al., 2007, Mol. Cell. Biol. 27, 8330), and plasma biochemistry (Argmann and Auwerx, 2006a, Curr. Protoc. Mol. Biol. Chapter 29, Unit 29A, 22). Tissues and blood were collected and processed for histopathology, blood chemistry, and gene expression according to standardized procedures (Argmann and Auwerx, 2006a; Feige et al., 2008b; Mark et al., 2007; Watanabe et al., 2006). Hyperinsulinemic euglycemic clamp studies were performed as described (Feige et al., 2008b), with minor modifications including a change in the initial insulin bolus (30 mU/kg) and insulin infusion rate (10 mU/min/kg). Plasma GLP-1 levels were measured by ELISA (Millipore) on blood collected by retro-orbital puncture. Experiments with db/db mice (Charles River) were performed in 14-week-old animals fed a CD without or with compound Ih3e (30 mg/kg/d) for 6 weeks (Feige et al., 2008a).

Gene Expression Profiling

Gene expression profiling was performed by real-time quantitative PCR (Feige et al., 2008b; Watanabe et al., 2006). Primer sequences used have been previously published, except those used for the Kir6.2 gene: R-5' AGATGCTAAACTTGGGCTTG (SEQ ID NO. 1), F-5' TAAAGTGCCCACACCACTC (SEQ ID NO. 2).

Statistics

Statistical analyses were performed by using the unpaired Student's t test. Data are expressed as mean±SEM, and P values smaller than 0.05 were considered statistically significant.

Example 17

TGR5 mRNA Expression

Figure 17A:
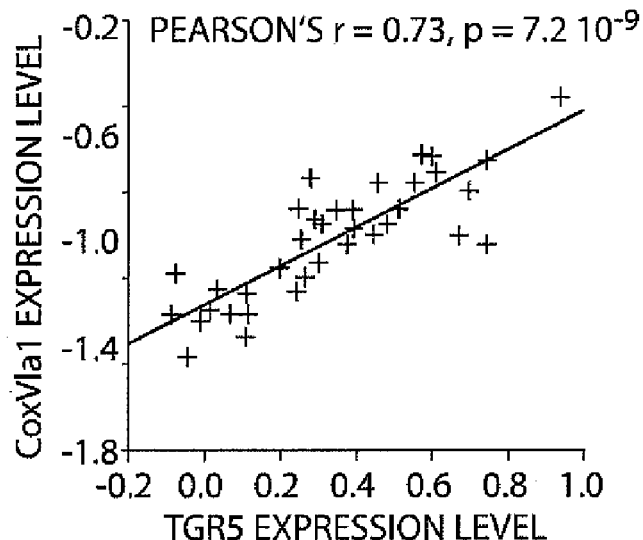
FIG. 17A shows correlation plots for liver mRNA expression of TGR5 and CoxVI1 a in the mouse BxD genetic reference population (n=41).
Figure 17B:
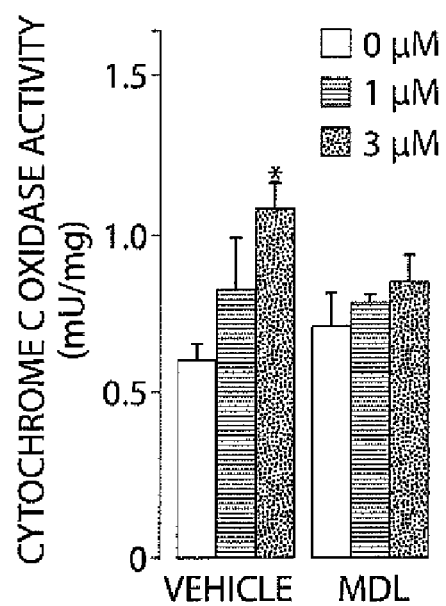
FIG. 17B is a bar graph that shows Cox activity in STC-1 cells treated for 1 hr with compound Ih3e at the concentration indicated. Vehicle or adenylate cyclase inhibitor MDL-12330-A (MDL) (1 μM) was added 15 min prior to treatment (n=3).
Figure 17C:
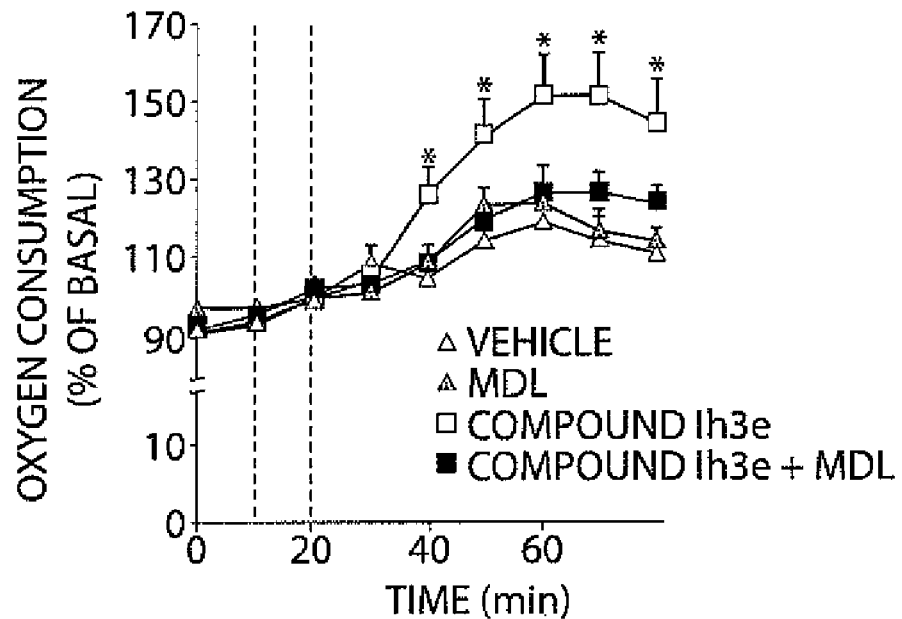
FIG. 17C is a graph showing oxygen consumption in STC-1 cells as measured using the XF24 extracellular flux analyzer (Seahorse Bioscience). The first vertical dotted line indicates the addition of vehicle or MDL-12330-A (MDL) to culture medium, and the second dotted line depicts the treatment with compound Ih3e at 1 μM (n=10).
Figure 17D:
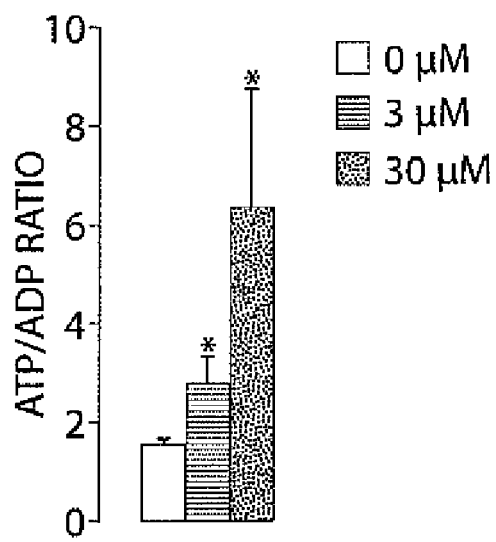
FIG. 17D is a bar graph that shows ATP/ADP ratio in STC-1 cells treated as in Figure B (n=3).
Figure 17E:
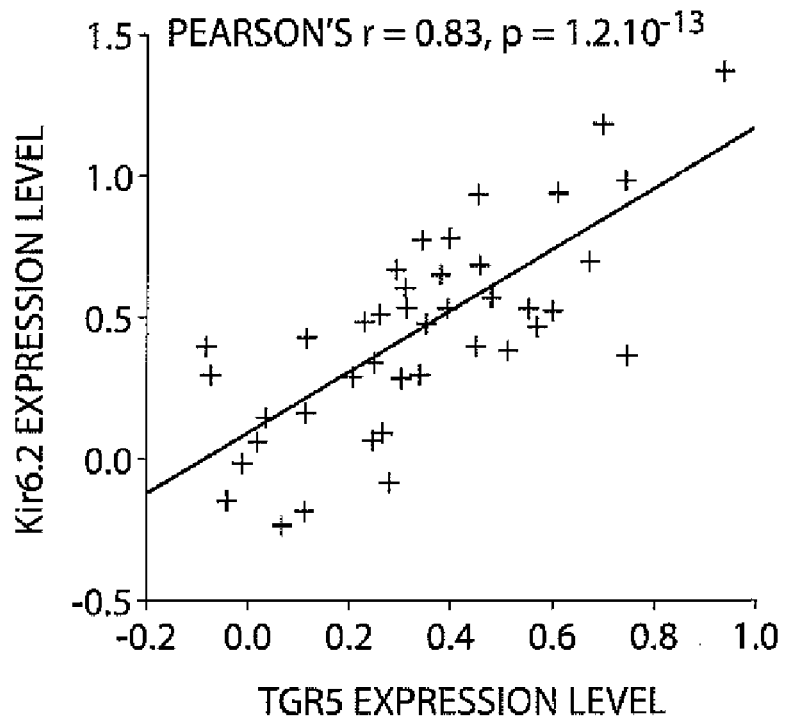
FIG. 17E shows correlation plots for liver mRNA expression of TGR5 and Kir6.2 in the mouse BxD genetic reference population according to a similar strategy as described Figure A.
Figure 17F:
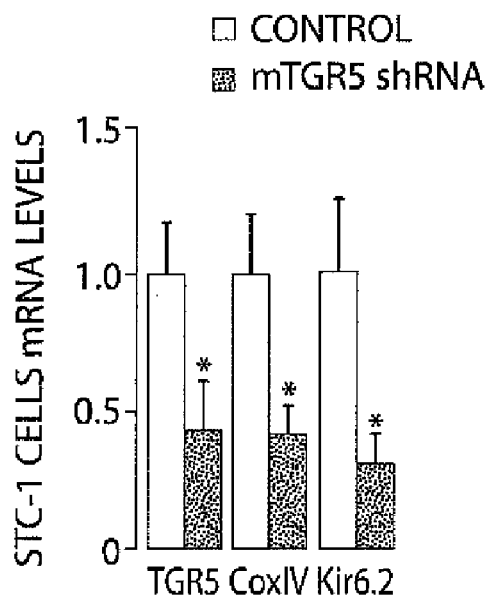
FIG. 17F is a bar graph that shows mRNA expression levels of TGR5, CoxIV, and Kir6.2 in STC-1 cells transfected for 36 hr with control or mTGR5 shRNA as was measured by real-time quantitative PCR. Target mRNA levels were normalized to 36B4 mRNA levels (n=3). The data are represented as mean±SE; Student's unpaired t test; *$p<0.05$.

A link between BAs and energy expenditure in vivo (Watanabe et al., 2006, Nature, 439, 484-489) has been previously established, thus it was speculated that activation of TGR5 signaling could impact mitochondrial activity in a more general fashion. To find initial support for this hypothesis, TGR5 mRNA expression was analyzed via the GeneNetwork liver mRNA database in the BxD genetic reference population as found on the GeneNetwork Univeristy of Tennessee website. A wide range of variation in TGR5 mRNA expression was evident among the different BxD mouse strains. Interestingly, TGR5 mRNA expression was highly significantly correlated with the expression of several genes encoding for subunits of complexes involved in oxidative phosphorylation, such as cytochrome c oxidase (Cox) (e.g., CoxyIIa; FIG. 17A) and ATP synthase (Atp6v0b, ATPase H$^+$ transporting VO subunit B; Atpaf2, ATP synthase mitochondrial F1 complex assembly factor 2; Atp1 a3, ATPase Na$^+$/K+ transporting alpha 3 polypeptide; Atp6v1b2, ATPase H$^+$ transporting V1 subunit β isoform 2). Consistent with this observation, treatment of STC-1 cells with compound Ih3e resulted in a cAMP-dependent increase in Cox activity (FIG. 17B), which was associated with an increase in cellular oxygen consumption (FIG. 17C) and a rise in the ATP/ADP ratio (FIG. 17D). This result was confirmed in the human enteroendocrine cell line NCI-H716, in which compound Ih3e treatment increased ATP production in a cAMP-dependent manner. Interestingly, TGR5 expression was also strongly correlated with that of Kir6.2, a component of the ATP-dependent potassium channel ($K_{ATP}$) (FIG. 17E). These correlations were further corroborated by TGR5RNA interference in STC-1 cells, which resulted in a concomitant drop in the expression of CoxIV and Kir6.2 mRNAs (FIG. 17F).

Example 18

Figure 18A:
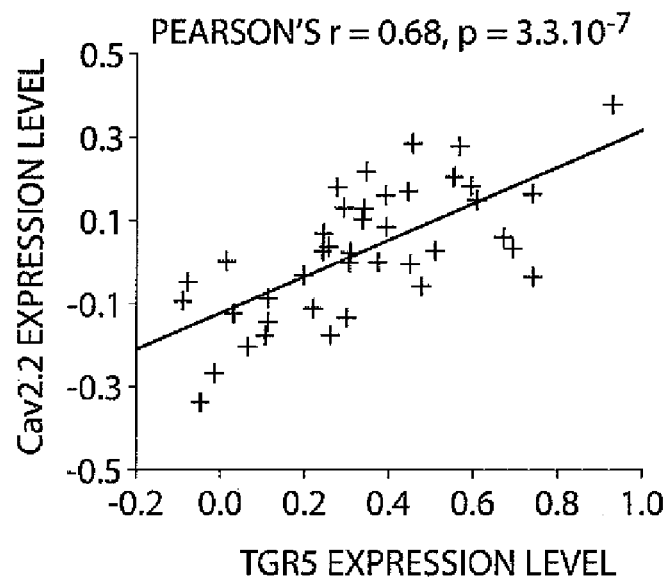
FIG. 18A shows correlation plots for liver mRNA expression of TGR5 and Cav2.2 in the mouse BxD genetic reference population (n=41) as found at the GeneNetwork University of Tennessee website.
Figure 18B:
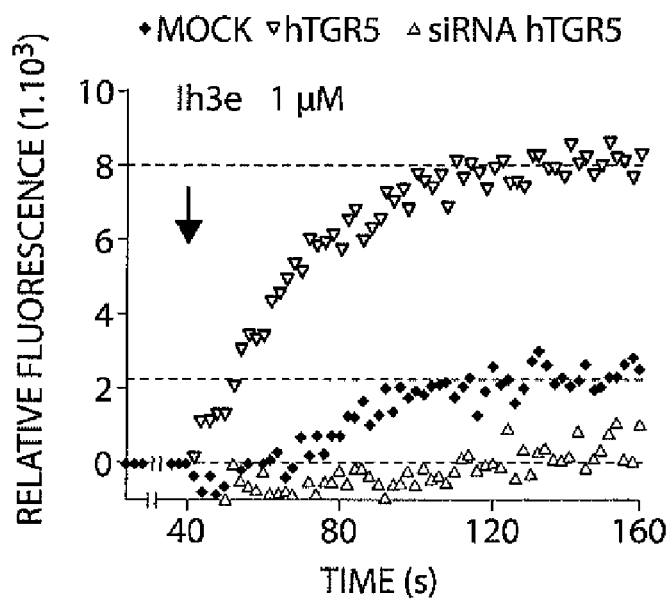
FIGS. 18B and 18C are graphs that show intracellular calcium level in NCI-H716 cells transfected with mock vector, hTGR5 expression vector, or hTGR5 siRNA for 36 hr and treated with 1 (B) or 10 μM (C) of compound Ih3e. The arrow represents compound Ih3e treatment (n=3).
Figure 18C:
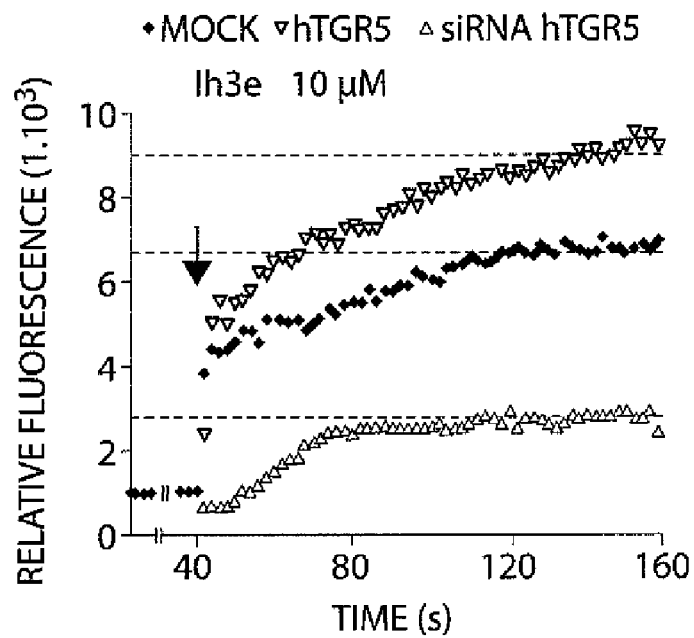
Figure 18D:
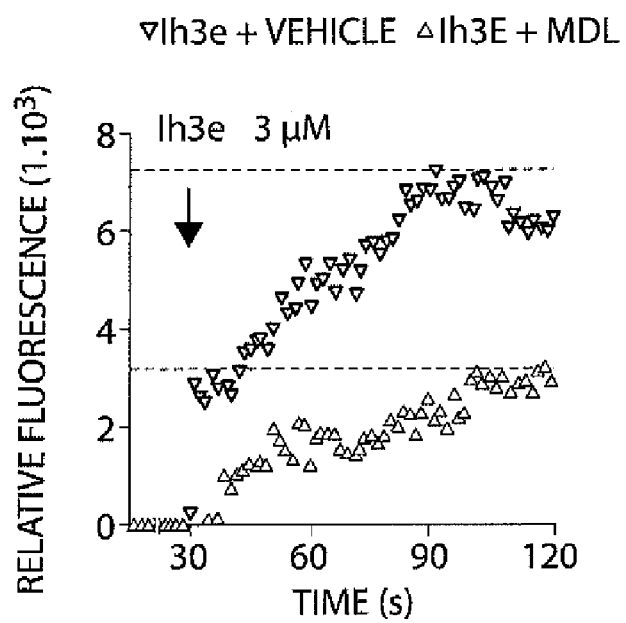
FIG. 18D is a graph that shows the intracellular calcium level in NCI-H716 cells treated with 3 μM of compound Ih3e (indicated by the arrow) in the presence of vehicle or adenylate cyclase inhibitor MDL-12330-A (MDL) (10 μM). MDL or vehicle was added 15 min prior to compound Ih3e treatment (n=3).
Figure 18E:
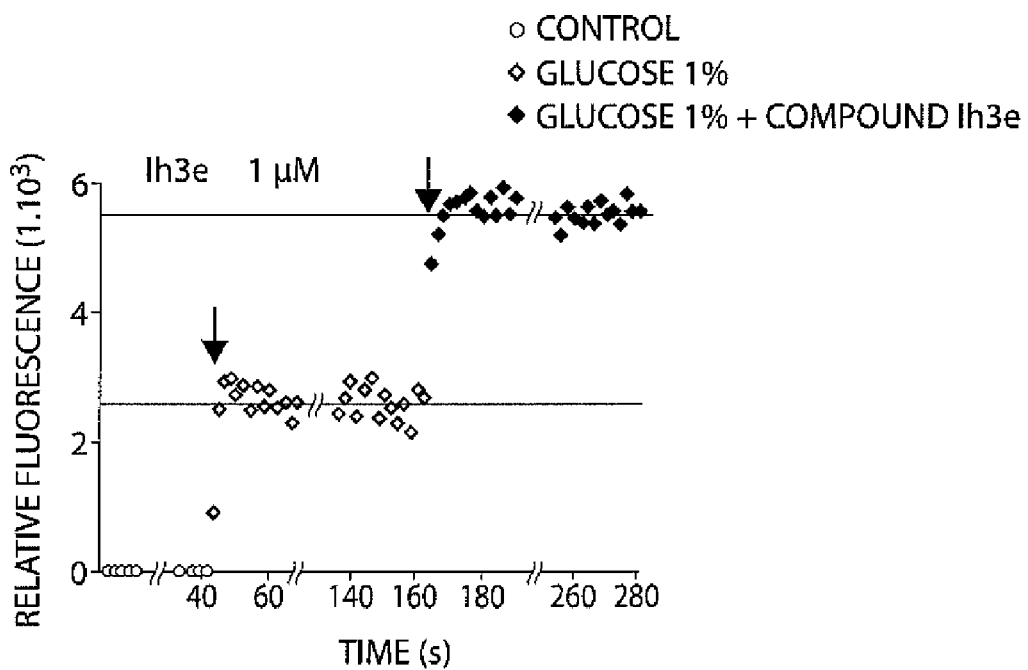
FIG. 18E is a graph that shows the intracellular calcium level in NCI-H716 cells treated with 1% glucose and then with 1 μM of compound Ih3e (n=3).
Figure 18F:
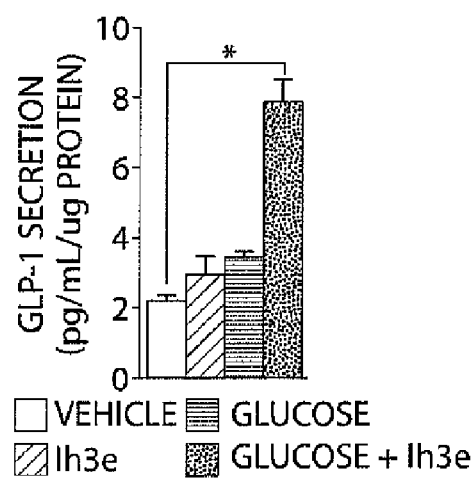
FIG. 18F is a bar graph that shows GLP-1 release in NCI-H716 cells treated with 1% glucose or 1 μM compound Ih3e, or a combination of both agents (n=3).

Activation of TGR5Signaling Pathway Increases Iintracellular Calcium Levels and Stimulates GLP-1 Release in Enteroendocrine L Cells In pancreatic β cells, it is well established that an increase in the ATP/ADP ratio derived from glucose metabolism closes the $K_{ATP}$ channels, resulting in depolarization of the plasma membrane. This membrane depolarization in turn opens calcium-gated voltage channels ($Ca_v$), causing calcium influx. The resultant increase in intracellular calcium then triggers the direct interaction between exocytotic proteins situated in the insulin-containing granule membrane and those located in the plasma membrane (Yang and Berggren, 2006, Endocr. Rev. 27, 621-676), leading to the subsequent release of insulin (Nichols, 2006, Nature, 440, 470-476). Recent findings support the hypothesis that $K_{ATP}$ and $Ca_v$ channels also play a pivotal role in GLP-1 release from enteroendocrine L cells (Reimann and Gribble, 2002, Diabetes 51, 2757-2763; Reimann et al., 2008, Cell Metab. 8, 532-539). Fascinatingly, in the BxD reference population, we also found that TGR5 expression correlated with the expression of $Ca_v2.2$ (FIG. 18A), whose expression was previously described in enteroendocrine cells (Reimann et al., 2005, J. Physiol. 563, 161-175) and which participates in calcium-stimulated insulin release in pancreatic 3 cells (Yang and Berggren, 2006, Endocr. Rev. 27, 621-676). Along with this, compound Ih3e robustly increased calcium influx in the human enteroendocrine cell line NCI-H716, an effect that was potentiated by TGR5 overexpression and, by contrast, blunted by TGR5RNA interference (FIGS. 18B and 18C) or by the addition of the adenylate cyclase inhibitor MDL-12330A(MDL) (FIG. 18D). In addition, the presence of glucose enhanced the TGR5-dependent increase in intracellular calcium (FIG. 18E). This effect was correlated with a rise in GLP-1 release from the NCI-H716 cells (FIG. 18F), which was inhibited by MDL-12-330A.

Figure 18G:
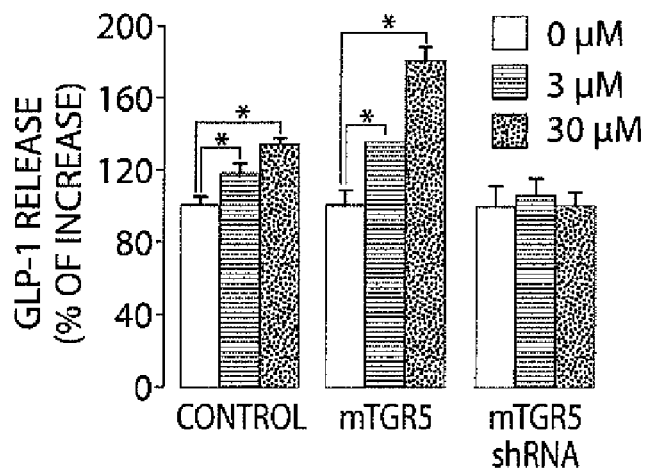
FIG. 18G is a bar graph that shows GLP-1 release in STC-1 cells transfected for 36 hr with control, mTGR5 expression vector, or mTGR5 shRNA and then exposed 30 min to compound Ih3e at the indicated concentration. A DPP4 inhibitor (Millipore) was added into culture medium at 0.1% (n=3).
Figure 18H:
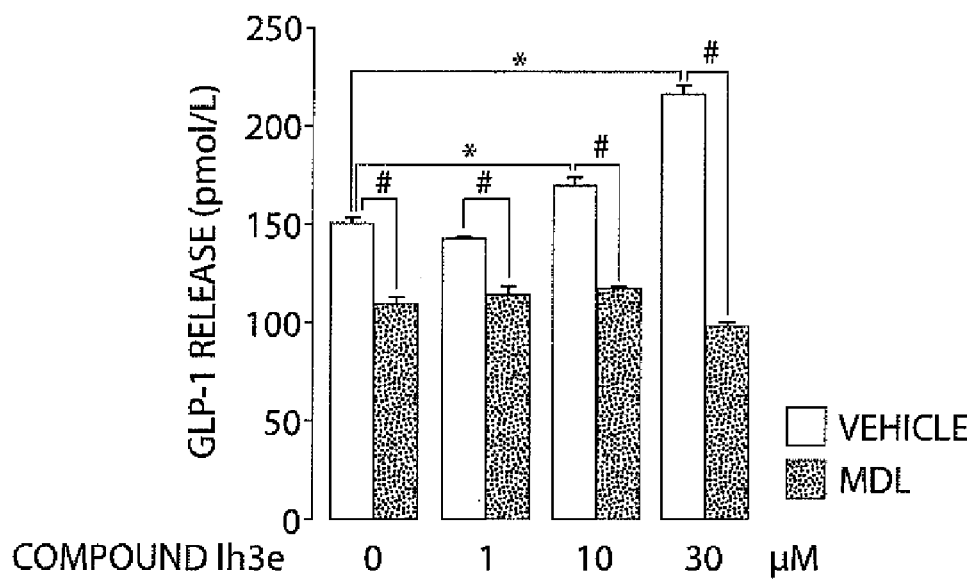
FIG. 18H is a bar graph that shows the impact of 30 min of compound Ih3e treatment on GLP-1 release in STC-1 cells transfected with mTGR5 expression vector in the presence of vehicle or adenylate cyclase inhibitor MDL-1 2330-A (10 μM). MDL or vehicle was added 15 min prior to compound Ih3e treatment. A DPP4 inhibitor (Millipore) was added into culture medium at 0.1% (n=3). The data are represented as mean±SE. Student's unpaired t test; #$p<0.05$ vehicle versus compound Ih3e treatment; #$p<0.05$ vehicle versus MDL-1 2330-A treatment.

The TGR5-mediated GLP-1 release triggered by compound Ih3e was further confirmed in the mouse enteroendocrine STC-1 cells in which the impact of compound Ih3e on GLP-1 release was enhanced by TGR5 overexpression, while being prevented either by RNA interference (FIG. 18G) or by MDL-12-330A, further underscoring the cAMP dependence of TGR5-mediated GLP-1 release (FIG. 18H). Taken together, these data demonstrate that TGR5 regulates a key pathway governing the release of GLP-1 from enteroendocrine L cells.

Example 19

TGR5Overexpression Modulates GLP-1 Secretion In Vivo

Figure 19A:
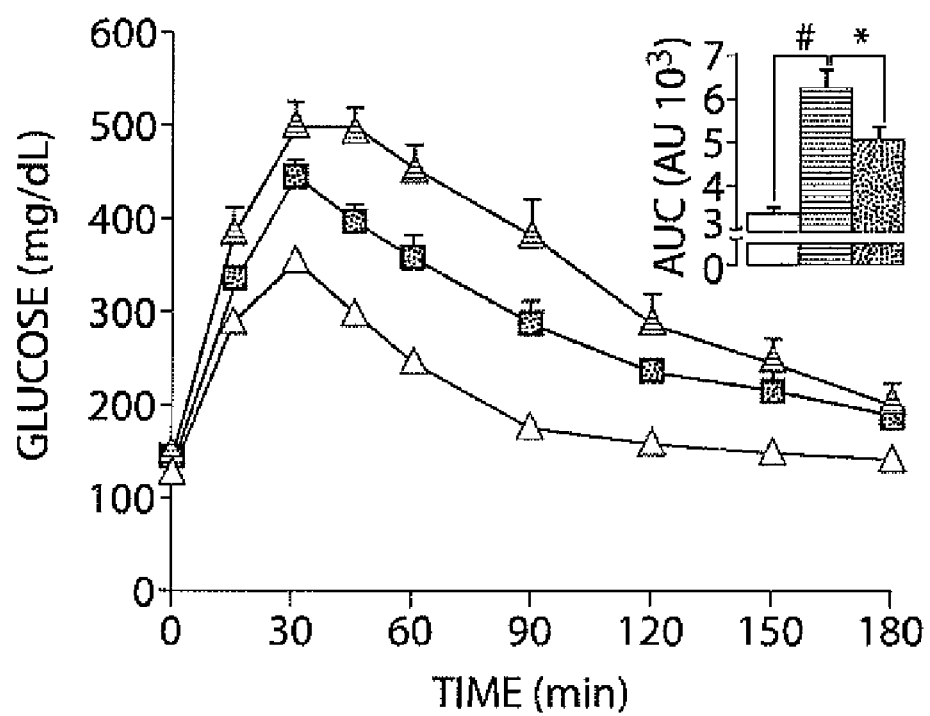
FIG. 19A is a graph which shows the results of an oral glucose tolerance test (OGTT) in male TGR5-Tg mice fed for 10 weeks with HF diet and in age-matched male littermates fed with a CD or a HF diet for the same duration. All mice were 8 weeks old at the initiation of the HF diet. Bodyweight of TGR5-Tg and control littermates was 37.9±1.7 g and 37.0±1.8 g, respectively (n=8; not statistically different). The adjacent bar graph represents the average area under the curve (AUC) (n=8).

To further evaluate the metabolic role of enhanced TGR5 signaling, we assessed the impact of transgenic overexpression of TGR5 in vivo in the context of DIO in mice. TGR5 transgenic mice (TGR5-Tg) were generated by oocyte injection of the bacterial artificial chromosome (BAC) RP23-278N1. By quantitative real-time PCR, TGR5-Tg mice were shown to have integrated six copies of the RP23-278N1 1 BAC clone, leading to a robust TGR5 mRNA expression, restricted to most tissues that express TGR5 normally. Glucose tolerance was markedly improved in TGR5-Tg mice challenged for 10 weeks with a high-fat (HF) diet compared to control HF-fed litter-mates (FIG. 19A), whereas no difference was noticed in mice on chow diet (CD) (data not shown). In contrast to our expectations, no differences were observed in body weight gain between wild-type and TGR5-Tg mice on CD or HF diet, demonstrating that improvement of glucose tolerance in TGR5-Tg mice could not be attributed to the confounding effects of weight loss. The absence of weight gain in TGR5-Tg mice, in the wake of an increase in energy expenditure, was explained by a reduction of locomotor activity. Since GLP-1 receptor knockout mice display a marked hyperactivity (Hansotia et al., 2007, J. Clin. Invest. 117, 143-152), we administered the GLP-1 receptor agonist Ex-4 to wild-type mice in order to assess whether the decrease in locomotor activity in TGR5-Tg mice could be linked to GLP-1 secretion. Ex-4 efficiently and dose-dependently reduced locomotor activity in mice. Interestingly, at 1 nmol/Kg, we noticed a significant decrease in locomotor activity while the mice were still eating properly.

Figure 19B:
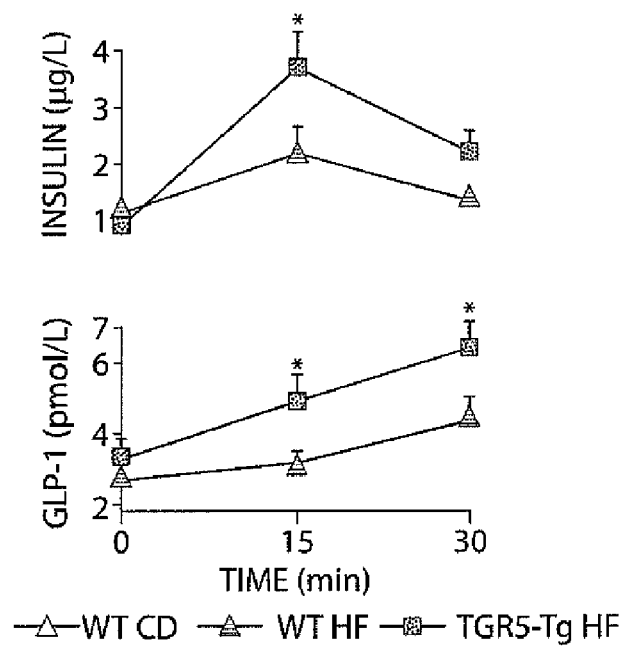
FIGS. 19B and 19C show plasma levels of insulin (top panel) and GLP-1 (bottom panel) during OGTT (19B) or before and after a test meal challenge (19C) (n=8).
Figure 19C:
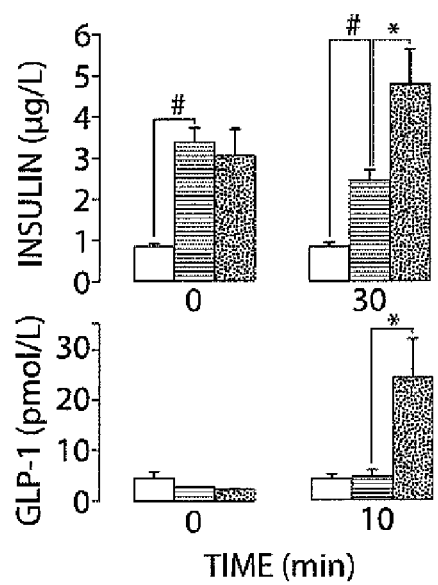
Figure 19D:
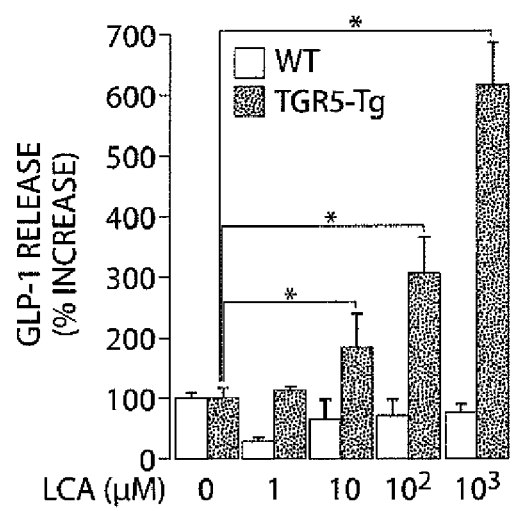
FIG. 19D is a bar graph that shows GLP-1 release from ileal explants isolated from control and TGR5-Tg male mice fed for 18 weeks with HF diet and exposed for 1 hr to the indicated concentrations of LCA (n=4).
Figure 19E:
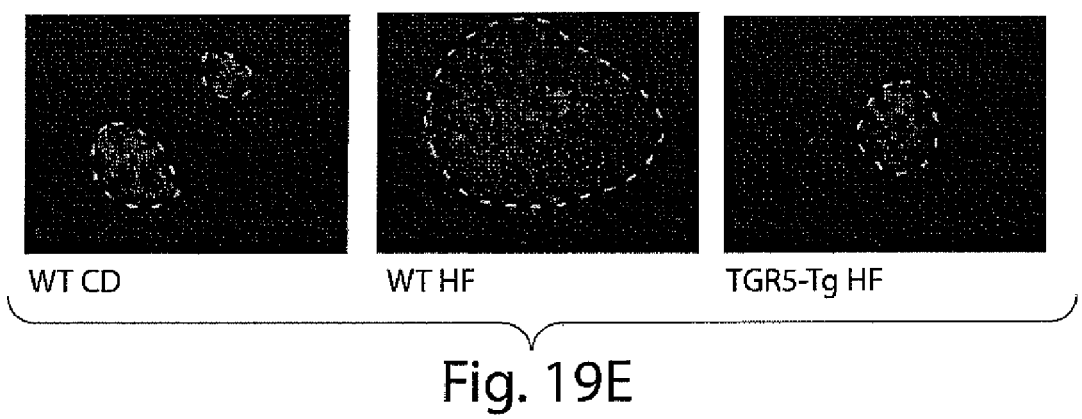
FIG. 19E is a series of pictures which are representative immunofluorescent insulin-stained pancreatic sections from TGR5-Tg male mice fed with a HF diet for 20 weeks or from male age-matched littermates fed with a CD or a HF diet for the same duration.
Figure 19F:
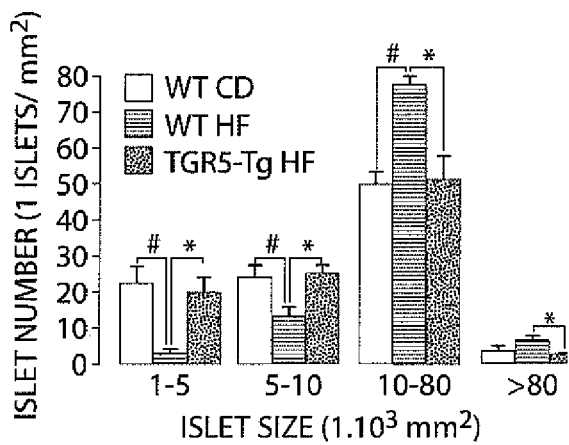
FIG. 19F is a bar graph that shows a distribution profile of pancreatic islets from male TGR5-Tg mice and control littermates fed with a CD or a HF diet as described in (FIG. 19E). Islets were counted and sized by the ImageJ analysis software on four H&E-stained alternated pancreatic sections spaced each by 150 μM (n=5).
Figure 19G:
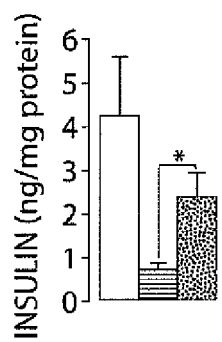
FIG. 19G is a bar graph that shows insulin content in collagenase-isolated pancreatic islets from male TGR5-Tg mice and control littermates fed with a CD or a HF diet as described in (FIG. 19E).

Interestingly, and according to our expectations, glucose tolerance in TGR5-Tg mice was associated with a robust GLP-1 secretion and insulin release in response to an oral glucose load (FIG. 19B). The significance of the enhanced GLP-1 secretion was underscored by the fact that measurements of plasma GLP-1 levels were performed without preliminary oral administration of a dipeptidyl peptidase-4 (DPP4) inhibitor to the mice. This enhanced GLP-1 release in TGR5-Tg mice helps to explain the decreased locomotor activity in these mice. To further investigate the impact of TGR5 overexpression on GLP-1 secretion, the HF-fed mice were subsequently challenged with a test meal to stimulate BA release from the gallbladder. Interestingly, the impact of TGR5 overexpression on insulin and GLP-1 secretion was more pronounced postprandially than after simple glucose challenge (FIG. 19C). It is speculated that these effects are due to the increased BA flux triggered by the test meal as compared to the glucose challenge. In line with this hypothesis, the treatment of ileal explants from TGR5-Tg and control mice with lithocholic acid (LCA) confirmed that BAs provide an excellent signal to induce GLP-1 release in the context of high TGR5 expression (FIG. 19D). These data are furthermore in accordance with results obtained in mTGR5-transfected STC-1 cells in which GLP-1 release was also boosted by increased expression of TGR5 (FIG. 19G). We speculate that in the context of wild-type ileal explants, the quick degradation of GLP-1 by DPP4 enzyme might mask the moderate increase in GLP-1 release triggered by LCA.

The impact of GLP-1 on pancreatic function has been extensively documented during the last decade and ranges from insulin-secretagogue effects to the promotion of pancreatic islet survival and proliferation (Drucker, 2006, Cell Metab. 3, 153-165). In this context, immunofluorescent staining of insulin on pancreatic sections revealed that, in contrast to hypertrophic islets with low insulin content, as observed in HF-fed control mice, islets of HF-fed TGR5-Tg mice were not hypertrophic and stained more intensively for insulin (FIG. 19E). In line with these data, counting and sizing of pancreatic islets confirmed that TGR5 expression results in the maintenance of a normal islet distribution profile (FIG. 19F), likely due to enhanced plasma GLP-1 levels. In addition, the insulin content of isolated pancreatic islets was significantly higher in HF-fed TGR5-Tg mice than in controls (FIG. 19G).

Figure 19H:
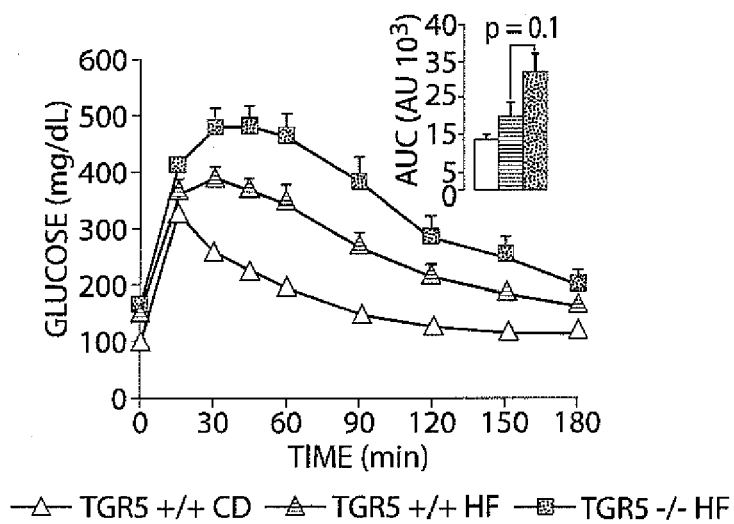
FIG. 19H is a graph that shows the results of an OGTT in TGR5$^{-/-}$ and TGR5$^{+/+}$ male mice fed with a HF diet for 8 weeks. The inset represents the average AUC. Body weight of TGR5$^{-/-}$ and TGR5$^{+/+}$ male mice at time of analysis was 46.3±3.9 g and 51.9±2.0 g, respectively (n=8; not statistically different).
Figure 19I:
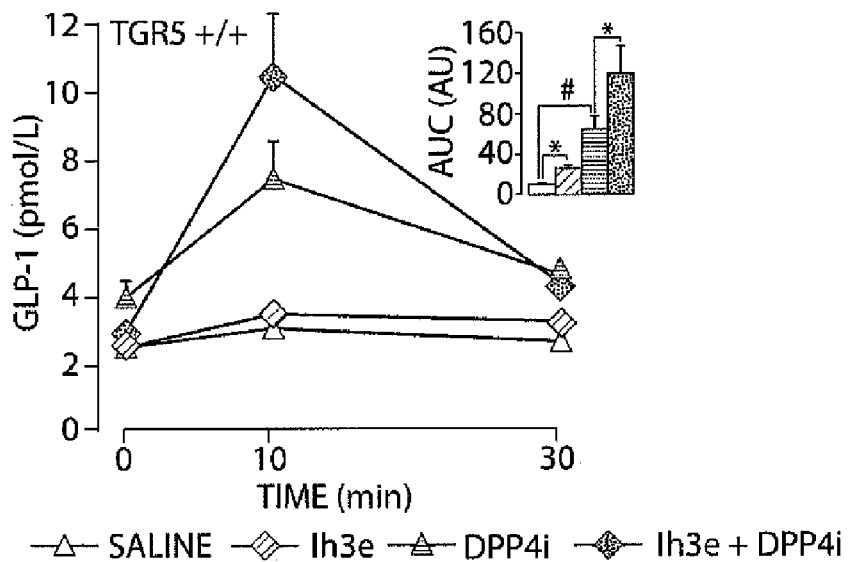
FIGS. 19I and 19J are graphs that show plasma GLP-1 levels in CD-fed TGR5$^{+/+}$ (FIG. 19I) and TGR5$^{-/-}$ mice (FIG. 19J) after an oral glucose challenge, preceded 30 min before by the oral administration of saline or compound Ih3e (30 mg/kg), alone or in combination with a dipeptidyl-peptidase-4 inhibitor (DPP4i, 3 mg/kg) (n=6). The data are represented as mean±SE. Student's unpaired t test; #$p<0.05$, HF-fed compared to HF-fed compound Ih3e-treated mice; and #$p<0.05$, HF-fed versus CD-fed mice except for (I) and (J), where * assessed saline- or DPP4i-treated mice versus compound Ih3e or Ih3e+DPP4i-treated mice, and #saline- versus DPP4i-treated mice.
Figure 19J:
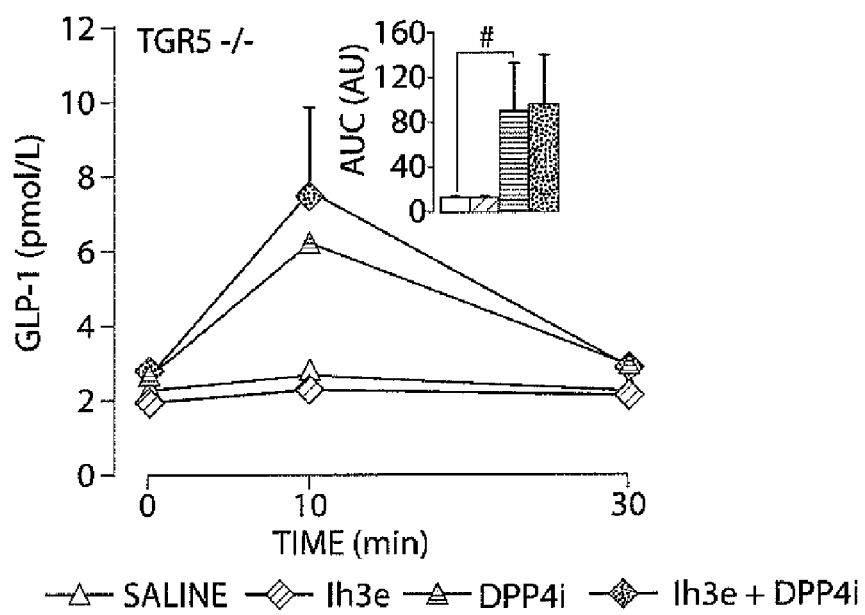

To further establish a role of TGR5 signaling in the maintenance of glucose homeostasis, we assessed the glucose tolerance of germline TGR5-deficient mice (TGR5$^{-/-}$), generated by breeding mice in which the TGR5 allele was floxed with CMV-Cre transgenic mice. In direct contrast with what was observed in TGR5-Tg mice, glucose tolerance was impaired in TGR5$^{-/-}$ mice challenged with a HF-diet for 8 weeks (FIG. 19H), whereas no difference was observed in CD-fed mice (data not shown). GLP-1 secretion was then tested by challenging TGR5$^{+/+}$ and TGR5$^{-/-}$ mice with an oral glucose load 30 min after the administration of saline or compound Ih3e alone, or in combination with the DPP4 inhibitor (DPP41), sitagliptin. Preadministration of compound Ih3e moderately increased GLP-1 release after a glucose challenge in TGR5$^{+/+}$ mice (FIG. 19I). This effect was, however, markedly more pronounced when DPP41 was coadministered as a consequence of its ability to prolong the half-life of plasma GLP-1 (Drucker and Nauck, 2006, Lancet, 368, 1696-1705) (FIG. 19I). In contrast, the effects of compound Ih3e on plasma GLP-1 levels were blunted in TGR5$^{-/-}$ mice (FIG. 19J). Together, these data underscore the critical role of TGR5 signaling in the control of GLP-1 release and further demonstrate the specificity of the semisynthetic agonist compound Ih3e in vivo.

Example 20

Figure 20A:
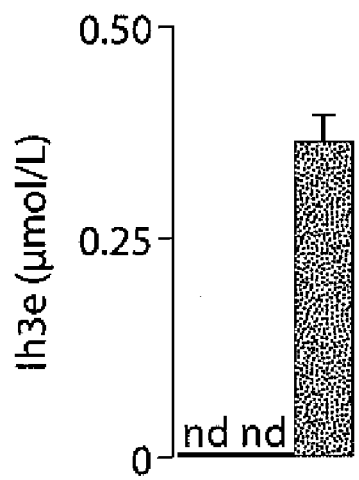
FIG. 20A is graph which shows the results of measurement by HPLC of plasma compound Ih3e levels in CD-, HF-, and HF-fed Ih3e-treated male C57BL6/J mice.

The TGR5Agonist Compound Ih3e Increases Energy Expenditure and Reduces Hepatic Steatosis and Obesity Upond High-Fat Feeding In view of the improved glucose and insulin profile in TGR5-Tg mice, we next assessed the therapeutic potential of compound Ih3e admixed at a dose of 30 mg/kg/day (mkd) with the diet in an intervention study in C57BL/6J mice in which diabesity was induced by HF feeding for 14 weeks. As expected, the HPLC profile of plasma BAs confirmed the presence of compound Ih3e in the treated mice only (FIG. 20A). The plasma levels of compound Ih3e were within the range of those of CA and 3-muricholic acid. It is noteworthy that compound Ih3e treatment affected neither plasma BA composition nor the expression profile of the enzymes involved in BA synthesis, whose expression is mainly under the control of nuclear receptors. The complete absence of changes in the expression level of classical target genes of FXR in the liver, such as cholesterol 7α-hydroxylase (CYP7A1) and bile salt export pump (BSEP) (Thomas et al., 2008, Nat. Rev. Drug Discovery 7, 678-693), further confirmed the specificity of compound Ih3e toward TGR5.

Figure 20B:
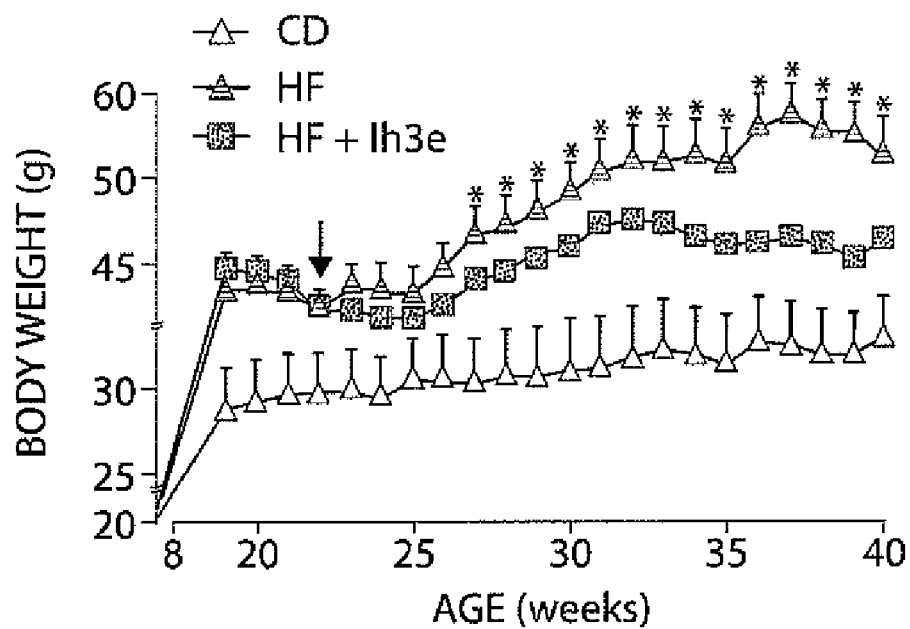
FIG. 20B is a graph that shows the result of dietary intervention with compound Ih3e (30 mg/kg/d) was started after a 14-week period of HF feeding at the time indicated by the arrow. Body weight evolution in all groups was followed throughout the study (n=8).
Figure 20C:
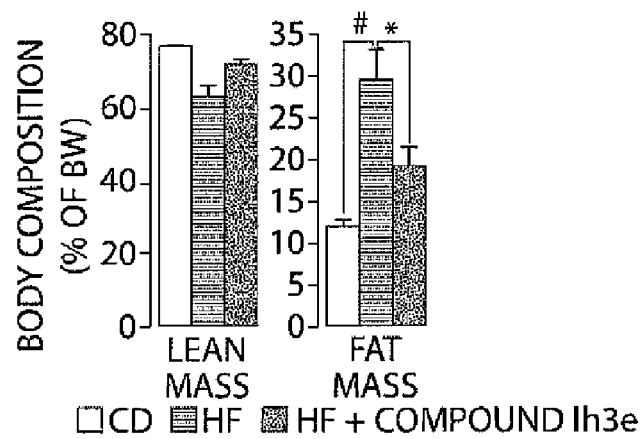
FIG. 20C is a bar graph that shows body composition as assessed by qNMR after 8 weeks of dietary intervention (n=8).
Figure 20D:
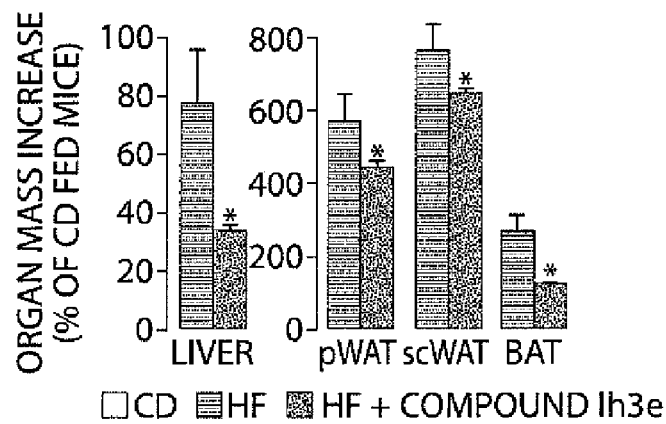
FIG. 20D is a bar graph that shows organ mass as expressed as percent of the weight of CD-fed control mice.
Figure 20E:
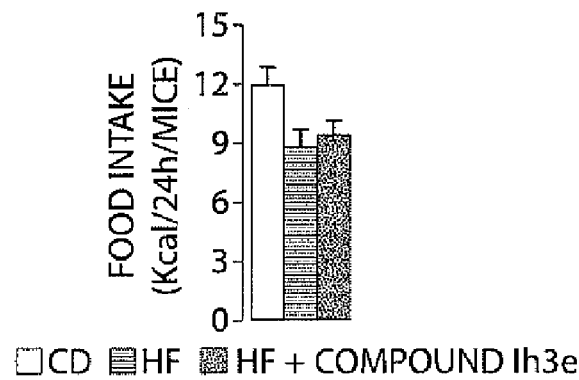
FIG. 20E is a bar graph that shows food intake (n=8).
Figure 20F:
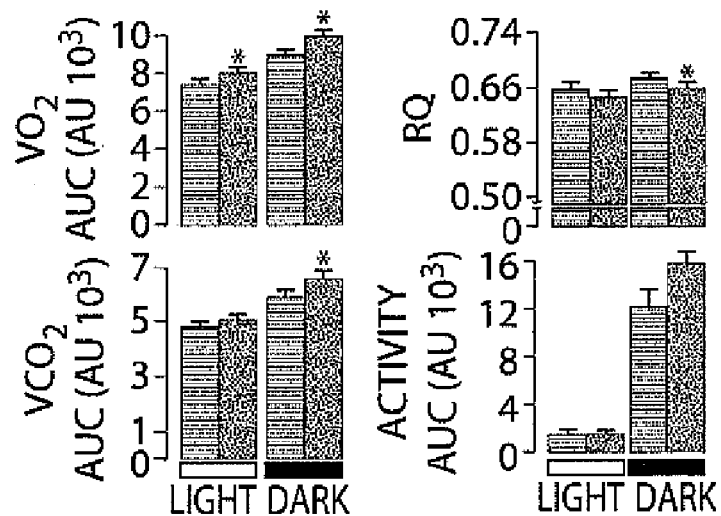
FIG. 20F is a series of bar graphs which show spontaneous horizontal activity and energy expenditure, evaluated by the measurement of oxygen consumption ($VO_2$) and carbon dioxide release ($VCO_2$), that were monitored over a 18 hr period 6 weeks after the initiation of the dietary intervention. The respiratory quotient (RQ) was calculated as the ratio $VCO_2/VO_2$. Bar graphs represent the average AUC. For the RQ, bar graphs represent the average (n=8).
Figure 20G:
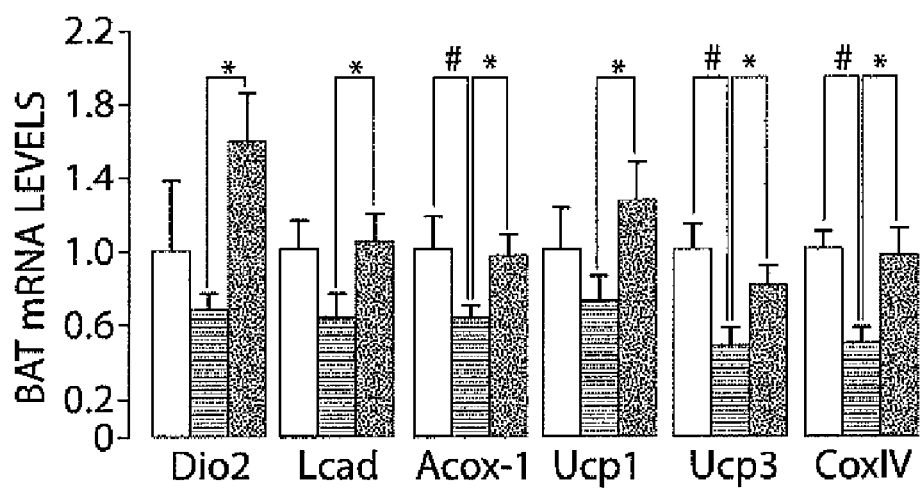
FIG. 20G is a bar graph that shows gene expression in BAT by real-time quantitative PCR after 18 weeks of dietary intervention. Target mRNA levels were normalized to 36B4 mRNA levels (n=8).
Figure 20H:
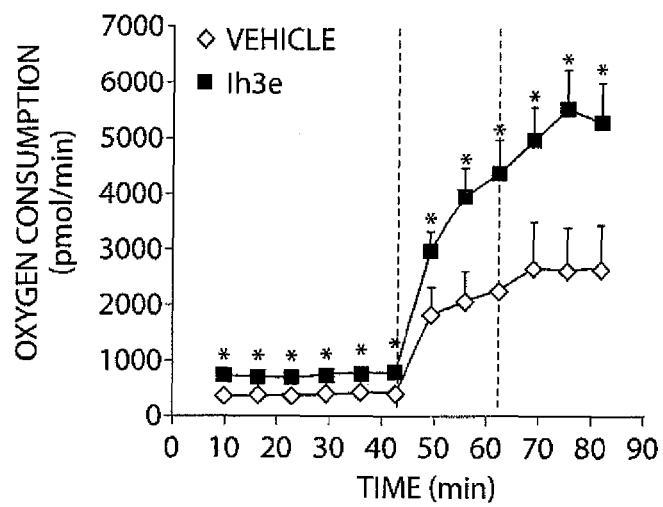
FIG. 20H is a graph that shows primary brown adipocytes isolated from CD-fed C57BL/6J male mice were cultured for 12 hr with vehicle or 3 µM compound Ih3e, and $O_2$ consumption was measured by using the XF24 extracellular flux analyzer (Seahorse Bioscience) (n=5). The dotted lines illustrate the addition of the uncoupling agent FCCP at successive doses of 250 and 500 nM.
Figure 20I:
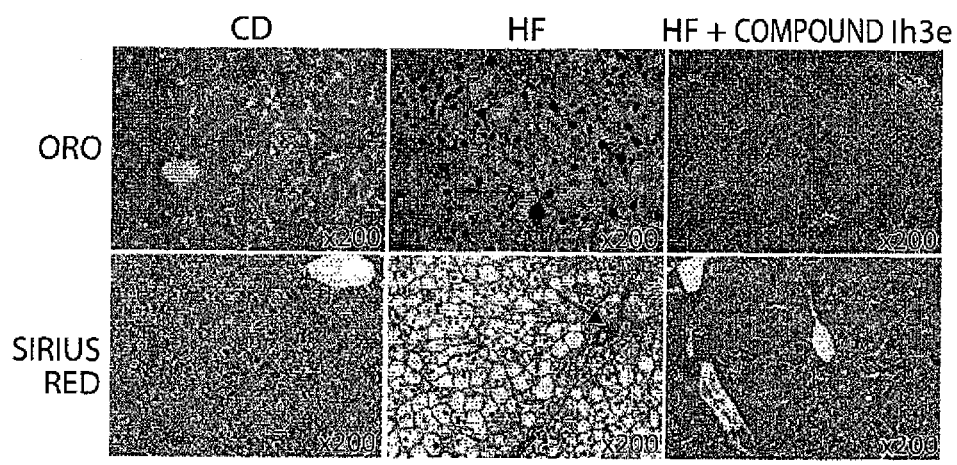
FIG. 20I is a series of pictures that are representative pictures of oil redO (ORO) staining of cryosections (top panel) and Sirius red staining of paraffin-embedded sections (bottom panel) of the liver at the end of the dietary intervention. Fibrosis is indicated by the arrow.
Figure 20J:
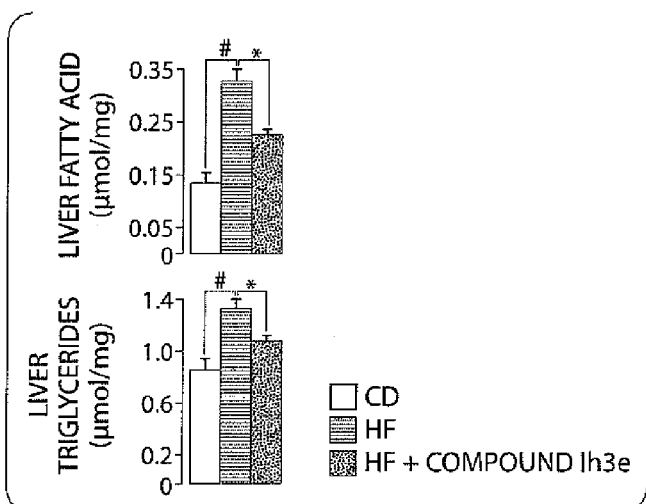
FIG. 20J is a series of bar graphs that show 1 Lipid content in liver samples extracted according to Folch's method (n=8).
Figure 20K:
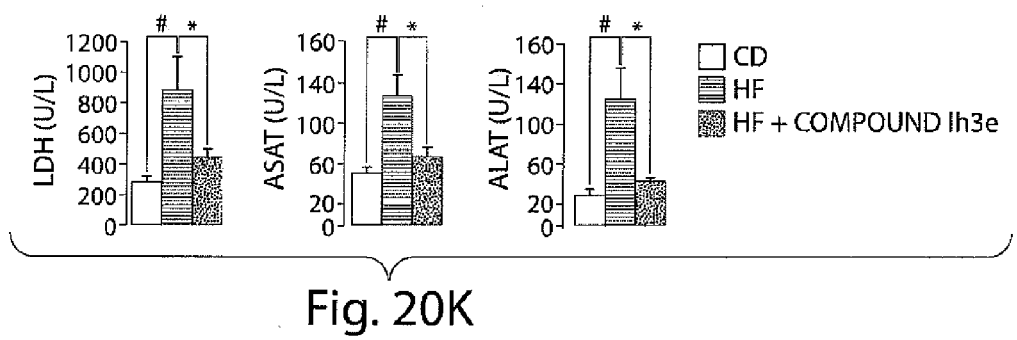
FIGS. 20K and 20L is a series of bar graphs that show plasma levels of liver enzymes (FIG. 20K) and lipids (FIG. 20L) at the end of the dietary intervention (n=8). The data are represented as the mean±SE. Student's unpaired t test; *p<0.05, HF-fed compared to HF-fed Ih3e-treated mice; and #p<0.05, HF-fed versus CD-fed mice.
Figure 20L:
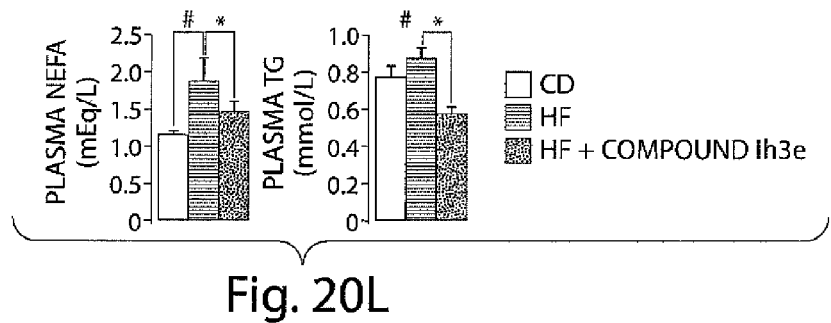

After 10 weeks of treatment with compound Ih3e, a significant attenuation of body weight gain of about 15%, in association with a sharp reduction in fat mass, was observed in HF-fed Ih3e-treated mice relative to HF-fed controls (FIGS. 20B and 20C). The increase in liver and fat pad mass was also attenuated in HF-fed Ih3e-treated mice (FIG. 20D). As noticed in our previous study with CA (Watanabe et al., 2006, Nature, 439, 484-489), the decrease in BAT mass was related to a diminution of white adipose tissue (WAT) in the interscapular region (FIG. 20D and data not shown). The metabolic changes between control HF-fed and Ih3e-treated HF-fed mice were not caused by a reduced calorie intake (FIG. 20E) or fecal energy loss, but rather were the consequence of enhanced energy expenditure, as indicated by the measurement of $O_2$ consumption and $CO_2$ production during indirect calorimetry (FIG. 20F). During the dark period, the respiratory quotient of Ih3e-treated mice was significantly reduced, consistent with increased fat burning (FIG. 20F). Gene expression profiling of BAT confirmed that activation of the TGR5 signaling pathway triggers the increase of several mitochondrial genes involved in energy expenditure along with an induction of type 2 deiodinase gene expression (FIG. 20G). The activation of the mitochondrial respiratory chain by compound Ih3e was further evidenced by measuring $O_2$ consumption in primary brown adipocytes isolated from C57BL/6J mice treated for 12 hr with compound Ih3e. Addition of the uncoupling agent, carbonylcyanide-ptrifluoromethoxyphenylhydrazone (FCCP), boosted basal $O_2$ consumption in all conditions but was significantly more pronounced in those treated with compound Ih3e (FIG. 20H). In addition to the enhanced energy expenditure, liver function was also improved, as evidenced by the reduction in liver steatosis, which was assessed by oil red O staining (FIG. 20I) and biochemical quantification of liver lipid content (FIG. 20J). Moreover, plasma levels of liver enzymes were markedly reduced compared to HF-fed controls, correlating with the absence of liver fibrosis in liver sections of Ih3e-treated mice stained with Sirius red (FIGS. 20I and 20K). The improvement in liver function was also reflected by the significant drop in plasma triglycerides and nonesterified fatty acids (NEFAs) in HF-fed mice treated with compound Ih3e (FIG. 20L).

Example 21

The TGR5 Agonist Compound Ih3e Improves Insulin Sensitivity in Obese Mice

Figure 21A:
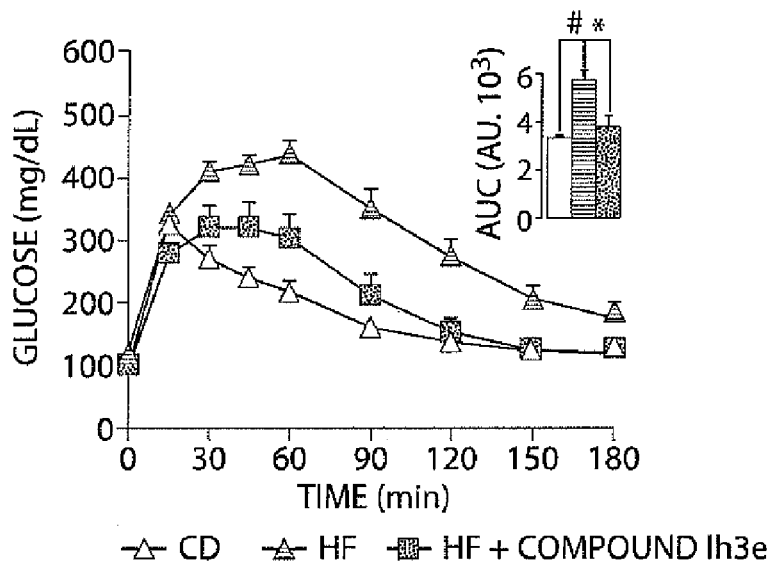
FIG. 21A is a graph that shows the result of an OGTT in CD- and HF-fed male C57BL6/J mice supplemented with 30 mg/kg/d compound Ih3e for 8 weeks following the onset of obesity induced by feeding a HF diet during 10 weeks. The inset represents the average AUC. Body weight of vehicle and compound Ih3e treated mice was 38.08±1.83 g and 32.26±0.95 g, respectively (n=8; p<0.05).
Figure 21B:
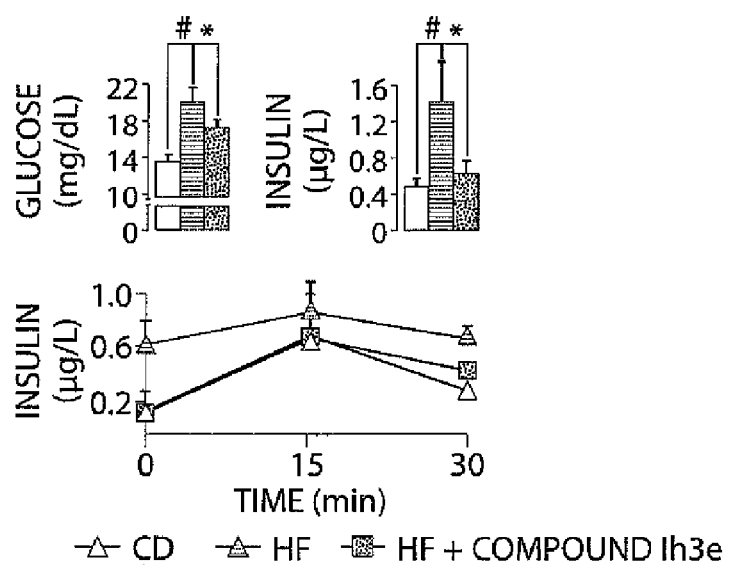
FIG. 21B is a graph that shows fasting glycemia and insulinemia (4 hr fasting) in DIO mice after 3 weeks of dietary intervention with compound Ih3e (top panel). Plasma insulin levels during OGTT in DIO mice (bottom panel).
Figure 21C:
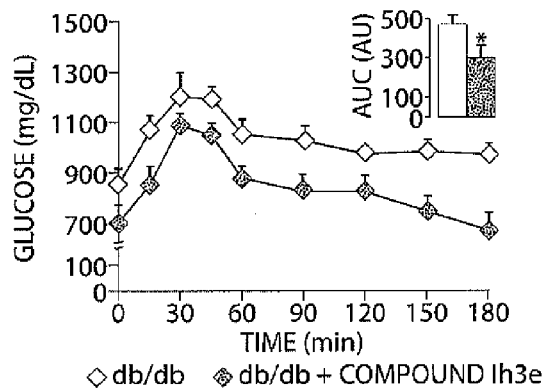
FIG. 21C is a graph that shows the result of an OGTT in 14-week-old CD-fed db/db male mice treated with 30 mg/kg/d compound Ih3e for 6 weeks. The inset shows the average AUC (n=8).
Figure 21D:
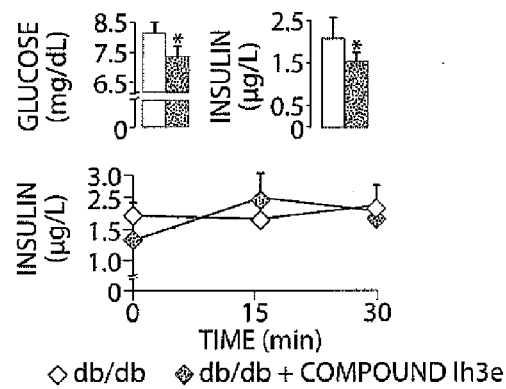
FIG. 21D is a graph that shows fasting (4 hr) glycemia and insulinemia in db/db mice after 6 weeks of treatment with compound Ih3e (top panel). Plasma insulin levels during OGTT in DIO mice (bottom panel).
Figure 21E:
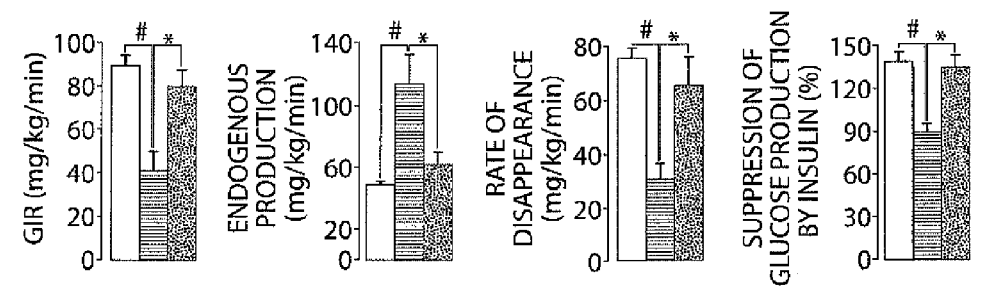
FIG. 21E is a series of two bar graphs that show insulin sensitivity evaluated through the average glucose infusion rate at equilibrium (euglycemia) in a hyperinsulinemic euglycemic clamp (10 mU insulin/min/kg) in DIO mice (following the onset of obesity induced by feeding a HF diet during 10 weeks) after 10 weeks of dietary intervention with compound Ih3e (30 mg/kg/d) (n=5). The evaluation of liver glucose production and its suppression by insulin, as well as the rate of glucose disappearance, was assessed at equilibrium using 3H-glucose (n=5).
Figure 21F:
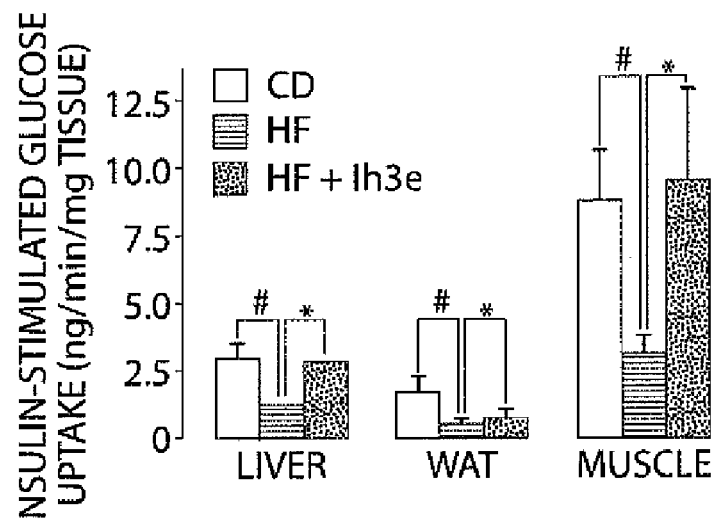
FIG. 21F is a series of bar graphs that show insulin-stimulated glucose uptake in the indicated tissues was measured by using 14C-2-deoxyglucose tracers (n=5).
Figure 21G:
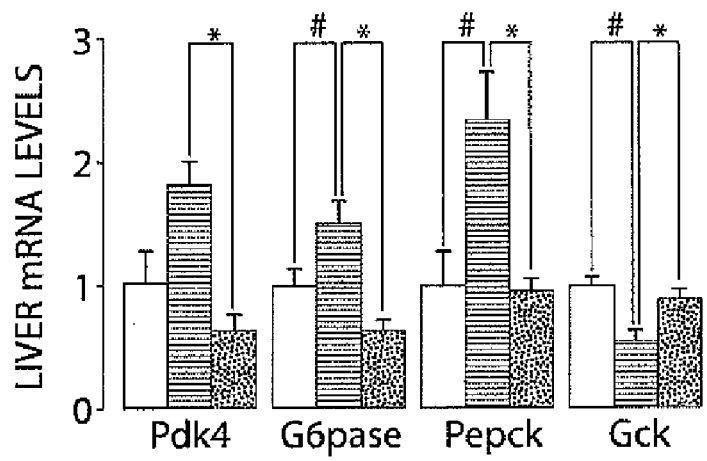
FIG. 21G is a series of bar graphs that show gene expression profiling in liver that was performed by real-time quantitative PCR. Target mRNA levels were normalized to 36B4 levels (n=8). The data are represented as mean±SE. Student's unpaired t test; *p<0.05, HF-fed compared to HF-fed compound Ih3e treated mice; and #p<0.05, HF-fed versus CD-fed mice.

The ability of compound Ih3e to improve glucose homeostasis was determined. In both DIO and db/db mice, an environmental and genetic model of diabesity, respectively, treatment with compound Ih3e (30 mkd) admixed with the diet robustly improved glucose tolerance after an oral challenge with glucose (FIGS. 21A and 21C), along with an improvement of the glucose-stimulated insulin secretion profile (FIGS. 21B and 21D, lower panel). This feature is consistent with a GLP-1-mediated improvement in pancreatic function. Furthermore, fasting glucose and insulin levels were decreased in both DIO and db/db mice that were treated with compound Ih3e (FIGS. 21B and 21D, top panel). To further characterize the impact of compound Ih3e on glucose homeostasis and insulin sensitivity, a hyperinsulinemic euglycemic glucose clamp was performed on these DIO mice. Consistent with the improved glucose tolerance, the glucose infusion rate required to maintain euglycemia in DIO mice treated with compound Ih3e was virtually identical to that observed in CD-fed control mice (FIG. 21E). While insulin-resistant HF-fed mice showed an increased endogenous production of hepatic glucose, together with a reduction of both glucose disposal rate and the suppression of glucose production by insulin, compound Ih3e treatment of HF-fed mice normalized these parameters to the values observed in CD-fed mice (FIG. 21E). Measurement of insulin-stimulated $^{14}C$-deoxyglucose uptake during the hyperinsulinemic euglycemic glucose clamp indicated that the improvement in glucose homeostasis by compound Ih3e could be mainly attributed to reduced insulin resistance in liver and muscle (FIG. 21F). These effects correlated with normalization in the expression of key genes involved in hepatic glucose homeostasis (FIG. 21G).

Figure 6A:
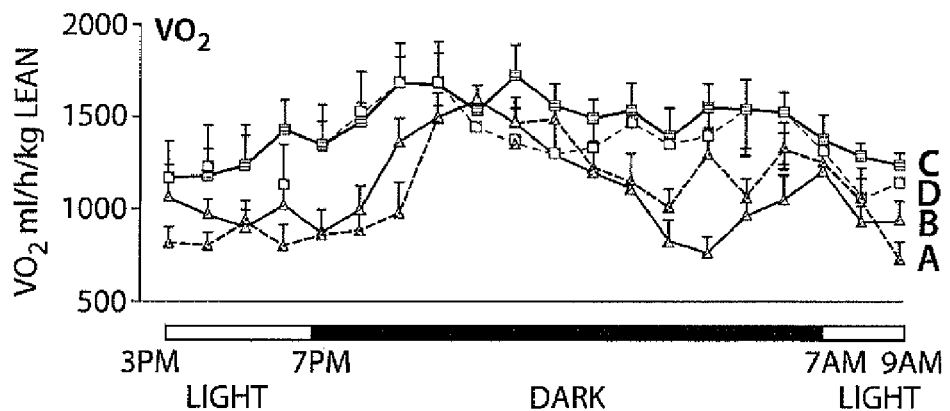
FIG. 6A is a graph that shows a comparison of oxygen consumption ($VO_2$) from 3 pm to 9 am.
Figure 6B:
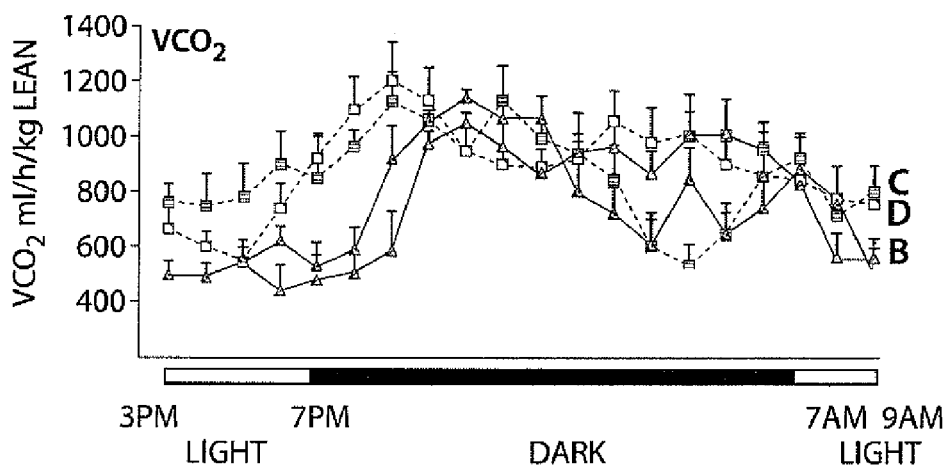
FIG. 6B is a graph that shows a comparison of carbon dioxide release ($VCO_2$) from 3 pm to 9 am.
Figure 6C:
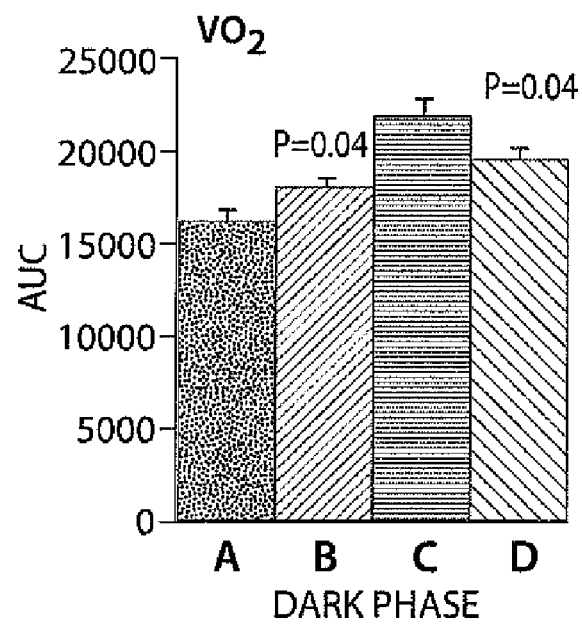
FIG. 6C is a bar graph that shows a comparison of oxygen release ($VO_2$) during dark phase.
Figure 6D:
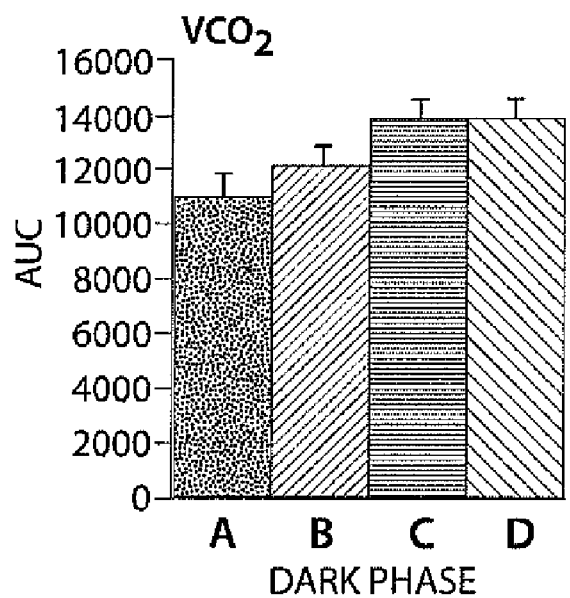
FIG. 6D is a bar graph that shows a comparison of carbon dioxide release (VO2) during dark phase.
Figure 7A:
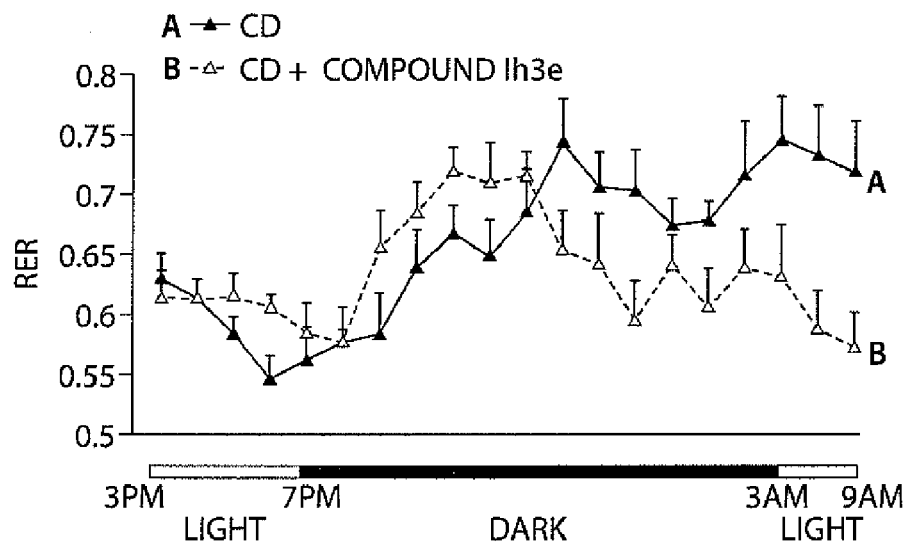
FIG. 7 are three graphs (A-C) that show the respiratory exchange ratio (RER) value as calculated after indirect calorimetry in chow and high fat fed mice treated with compound Ih3e.
Figure 7B:
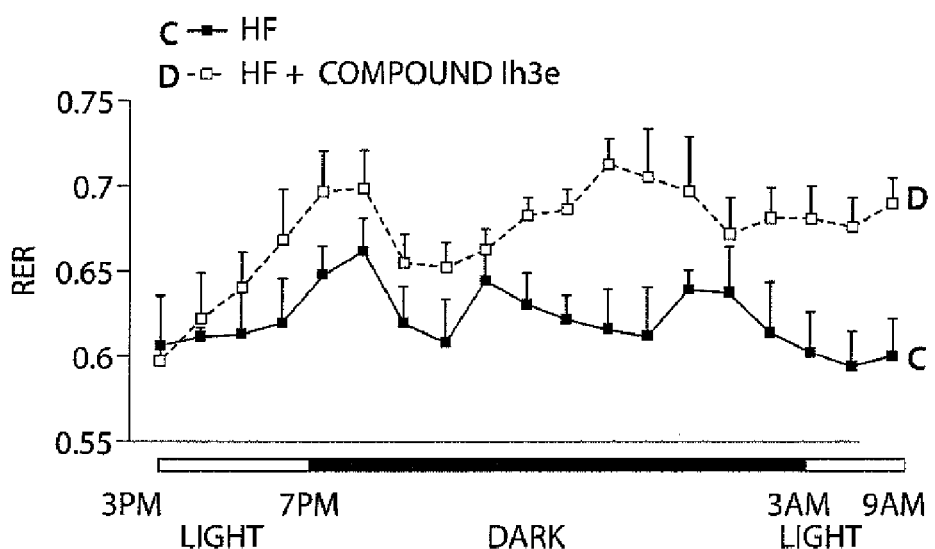
Figure 7C:
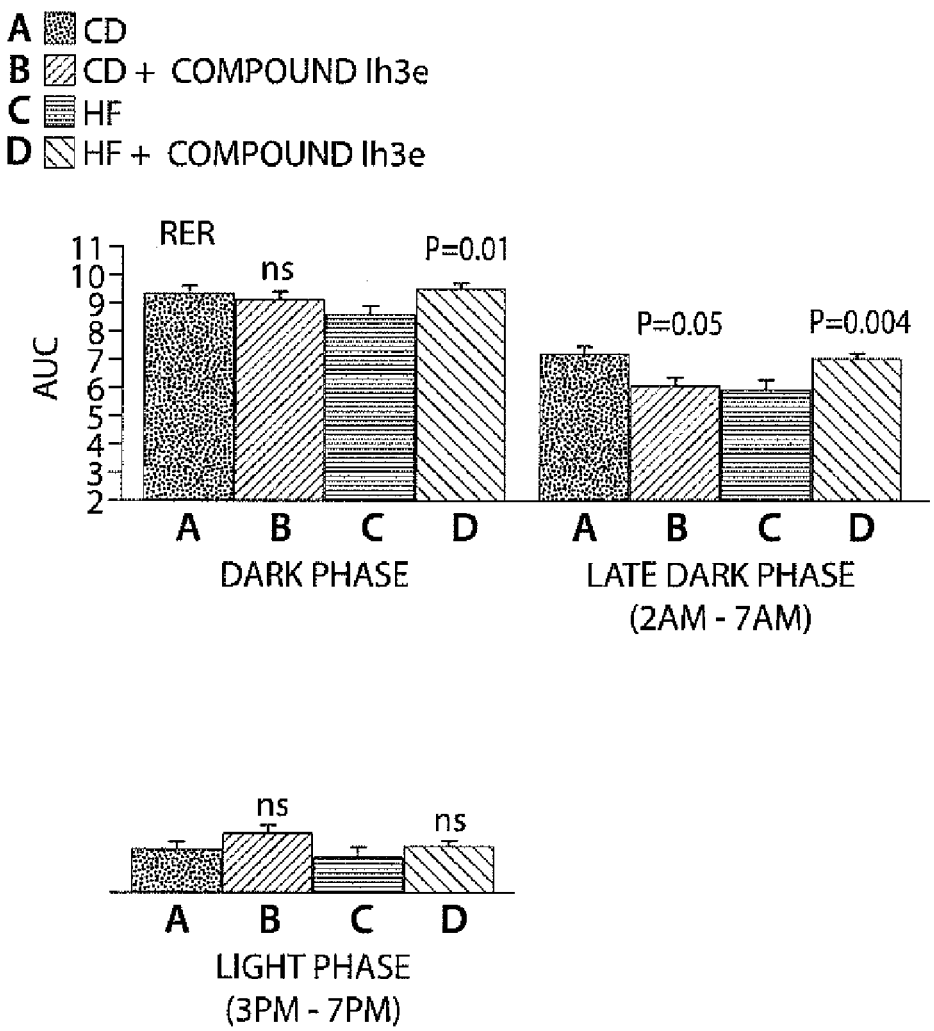
Figure 22A:
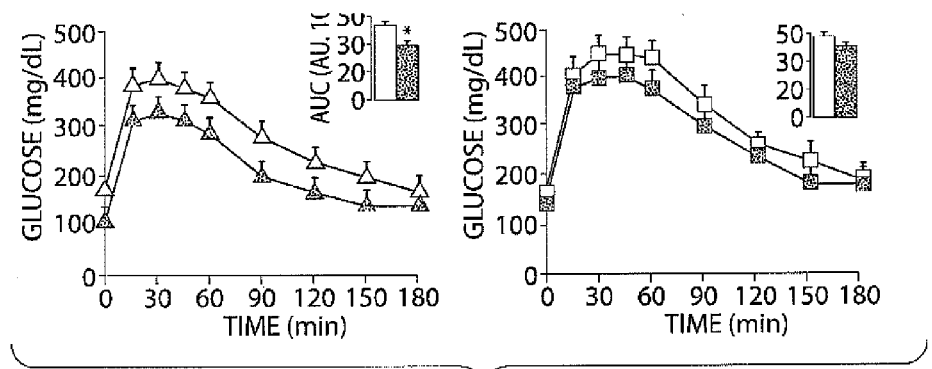
FIG. 22A is a series of graphs that shows the results of a study where $TGR5^{+/+}$ and $TGR5^{-/-}$ male mice were fed a HF diet for 9 weeks, and a first OGTT was performed thereafter. HF was then supplemented with compound Ih3e at 30 mg/kg/d. A second OGTT was performed 4 weeks after treatment with compound Ih3e was initiated. Curves represent glucose tolerance before and after 4 weeks' treatment with compound Ih3e in $TGR5^{+/+}$ (left panel) and $TGR5^{-/-}$ (right panel) mice. The inset represents the average AUC. In $TGR5^{+/+}$ mice, body weight before and after compound Ih3e treatment was 46.86±3.54 g and 43.50±3.47 g, respectively (n=8; not statistically different). In TGR5~/mice, body weight before and after compound Ih3e treatment was 54.34±2.23 g and 52.30±2.72 g, respectively (n=8; not statistically different).
Figure 22B:
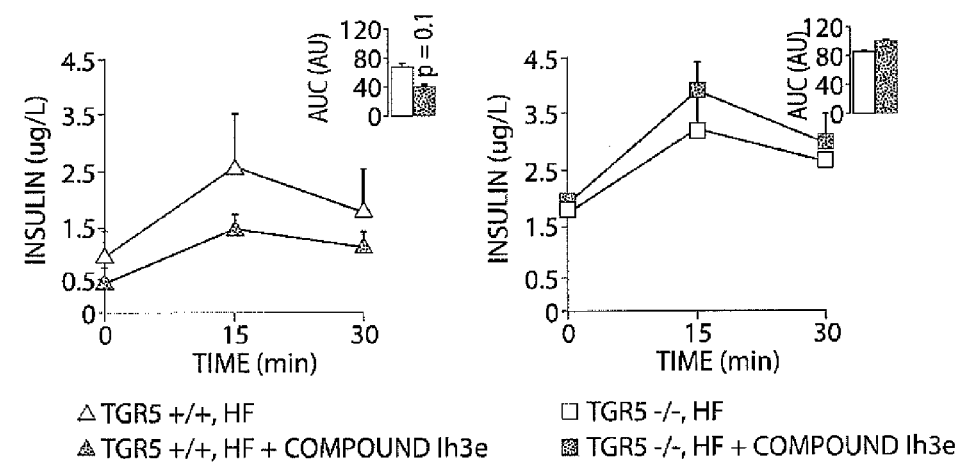
FIG. 22B is a series of graphs which show plasma insulin levels that were concurrently measured during the OGTT in DIO in $TGR5^{+/+}$ (left panel) and $TGR5^{-/-}$ (right panel) mice before and after 4 weeks' treatment with compound Ih3e. The inset represents the average AUC (n=8). The data are represented as mean±SE. Student's unpaired t test; *p<0.05, vehicle compared to compound Ih3e 7-treated mice.

To address the specificity of compound Ih3e with regard to TGR5 in vivo, the impact of 4 weeks' treatment with compound Ih3e at 30 mkd on glucose tolerance was compared in TGR5' and TGR5/mice, primed by HF feeding for 9 weeks. Even over this short time period, compound Ih3e significantly improved glucose tolerance in TGR5$^{+/+}$ fed a HF diet (FIG. 6A), along with a normalization of insulin secretion during oral glucose challenge (FIG. 6B). These effects were blunted in TGR5$^{-/-}$ mice, thereby providing further arguments to support the specificity of compound Ih3e for TGR5 (FIGS. 22A and 22B).

Example 22

Figure 23:
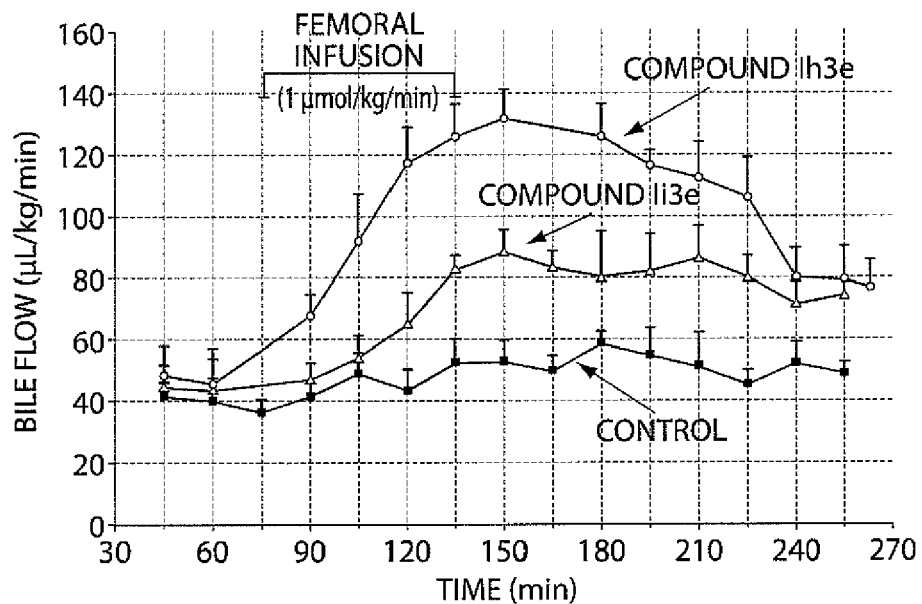
FIG. 23 is a graph that shows compounds Ih3e and Ii3e bile flow rates in a femoral infusion experiment at 1 µmol/min/kg for 1 h and bile flow rate in a femoral experiment as control infusing 3% BSA physiological solution for 1 h.

Pharmacokinetics and Metabolism in Bile-Fistula Rat After IV Administration for compounds Ih3e and Ii3e The difference between the two pure diasteroisomers, Ih3e and Ii3e, is that the C-23 methyl group is oriented differently, thus generating the 23S and 23R forms. This structure modification could in part modify the physicochemical properties, metabolism and pharmacokinetics of the two compounds. The introduction of a C-23 methyl group in the side chain differently oriented produced two isomers where also the carboxy group is differently oriented and its reactivity in the amidation process or in the deconjugation of the amidated form can be different among the two diasteroisomers. The different carboxy group orientation is also responsible for a different hydrophobic/hydrophilic balance of the two molecules which could result in different bilological properties and metabolism. In order to clarify this point the two pure isomers were administered by femoral infusion (i.v.) to a bile fistula rat model at a single dose of 1 μmol/min/kg bw for 1 hour and bile samples were collected for 3 hours. The effect on bile flow, on biliary secretion of the parent compound and of the main metabolite were also evaluated.
Bile Flow. Choleretic Effect
Methods This study was performed by administration of the two compounds via femoral infusion (iv); 6 rats (body weight 267±12 g) were treated with each diasteroisomer at a dose of 1 μmol/min/kg. Femoral infusion started after 75 minutes of steady-state and continued for 60 minutes. Bile samples were collected every 15 minutes for 2 hours. In addition, 3 rats were treated with 3% BSA saline solution under the same conditions for times and sampling (femoral control rats).
Results The bile flow during iv infusion of the control 3% BSA saline vehicle maintained a value ranging from 40 to 60 μL/min/kg for the entire period of the experiments. The iv infusion of compound Ih3e significantly increased the bile flow rate and this phenomenon started 15 minutes after the beginning of the infusion period and continued for at least 2 hours after the end of the infusion period (FIG. 23). The iv infusion of compound Ii3e also increased the bile flow rate but this effect is significantly lower than that observed for the isomer compound Ih3e (FIG. 23).

Pharmacokinetics (Biliary Secretion) of the Administered Isomers after iv Infusion Bile samples collected at different times during the iv experiments were analyzed to determine the biliary secretions of the administered isomers and their main metabolites recovered in bile.

Materials

Pure crystalline powder of each compound was obtained from R. Pellicciari's laboratory at the University of Perugia. Stock solutions were prepared in methanol at 1 mmol/L and working solutions were prepared by diluting appropriate volumes of the primary solution. Methanol and acetonitrile were of HPLC-grade purity Ammonia was 30% pure and acetic acid was 99.8% pure. All reagents were obtained from Carlo Erba Reagents. HPLC-grade water was prepared by a Milli-Q system.

Sample Preparation

Rat bile samples were brought to room temperature, briefly stirred, and diluted 1:100 or 1:200 v/v with 15 mM ammonium acetate buffer (pH=5.0): acetonitrile (70:30, v/v). The final solution was transferred in an autosampler vial and 10 µL was injected onto the chromatographic column. When samples were found out of linearity range, they were diluted and reanalyzed.

HPLC-ESI-MS/MS Method

Rat bile samples were analyzed by HPLC-ESI-MS/MS using the ESI source in negative ionization mode. For liquid chromatography a Waters Alliance 2695 separation module coupled with autosampler was used. The autosampler was maintained at 7° C. Separation was performed on a Synergi Hydro-RP C18 column (150×2.0 mm i.d., 4 µm particle size), protected by a SecurityGuard ODS 4×2.0 mm i.d. precolumn, both supplied from Phenomenex. The analyte was eluted using 15 mM ammonium acetate buffer (pH=5.0) as mobile phase A and acetonitrile as mobile phase B. Mobile phase B was increased from 30% to 64% in 10 minutes, then to 100% in 10 minutes, and held constant for 10 minutes. Flow rate was 150 µL/min and the column was maintained at 45° C. The column effluent was introduced into the ESI source connected to a triple quadruple MS (Quattro-LC, Micromass) operating in multiple reaction monitoring (MRM) acquisition mode. Nitrogen was used as nebulizer gas at 100 L/h flow rate and as desolvation gas at 930 L/h. The ion source block and desolvation temperatures were set respectively to 80° C. and 180° C. Capillary voltage was 3.0 kV. MassLynx software version 4.0 was used for data acquisition and processing. In addition, using mass spectrometry both in single MS and tandem MS/MS configurations, experiments were performed to identify metabolites.

Quantification

A 5-point calibration curve was prepared daily and injected in duplicate. Calibration samples were obtained in the 0.1-20 µmol/L concentration range prepared in the mobile phase. Linear calibration curve parameters were obtained from the plot of the analyte peak area versus analyte concentration using a least squares regression analysis (weight=1/x2). Correlation coefficients were $\geq 0.994$. The taurine conjugated metabolites of compounds Ih3e and Ii3e were also estimated even if standards were not available to us. A A corrective factor, to take into account the different responses in ES-MS/MS between free and taurine conjugated species, previously estimated was applied to the area values obtained from HPLC-MRM dataset chromatograms. Finally, calibration curves obtained for the free BA were used to estimate taurine conjugated metabolites.

Results-Biliary Secretion-Compound Ih3e

Figure 24:
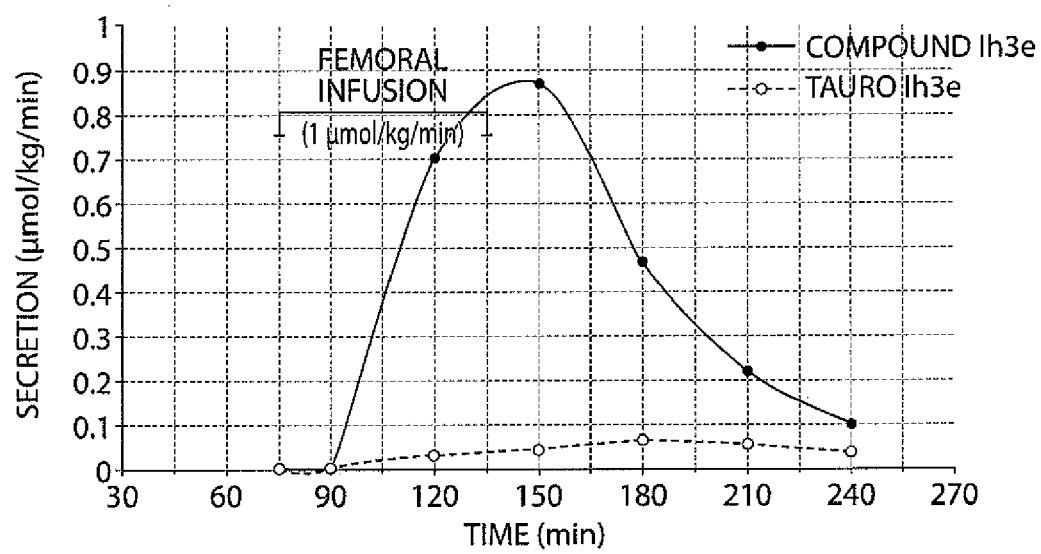
FIG. 24 is a graph that shows compound Ih3e and tauro-Ih3e secretion rates vs. time in a femoral experiment at 1 µmol/min/kg for 1 h.
Figure 26:
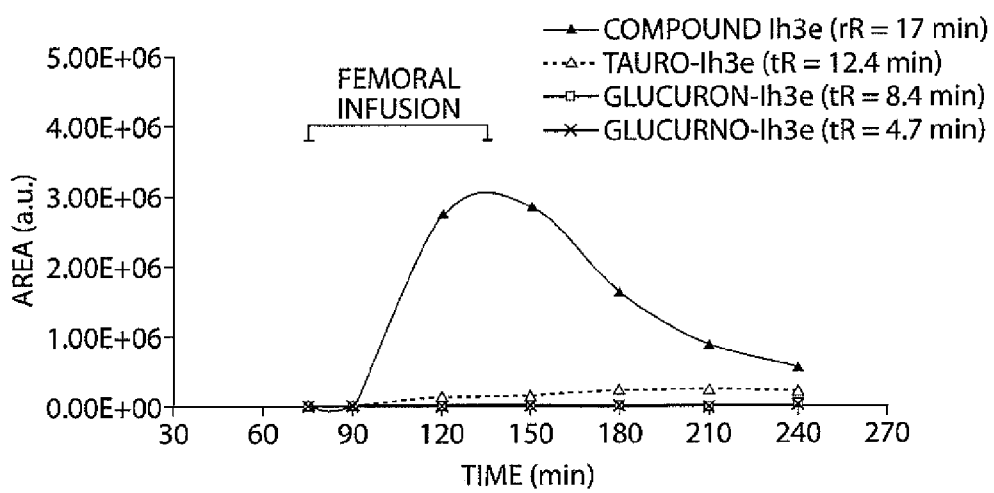
FIG. 26 is a graph that shows compound Ih3e and its main metabolites identified in bile samples collected during the femoral infusion experiment. Data are reported as absolute area values.
Figure 27:
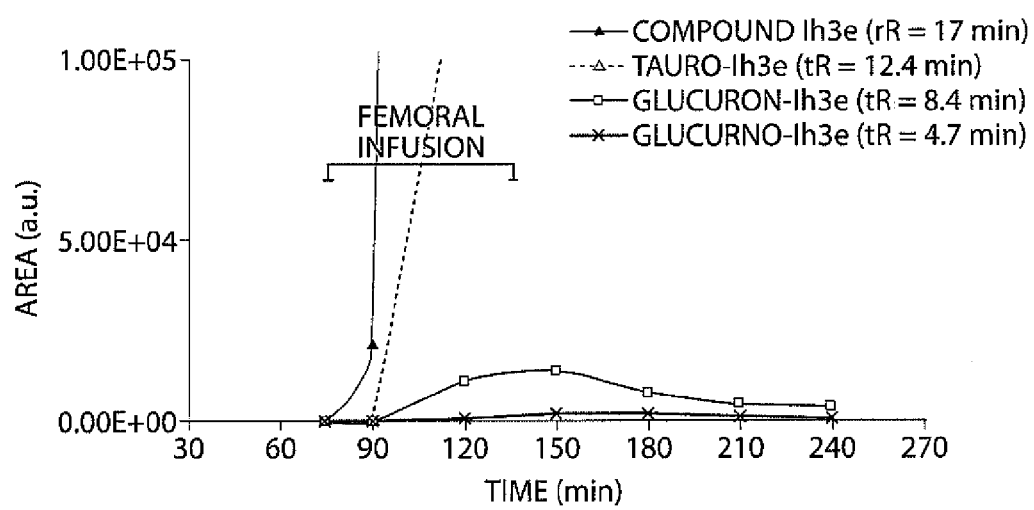
FIG. 27 is a zoom display of FIG. 26.

The biliary secretion of compound Ih3e after iv administration was efficient and the compound was recovered in bile at a relatively high percentage of the administered dose. The kinetic profile indicates that compound Ih3e was efficiently taken up by the liver and secreted in bile mainly unmodified and also, to a lesser extent conjugated with taurine (FIG. 24); other minor metabolites including glucuronides have been identified in bile in trace amounts (FIGS. 26 and 27).

The presence of the methyl group in the C-23 position hinders the physiological conjugation process with taurine and glycine which is relevant for efficient secretion of almost all naturally occurring carboxylated BA; this is crucial for dihydroxy-BA and to a lesser extent for trihydroxy-BA. The extent of its recovery in bile is also related to the administered dose like it has been observed for cholic acid (Roda A. et al. Hepatology. 8,1571-6,1988).

Taking into account the compound Ih3e physicochemical properties, we expected that this compound would be absorbed by a passive diffusion mechanism (Log P=1.44) and an active mechanism did not seem to be involved. The presence of three hydroxyl groups allows the molecule to be efficiently taken up by the liver and secreted into bile. The 6-ethyl group prevents also the intestinal bacteria 7-dehydroxylation as shown in the previous report.

Results-Biliary Secretion-Compound Ii3e

Figure 25:
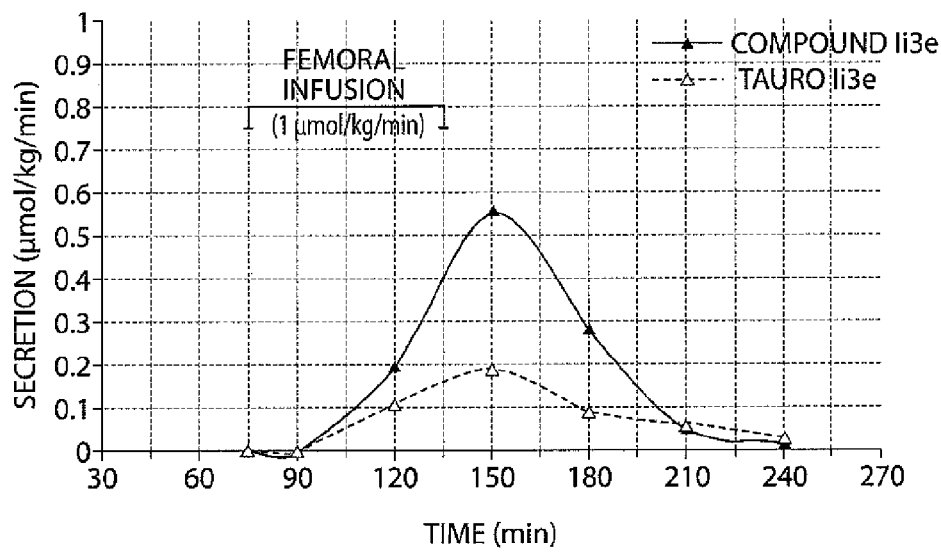
FIG. 25 is a graph that shows compound Ii3e and tauro-Ii3e secretion rates vs. time in femoral experiment at 1 µmol/min/kg for 1 h.

The biliary secretion of compound Ii3e after iv infusion is reported in FIG. 25. The kinetic profile indicates that the compound is metabolized by the liver more extensively than compound Ih3e. The parent compound is secreted in bile as such and to a less extent as taurine conjugate.: In respect to its diasteroisomer compound Ih3e, the percentage of conjugation is higher and the maximum secretion rate of the unconjugared form is lower. This suggests that the C-23(R) isomer presents a side chain geometry and orientation more suitable for the amidation process in respect to the isomer (S) which is secreted as unconjugated form at higher percentage. The conjugation with taurine contributes to improve compound Ii3e recovery in bile which is approx. 70-80% of the administered dose. Other minor metabolites including glucuronides have been identified in bile in trace amount (FIG. 28-29).

Hepatic Metabolism

Methods

Using data obtained from previous experiments as well as structural and physicochemical properties of the studied analogues, a preliminary screen was carried out to search for possible metabolites.

Compound Ih3e

This molecule was mainly secreted as parent compound (unmodified) and was only slightly metabolized by the liver. The main metabolite was the taurine conjugated species and, at very low levels, the mono-glucuronide species was detected (FIG. 26-27). The presence of the methyl group in C-23 position hinders the conjugation process with taurine and glycine which is required for an efficient secretion of almost all naturally occurring carboxylated BAs; this is crucial for dihydroxy BA and to a lesser extent for trihydroxy BA since they are already quite polar. Formation of glucuronides could become relevant if administered at higher doses.

Compound Ii3e

This molecule was mainly secreted as parent compound (unmodified) and was also metabolized by the liver to form the taurine conjugated specie and, at very low levels, the mono-glucuronide specie. (FIG. 27-29).

The presence of the methyl group in C-23 position hinders the conjugation process with taurine and glycine which is required for an efficient secretion of almost all naturally occurring carboxylated BAs; this is crucial for dihydroxy BA and to a lesser extent for trihydroxy BA, since they are already quite polar. Formation of glucuronides could become relevant if the molecule is administered at higher doses.

Compound Ii3e is secreted in bile in higher percentage than the diasteroisomer compound Ih3e as taurine conjugated form, 20-30% vs 5-10% and this accounts for the different side chain geometry and to a slightly higher lipophilicity of compound Ii3e.

Compound Ih3e is moderately hydrophilic and has a mild detergency. Its hepatic uptake seems efficient. The biliary secretion is also efficient considering that the compound is secreted mainly unmodified and, to a limited extent, conjugated with taurine. The intestinal absorption occurs via passive mechanism like naturally occurring unconjugated BA and the kinetics is similar to that of cholic acid slightly lower that dihydroxy bile acids (Aldini R. et al. Steroids 61, 590-7, 1996).

Compound Ih3e does not require extensive hepatic metabolism at the administered dose to be secreted into bile. The presence of the methyl group in the C-23 (S) position prevents extensive conjugation with taurine and the molecule can be efficiently secreted unmodified. An increased hepatic residence time of the molecule results from a ductular absorption since this molecule undergoes to a cholehepatic shunt pathway, which is responsible for its potent choleretic effect.

Compound Ii3e is the diasteroisomer of compound Ih3e. Compound Ii3e is characterized by a slightly lower hydrophilicity as a result of the different side chain geometry. Therefore, the C-23 carboxy group is differently oriented and this accounts for the different hydrophilic-hydrophobic balance of the molecule. As a consequence of its higher lipophilicity the molecule requires a more extensive conjugation with taurine in respect to compound Ih3e. The side chain geometry of the last compound probably produces a BA with a lower substrate specificity toward the enzyme responsible for the conjugation mediated by CoA activation process. The final result is that compound Ii3e is secreted in bile in an higher conjugated percentage than compound Ih3e.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

What is claimed:

1. A compound Ih3e of the chemical structure:

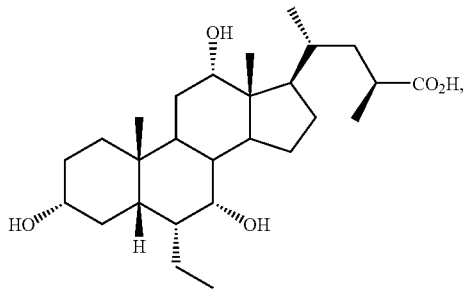

or a pharmaceutically acceptable salt, or glycine or taurine amino acid conjugate thereof.

2. The compound according to claim 1, wherein the compound is a pharmaceutically acceptable salt.

3. A pharmaceutically acceptable composition comprising a compound according to claim 1 or a pharmaceutically acceptable salt thereof, and at least one pharmaceutically acceptable excipient.

4. A method of treating diabetes or obesity in a subject in need of said treatment comprising administering a compound Ih3e of the chemical structure:

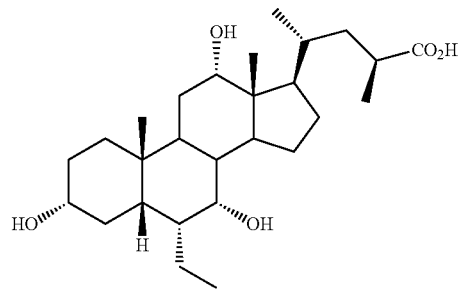

or a pharmaceutically acceptable salt thereof.

5. A kit for treating diabetes or obesity in a subject in need of said treatment, wherein the kit comprises a compound Ih3e of the chemical structure:

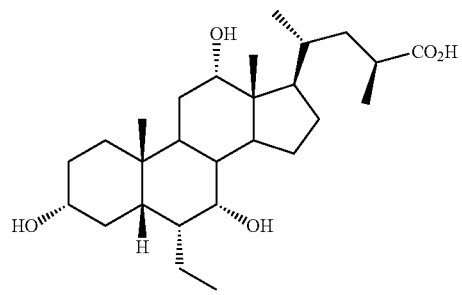

or a pharmaceutically acceptable salt thereof.

6. The compound according to claim 1, wherein the compound is a glycine amino acid conjugate.

7. The compound according to claim 1, wherein the compound is a taurine amino acid conjugate.

8. The method of claim 4 of treating diabetes.

9. The method of claim 4 of treating obesity.